United States Patent
Alt et al.

(10) Patent No.: US 10,640,820 B2
(45) Date of Patent: May 5, 2020

(54) METHODS RELATING TO THE DETECTION OF RECURRENT AND NON-SPECIFIC DOUBLE STRAND BREAKS IN THE GENOME

(71) Applicant: CHILDREN'S MEDICAL CENTER CORPORATION, Boston, MA (US)

(72) Inventors: Frederick W. Alt, Cambridge, MA (US); Richard L. Frock, Jamaica Plain, MA (US); Jiazhi Hu, Boston, MA (US); Robin M. Meyers, Cambridge, MA (US)

(73) Assignee: CHILDREN'S MEDICAL CENTER CORPORATION, Boston, MA (US)

(*) Notice: Subject to any disclaimer, the term of this patent is extended or adjusted under 35 U.S.C. 154(b) by 192 days.

(21) Appl. No.: 15/527,790

(22) PCT Filed: Nov. 20, 2015

(86) PCT No.: PCT/US2015/061758
§ 371 (c)(1),
(2) Date: May 18, 2017

(87) PCT Pub. No.: WO2016/081798
PCT Pub. Date: May 26, 2016

(65) Prior Publication Data
US 2018/0346977 A1    Dec. 6, 2018

Related U.S. Application Data

(60) Provisional application No. 62/082,395, filed on Nov. 20, 2014.

(51) Int. Cl.
*C12Q 1/6869* (2018.01)
*G16B 30/00* (2019.01)

(52) U.S. Cl.
CPC .......... *C12Q 1/6869* (2013.01); *G16B 30/00* (2019.02); *C12Q 2523/303* (2013.01);
(Continued)

(58) Field of Classification Search
None
See application file for complete search history.

(56) References Cited

U.S. PATENT DOCUMENTS

| 6,183,969 B1 | 2/2001 | Gabriel |
| 2003/0104382 A1 | 6/2003 | Hogan et al. |

(Continued)

FOREIGN PATENT DOCUMENTS

| WO | 2000024929 A3 | 5/2000 |
| WO | 2001/066802 A1 | 9/2001 |

(Continued)

OTHER PUBLICATIONS

Chiarle et al. (Cell, 2011, vol. 147, p. 107-119) (Year: 2011).*
(Continued)

*Primary Examiner* — Stephanie K Mummert
(74) *Attorney, Agent, or Firm* — Nixon Peabody LLP; David S. Resnick; Nicole D. Kling

(57) ABSTRACT

Described herein are methods and systems relating to high throughput, genome-wide translocation sequencing (HT-GTS) and/or detection of double-stranded DNA break (DSB) locations. The methods described herein can comprise generating DSBs in a nucleic acid sequence and performing nested PCR with the primers described herein. Described herein is an enhanced HTGTS approach. The assays and methods described herein permit the measurement of various DNA double-strand break (DSB) activities either intrinsic to the biological system or from outside agents.

20 Claims, 50 Drawing Sheets
Specification includes a Sequence Listing.

(52) U.S. Cl.
CPC . *C12Q 2525/191* (2013.01); *C12Q 2535/122* (2013.01); *C12Q 2549/119* (2013.01); *C12Q 2563/131* (2013.01)

(56) References Cited

U.S. PATENT DOCUMENTS

| | | |
|---|---|---|
| 2009/0047680 A1 | 2/2009 | Lok |
| 2014/0214334 A1 | 8/2014 | Plattner et al. |
| 2014/0234847 A1 | 8/2014 | Alt et al. |

FOREIGN PATENT DOCUMENTS

| | | |
|---|---|---|
| WO | 2006/003721 A1 | 1/2006 |
| WO | 2006053259 A2 | 5/2006 |
| WO | 2011/017596 A2 | 2/2011 |
| WO | 2013006745 A2 | 1/2013 |

OTHER PUBLICATIONS

Paruzynski et al. (Nature Protocols, 2010, 5(8):1379-1395) (Year: 2010).*

Bredemeyer et al., "ATM stabilizes DNA double-strand-break complexes during V (D) J recombination." Nature 442 (7101):466-470 (2006).

Chiang et al., "High-resolution mapping of copy-number alterations with massively parallel sequencing." Nature Methods 6(1):99-130 (2009).

Honma et al., "Non-homologous end-joining for repairing I-SceI-induced DNA double strand breaks in human cells." DNA Repair 6(6):781-788 (2007).

Puchta "The repair of double-strand breaks in plants: mechanisms and consequences for genome evolution." Journal of Experimental Botany 56(409):1-14 (2004).

Ochman et al., "Genetic applications of an inverse polymerase chain reaction." Genetics 120(3):621-623 (1988).

Chiarle et al., "Genome-wide translocation sequencing reveals mechanisms of chromosome breaks and rearrangements in B cells." Cell 147(1):107-119 (2011).

Klein et al., "Translocation-capture sequencing reveals the extent and nature of chromosomal rearrangements in B lymphocytes." Cell 147(1):95-106 (2011).

Langmead et al., "Fast gapped-read alignment with Bowtie 2", Nat Methods, 9(4):357-9 (2012).

Mahowald et al., "Aberrantly resolved RAG-mediated DNA breaks in Atm-deficient lymphocytes target chromosomal breakpoints in cis", PNAS 106(43):18339-18344 (2009).

Paruzynski et al., "Genome-wide high-throughput integrome analyses by nrLAM-PCR and next-generation sequencing", Nat Protoc, 5(8):1379-95 (2010).

Siebert et al., "An improved PCR method for walking in uncloned genomic DNA", Nucleic Acids Research 23 (6):1087-1088 (1995).

Wu et al., "High efficiency restriction enzyme-free linear amplification-mediated polymerase chain reaction approach for tracking lentiviral integration sites does not abrogate retrieval bias", Hum Gene Ther, 24(1):38-47 (2013).

* cited by examiner

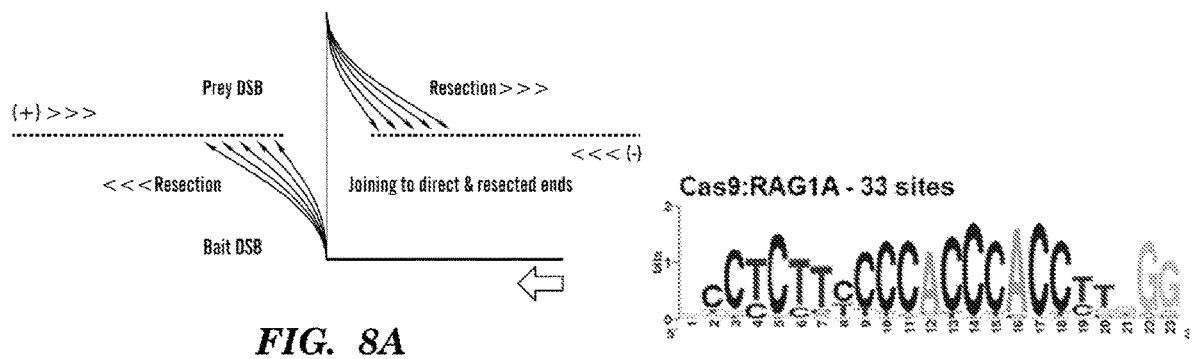
FIG. 8A
Fig. 8B
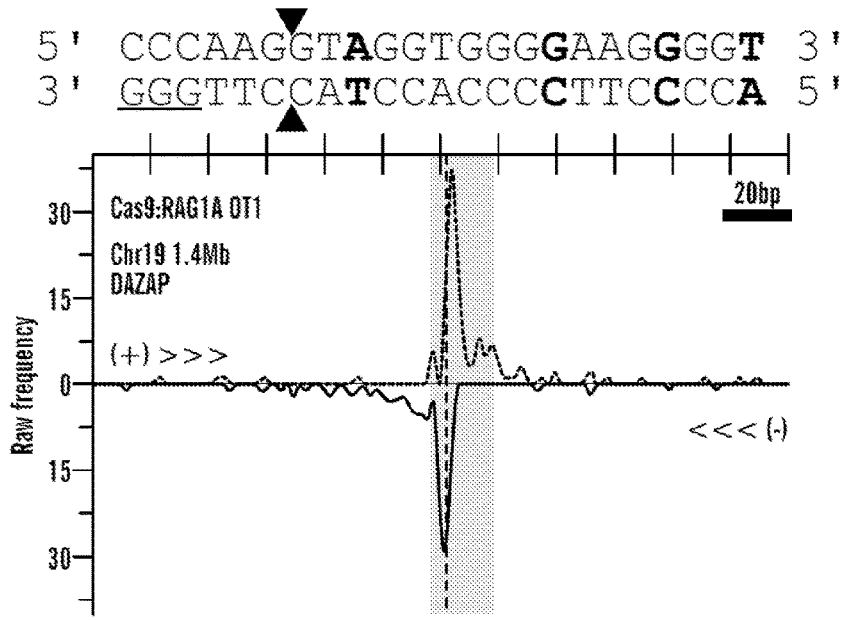
FIG. 8C

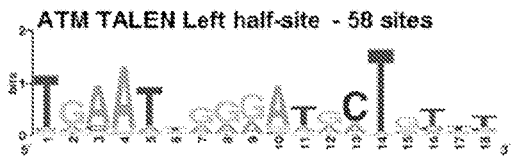
Fig. 11D
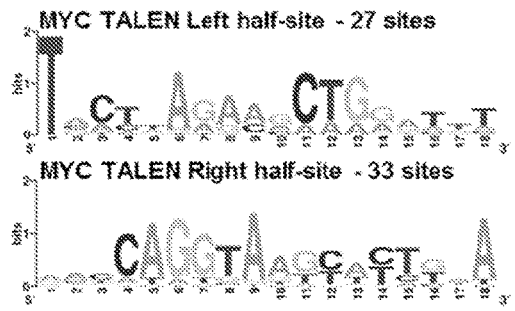
Fig. 11E
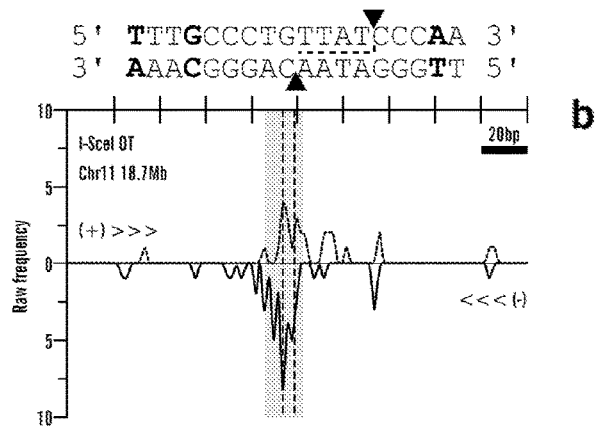
FIG. 12A
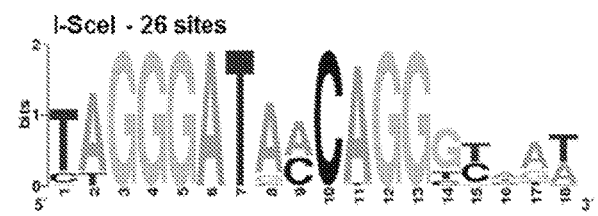
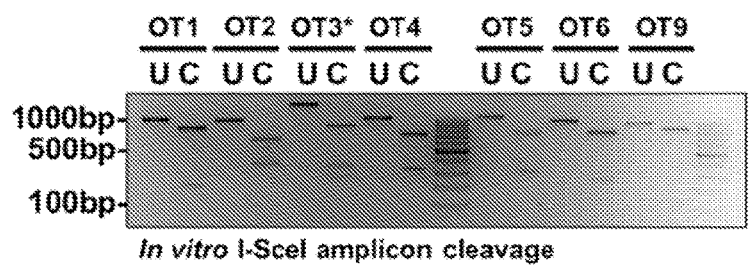
Figs. 12A-12C

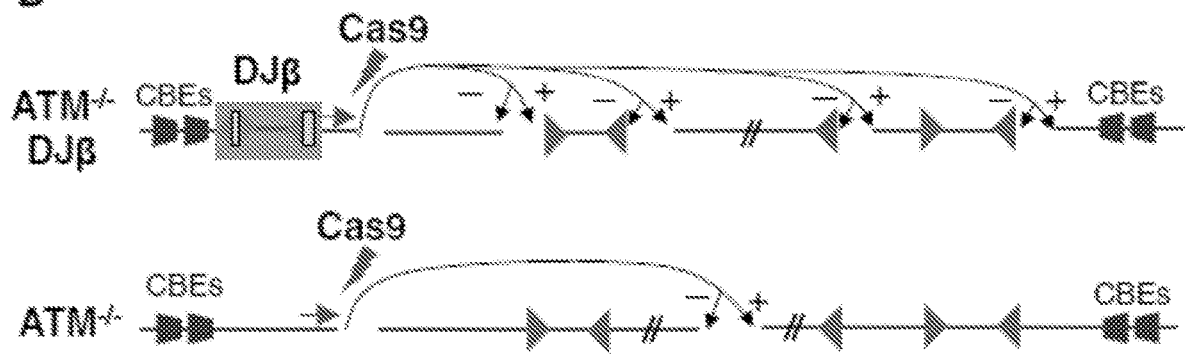
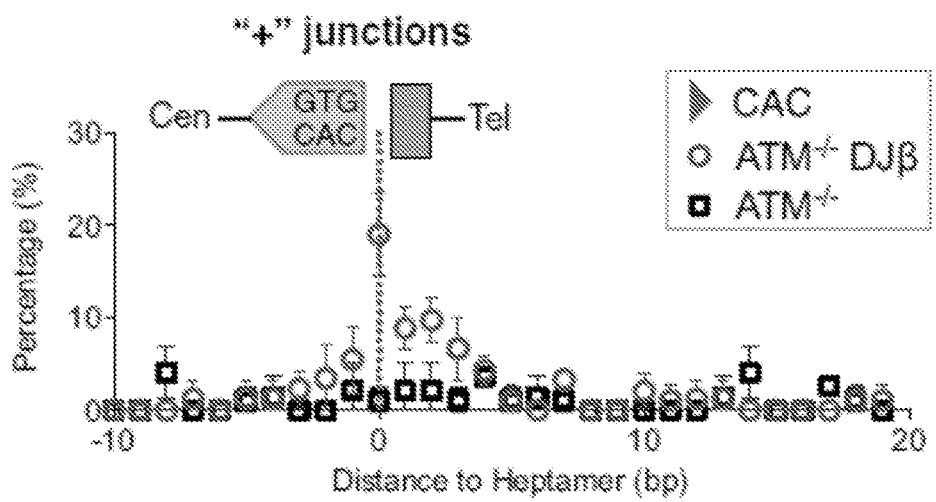
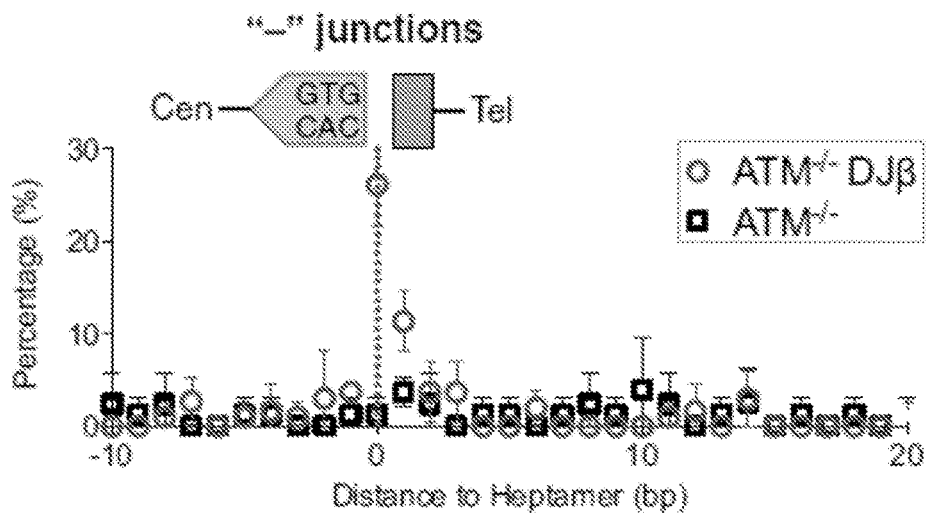
Figs. 28A-28F (cont.)

SEQUENCE LISTING

<160> NUMBER OF SEQ ID NOS: 360

<210> SEQ ID NO 1

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(26)
<223> OTHER INFORMATION: a, c, t, g, unknown or other

<400> SEQUENCE: 1
gcctctttcc cacccacctt gggnnn                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
accccttccc cacctacctt gggtcg                                          26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcctcctccc cacccacctt cagact                                          26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccctccttcc cacccacttt gggtga                                          26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcctctctcc cacccacctc cggctc                                          26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acgtcttccc cacccacctg gggcct                                          26
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acttccttcc cacccacctt cagcca                                              26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcctcttctc cacccacctc tggttt                                              26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtctctttct cacccacttt gggttg                                              26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caccctttcc catccacctt tggata                                              26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcctcttcca cacccaccct gggccc                                              26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcctctttac cacctcacct tgggca                                              26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttctcttccc cacccacctt tgagct                                          26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcctcttctc cacccaccat agggtg                                          26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtctctttcc catccacctt tgataa                                          26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcccctaccc cacccacctg ggtgga                                          26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acctcttatc cacccacctt ggcctc                                          26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcctctcccc acccaccctt ggcttg                                          26

```
<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acctccttcc cgcccacctg gggctc                                              26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
accccttccc cactcacctc cgggat                                              26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcttcttccc cacccacact tggtgg                                              26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cacccttccc cacccaccct gggacc                                              26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 gccccctcccc cacccaccct ggggga                                             26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgctcttccc cacccaccca aggcct                                              26

<210> SEQ ID NO 25
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
acctccatcc tccccacctt gggtct                                            26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggctcctcct cacccacctc tgggtc                                            26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gactcttttc cacccaccct agggga                                            26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
acctcttccc tccccacctt tggagg                                            26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
acctctttcc atcccacctt gggaaa                                            26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtgtattccc cacccacctt gggaag                                            26

<210> SEQ ID NO 31
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gccccttccc cacccaccct gtggaa                                              26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
accttgtccc cacccaccag gggatc                                              26

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gccccttacc catccaccct gggtgc                                              26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 gccctgccc cacccacctg tggagc                                               26

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgaattggga tgctgttt                                                       18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggataggga tgatgtgc                                                       18

<210> SEQ ID NO 37
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
tgaatagaac tgcttttc                                              18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
taaataggga ttctgagc                                              18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgaaatgggg ttttgatt                                              18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgaataggaa caaagatt                                              18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgaatcggga agatattc                                              18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcaattgaaa agctgagg                                              18

<210> SEQ ID NO 43
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
cgaataggaa tgctctgc                                                       18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgaatagaaa tgctgtca                                                       18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaaattggga tgattttc                                                       18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttgaatagaa tgatgtat                                                       18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgaatgagaa tgctcatt                                                       18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgaacaagga tgctgcat                                                       18

<210> SEQ ID NO 49
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
tcacttaaaa tactgttt                                                  18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tagatagtga tactgttt                                                  18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
taaatagtga tgctgtgg                                                  18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
taaattagga agctgagg                                                  18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgaatcagga aactgtcc                                                  18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgacttcaga tgctgcct                                                  18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 55
tgaattggaa agcagtag                                                18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tggactagag tgctggtt                                                18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttagttggga tactgctt                                                18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggaatcagga tactcctc                                                18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tggattagaa tgatctac                                                18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgaatggaga tgattaca                                                18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 61
tgaataggca cgctgttc                                               18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgatttgaga tgctctta                                               18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgcatagggg agatgttt                                               18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tgaagcagga tactgcat                                               18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgcataaaga tgctattg                                               18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgcatagtga agctgctt                                               18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 67
tgaataggga acctatag                                                18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgagtgaggg ttctagtt                                                18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgagatgaga gactcact                                                18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgaattaaga tactgttt                                                18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgcattgaaa aactatct                                                18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
taaataagaa agctttct                                                18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
```
tgaaaggaaa tactgtct                                                 18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tgaaatagga tattatat                                                 18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
taaattgaaa ggctgttg                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggcattgcgt tgaattgt                                                 18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggaaatggaa acctgttt                                                 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tgaaatgaga tgatttat                                                 18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgaagtgggg tgctgcct                                          18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ttgattggga ttatgttt                                          18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tgaatgaggc tgctctttt                                         18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tgaatgtgga gaatgtgg                                          18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tgaacaggga tgctttgt                                          18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
taaattgaga tattgctt                                          18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tacattagaa tgatgtcc                                          18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgaatgtgaa tgctaatg                                                 18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttaattggga ccctgcct                                                 18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tgcatctggc taatgttt                                                 18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
taaatgaagc aactgttt                                                 18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tgaatatgta tactgctt                                                 18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tgaattggaa gactattg                                                 18

```
<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
agaatgctgt tgctctttt                                                   18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccaatgggga gaatgttt                                                    18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tttattttac tgtcttta                                                    18

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
actattttac tgtctttc                                                    18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gacactctac tgtcttca                                                    18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgcttagacg ctggattt                                                    18
```

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tacttagaac ctgggttt                                                   18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tactcagaaa atgaatta                                                   18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcccgagaag ctggaatt                                                   18

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgattaaacc ctgattct                                                   18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tccttgaaca ctggcttt                                                   18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tcccaagaag ctgggatt                                                   18

<210> SEQ ID NO 104

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tactaaaaga caaggttt                                                 18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tactcatgag ctaaatat                                                 18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgctaagaag ctggactc                                                 18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tgcttagaag caggtctt                                                 18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tacataaaag caagattc                                                 18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
taataagaca caagatac                                                 18

<210> SEQ ID NO 110
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tgcttctctg ctgaatta                                                  18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
taaatagaag aaggcttg                                                  18

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tgattagaac atagatcc                                                  18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tccatagaca ctgcatct                                                  18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tcctgagtag ctggatta                                                  18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tacctagaaa aagaatgt                                                  18

<210> SEQ ID NO 116
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 116
tgtatagaag ctgggtgt                                              18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tcccaaagca ctaggatt                                              18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
taatgaagcc ctgaacat                                              18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tcccaagaag ctgggttt                                              18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
taatgaagcc ctgaacat                                              18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgcttaaaaa aagaatat                                              18

<210> SEQ ID NO 122
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 122
tacctagaag ctgatgga                                                    18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgctttggcc ctgtgagt                                                    18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tctcgagaag ctgaaatt                                                    18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
aaccaggtaa gcaccgaa                                                    18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ggccagggtg gcatctga                                                    18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tattagttaa gtacttgt                                                    18

<210> SEQ ID NO 128
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 128
ccacaggtaa gtacttaa                                                 18

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
acccaggcac acacagaa                                                 18

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cctcaggtat gcattgaa                                                 18

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aaccaggtaa tctttgta                                                 18

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ttacaggagt gcactgcc                                                 18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aacacgagaa tcgcttga                                                 18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued

```
oligonucleotide

<400> SEQUENCE: 134
aaccaggtaa ttttgta                                                    18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aagcaggtaa ggacctta                                                   18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
aaccagggaa gtatccaa                                                   18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gatcaggtag gcattcaa                                                   18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agtcaggtaa gcacacca                                                   18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
aaccaggtaa ttttgta                                                    18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 140
catctggtga gtgctgaa                                                   18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
aatgaggcag gcacataa                                                   18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
aaccaggtag ggaactat                                                   18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
atgcttgtaa tcccagca                                                   18

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aaccaggtac tttcttaa                                                   18

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
taccaggtat gtcttgaa                                                   18

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 146
gcccaagtaa gcatccaa                                                 18

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcgcaggtaa gcatctaa                                                 18

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gggaaggtaa acattgaa                                                 18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aaccagtcaa gcactttt                                                 18

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gcccaggtaa tttttgta                                                 18

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cagcaagtat gcactgga                                                 18

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
```
gtccagttaa gctcttta                                                  18

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
acccagctaa tttttgta                                                  18

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gtccagttaa gctcttta                                                  18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aatatggtaa actttgaa                                                  18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aatcaggtaa gtatttca                                                  18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gagataggaa gcacttaa                                                  18

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158

```
gcccaggtaa tttttgta                                                    18
```

<210> SEQ ID NO 159
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (24)..(26)
<223> OTHER INFORMATION: a, c, t, g, unknown or other

<400> SEQUENCE: 159

```
gagtccgagc agaagaagaa gggnnn                                           26
```

<210> SEQ ID NO 160
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 160

```
gagtctaagc agaagaagaa gagagc                                           26
```

<210> SEQ ID NO 161
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 161

```
gagttagagc agaagaagaa aggcat                                           26
```

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 162

```
aagtctgagc acaagaagaa tggtga                                           26
```

<210> SEQ ID NO 163
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 163

```
gaggccgagc agaagaaaga cggcga                                           26
```

<210> SEQ ID NO 164
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide -continued

<400> SEQUENCE: 164
aagcccgagc aaaggaagaa aggaga                                              26

<210> SEQ ID NO 165
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gagtcctagc aggagaagaa gaggca                                              26

<210> SEQ ID NO 166
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gagtccggga aggagaagaa aggctc                                              26

<210> SEQ ID NO 167
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gagccggagc agaagaagga gggagg                                              26

<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gaatccaagc agaagaagag aaggag                                              26

<210> SEQ ID NO 169
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aagtcagagc agaaaaagag aggaca                                              26

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 170
acgtctgagc agaagaagaa tggaca                                          26

<210> SEQ ID NO 171
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aagtccgagg agaggaagaa agggtt                                          26

<210> SEQ ID NO 172
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gagtaggagc aggagaagaa ggagga                                          26

<210> SEQ ID NO 173
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(26)
<223> OTHER INFORMATION: a, c, t, g, unknown or other

<400> SEQUENCE: 173
gggtgggggg agtttgctcc tggnnn                                          26

<210> SEQ ID NO 174
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ggatggaggg agtttgctcc tggggt                                          26

<210> SEQ ID NO 175
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tagtggaggg agcttgctcc tggctg                                          26

<210> SEQ ID NO 176
<211> LENGTH: 26
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 176
ggggagggga agtttgctcc tggcat                                      26

<210> SEQ ID NO 177
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
gggagggtgg agtttgctcc tgggga                                      26

<210> SEQ ID NO 178
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
cgggggaggg agtttgctcc tgggga                                      26

<210> SEQ ID NO 179
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
gggtgggggg agtttgccccc aggcca                                     26

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
gtgggggtag agtttgctcc aggtgt                                      26

<210> SEQ ID NO 181
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181 gaggggagc agtttgctcc aggtga                                       26

<210> SEQ ID NO 182
<211> LENGTH: 26
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 182
gcgtgggggg tgtttgctcc cgggca                                              26

<210> SEQ ID NO 183
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ctggtggggg agcttgctcc agggaa                                              26

<210> SEQ ID NO 184
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aggaaggagg agttagctcc tggggg                                              26

<210> SEQ ID NO 185
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggtgggggtg ggtttgctcc tggtat                                              26

<210> SEQ ID NO 186
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gggcaagggg aggttgctcc tggaga                                              26

<210> SEQ ID NO 187
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aggtggtggg agcttgttcc tggctt                                              26

<210> SEQ ID NO 188
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ggaggagggg agtctgctcc aggttt                                              26

<210> SEQ ID NO 189
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
agctgagggg agcttgctct gggctg                                              26

<210> SEQ ID NO 190
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gagtgggtgg agtttgctac aggcag                                              26

<210> SEQ ID NO 191
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggttgagggg agtctgctcc aggctt                                              26

<210> SEQ ID NO 192
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gggtgggtgg agtttgctac tggcat                                              26

<210> SEQ ID NO 193
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
agggaggagg aatttgctcc aggagt                                              26

<210> SEQ ID NO 194
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 194
gggggtgggg actttgctcc agggcc                                              26

<210> SEQ ID NO 195
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gggcagaggg agttagcacc gggcgt                                              26

<210> SEQ ID NO 196
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
aagtaaggga agtttgctcc tggtcc                                              26

<210> SEQ ID NO 197
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aggaaggagg agttagctcc tggggg                                              26

<210> SEQ ID NO 198
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
aggaaggagg agttagctcc tggggg                                              26

<210> SEQ ID NO 199
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
agctggaggg agtttgcccc aggtga                                              26

<210> SEQ ID NO 200
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
```
gagggtgggg agtttactcc tggaag                                              26

<210> SEQ ID NO 201
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gggtgagggg aataaactcc aggtg                                               26

<210> SEQ ID NO 202
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
aggtcggggg agttagatcc cggggt                                              26

<210> SEQ ID NO 203
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggggaggggg agggtgctcc aggcag                                              26

<210> SEQ ID NO 204
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204 gggagggag agtttgttcc aggaaa                                               26

<210> SEQ ID NO 205
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
aagtgggaag agtttgttcc aggctc                                              26

<210> SEQ ID NO 206
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206

```
gggaggggc aggttgctcc aggata                                          26
```

<210> SEQ ID NO 207
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207

```
aggtaggaga agcttgctcc tgagat                                         26
```

<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208

```
ggtgggggag agctagctcc gggagg                                         26
```

<210> SEQ ID NO 209
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209

```
aagtgggagg agactgctcc aggtag                                         26
```

<210> SEQ ID NO 210
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210

```
aaatgggggg agtttgcccc ccggag                                         26
```

<210> SEQ ID NO 211
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211

```
gggggcgggg aggttgcccc ggggaa                                         26
```

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212

```
agccccgtct tctctgaatg                                                20
```

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cgttgagctg cttttttcctc                                              20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gcaacacggt gtggtatttc                                               20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tgaaccaatc ctgacattgc                                               20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tttggaaaca agcccagttg                                               20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tgaccccaga ttccttcttc                                               20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ggtggttcct gagtgtttcc                                               20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tggccaaaag tcatgaagtg                                           20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ggttgccatt gtgattcctc                                           20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ggcataaacc cacaaaaagg                                           20

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ccttagccca tggattctac c                                         21

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tcagtttacc ccaaccaagc                                           20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tgctgtggct tgaatgtctc                                           20

```
<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
acttctgagg ggcctttgtc                                               20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ccccctggaa gactgcttta                                               20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
aggactgctg gagattgctc                                               20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ttggttgccc atcttattcc                                               20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
agctaaacct gcctgcagaa                                               20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
aataacttgc agccattcca                                               20

<210> SEQ ID NO 231
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
taaattgccc atgattgcac                                                     20

<210> SEQ ID NO 232
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
taaccagccc t                                                              11

<210> SEQ ID NO 233
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gtaatacgac tcactatagg gcacgcgtgg tcgacggccc gggctggtta t                  51

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
aggactgctg gagattgctc                                                     20

<210> SEQ ID NO 235
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tacactcttt ccctacacga cgctcttccg atctgagagg gtttcccctc aaag              54

<210> SEQ ID NO 236
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tacactcttt ccctacacga cgctcttccg atcttggaga gggtttcccc tcaaag            56

<210> SEQ ID NO 237
<211> LENGTH: 57
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tacactcttt ccctacacga cgctcttccg atctcatgag agggtttccc ctcaaag        57

<210> SEQ ID NO 238
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tacactcttt ccctacacga cgctcttccg atctgctcga gagggtttcc cctcaaag       58

<210> SEQ ID NO 239
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
tacactcttt ccctacacga cgctcttccg atctgccatg agagggtttc cctcaaag       59

<210> SEQ ID NO 240
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tacactcttt ccctacacga cgctcttccg atctatatcg gagagggttt ccctcaaag      60

<210> SEQ ID NO 241
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tctcggcatt cctgctgaac cgctcttccg atctactata gggcacgcgt ggt            53

<210> SEQ ID NO 242
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
aatgatacgg cgaccaccga gatctacact ctttccctac acgacgct                  48

<210> SEQ ID NO 243
<211> LENGTH: 48
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 243
caagcagaag acggcatacg agatcggtct cggcattcct gctgaacc                48

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
cctgagaaca atgaaaacaa gtc                                           23

<210> SEQ ID NO 245
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tacactcttt ccctacacga cgctcttccg atctaccaat atcaatatcc cactgatg    58

<210> SEQ ID NO 246
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tacactcttt ccctacacga cgctcttccg atctcgacca atatcaatat cccactgatg  60

<210> SEQ ID NO 247
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tacactcttt ccctacacga cgctcttccg atctcacgac caatatcaat atcccactga  60
tg                                                                  62

<210> SEQ ID NO 248
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tacactcttt ccctacacga cgctcttccg atctgactcg accaatatca atatcccact  60
gatg                                                                64

```
<210> SEQ ID NO 249
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(27)
<223> OTHER INFORMATION: a, c, t, g, unknown or other

<400> SEQUENCE: 249
gcgactatag ggcacgcgtg gtnnnnn                                          27

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ccacgcgtgc cctatagtcg c                                                21

<210> SEQ ID NO 251
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
accacgcgtg ccctatagtc gc                                               22

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ttccctgtaa cttgggatgg                                                  20

<210> SEQ ID NO 253
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tacactcttt ccctacacga cgctcttccg atcttgccca gaaatcagaa caac            54

<210> SEQ ID NO 254
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
```
tacactcttt ccctacacga cgctcttccg atctagtgcc cagaaatcag aacaac    56

<210> SEQ ID NO 255
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tacactcttt ccctacacga cgctcttccg atcttcatgc ccagaaatca gaacaac    57

<210> SEQ ID NO 256
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tacactcttt ccctacacga cgctcttccg atctgatctg cccagaaatc agaacaac    58

<210> SEQ ID NO 257
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tacactcttt ccctacacga cgctcttccg atctctgaat gcccagaaat cagaacaac    59

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ggacaacaac ccccagttag    20

<210> SEQ ID NO 259
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tacactcttt ccctacacga cgctcttccg atcttgtggt aaaggagaca atgct    55

<210> SEQ ID NO 260
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tacactcttt ccctacacga cgctcttccg atctcttgtg gtaaaggaga caatgct    57

<210> SEQ ID NO 261
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tacactcttt ccctacacga cgctcttccg atctgactgt ggtaaaggag acaatgct          58

<210> SEQ ID NO 262
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tacactcttt ccctacacga cgctcttccg atctacgttg tggtaaagga gacaatgct         59

<210> SEQ ID NO 263
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tacactcttt ccctacacga cgctcttccg atcttgacat gtggtaaagg agacaatgct        60

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ctgctgccgt caactagaac                                                    20

<210> SEQ ID NO 265
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tacactcttt ccctacacga cgctcttccg atctatttaa gcgcctgatt cgag              54

<210> SEQ ID NO 266
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tacactcttt ccctacacga cgctcttccg atctcgattt aagcgcctga ttcgag            56

<210> SEQ ID NO 267
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 267
tacactcttt ccctacacga cgctcttccg atcttcaatt taagcgcctg attcgag     57

<210> SEQ ID NO 268
<211> LENGTH: 58
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 268
tacactcttt ccctacacga cgctcttccg atctatctat ttaagcgcct gattcgag    58

<210> SEQ ID NO 269
<211> LENGTH: 59
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 269
tacactcttt ccctacacga cgctcttccg atctccgcga tttaagcgcc tgattcgag   59

<210> SEQ ID NO 270
<211> LENGTH: 59
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 270
tacactcttt ccctacacga cgctcttccg atcttgtaca tttaagcgcc tgattcgag   59

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 271
cgaaactttg cccatagcag                                              20

<210> SEQ ID NO 272
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 272
tacactcttt ccctacacga cgctcttccg atctcttaca cacccgagc aagg          54

```
<210> SEQ ID NO 273
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tacactcttt ccctacacga cgctcttccg atctagcctt acaacacccg agcaagg         57

<210> SEQ ID NO 274
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tacactcttt ccctacacga cgctcttccg atctctcgct tacaacaccc gagcaagg        58

<210> SEQ ID NO 275
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tacactcttt ccctacacga cgctcttccg atcttgtatc ttacaacacc cgagcaagg       59

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(26)
<223> OTHER INFORMATION: a, c, t, g, unknown or other

<400> SEQUENCE: 276
gacttgtttt cattgttctc aggnnn                                           26

<210> SEQ ID NO 277
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tccttgtttt cattgttctc tggtgg                                           26

<210> SEQ ID NO 278
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
```
catttgtttt cattgttctc tggctg						26

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (22)..(24)
<223> OTHER INFORMATION: a, c, t, g, unknown or other

<400> SEQUENCE: 279
nnntagggat aacagggtaa tnnn						24

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gtcttgggat aacagggcaa agca						24

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
attttgggat aacagggcaa tact						24

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ttgtagggat accaggttta tttc						24

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggctagggat accaggtcaa acaa						24

<210> SEQ ID NO 284
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 284
cactagggat aacaggctat tcgg                                           24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tactagggat accagggtca ttca                                           24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tgctagggat aacaggttga aggt                                           24

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
cagtagggat aacagggctg ttga                                           24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cactagggat gccagggtga acaa                                           24

<210> SEQ ID NO 289
<211> LENGTH: 9
<212> TYPE: PRT
<213> ORGANISM: Unknown
<220> FEATURE:
<223> OTHER INFORMATION: Description of Unknown:
      Homing endonuclease sequence

<400> SEQUENCE: 289

Leu Ala Gly Leu Ile Asp Ala Asp Gly
1               5

<210> SEQ ID NO 290
<211> LENGTH: 99
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (72)..(81)
<223> OTHER INFORMATION: a, c, t, g, unknown or other

<400> SEQUENCE: 290
gcgggtgctg aatttcatct ggggcagaac tgagtcccaa gcttgggact cagttctgcc    60
ccagatgaaa tnnnnnnnnn nctttgaggg gaaaccctc                            99

<210> SEQ ID NO 291
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(28)
<223> OTHER INFORMATION: a, c, t, g, unknown or other

<400> SEQUENCE: 291
gagggtttcc cctcaaagnn nnnnnnnnat ttcatctggg gcagaactga gtcccaagct    60
tgggactcag ttctgcccca gatgaaattc agcacccgc                            99

<210> SEQ ID NO 292
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (73)..(82)
<223> OTHER INFORMATION: a, c, t, g, unknown or other

<400> SEQUENCE: 292
ggtccgctgc tgggaaagag gctgccatgc tggctgaggt acctgagaac aatgaatccc    60
acccaccttg ggnnnnnnnn nnctttgagg ggaaaccctc tc                       102

<210> SEQ ID NO 293
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (21)..(30)
<223> OTHER INFORMATION: a, c, t, g, unknown or other

<400> SEQUENCE: 293
gagagggttt cccctcaaag nnnnnnnnnn cccaaggtgg gtgggattca ttgttctcag    60
gtacctcagc cagcatggca gcctctttcc cagcagcgga cc                       102

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 294
cccaaggtag gtggggaagg ggt        23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ctgaaggtgg gtggggagga gga        23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
tccttgtttt cattgttctc tgg        23

<210> SEQ ID NO 297
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (64)..(76)
<223> OTHER INFORMATION: a, c, t, g, unknown or other

<400> SEQUENCE: 297
cttgttttca ttgttctcag gtacctcagc cagcatggca gcctctttcc cacccacctt        60
gggnnnnnnn nnnnnnctttt gaggggaaac cctctc        96

<210> SEQ ID NO 298
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(33)
<223> OTHER INFORMATION: a, c, t, g, unknown or other

<400> SEQUENCE: 298
gagagggttt cccctcaaag nnnnnnnnnn nnncccaagg tgggtgggaa agaggctgcc        60
atgctggctg aggtacctga gaacaatgaa aacaag        96

<210> SEQ ID NO 299
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tttgccctgt tatcccaa                                                    18

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gccctaacac ccaggaacag ggg                                              23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gccctaacat ccagaaacag ggg                                              23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
acccttacat ccaggaacag cgg                                              23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
accctaccac tcaggaacag agg                                              23

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304 gggtggggg agtttgctcc tgg                                               23

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
aggagggagg ggtttgctcc cgg                                                23

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306 agtgggggg agtttgcccc ggg                                                 23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
acgtgagggg agcttgctcc agg                                                23

<210> SEQ ID NO 308
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(27)
<223> OTHER INFORMATION: a, c, t, g, unknown or other

<400> SEQUENCE: 308
gcgactatag ggcacgcgtg gnnnnnn                                            27

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
ccacgcgtgc cctatagtcg c                                                  21

<210> SEQ ID NO 310
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
acactctttc cctacacgac gctcttccga tct                                     33

<210> SEQ ID NO 311
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 311
ctcggcattc tgctgaacc gctcttccga tctgactata gggcacgcgt gg         52

<210> SEQ ID NO 312
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
aatgatacgg cgaccaccga gatctacact ctttccctac acgacgctct tccgatct    58

<210> SEQ ID NO 313
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
caagcagaag acggcatacg agatcggtct cggcattcct gctgaaccgc tcttc        55

<210> SEQ ID NO 314
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
catgagagct ggagctagta tgaaggtg                                     28

<210> SEQ ID NO 315
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
actgactgac tgagtgtcct ctcaac                                       26

<210> SEQ ID NO 316
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
cagtcacaga gaaactgatc caggtgag                                     28

<210> SEQ ID NO 317
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
ccatagcagt tggtcaatcc ttgtctcc                                              28

<210> SEQ ID NO 318
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
gcgccatcga tggactgctg tgggtttcac ccag                                       34

<210> SEQ ID NO 319
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ggccggtcga caggcgcgca ctgacaccac taag                                       34

<210> SEQ ID NO 320
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 320
cctgggtagg ttacaggtca aggct                                                 25

<210> SEQ ID NO 321
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
ctgcagagac agtgaccaga gtcccttggc cccagtaagc aaaccagggt agctactacc           60
gtagtaataa a                                                                71

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tgatgttggg ctagcgcag                                                        19

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 323
agggatgtga ccgattcgtt g                                            21

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gaccttacac agtcctgctg                                              20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gtagacggca tcgcagcttg                                              20

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
caaaagacgg caatatggtg g                                            21

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
acgcacaccg gccttattcc                                              20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gacaaccact acctgagcac                                              20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ccaacgagaa gcgcgatcac                                                20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gaataggtct tttatctgaa                                                20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gagcaatata cctgagtctg                                                20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gacgagcgtc actgatagta                                                20

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gcctcggctc ttagcagact g                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
cctctgaagc caaggccgat g                                              21

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 335
gcagtgtctg ctgagtgact                                              20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tgatgagagc cactcagctc                                              20

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
cctaagctga tgctgagctt g                                            21

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
caatggccct gattgtgctg                                              20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
cctattttct ccgactagcc                                              20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gaagcacaca tgtggcttgc                                              20

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
```
ctggtgctta caccattaga g                                              21

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gtgaggtatg aagccatgac c                                              21

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tgtcgggagt tagcttccag                                                20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ctgtcctcac actcaggttc                                                20

<210> SEQ ID NO 345
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
caagtggcga acatgaccta gc                                             22

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ctgctactat tgctcctctg                                                20

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ctaagacagt aaggtagaca cac                                           23

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
ctagttggtt atgcgtatga c                                             21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gaagtagaac agaagggaaa g                                             21

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
ccgcactctt tgacacagac                                               20

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gttcatattc aaagtttagt cgcc                                          24

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ctctagccaa aagctggctt c                                             21

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ggaaaactct gtaggactac                                               20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
tgggacatgt aaactgtaac                                                   20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cttgctccct aggaccttcc                                                   20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
actgaaactc aaccgtgctg                                                   20

<210> SEQ ID NO 357
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(30)
<223> OTHER INFORMATION: a, c, t, g, unknown or other

<400> SEQUENCE: 357
cacggtgnnn nnnnnnnnn nnnnnnnnnn acaaaaacc                                39

<210> SEQ ID NO 358
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(32)
<223> OTHER INFORMATION: a, c, t, g, unknown or other

<400> SEQUENCE: 358 ggttttgtn nnnnnnnnn nnnnnnnnnn nncaccgtg                                39

<210> SEQ ID NO 359
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(21)
<223> OTHER INFORMATION: a, c, t, g, unknown or other

<400> SEQUENCE: 359
tatttttctn nnnnnnnnnn ncactgtg                                          28

<210> SEQ ID NO 360
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(19)
<223> OTHER INFORMATION: a, c, t, g, unknown or other

<400> SEQUENCE: 360
cacagtgnnn nnnnnnnnna gaaaaata                                          28
```

METHODS RELATING TO THE DETECTION OF RECURRENT AND NON-SPECIFIC DOUBLE STRAND BREAKS IN THE GENOME

CROSS-REFERENCE TO RELATED APPLICATIONS

This application is a 35 U.S.C. § 371 National Phase Entry Application of International Application No. PCT/US15/061758 filed Nov. 20, 2015, which designates the U.S. and claims benefit under 35 U.S.C. § 119(e) of U.S. Provisional Application No. 62/082,395 filed Nov. 20, 2014, the contents of which are incorporated herein by reference in their entireties.

GOVERNMENT SUPPORT

This invention was made with federal funding under Grant Nos. P01CA109901 and P01AI076210 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Nov. 19, 2015, is named 701039-083171-PCT_SEtxt and is 87,609 bytes in size.

TECHNICAL FIELD

The technology described herein relates to methods and assays for detecting and analyzing double-strand breaks and resulting translocations in the genome of a cell.

BACKGROUND

Chromosomal translocations fuse sections of two heterologous chromosomes or two separated regions on homologous chromosomes. Other than from resection at a fixed break, such junctions are expected to result mostly from end-joining of double-strand breaks (DSBs) to other genomic DSBs. DSBs can arise from a number of stresses and sources. The frequency and location of such DSBs and resulting chromosomal translocations is of particular interest in cancer, V(D)J recombination, and within the context of the use of engineered nucleases, e.g., for gene therapy. Existing methods of high-throughput genome-wide translocation sequencing (HTGTS) uses engineered "bait" DSBs to detect other "prey" cellular DSBs genome-wide.

SUMMARY

Described herein is an enhanced HTGTS approach. The assays and methods described herein permit the measurement of various DNA double-strand break (DSB) activities either intrinsic to the biological system or from outside agents. As but one example, the methods and assays described herein can, e.g., identify custom nuclease generated on-target and off-target DSBs, as well as non-specific DSBs and collateral genomic damage such as recurrent translocations. The presently described methods have increased sensitivity in identifying off-target hotspots as well as non-specific DSB occurrences and additionally, are much cheaper, faster and more robust than prior methods.

In one aspect, described herein is a method for high throughput, genome-wide translocation sequencing (HT-GTS) and detection of double-stranded DNA break (DSB) locations, the method comprising the steps of: (a) exposing a cell to an agent known or suspected of being capable of producing at least one DSB; (b) optionally, allowing the cell to divide for at least a half cell cycle after exposure; (c) extracting genomic DNA from the cells; (d) optionally, producing a fragmented DNA sample; (e) producing a single-stranded PCR product by Linear Amplification Mediated (LAM)-PCR with a first locus-specific primer; (f) producing a ligated DNA product by ligating the single-stranded PCR product produced in step (e) to an adapter, wherein the adapter comprises: a distal portion of known DNA sequence that can be used to design PCR primers for a nested PCR amplification; a proximal portion of random nucleotides comprising a 3' overhang; (g) producing a nested PCR product by performing a nested-PCR with an adapter- and a locus-specific primer using the ligated DNA product thereby amplifying the nucleic acid sequence surrounding the junction around the at least one DSB; (h) optionally, digesting the ligated DNA sample with a blocking enzyme; (i) producing a sequenced nested PCR product by sequencing the nested PCR product; (j) aligning the sequenced nested PCR product against a reference sequence to identify a chromosomal location of the translocation and the chromosomal location of the at least one DSB.

In some embodiments, the first locus-specific primer comprises an affinity tag. In some embodiments, the method further comprises isolating the PCR products produced in step (e) by affinity purification. In some embodiments, the affinity tag is biotin. In some embodiments, the affinity purification comprises binding biotin with streptavidin. In some embodiments, the affinity purification comprises binding the PCR products produced in step (d) to a substrate. In some embodiments, the substrate is a bead.

In some embodiments, the primers used for the nested PCR step comprise barcode sequences.

In some embodiments, the fragmenting is performed by sonication or restriction digest. In some embodiments, the fragmenting is performed by randomly shearing genomic DNA or with a frequently cutting restriction enzyme.

In some embodiments, ligating the single-stranded PCR products to an adapter comprises contacting the PCR product with a population of adapters having the same distal portion and random proximal portion sequences. In some embodiments, the proximal portion of the adaptor is 3-10 nucleotides in length. In some embodiments, the proximal portion of the adaptor is 5-6 nucleotides in length. In some embodiments, the adaptor comprises barcode sequences between distal and proximal portions. In some embodiments, the PCR products produced in step (i) are size selected prior to sequencing.

In some embodiments, the agent is Cas9. In some embodiments, the agent is selected from the group consisting of a nuclease; a custom nuclease; a meganuclease; a TALEN; a zinc-finger nuclease; a chemotherapeutic; and radiation. In some embodiments, the cell is exposed to two agents, wherein one agent will generate at least one DSB within 400 bp of the locus-specific primer. In some embodiments, the method further comprises a step of inserting into a cell to be analyzed at least one target sequence for the agent that is known to be absent in the genome of the cell to be analyzed prior to step (a).

In some embodiments, the cells are allowed to divide for at least 12 hours. In some embodiments, the cells are allowed to divide for 1-5 days. In some embodiments, the cells are allowed to divide for 2-4 days.

In some embodiments, the sequencing is performed using a next generation sequencing method. In some embodiments, the step of aligning is performed by a non-human machine. In some embodiments, the non-human machine comprises a computer executable software. In some embodiments, the method further comprises a display module for displaying the results of the step of aligning.

In some embodiments, the cell is a mammalian cell. In some embodiments, the cell is a plant cell. In some embodiments, the cell division step (b) is omitted. In some embodiments, the blocking digestion step (h) is omitted. In some embodiments, the fragmentation step (d) is omitted. In some embodiments, end repair is not performed between steps (d) and (e).

In one aspect, described herein is a kit comprising: an agent known to cause at least one DSB in a cell; and a locus-specific primer that will anneal within 400 bp of the DSB generated by the agent. In some embodiments, the kit can further comprise an adapter, the adapter comprising: a distal portion of known DNA sequence that can be used to design PCR primers for a nested PCR amplification; and a proximal portion of random nucleotides comprising a 3' overhang. In some embodiments, the kit further comprises at least one nested PCR primer. In some embodiments, the kit further comprises a substrate comprising an affinity domain, wherein the locus-specific primer comprises an affinity tag. In some embodiments, the kit further comprises a cell. In some embodiments, the kit further comprises an additional agent known or suspected to cause at least one DSB in the cell.

In one aspect, described herein is a computer implemented method for high throughput, genome-wide translocation sequencing (HTGTS) and detection of double-stranded DNA break (DSB) locations, comprising: on a device having one or more processors and a memory storing one or more programs for execution by the one or more processors, the one or more programs including instructions for: aligning a sequenced nested PCR product against a reference sequence to identify a chromosomal location of a translocation and the chromosomal location of at least one DSB. In some embodiments, the aligning step is performed by an aligning program. In some embodiments, the aligning program is Bowtie2. In some embodiments, the aligning step comprises a best-path search algorithm to determine prey and bait alignments. In some embodiments, the aligning step comprises de-multiplexing sequence reads. In some embodiments, the de-multiplexing sequence reads comprises using a fastq-multx tool. In some embodiments, the aligning step comprises trimming an adapter sequence. In some embodiments, trimming the adapter sequence comprises using a SeqPrep utility. In some embodiments, the aligning step comprises mapping reads to an hg19 reference genome using the Bowtie2 with the top fifty alignments reported that had an alignment score above 50, representing a perfect 25 nt local alignment. In some embodiments, on average, 94% of the demultiplexed reads per library harbor a bait sequence alignment with <10% of these reads containing an alignable prey junction. In some embodiments, the aligning step comprises a best-path searching algorithm to select an optimal sequence of alignments that describe the read's composition. In some embodiments, the aligning step comprises filtering. In some embodiments, the filtering comprises a bait alignment and a prey alignment. In some embodiments, the bait alignment does not extend more than 10 nucleotides beyond a targeted site. In some embodiments, the aligning step comprises vector controls, off-set nicking with multiple sites, and use of a distal targeted site. In some embodiments, the aligning step comprises comparing discarded alignments to a selected prey alignment. In some embodiments, if any of the discarded alignments surpasses both a coverage and score threshold with respect to the prey alignment, the read is filtered due to low mapping quality. In some embodiments, the aligning step comprises extending the bait alignment 10 nucleotides past the primer to remove possible mispriming events and other artifacts. In some embodiments, the aligning step comprises removing potential duplicates by comparing coordinates of an end of a bait alignment and a start of a prey alignment across all reads. In some embodiments, the aligning step comprises marking a read as a duplicate if it has a bait alignment off-set within 2 nt and a prey alignment offset within 2 nt of another read's bait and prey alignments. In some embodiments, the aligning step comprises applying post-filter stringency to remove junctions with gaps larger than 30 nt and bait sequences shorter than 50 nt. In some embodiments, the aligning step comprises removing reads with prey alignments to telomere repeat sequences. In some embodiments, the aligning step comprises filtering genome mixing experiments using a combined hg19/mm9 reference or *Homo sapiens/Mus musculus* genome builds.

In some embodiments, the computer implemented method is used with a method for high throughput, genome-wide translocation sequencing (HTGTS) and detection of double-stranded DNA break (DSB) locations, the method comprising the steps of: (a) exposing a cell to an agent known or suspected of being capable of producing at least one DSB; (b) optionally, allowing the cell to divide for at least a half cell cycle after exposure; (c) extracting genomic DNA from the cells; (d) optionally, producing a fragmented DNA sample; (e) producing a single-stranded PCR product by Linear Amplification Mediated (LAM)-PCR with a first locus-specific primer; (f) producing a ligated DNA product by ligating the single-stranded PCR product produced in step (e) to an adapter, wherein the adapter comprises a distal portion of known DNA sequence that can be used to design PCR primers for a nested PCR amplification and a proximal portion of random nucleotides comprising a 3' overhang; (g) producing a nested PCR product by performing a nested-PCR with an adapter- and a locus-specific primer using the ligated DNA product thereby amplifying the nucleic acid sequence surrounding the junction around the at least one DSB; (h) optionally, digesting the ligated DNA sample with a blocking enzyme; (i) producing a sequenced nested PCR product by sequencing the nested PCR product; (j) aligning the sequenced nested PCR product against the reference sequence to identify the chromosomal location of the translocation and the chromosomal location of the at least one DSB.

In one aspect, described herein is a computer system for high throughput, genome-wide translocation sequencing (HTGTS) and detection of double-stranded DNA break (DSB) locations, comprising: one or more processors and memory to store one or more programs, the one or more programs comprising instructions for: aligning a sequenced nested PCR product against a reference sequence to identify a chromosomal location of a translocation and the chromosomal location of at least one DSB. In one aspect, described herein is a non-transitory computer-readable storage medium storing one or more programs for high throughput, genome-wide translocation sequencing (HTGTS) and detection of double-stranded DNA break (DSB) locations, the one or more programs for execution by one or more processors of a computer system, the one or more programs comprising instructions for: aligning a sequenced nested PCR product against a reference sequence to identify a chromosomal location of a translocation and the chromosomal location of at least one DSB.

BRIEF DESCRIPTION OF THE DRAWINGS

FIG. 1A depicts a schematic of LAM-PCR HTGTS method overview. Major modifications of prior HTGTS method include enriching for translocations directly from sonicated DNA via LAM-PCR and ssDNA ligation using a bridge adapter. FIG. 1B depicts positions of Cas9:RAG1A-D gRNA target sites within the RAG1 locus on Chromosome (Chr) 11. White arrow indicates the cloning primer used to capture the 3' DSB ends from the RAG1A site (white box); RAG1B uses the same primer but with longer bait. RAG1 C & D use a separate primer strategy. Cas9:RAG1 DSBs occur 3 bp proximal to the PAM within the gRNA target sequence (bars shaded with negative sloped lines inside gRNA targets) FIG. 1C depicts a bar graph of average junction frequency per 10,000 unique junctions for each OT site not located on bait chromosomes 7, 11, 12, and 19. Error bars are displayed as S.E.M.

FIG. 2A depicts a schematic of prey joining outcomes of 3' DSB ends at the break-site. Light grey box indicates the break-site and the short arrow indicates the (−) orientation and position of the cloning primer used. Most junctions represent rejoining of the processed 5' DSB end (resection) followed by joins to other DSB ends which can result in deletions and excision circles and inversions to the (+) orientation (see FIG. 9A). Additional types of joins can occur from the homologous chromosome (see FIG. 9B) leading to tandem duplications, and translocations which can form dicentric chromosomes. FIGS. 2B-2C depict graphs of HTGTS libraries displaying prey junction enrichment within 1 kb regions flanking the break-site for (FIG. 2B) RAG1A and (FIG. 2C) RAG1A OT on Chr 19. Diagrams above each graph indicate the target break-site position; the number within the lower left grid of each graph indicates total junctions for each quadrant. FIG. 2D depicts the sequence of a RAG1A head-to-head inversion joined from the break-site on the homologous chromosome and corresponds to "1" indicated in FIG. 2B. PAM is boxed in solid black, RAG1A target sequence is boxed in small dashed lines, and primer sequence is boxed in bolded dashed lines. Identical sequences between the bait and prey are underlined. Sequences disclosed as SEQ ID NOS 290-291, respectively, in order of appearance.

FIG. 3A depicts a schematic of RAG1A paired with nearby gRNAs RAG1G, E, and F which target the opposing strand and generate DSBs with 5' overhangs of 28, 36, and 51 nt in length when used in combination with Cas9n. Red arrows indicate the orientation and position of the cloning primer used. White box indicates the gRNA target sites with grey bars indicating the position of Cas9 cleavage. FIG. 3B depicts a schematic of prey junction enrichment within 500 bp of the RAG1A target site for Cas9n:RAG1A/F (N=2). White arrows indicate position of the bait primer and the left dashed line indicates the position of the opposing strand gRNA target (RAG1F). Numbers in the lower left grid indicate total junctions for each region including the region between the paired off-set target sites (middle). FIG. 3C depicts sequence indicating a head-to-head inversion of the RAG1A bait to the RAG1F "prey" on the homologous chromosome as indicated as "1" in FIG. 3C. PAM is boxed in solid lines and the light dashed lines and grey highlights indicate RAG1A and RAG1F target sites respectively. Identical sequences between the two RAG1A target sites are underlined. Sequences disclosed as SEQ ID NOS 292-293, respectively, in order of appearance.

FIG. 4A depicts a plot of on-target and OT frequencies per 10,000 unique junctions from I-SceI, Cas9:EMX1, and Cas9:VEGFA (N=3 each) using Cas9:RAG1B as the bait. FIG. 4B depicts average junction frequencies for the top 50 recurrent ATM and c-MYC TALEN sites are listed. Error bars are displayed as S.E.M.

FIG. 5A depicts a graph of multiple RAG1B bait ATM TALEN titration HTGTS libraries plotting the ATM on-target frequency, the sum of the top 5 ATM TALEN OT sites and the average of junction frequencies along the break-site chromosome (ATM TALEN non-specific DSB activity; 100 regions minus bait break-site region and known ATM OT sites: 174 sites on chromosome 11, 880 bp mean size/site) ranging from 1 μg to 100 μg each (1 μg N=2; 3-10 μg N=3; 20-100 μg N=2). Libraries were normalized to RAG1B OT1 junction enrichment. FIG. 5B depicts the fold enrichment of the ATM TALEN on-target and the sum of the top 5 ATM OTs over the ATM TALEN non-specific DSB activity junctions is indicated for each transfected ATM TALEN plasmid concentration assayed.

FIG. 7A depicts a schematic demonstrating that filtered DNA sequence reads are composed of (from right to left) the bait primer (white arrow), the bait sequence (black rectangle) leading up to the junction (white box), followed by the aligned prey sequence (white rectangle). FIGS. 7B-7C demonstrate that bait sequence junction distribution corresponds to predicted break-site position for Cas9:RAG1A-D libraries displayed as either (FIG. 7B) total junctions or (FIG. 7C) percent junctions (black dashed lines; N=6 each). Due to the constraints of sequencing length for Miseq and, correspondingly, primer positions from the bait DSB, bait junctions predominately display short resections (up to 25 bp for most junctions) with some displaying longer resections leading up to the primer position; bait resections beyond the primer position are not detected with this method. However, this is not true for prey junctions, and for those which map to the break-site (See FIGS. 9A-9E), it was observed that >99% of resection events are within 15 kb with an average of around 2-3 kb while less than 1% extends for up to 250-300 kb. FIGS. 7D-7G demonstrate that junctions from HTGTS libraries are primarily composed of short micro-homologies and direct joins with a smaller proportion of junctions containing base pair insertions of variable lengths.

FIGS. 8A-8E demonstrate that hotspots are related to recurrent off-target nuclease activity. FIG. 8A depicts a diagram of bait 3' DSB ends translocating to a separate broken end resulting in direct and resected joins in both orientations. FIG. 8B depicts a schematic of guide RNA sequence preference extrapolated from RAG1 OT sites. FIGS. 8A-8E demonstrate prey joining distribution to select OT sites from (FIGS. 8C-8D) Cas9:RAG1A (SEQ ID NOS 294-295, respectively, in order of appearance) or (FIG. 8E) Cas9:RAG1B (SEQ ID NO: 296) bait DSBs. Plus and minus orientation junction enrichment are indicated by dashed and solid curves respectively. Dashed lines indicate predicted off-target cleavage site. Shaded area represents off-target sequence listed above each plot; bold text indicates mismatch from targeted sequence and underlined nucleotides indicate the PAM.

FIG. 9A depicts a schematic demonstrating that from a single bait DSB, nearby prey junctions are primarily derived from rejoining the original, but resected, DSB. Joining to broken ends of nearby spontaneous DSBs can result in deletions, inversions and excision circles depending on the position of the $2^{nd}$ DSB relative to the bait and which broken end of the $2^{nd}$ DSB is joined. FIG. 9B demonstrates that targeting endogenous loci typically include the homologous chromosome and the homologous target site. Thus, joins to the homologous chromosome can occur which can lead to the formation of dicentric chromosomes. FIGS. 9C-9E depicts graphs of break-site prey junction enrichment for (FIG. 9C) Cas9:RAG1B, (FIG. 9D) Cas9:RAG1C, and (FIG. 9E) Cas9:RAG1D (1 kb regions flanking the break-site). White boxes indicate Cas9 targeted site for the respective gRNA. Boxed with negative-slope line shading indicate cleavage site. Total junctions for each quadrant are listed (N=6 for each).

FIG. 10A depicts sequences specific for RAG1A, G, E, and F gRNAs (labelled highlights) with variable length 5' overhangs (dashed lines connecting red arrowheads; PAM is underlined). Sequences disclosed as SEQ ID NOS 297, 298, 297, 298, 297 and 298, respectively, in order of appearance. FIGS. 10B-10C demonstrate prey junction distribution at the break-site for (FIG. 10B) Cas9n: RAG1A/G (N=6) and (FIG. 10C) Cas9n:RAG1A/E (N=2). Left-hand dashed lines indicate the (FIG. 10B) RAG1G or (FIG. 10C) RAG1E site relative to the RAG1A site (black dashed line). Break-site prey junction totals within 0.3 kb are listed for each section including prey junctions between off-set nick sites. Preliminary data of RAG1A single nicking experiments do not yield high numbers of HTGTS junctions and no HTGTS hotspots of any kind. However, we detect small numbers of junctions at the break-site, which are 2-fold greater than vector control, indicating that nicks indeed can be converted into DSBs. In these controls, there appears to be few if any translocations to the homologous chromosome. Future studies using a separate bait-site (using a different nuclease class) to capture single nick DSBs (co-expression assay) will yield more information into the mechanisms associated with Cas9n-related single nick-driven DSBs.

FIGS. 11A-11E depict ATM and c-MYC TALEN HTGTS libraries. FIG. 11A demonstrates cloning from 5' bait DSBs in TALEN libraries and outcomes associated with local joining (see FIG. 9A-9B). FIGS. 11B-11C depict graphs demonstrating that relative to the primer (white arrow), downstream prey junctions beyond the break-site (middle dashed line) predominantly represent resections and deletions. Dicentric-forming upstream inversions at the break-site are enriched. Numbers in the lower left corner are total frequencies for each quadrant (N=3 each). FIGS. 11D-11E depict schematics of (FIG. 11D) ATM and (FIG. 11E) C-MYC TALEN sequence preference derived from OT half-sites. No ATM TALEN right half-site analysis was performed since only two sites were described.

FIGS. 12A-12C demonstrate analysis of I-SceI OT sites recovered by Cas9:RAG1B bait DSBs. FIG. 12A depicts a graph of select I-SceI OT site showing focal prey junction enrichment. Vertical dashed lines indicate predicted off-target cleavage site. Shaded area represents off-target sequence listed above the plot; bold text indicates mismatch from targeted sequence (SEQ ID NO: 299). FIG. 12B depicts a schematic of nuclease sequence preference derived from both human and mouse[6] I-SceI OT sites. FIG. 12C demonstrates that I-SceI off-target sites were PCR amplified and either mock digested (U) or digested with I-SceI (C) with most sites efficiently cleaved. Asterisk indicates site with 2 identical off-target sequences.

FIGS. 13A-13B depict Dot plot of Cas9:RAG1A and Cas9:RAG1A +IR (FIG. 13A) across the break-site chromosome 11 and (FIG. 13B) across a similar sized chromosome 12. Dot scale: 100 kb. Enlarged dots with asterisks signify RAG1A OT sites or the on-target site (at the dashed line).

FIG. 14A depicts a schematic of nuclease sequence preference derived from Cas9:EMX1 and Cas9:VEGFA OT sites. FIG. 14B depicts a T7 Endonuclease I cleavage assay of RAG1B, VEGFA, and EMX1 gRNA on- and off-target sites. 293T genomic DNA sources were from non-transfected, Cas9:RAG1B alone, or in combination with VEGFA or EMX1 gRNAs. For Cas9:EMX on-target, black triangles indicate correct germline band. See online methods for measuring amplicon cleavage.

FIGS. 15A-15D depict dot plot of break-site chromosome junctions from (FIGS. 15A-15B) RAG1B (N=6), (FIG. 15A) RAG1B+IR (N=3), and (FIG. 15B) RAG1B+C-MYC TALEN (N=3) HTGTS libraries using RAG1B as bait. A similar sized chromosome (12) is also displayed for (FIGS. 15C-15D) RAG1B, (FIG. 15C) RAG1B+IR, and (FIG. 15D) RAG1B+C-MYC TALEN. Dot scale: 100 kb. Dashed line indicates break-site with enlarged dots representing the 100 kb region of the break-site. For all HTGTS libraries shown in the figure, junctions within C-MYC OT sites (200 chromosome 11 sites, mean size/site: 990 bp) were removed prior to normalization at 59,830 junctions.

FIG. 18A—the original HTGTS method requires end processing and adapter ligation of sheared genomic DNA fragments prior to PCR amplification, enrichment of biotinylated products, and further amplification steps to increase specificity and to label ends for Miseq sequencing. FIG. 18B—LAM-HTGTS directly amplifies junctions from sheared genomic DNA using LAM-PCR followed by enrichment and bridge adapter ligation to allow for exponential amplification and Miseq labeling of enriched products. FIG. 18C—The final amplified products will contain the following sequence components in the order listed: Illumina P545, nested primer, bait, junction, prey, adapter, Illumina P7-17. The bait is composed of the nested primer binding sequence leading up to the targeted DSB site. The prey represents the unique genome alignment with the junction representing the resulting join between the bait and prey sequences.

FIG. 22A—Top, Igh CH locus with AID targeting (lightning bolts) in Sµ and Sγ1. Botttom, productive (left) CSR via deletional Sµ to Sγ1 joins plus excision circles; and inversional (right) CSR. 3'RR, 3' regulatory region. FIGS. 22B-22C—Joining outcomes from 3' or 5' (arrows) bait broken ends (BEs; bolts) to prey broken ends. CEN, centromere; TEL, telomere. FIG. 22D—Top, joining between I-SceI DSBs at Sγ1 and Sµ in ΔSγ1$^{2xI}$ B cells. Middle, location of bait BE junctions to I-SceI-generated ΔSµ$^{2xI}$ or AID-initiated Sε prey broken ends in either 1 or 2 orientation (five experiments) as a percentage of total Igh junctions (2-kb bins). Bottom, junction distribution to the 10-kb region encompassing I-SceI prey DSBs at Sµ and AID-initiated prey DSBs at Sε. FIG. 22E—Results from Sγ1$^{2xI}$/1B cells plotted as in FIG. 22D. Grey box indicates prey junctions not assignable to single core-Sµ sequence. Numbers in parenthesis denote total unique junctions.

FIG. 23A, 23B—Top, HTGTS in CSR-activated CH12F3 cells for joining between 3'-broken ends of I-SceI DSB in the cassette replacing Sα and AID-initiated Sµ DSBs in which Sµ is in the normal (FIG. 23A; WT) or inverted (FIG. 23B; Inv) orientation. Bottom, junctions from I-SceI DSB 3'-broken ends to normal (left) or inverted (right) Sµ plotted as in FIG. 22D. FIG. 22C, Plot showing ratio (average 6 s.d.) of 1 (deletional) to 2 (inversional) joins in wild-type Sµ (squares, n=3) and Sµ (Inv) (circles, n=3) cells, with significance calculated by unpaired two-tailed t-test (P=0.307). NS, not significant. FIG. 23D—Top, HTGTS junctions from ΔSγ1$^{2xI}$ 3'-broken ends to AID-induced Sµ broken ends on trans chromosome in 1 and 2 orientations in activated ΔSγ1$^{2xI}$ ΔSµ$^{xI}$ cells. Bottom, distribution of junctions in 10-kb trans Sµ (n=5). FIG. 23E—Top, joining of bait I-SceI 5'-broken ends of c-myc253I cassette4 on chromsome 15 and AID-induced Sµ and Sε Igh breaks in 1 or 2 orientations as in FIG. 23D—Bottom, linear distribution of junctions in Sµ (left) or Sε(right) (n 5 4). Numbers in brackets in FIG. 23D and 23E denote biological replicates.

FIG. 24A-Left, 150-bp 5'Sµ sequence used as HTGTS bait. Arrow denotes 5'Sµ primer. Vertical lines indicate AGCT or other AID-targeting motifs. Right, distribution and frequency of 5"m break points in junctions to downstream S regions recovered from anti-CD40/IL4—stimulated wild-type B cells. Asterisks indicate positions of AGCT or other RGYW motifs. FIG. 24B—Junctional outcomes from 5' Sµ AID-initiated broken end joining to AID-initiated DSBs in Sγ1 and Sε including deletions (2) or inversions (1); long resections indicated by grey arrows. Break site 5'Sµ resections also are depicted. FIGS. 24C-24E—Linear distribution of pooled junctions along 200-kb CH locus (left) or at Sγ1 and Sε (middle and right) recovered from anti-CD40/IL4-stimulated wildtype (n=5) (FIG. 24C), ATM$^{-/-}$ (n=3) (FIG. 24D) or 53BP1$^{-/-}$ (n=5) (FIG. 24E) B cells. Grey boxes indicate repetitive sequences with junctions mapping to multiple locations in Sγ1; asterisks indicate G-rich Sγ1 regions devoid of AID motifs and junctions.

FIG. 25A— Ratios of inversional to deletional 5' Sµ joins to Sγ1 (left) or Sε (right) in wild-type and mutant cells. Average±s.d. calculated from at least three separate experiments. FIG. 25B— Sγ1 and Sε resection junctions mapping to deletional (2) resection regions where the incidence of wild-type junctions decreases to background plotted as the percentage of total junctions in the deletional orientation from cells in FIG. 25A. For panels FIGS. 25A and 25B, more than 1,000 unique junctions (up to tens of thousands in some cases) were analysed. Statistical significance or insignificance of key comparative results calculated by unpaired two-tailed t-test from at least three biological repeats. Ai: ATM inhibitor. FIG. 25C-25D—Working model for orientation-biased joining (FIG. 25C) and functions of DSBR proteins (FIG. 25D) in maintaining directional CSR.

FIG. 27A depicts a diagram of c-Myc-DJβ and sequences of Dβ1 23RSS (SEQ ID NOS 357-358, respectively, in order of appearance) and Jβ1-1 12RSS (SEQ ID NOS 359-360, respectively, in order of appearance). Small triangles indicate RAG cleavage-sites. FIG. 27 dmonstrates that RAG-initiated DSBs in c-Myc-DJβ cassette participate in cassette DJβ rearrangements but rarely to translocations involving DSBs on other chromosomes. Small arrows indicate HTGTS primer positions. FIG. 27C depicts a linear plot with a broken y axis showing HTGTS junction profiles in indicated 20-Mb region containing c-Myc-DJβ. FIG. 27D depicts potential junctional outcomes between bait Dβ1 23RSS coding ends and other DSBs in cis include deletions, excision circles, and inversions. FIG. 27E depicts HTGTS junction profiles in v-Ab1 cells within indicated 2-Mb region containing c-Myc-DJβ. For all panels, unmarked ticks represent 0. Black lines in the middle show hotspot (HS) positions. Junction numbers and percentages in + or – orientation downstream of c-Myc-DJβ are shown. Cassette location is shadowed in gray. Star indicates a good cryptic RSS. FIG. 27F depicts ChIP-seq profiles of CTCF and Rad21 in the 2-Mb region defined in (FIG. 27E). CBE orientation is indicated by triangles. FIG. 27G depicts a heatmap showing the 1.8-Mb c-Myc loop domain defined by in situ Hi-C data in CH12-LX cell line.

FIG. 28A depicts a schematic of translocations between Dβ1 downstream coding ends and cryptic RSSs mostly represented by CAC motifs in the 1.8-Mb c-Myc domain in c-Myc-DJβ vAb1 pro-B cells. FIGS. 28B-28C depict the distance of Dβ1 downstream coding-end junctions to reverse CACs (FIG. 28B) or forward CACs (FIG. 28C) within the 1.8-Mb domain in c-Myc-DJβ vAb1 pro-B cells. Direct joining to the nucleotide immediately adjacent to CAC is defined as 0 in this and following panels. Mean±SD, n=3. FIG. 28D depicts a schematic of translocations between Cas9/gRNA-initiated bait DSBs and DSBs in the c-Myc domain in ATM-deficient pro-B cells with (top) or without (bottom) the c-Myc-DJβ cassette. FIG. 28E-28F depict the distance of 50 Cas9 junctions in + (FIG. 28E) or – (FIG. 28F) orientation to reverse CACs in the c-Myc domain in cells defined in (FIG. 28D). Means±SD, n=3.

FIG. 29A depicts a diagram showing major RAG-initiated joins in DEL-SJ-containing v-Ab1 pro-B cells. FIG. 29B depicts potential junctional outcomes between bait 12RSS and DSBs in cis include deletions, excision circles, and inversions. FIG. 29C depicts profiles of 12RSS junctions within chromosome X in ATM-deficient vAb1 pro-B cells. Black triangles indicate insertion site of DEL-SJ. Junction numbers and percentages in + or – orientation upstream or downstream of bait 12RSS are shown separately. FIGS. 29D-29E depict profiles of 23RSS junctions in the indicated 3.5-Mb region containing DEL-SJ on chromosome X. FIG. 29F depicts ChIP-seq profiles of CTCF/Rad21 (top) and heatmap of in situ Hi-C (bottom) in this 3.5-Mb region. FIGS. 29G-29K demonstrate 12RSS and 23RSS junctions across the 1-Mb DEL-SJ-containing loop domain on chromosome 4. Stars indicate stronger cryptic RSSs.

FIG. 30A depicts a schematic of translocation between bait 12RSS and CACs within the DEL-SJ-containing loop domain on chromosome X in ATM-deficient v-Ab1 pro-B cells. FIG. 30B depicts the distance of 12RSS junctions upstream of bait 12RSS to forward CACs; no correlation was found with reverse CACs. FIG. 30C depicts the distance of 12RSS junctions downstream of bait 12RSS to reverse CACs; no correlation was found with forward CACs. FIG. 30D depicts a diagram of recombination output generated by RAG re-cleavage at perfect 12-23RSS joins. FIG. 30E depicts profiles of 12RSS junctions of 12-23RSS join within chromosome X in ATM-deficient vAb1 pro-B cells. Star indicates a relatively stronger cryptic RSS, and loop domain is shadowed in gray, also in (FIG. 30G). FIG. 30F depicts a diagram of bait surrogate coding ends associated with DEL-SJ 12RSS and the potential outcomes. FIG. 30G depicts profiles of GFP primer junctions within chromosome X in ATM-deficient vAb1 pro-B cells. FIG. 30H depicts the distance of GFP primer junctions downstream of bait surrogate coding ends to forward CACs.

FIG. 31A depicts the consensus sequence of cryptic RSS heptamer extrapolated from the 107 identified cryptic RSSs. FIG. 31B depicts paired cryptic RSSs on chromosome 1 (left) and 15 (right). Arrows indicate the position and orientation of cryptic RSSs in these four translocation hotspots. FIG. 31C depicts a Venn diagram showing number of identified cryptic RSSs that overlap with H3K27Ac and H3K4me3. FIG. 31D depicts a pie chart showing number of identified cryptic RSSs that overlap with typical enhancers and super-enhancers.

DETAILED DESCRIPTION

Figure 1A:
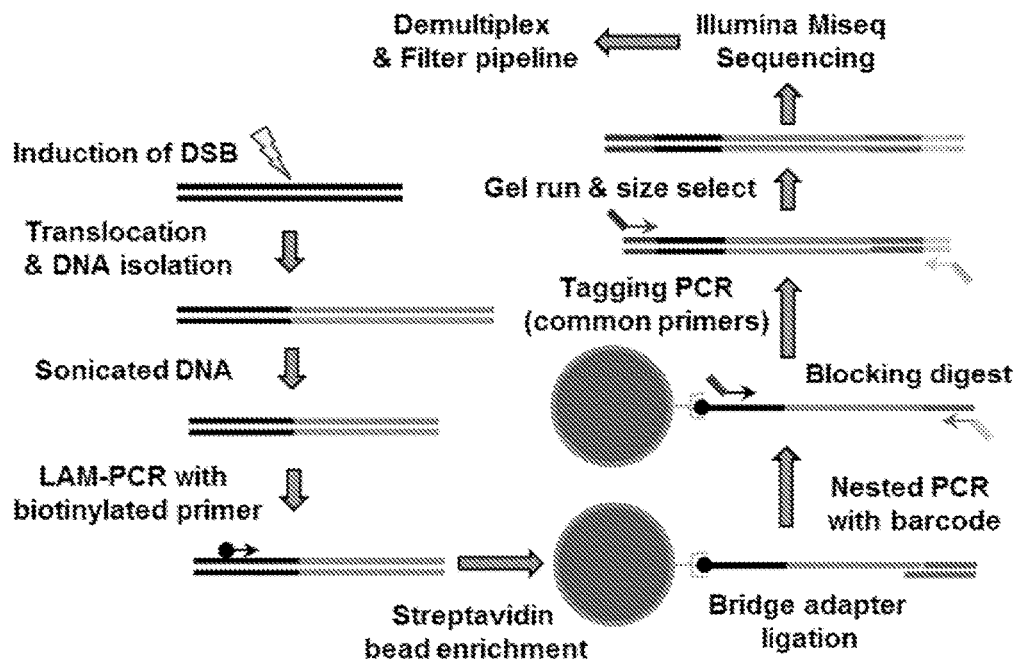
FIGS. 1A-1C demonstrate LAM-PCR HTGTS from Cas9:RAG1A on-target and off-target bait sites.

Described herein is a robust linear amplification-mediated high-throughput genome-wide translocation sequencing (HTGTS) method that identifies endogenous or ectopic "prey" DNA double-stranded breaks (DSBs) across a genome, such a mammalian genome, e.g. the human genome, based on their translocation to "bait" DSBs generated by, e.g., nucleases, including custom nucleases. The methods described herein are widely applicable to any cell in which one wishes to identify a "translocatome" in, i.e., the universe of translocations arising from any specific DSB, and to application with any agent that can cause a DSB, such as meganucleases, zinc-finger nucleases, TALENs and even chemical agents designed for and used in, e.g., genome engineering or genome editing.

The method is therefore useful, for example, for anyone wishing to scan for possible translocations arising from use of any specific agent, such as an enzyme used to create a DSB for, e.g., genetic or genome engineering. The same method can also be used to screen the specificity of DSB causing agents, such as enzymes. For example, one can screen enzymes for risk of unwanted breaks or recombinations to be used in applications such as inserting a gene to a genome. Optimizing the specificity and recombination risks, one can avoid using enzymes that pose a high risk of unwanted recombination events, such as those that disrupt genes or other DNA sequences that are important for the integrity of the normal cellular functions. The agent may also be a therapeutic agent, such as a chemotherapy agent. In such a case, one can use the method to screen for potential DSBs and/or translocation events that may occur as a result of exposing a cell to the chemotherapeutic agent. The present method allows for mapping or screening for potential off-target recombinations that may result from using a specific enzyme, such as rare cutting enzymes, e.g., a meganuclease. Thus, the method allows optimizing the types of enzymes or agents used in genome engineering applications.

The HTGTS assay described herein has several key advantages versus the prior HTGTS method which make the identification of genome-wide translocations cheaper and more efficient. First, a biotinylated locus-specific primer can be used directly on the sheared DNA fragments without the need to repair the broken ends. Second, the amplified single-strand DNA fragments can be directly ligated on-bead to adapters with a 3' overhang comprised of 5-6 random nucleotides, which suppresses non-specific amplification in following PCR steps necessary for including next generation sequencing-specific nucleotides. Third, the use of a common bait site in the presently described methods permits the characterization and comparison of cutting efficiency, off-target sites, and/or non-specific activity of DSB-generating agents.

In one aspect, described herein is a method for high throughput, genome-wide translocation sequencing (HT-GTS) and detection of double-stranded DNA break (DSB) locations, the method comprising the steps of: (a) exposing a cell to an agent known or suspected of being capable of producing at least one DSB; (b) optionally, allowing the cell to divide for at least a half cell cycle after exposure; (c) extracting genomic DNA from the cells; (d) optionally producing a fragmented DNA sample; (e) producing a single-stranded PCR product by Linear Amplification Mediated (LAM)-PCR with a first locus-specific primer; (f) producing a ligated DNA product by ligating the single-stranded PCR product produced in step (e) to an adapter, wherein the adapter comprises: a distal portion of known DNA sequence that can be used to design PCR primers for a nested PCR amplification; a proximal portion of random nucleotides; and a 3' overhang; (g) producing a nested PCR product by performing a nested-PCR with an adapter- and a locus-specific primer using the ligated DNA product thereby amplifying the nucleic acid sequence surrounding the junction around the at least one DSB; (h) optionally, digesting the ligated DNA sample with a blocking enzyme; (i) producing a sequenced nested PCR product by sequencing the nested PCR product; and (j) aligning the sequenced nested PCR product against a reference sequence to identify a chromosomal location of the translocation and the chromosomal location of the at least one DSB.

In one aspect, described herein is a method for high throughput, genome-wide translocation sequencing (HT-GTS) and detection of double-stranded DNA break (DSB) locations, the method comprising the steps of: (a) exposing a cell to an agent known or suspected of being capable of producing at least one DSB; (b) optionally, allowing the cell to divide for at least a half cell cycle after exposure; (c) extracting genomic DNA from the cells; (d) optionally producing a fragmented DNA sample; (e) producing a single-stranded PCR product by annealing and extension with a first locus-specific primer; (f) producing a ligated DNA product by ligating the single-stranded PCR product produced in step (e) to an adapter, wherein the adapter comprises: a distal portion of known DNA sequence that can be used to design PCR primers for a nested PCR amplification; a proximal portion of random nucleotides; and a 3' overhang; (g) producing a nested PCR product by performing a nested-PCR with an adapter- and a locus-specific primer using the ligated DNA product thereby amplifying the nucleic acid sequence surrounding the junction around the at least one DSB; (h) optionally, digesting the ligated DNA sample with a blocking enzyme; (i) producing a sequenced nested PCR product by sequencing the nested PCR product; and (j) aligning the sequenced nested PCR product against a reference sequence to identify a chromosomal location of the translocation and the chromosomal location of the at least one DSB.

Methods of extracting genomic DNA are well-known in the art, see, e.g., Tan and Yiap. J Biomed and Biotechnol 2009; and Varma et al. Biotechnol J 2007 2:386-392; each of which is incorporated by reference herein in its entirety. In some embodiments, genomic DNA extraction can be performed using a commercially available kit, e.g. WIZARD Genomic DNA Purification Kit (Cat. No. A1120; Promega, Madison, Wis.).

DNA samples can be fragmented by any method known in the art, including by not limited to sonication, restriction enzyme digest, random shearing, restriction with a frequently-cutting restriction enzyme, nebulization, acoustic shearing, point-sink shearing, needle shearing, and a French press. In some embodiments, the fragmenting of a DNA sample can be performed by restriction enzyme digest. Frequently cutting enzymes, which typically cut every 4 bp are well known to one skilled in the art and one can screen for any their effect on a target genome in silico using a target genome sequence as a template. For example, MspI is a suitable frequently-cutting enzyme in human cells, but a skilled artisan can easily substitute the enzymes according to the need for any given genome. As used herein, the term "fragmented DNA sample" refers to a sample of DNA which has been subjected to a fragmentation process such that a statistically significant greater number of DSBs exist in the sample as compared to prior to the fragmentation process. In some embodiments, a fragmented DNA sample no longer comprises intact chromosomes. One of skill in the art can readily selected a fragmentation process, including strength and duration thereof, that will provide a desired degree of fragmentation, e.g., that will result in a population of DNA molecules of the desired sizes.

In some embodiments, the fragmenting of a DNA sample can be performed by sonication. Sonication provides random, unbiased fragmentation, which differs from the specific fragmentation achieved by restriction digest, e.g, as described in US Patent Publication 20140234847; which is incorporated by reference herein in its entirety. In some embodiments, end repair is performed after fragmentation and before LAM-PCR. In some embodiments, end repair is not performed after fragmentation but before LAM-PCR. In some embodiments of the various aspects described herein, genomic DNA is sheared, rather than digested by specific frequent cutter enzymes. As described herein, enzyme digest is revealed to have a bias in junction enrichment genome-wide.

The methods and compositions described herein relate to performing a polymerase chain reaction (PCR). PCR refers to a process of specifically amplifying, i.e., increasing the abundance of, a nucleic acid sequence of interest, and more particularly, the exponential amplification occurring when the products of a previous polymerase extension serve as templates for the successive rounds of extension. A PCR amplification regimen according to the invention comprises at least one, e.g., at least 1, at least 2, at least 5, 10, 15, 20, 25, 30, 35 or more iterative cycles, where each cycle comprises the steps of: 1) strand separation (e.g., thermal denaturation); 2) oligonucleotide primer annealing to template molecules; and 3) nucleic acid polymerase extension of the annealed primers. Conditions and times necessary for each of these steps can be devised by one of ordinary skill in the art. An amplification regimen according to the methods described herein is preferably performed in a thermal cycler, many of which are commercially available. Linear Amplification Mediated PCR (LAM-PCR) is a type of PCR in which a primer to a known sequence (bait) is used to produce ssDNA from a target nucleic acid sequence, where the PCR product comprises sequence downstream from the site at which the primer anneals. The PCR product's sequence can be unknown, e.g. if a translocation has occurred near the bait sequence. The ssDNA is then converted to a dsDNA and further PCR amplification reactions are conducted. LAM-PCR is described in further detail at, e.g., Schmidt et al. Nature Methods 2007 4:1051-7; U.S. Pat. No. 6,514,706; U.S. Pat. App. US2007/0037139 and Harkey et al., (2007) Stem Cells Dev., June; 16(3): 381-392; each of which is incorporated by reference herein in its entirety.

A locus-specific primer is a primer that can specifically anneal to a known sequence at a locus which is to be analyzed for the occurrence of DSBs and/or transcloations. The locus can be a naturally-occuring locus and/or an engineered or introduced locus. In some embodiments, the locus-specific primer can be designed to anneal within 1 kb of a location at which a DSB can be induced, e.g., within 1 kb, within 500 bp, within 400 bp, within 300 bp, within 200 bp, or within 100 bp of a location at which a DSB can be induced. In some embodiments, the locus-specific primer can be designed to anneal within 400 bp of a location at which a DSB can be induced. Such a location can be, e.g, a sequence targeted by an nuclease that the cell is contacted with in accordance with the methods described herein.

In some embodiments, the first locus-specific primer can comprise an affinity tag, e.g. for affinity purification using a substrate with the appropriate affinity domain. An affinity domain and tag pair can complex two molecules by non-covalent means. In some embodiments, the first locus-specific primer can comprise an affinity tag to which the affinity domain can specifically bind. A number of affinity tags and domains are well known in the art and are described, e.g., in Lichty et al. Protein Expr Purif 2005 41:98-105; Zhao et al. J Analytical Methods in Chemistry 2013; Kimple et al. Current Protocols in Protein Science 2004 36:939:9.1-9.9.19; and Giannone et al. Methods and Protocols "Protein Affinity Tags" Humana Press 2014; each of which is incorporated by reference herein in its entirety. Non-limiting examples of compatible affinity domain and affinity tag pairings can include an antibody or antigen-binding fragment thereof and an epitope; an anti-His antibody or antigen-binding fragment thereof and a His tag; an anti-HA antibody or antigen-binding fragment thereof and a HA tag; an anti-FLAG antibody or antigen-binding fragment thereof and a FLAG tag; an anti-myc antibody or antigen-binding fragment thereof and a myc tag; an anti-V5 antibody or antigen-binding fragment thereof and a V5 tag; an anti-GST antibody or antigen-binding fragment thereof and a GST tag; an anti-MBP antibody or antigen-binding fragment thereof and a MBP tag; an aptamer and the target molecule recognized by that aptamer; streptavidin and biotin. In some embodiments, an affinity tag and/or domain is located at or near one terminus of the molecule, e.g. within 10 nucleotides of a terminus. Affinity tags and/or domains can be, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule. In some embodiments, the affinity domain can be an aptamer.

One example of using affinity domains and tags to complex two molecules is the biotin-avidin or biotin-streptavidin conjugation. In this approach, one of the members of molecules to be conjugated together (e.g., the nuclease or the template nucleic acid) is biotinylated and the other is conjugated with avidin or streptavidin. Many commercial kits are available for biotinylating molecules, such as proteins. For example, an aminooxy-biotin (AOB) can be used to covalently attach biotin to a molecule with an aldehyde or ketone group. Moreover, the primer can be coupled to a biotin acceptor peptide, for example, the AviTag or Acceptor Peptide (referred to as AP; Chen et al., 2 Nat. Methods 99 (2005)). The Acceptor Peptide sequence allows site-specific biotinylation by the *E. coli* enzyme biotin ligase (BirA; Id.). Another non-limiting example of using conjugation with an affinity domain/tag is the biotin-sandwich method. See, e.g., Davis et al., 103 PNAS 8155 (2006). In this approach, the two molecules to be conjugated together are biotinylated and then conjugated together using tetravalent streptavidin. In some embodiments, the affinity tag can be biotin.

In some embodiments, the method can further comprise isolating the PCR products produced in step (e) by affinity purification. In some embodiments, affinity purification can comprise binding the PCR products produced in step (d) to a substrate, e.g. a bead and/or a column. In some embodiments, the substrate can be a bead. In some embodiments, affinity purification can comprise binding biotin with streptavidin, e.g., binding biotin-tagged PCR products to beads, substrates, and/or columns comprising streptavidin.

The PCR product resulting from extension and/or PCR of the first locus-specific primer, optionally after isolation, can be ligated to an adapter molecule. In the ligation step, typically, one uses DNA that is concentrated at less than 1.5 ng/microL. Concentrations varying from about 1.0 to about 2.5 ng/microL can be used and a skilled artisan will be able to optimize the DNA concentrations using routine methods.

The adapter molecule is a double-stranded oligonucleotide, e.g. a dsDNA molecule comprising a distal portion of known DNA sequence that can be used to design PCR primers for a nested PCR amplification; and a proximal portion comprising random nucleotides and a 3' overhang. In some embodiments, the 3' ends of the distal and proximal portions of the adapter are modified to prevent self ligation, e.g. by providing a 3' dideoxynucleotide, e.g. a 3' ddC. In some embodiments, the end of the adapter which does not comprise the 3' overhang, e.g. the end comprising the distal portion, is blunt-ended. In some embodiments, the 3' overhang can anneal to the ss-DNA PCR product.

In some embodiments, the proximal portion of the adaptor can be 3-10 nucleotides in length. In some embodiments, the proximal portion of the adaptor can be 5-6 nucleotides in length. In some embodiments the proximal portion can have some nucleotides fixed.

In some embodiments, the proximal portion of the adapter molecule can consist of a 3' overhang. In some embodiments, proximal portion of the adaptor can be 3-10 nucleotides in length. In some embodiments, proximal portion of the adaptor can be 5-6 nucleotides in length.

In some embodiments, the adapter can further comprise a barcode sequence, e.g., between the distal and proximal portions. In some embodiments, the distal portion of the adapter comprises a sequence that is complementary to the adapter-specific primer used in the nested PCR step.

In some embodiments, ligating the single-stranded PCR products to an adapter can comprise contacting the PCR product with a population of adapters having the same distal portion and varying random proximal portion sequences.

Nested-PCR is a second PCR reaction using primers that anneal to the amplified sequence produced by a first PCR reaction, e.g., the LAM-PCR reaction to increase specificity of the final product. Accordingly, nested-PCR performed on the ligated DNA product with an adapter- and a locus-specific primer will amplify and/or replicate the nucleic acid sequence surrounding the junction around the at least one DSB. In theory, there is not a minimum or a maximum for how many rounds of nested PCR can be used. In some embodiments, the nested PCR comprises at least one round, at least 2 rounds, or at least 3 rounds. In some embodiments, the nested PCR comprises one round, 2 rounds, or 3 rounds. In some embodiments, the nested PCR comprises one round, 2 rounds, 3 rounds, 1-2 rounds, 1-3 rounds, or 1-5 rounds. More rounds can be less useful since they can just increase the amplification of already overrepresented sequences—Nested PCR (with typically 2 rounds) is used to increase specificity of the amplification reaction, by using independent sets of primers for the same locus. In some embodiments, a third round can add the barcodes necessary for sequencing, e.g., 454 sequencing. Such a third round can be skipped if barcoded primers are used at round 2 or if one uses other sequencing methods where additional bar codes are not needed. In some aspects of all the embodiments of the invention, one performs 1 round of nested PCR and an additional round to introduce a tag or a label into the PCR products thus allowing a specific sequencing protocol to be applied to analyze the sequences of the junctions. In some aspects of all the embodiments of the invention, one performs 2 rounds of nested PCR and an additional round to introduce a tag or a label into the PCR products thus allowing a specific sequencing protocol to be applied to analyze the sequences of the junctions.

In some embodiments, the locus-specific primer used in the nested-PCR step (the second locus-specific primer) can overlap with the locus-specific primer used in the LAM-PCR step (the first locus-specific primer). In some embodiments, the primers are designed such that 3' end of the second locus-specific primer anneals closer (e.g. at least one nucleotide closer, 1-2 nucleotides closer, 1-3 nucleotides closer, 1-5 nucleotides closer, etc.) to the bait DSB than the 3' end of the first locus-specific primer. In some embodiments, the sequence of the second locus-specific primer can comprise a portion of the sequence of the first locus-specific primer. In some embodiments, the sequence of the second locus-specific primer can comprise a 3' portion of the sequence of the first locus-specific primer. In some embodiments, the sequence of the second locus-specific primer can comprise the sequencd of the first locus-specific primer. In some embodiments, one or more of the primers used for the nested PCR step can comprise barcode sequences.

As used herein, "barcode" refers to a DNA sequence used as a barcode or tag for identification of a target molecule. In some embodiments, the DNA sequence is exogenous and/or foreign relative to the genomes of the organism being analyzed.

In some embodiments, the ligated DNA can be digested with a blocking enzyme, e.g., after nested PCR but prior to sequencing or prior to nested PCR. The blocking enzyme digestion can block amplification of germline or unrearranged targeted alleles in subsequent steps, e.g., during nested PCR. Blocking enzymes typically need to be selected in each individual case based on the DNA sequence of the locus where the bait location, e.g. a targeting cassette, such as the I-SceI casette is located, or based on the artificial sequence of the cassette itself—any common restriction enzyme that cuts in the unrearranged product past the enzyme restriction site, such as I-SceI restriction site, and therefore should be absent from the translocated product, can be used as a blocking enzyme. The selection is routine and based on each individual sequence. Thus, a skilled artisan can readily find a suitable blocking enzyme for the assays. In some embodiments, the blocking digestion is not performed, e.g., it is omitted.

As used herein, the term "blocking enzyme" refers to a restriction enzyme that cuts in the unrearranged product distal, relative to the locus-specific primer, of a site targeted by the agent of step (a). A blocking enzyme will not cut in the unrearranged product proximal, relative to the locus-specific primer, of the site targeted by the agent of step (a). Thus, a blocking enzyme, and its sequence specificity, is determined by the particular sequence of the DNA used in the method, the sequence of the locus-specific primer, and the agent(s) used in step (a). Any restriction enzyme with the appropriate specificity can be utilized. One of skill in the art is readily able to select a restriction enzyme with the necessary specificity given such parameters.

DNA sequencing of the nested-PCR product can be performed by any method known in the art. In some embodiments, the sequencing can be performed by a next generation sequencing method. As used herein "next-generation sequencing" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina)—SOLiD technology (Applied Biosystems); Ion semiconductor sequencing (ION Torrent); DNA nanoball sequencing (Complete Genomics); and technologies available from Pacific Biosciences, Intelligen Bio-systems, Oxford Nanopore Technologies, and Helicos Biosciences. In some embodiments, the sequencing primers can comprise portions compatible with the selected next-generation sequencing method. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/0252077; 2007/0070349; and 20070070349; which are incorporated by referene herein in their entireties).

In some embodiments, the nested-PCR products can be size selected prior to sequencing. Any reasonable size can be selected, e.g., to exclude non-specific amplification products, such as poly-primer amplification products. In some embodiments, nested-PCR products of from about 400 bp to about 1 kb can be selected for, e.g., to exclude non-specific poly-primer amplification products. In some embodiments, nested-PCR products of from about 200 bp to about 1 kb can be selected for, e.g., to exclude non-specific poly-primer amplification products.

The sequence of the nested-PCR product can be aligned against a reference sequence to identify a chromosomal location of the translocation and the chromosomal location of the at least one DSB. As used herein "reference sequence" refers to a sequence comprising the unrearranged DNA sequences targeted by an agent(s) of step (a). The reference sequence can be, e.g., a genomic sequence(s) from type of cell being analyzed. In some embodiments, the step of aligning can be performed by a non-human machine. In some embodiments, the non-human machine can comprise a computer executable software. In some embodiments, the method can further comprise a display module for displaying the results of the step of aligning.

Figure 17:
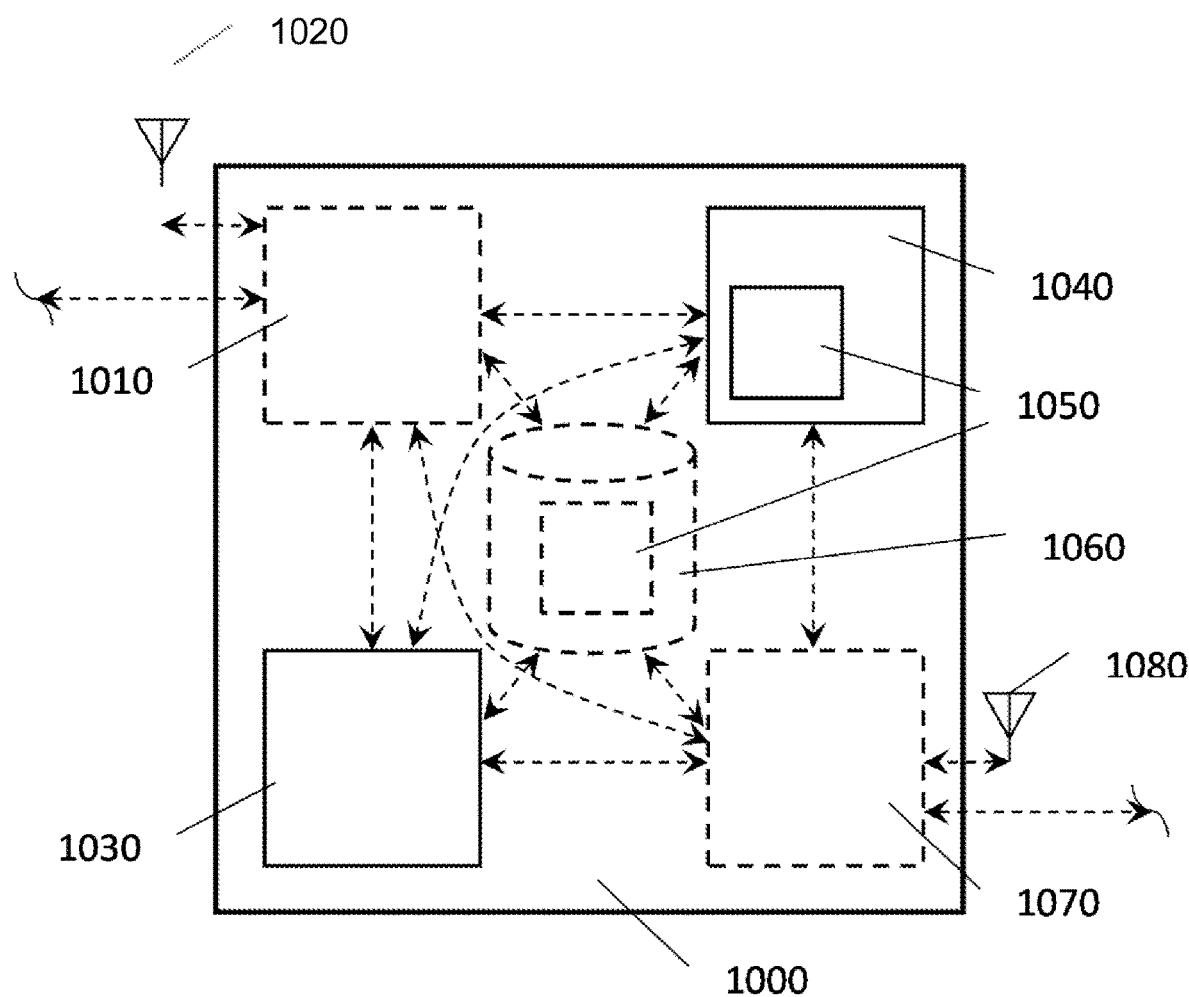
FIG. 17 depicts a computer device or system 1000 comprising one or more processors 1030 and a memory 1040 storing one or more programs 1050 for execution by the one or more processors 1030.

FIG. 17 depicts a computer device or system 1000 comprising one or more processors 1030 and a memory 1040 storing one or more programs 1050 for execution by the one or more processors 1030.

In some embodiments, the device or computer system 1000 can further comprise a non-transitory computer-readable storage medium 1060 storing the one or more programs 1050 for execution by the one or more processors 1030 of the device or computer system 1000.

In some embodiments, the device or computer system 1000 can further comprise one or more input devices 1010, which can be configured to send or receive information to or from any one from the group consisting of: an external device (not shown), the one or more processors 1030, the memory 1040, the non-transitory computer-readable storage medium 1060, and one or more output devices 1070. The one or more input devices 1010 can be configured to wirelessly send or receive information to or from the external device via a means for wireless communication, such as an antenna 1020, a transceiver (not shown) or the like.

In some embodiments, the device or computer system 1000 can further comprise one or more output devices 1070, which can be configured to send or receive information to or from any one from the group consisting of: an external device (not shown), the one or more input devices 1010, the one or more processors 1030, the memory 1040, and the non-transitory computer-readable storage medium 1060. The one or more output devices 1070 can be configured to wirelessly send or receive information to or from the external device via a means for wireless communication, such as an antenna 1080, a transceiver (not shown) or the like.

In one aspect, described herein is a computer implemented method for high throughput, genome-wide translocation sequencing (HTGTS) and detection of double-stranded DNA break (DSB) locations, comprising: on a device having one or more processors and a memory storing one or more programs for execution by the one or more processors, the one or more programs including instructions for: aligning a sequenced nested PCR product against a reference sequence to identify a chromosomal location of a translocation and the chromosomal location of at least one DSB.

In some embodiments, the aligning step is performed by an aligning program. In some embodiments, the aligning program is Bowtie2. In some embodiments, the aligning step comprises a best-path search algorithm to determine prey and bait alignments. In some embodiments, the aligning step comprises de-multiplexing sequence reads. In some embodiments, the de-multiplexing sequence reads comprises using a fastq-multx tool. In some embodiments, the aligning step comprises trimming an adapter sequence. In some embodiments, the trimming the adapter sequence comprises using a SeqPrep utility. In some embodiments, the aligning step comprises mapping reads to an hg19 reference genome using the Bowtie2 with the top fifty alignments reported that had an alignment score above 50, representing a perfect 25 nt local alignment.

In some embodiments, on average, 94% of the demultiplexed reads per library harbored a bait sequence alignment with <10% of these reads containing an alignable prey junction. In some embodiments, the aligning step comprises a best-path searching algorithm to select an optimal sequence of alignments that describe the read's composition. In some embodiments, the aligning step comprises filtering. In some embodiments, the filtering comprises a bait alignment and a prey alignment. In some embodiments, the bait alignment does not extend more than 10 nucleotides beyond a targeted site. In some embodiments, the aligning step comprises vector controls, off-set nicking with multiple sites, and use of a distal targeted site. In some embodiments, the aligning step comprises comparing discarded alignments to a selected prey alignment. In some embodiments, if any of the discarded alignments surpasses both a coverage and score threshold with respect to the prey alignment, the read is filtered due to low mapping quality. In some embodiments, the aligning step comprises extending the bait alignment 10 nucleotides past the primer to remove possible mispriming events and other artifacts. In some embodiments, the aligning step comprises removing potential duplicates by comparing coordinates of an end of a bait alignment and a start of a prey alignment across all reads. In some embodiments, the aligning step comprises marking a read as a duplicate if it has a bait alignment off-set within 2 nt and a prey alignment offset within 2 nt of another read's bait and prey alignments. In some embodiments, the aligning step comprises applying post-filter stringency to remove junctions with gaps larger than 30 nt and bait sequences shorter than 50 nt. In some embodiments, the aligning step comprises removing reads with prey alignments to telomere repeat sequences. In some embodiments, the aligning step comprises filtering genome mixing experiments using a combined hg19/mm9 reference.

In some embodiments, the computer implemented method is used with a method for high throughput, genome-wide translocation sequencing (HTGTS) and detection of double-stranded DNA break (DSB) locations, the method comprising the steps of:
  a. exposing a cell to an agent known or suspected of being capable of producing at least one DSB;
  b. optionally, allowing the cell to divide for at least a half cell cycle after exposure;
  c. extracting genomic DNA from the cells;
  d. optionally, producing a fragmented DNA sample;
  e. producing a single-stranded PCR product by Linear Amplification Mediated (LAM)-PCR with a first locus-specific primer;
  f. producing a ligated DNA product by ligating the single-stranded PCR product produced in step (e) to an adapter, wherein the adapter comprises:
    a distal portion of known DNA sequence that can be used to design PCR primers for a nested PCR amplification;
    a proximal portion of random nucleotides; and
    a 3' overhang;
  g. producing a nested PCR product by performing a nested-PCR with an adapter- and a locus-specific primer using the ligated DNA product thereby amplifying the nucleic acid sequence surrounding the junction around the at least one DSB;
  h. optionally, digesting the ligated DNA sample with a blocking enzyme;
  i. producing a sequenced nested PCR product by sequencing the nested PCR product;
  j. aligning the sequenced nested PCR product against the reference sequence to identify the chromosomal location of the translocation and the chromosomal location of the at least one DSB.

In one aspect, described herein is a computer system for high throughput, genome-wide translocation sequencing (HTGTS) and detection of double-stranded DNA break (DSB) locations, comprising: one or more processors and memory to store one or more programs, the one or more programs comprising instructions for: aligning a sequenced nested PCR product against a reference sequence to identify a chromosomal location of a translocation and the chromosomal location of at least one DSB.

In one aspect, described herein is a non-transitory computer-readable storage medium storing one or more programs for high throughput, genome-wide translocation sequencing (HTGTS) and detection of double-stranded DNA break (DSB) locations, the one or more programs for execution by one or more processors of a computer system, the one or more programs comprising instructions for: aligning a sequenced nested PCR product against a reference sequence to identify a chromosomal location of a translocation and the chromosomal location of at least one DSB.

In some embodiments, a modern alignment program, e.g., BOWTIE2™, is used to align to a reference genome. In some embodiments, a best-path search algorithm can used to determine prey and bait alignments. Use of such algorithms permits further characterization of the breakpoints at translocation junctions and/or use of paired-end reads.

In an exemplary embodiment, sequence reads can be de-multiplexed and adapter sequence trimmed using the FASTQ-MULTX™ tool from ea-utils (available on the World Wide Web at code.google.com/p/eautils/) and the SEQPREP™ utility (available on the World Wide Web at github.com/jstjohn/SeqPrep), respectively. Reads can be mapped to the reference sequence using BOWTIE2™ (available on the World Wide Web at bowtiebio.sourceforge.net/bowtie2/manual.shtml). The top alignments, e.g. the top ten, twenty, thirty, forty, fifty, or more alignments can be used. In some embodiments, alignments (or top alignments) with an alignment score above a threshold alignment score can be used. In some embodiments, the threshold alignment score can be 50, representing a perfect 25 nt local alignment.

In some embodiments, a best-path searching algorithm can be used to select the optimal sequence of alignments that describe the read's composition, typically finding the bait and prey alignments. Aligned reads can be filtered, e.g., on the following conditions: (1) reads must include both a bait alignment and a prey alignment and (2) the bait alignment cannot extend more than 10 nucleotides beyond the targeted site. In some embodiments, for vector controls and off-set nicking with multiple sites, the distal targeted site can be used. Discarded alignments can be compared to the selected prey alignment; if any of the discarded alignments surpass both a coverage and score threshold with respect to the prey alignment, the read can be filtered due to low mapping quality.

In some embodiments, to remove possible mispriming events and other potential artifacts, the bait alignment can extend 10 nucleotides past the primer. Potential duplicates can be removed by comparing the coordinates of the end of the bait alignment and the start of the prey alignment across all reads. A read can be marked as a duplicate if it has a bait alignment off-set within 2 nt and a prey alignment offset within 2 nt of another read's bait and prey alignments. Post-filter stringency can be applied to remove junctions with gaps larger than a predetermined nucleotide length (e.g., 10 nt, 20 nt, 30 nt, 40 nt, 50 nt, etc) and bait sequences shorter than a predetermined length (e.g., 70 nt, 60 nt, 50 nt, 40 nt, 30 nt, etc.). Reads with prey alignments to telomere repeat sequences can also be removed.

Each of the above identified modules or programs corresponds to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments, memory may store a subset of the modules and data structures identified above. Furthermore, memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

The cell of the methods and assays described herein can be any type of cell, including, but not limited to, a eukaryotic cell, a mammalian cell, a human cell, a plant cell, a neuronal cell, a fibroblast, an in vitro cell, or an in vivo cell. The cell can be of any type, so long as it contains DNA. In some embodiments, the cell can be a cell that can be maintained in culture. The cell can be a primary cell or an immortalized cell. One can also use differentiated cells as well as partially differentiated cells, pluripotent cells and stem cells, including embryonic stem cells.

Cell division is not strictly necessary to induce a DSB and translocations. However, if cells are T or B cells, activation of T and B cells helps to keep them alive in the culture for 4 days, to allow retroviral infection and to induce expression of DSB-generating enzymes (such as AID in B cells). Translocation per se can be obtained also in non-cycling G1 arrested cells. Accordingly, in some aspects of all the embodiments of the invention, the cells are non-dividing cells. In some instances, if one uses cells, such as T or B cells or macrophages, such cells can be activated using respective activating conditions well known to one skilled in the art to induce cell division and recombination events.

In some embodiments, the cell can be allowed to divide for at least half a cell cycle after the exposure step. In some embodiments, the cell can be allowed to divide for at least one cell cycle after the exposure step. In some embodiments, the cell can be allowed to divide for at least about 6 hours, e.g. 6 hours of more, 8 hours or more, 10 hours or more, 12 hours or more, 18 hours or more, or 24 hours or more after the exposure step. In some embodiments, the cell can be allowed to divide for at least about 12 hours. In some embodiments, the cell can be allowed to divide for at least 12 hours. In some embodiments, the cell can be allowed to divide for about 1 day to about 5 days. In some embodiments, the cell can be allowed to divide for 1-5 days. In some embodiments, the cell can be allowed to divide for about 2 days to about 4 days. In some embodiments, the call can be allowed to divide for 2-4 days. The length of the cell cycle will vary depending upon the cell type and species and is readily determined by one of skill in the art, e.g., by measuring the rate of cell division and/or the levels of cell cycle markers. In some embodiments, steps a and b can occur concurrently, e.g., the cell can progress through the cell cycle while being exposed to the agent (for example, the agent can be added to the cell medium and not removed while the cell is allowed to proceed through the cell cycle). In some embodiments, steps a and b can occur sequentially, e.g., the cell can be exposed to the agent and when the exposure is complete, the cell is permitted to proceed through the cell cycle without the agent being present. In some embodiments, the cell division step (e.g., step b) can be omitted, e.g., after exposing the cell to the agent, the DNA is extracted without any further incubation or wait.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

In some embodiments, the agent can be selected from the group consisting of a nuclease; a custom nuclease; a meganuclease; a TALEN; a zinc-finger nuclease; a CRISPR; a Cpf1 CRISPR effector; an integrating virus or viral vector; an endonuclease; a CAS9:gRNA nuclease; a chemotherapeutic; and radiation. In some embodiments, the agent can be Cas9.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

Radiation can include, but is not limited to, ionizing radiation and ultraviolet radiation.

As used herein, "nuclease" refers to an enzyme capable of cleaving the phosphodiester bonds between the nucleotide subunits of nucleic acids. Nucleases can be site-specific, i.e. site-specific nucleacses cleave DNA bonds only after specifically binding to a particular sequence. Therefore, nucleases specific for a given target can be readily selected by one of skill in the art. Nucleases often cleave both strands of dsDNA molecule within several bases of each other, resulting in a double-stranded break (DSB). Exemplary nucleases include, but are not limited to Cas9; meganucleases; TALENs; zinc finger nucleases; FokI cleavage domain; RNA-guided engineered nucleases; Cas9-derived nucleases; homing endonucleases (e.g. I-Anil, I-CreI, and I-SceI) and the like. Further discussion of the various types of nucleases can be found, e.g. in Silva et al. Curr Gene Ther 2011 11:11-27; Gaj et al. Trends in Biotechnology 2013 31:397-405; Humbert et al. Critical Reviews in Biochemistry and Molecular Biology 2012 47:264-281; and Kim and Kim Nature 2014 doi:10.1038/nrg3686; each of which is incorporated by reference herein in its entirety.

Examples of agents that can be used to create a double-stranded DNA break or DSB include meganucleases.

Thus, the methods of the invention can be used to evaluate the universe of recombination events a DSB caused by a meganuclease. Such screening of meganucleases would assist in selecting meganucleases for the purpose of genetic and genomic engineering. If one finds, for example, an enzyme that results in particularly large number of recombinations or particularly troublesome recombinations, e.g., a possibility to disrupt a gene disruption of which would lead to increased risk of malignant transformation, one can avoid using such meganucleases.

Any meganuclease, existing or newly engineered one, can be used in the methods as described using the recognition sequence as described in the methods.

Meganucleases are sequence-specific endonucleases originating from a variety of single-celled organisms such as Archaea or archaebacteria, bacteria, phages, fungi, yeast, algae and some plant organelles. Meganucleases have long recognition sites of between about 12 and 40 base pairs. As a result the recognition site generally occurs only once in any given genome. The high degree of specificity of these proteins makes them the perfect tools for genome customization: a meganuclease binding to its specific DNA recognition site induces a DNA double-strand break (DSB) at a unique site in the genome of a living cell. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes.

To date, about 600 meganucleases, from various unicellular organisms, have been identified and sequenced. However, the naturally occurring meganucleases have also been engineered for genome customization products. For example, meganucleases with 18-24 bp long recognition sites are commercially available.

Meganucleases are mainly represented by two main enzyme families collectively known as homing endonucleases: intron endonucleases and intein (intervening sequences that are spliced and excised post-translationally) endonucleases.

In nature, these proteins are coded by mobile genetic elements, introns or inteins. Introns propagate by intervening at a precise location in the DNA, where the expression of the meganuclease produces a break in the complementary intron- or intein-free allele. For inteins and group I introns, this break leads to the duplication of the intron or intein at the cutting site by means of the homologous recombination repair for double-stranded DNA breaks.

There are five families, or classes, of homing endonucleases (Stoddard BL., Homing endonuclease structure and function. Q Rev Biophys. 2005 February; 38(1):49-95. Epub 2005 Dec. 9.) Among meganucleases, the LAGLIDADG (SEQ ID NO: 289) family of homing endonucleases is the most studied and well known family, and it has become a valuable tool for the study of genomes and genome engineering. It is mostly found in the mitochondria and chloroplasts of eukaryotic unicellular organisms. By modifying the recognition sequence of these enzymes through protein engineering, the targeted sequence can be changed. Meganucleases are used to modify all genome types, whether bacterial, plant or animal. They can be used, for example, to to correct mutated genes.

The thus far best characterized endonucleases which are most widely used in research and genome engineering include I-SceI (discovered in the mitochondria of baker's yeast *Saccharomyces cerevisiae*), I-CreI (from the chloroplasts of the green algae *Chlamydomonas reinhardtii*) and I-DmoI (from the archaebacterium *Desulfurococcus mobilis*).

The best known LAGLIDADG (SEQ ID NO: 289) endonucleases are homodimers (for example I-CreI, composed of two copies of the same protein domain) or internally symmetrical monomers (I-SceI). The DNA binding site, which contains the catalytic domain, is composed of two parts on either side of the cutting point. The half-binding sites can be extremely similar and bind to a palindromic or semi-palindromic DNA sequence (I-CreI), or they can be non-palintromic (I-SceI).

To create tailor-made meganucleases, two main approaches have been adopted: (1) Modifying the specificity of existing meganucleases by introducing a small number of variations to the amino acid sequence and then selecting the functional proteins on variations of the natural recognition site (Mutations altering the cleavage specificity of a homing endonuclease. Seligman L M, et al., Nucleic Acids Res. 2002 Sep. 1; 30(17):3870-9; Sussman et al. Journal of Molecular Biology. 342:31-41, 2004; Rosen L E, et al. (2006) Homing endonuclease I-CreI derivatives with novel DNA target specificities. Nucleic Acids Research. 34:4791-4800); and (2) by exploiting a property that plays an important role in meganucleases' naturally high degree of diversification: the possibility of associating or fusing protein domains from different enzymes (Arnoud S, et al. (2006) Engineering of Large Numbers of Highly Specific Homing Endonucleases that Induce Recombination on Novel DNA Targets. Journal of Molecular Biology. 355:443-458; Smith J. et al., (2006) A combinatorial approach to create artificial homing endonucleases cleaving chosen sequences. Nucleic Acids Research. 34(22):e149. This option makes it possible to develop chimeric meganucleases with a new recognition site composed of a half-site of meganuclease A and a half-site of protein B. By fusing the protein domains of I-Dmol and I-CreI, two chimeric meganucleases have been created using this method: E-Drel and DmoCre (Chevalier B S., et al., 2002) Design, activity, and structure of a highly specific artificial endonuclease. Mol Cell. 10(4):895-905). These two approaches can be combined to increase the possibility of creating new enzymes, while maintaining a high degree of efficacy and specificity research laboratories and for industrial purposes.

For example, over 20,000 protein domains from the homodimeric meganuclease I-CreI as well as from other meganucleases scaffolds have been developed by commercial entities (Grizot S et al., Nucleic Acids Res. 2010 April; 38(6):2006-18. Epub 2009 Dec. 21). Precision Biosciences, a biotechnology company, has developed a fully rational design process called Directed Nuclease Editor (DNE) which is capable of creating engineered meganucleases that target and modify a user-defined location in a genome (Gao et al., Heritable Targeted Mutagenesis in Maize Using a Dedicated Meganuclease. Plant J. 2010 January; 61(1):176-87. Epub 2009 Oct. 7).

Evaluating the recombination events any meganuclease sequence can result in would provide important information regarding the genomic effects of using the meganuclease for any genetic or genomic engineering application.

Agents that produce DSBs or are suspected of being capable of producing DSBs can also be zinc-finger nucleases.

Zinc-finger nucleases (ZFNs) are artificial restriction enzymes generated typically by fusing a zinc finger DNA-binding domain to a DNA-cleavage domain. Zinc finger domains can be engineered to target desired DNA sequences and this enables zinc-finger nucleases to target unique sequences within complex genomes. By taking advantage of endogenous DNA repair machinery, these reagents can be used to precisely alter the genomes of higher organisms.

Zinc finger nucleases have become useful reagents for manipulating the genomes of many plants and animals including arabidopsis, tobacco, soybean, corn, Drosophila melanogaster, C. elegans, sea urchin, silkworm, zebrafish, frogs, mice, rats, rabbits, pigs, cattle, and various types of mammalian cells. Zinc finger nucleases have also been used in a mouse model of haemophilia and an ongoing clinical trial is evaluating Zinc finger nucleases that disrupt the CCR5 gene in CD4+ human T-cells as a potential treatment for HIV/AIDS. ZFNs are also used for the creation of a new generation of genetic disease models called isogenic human disease models.

Given the breath of potential applications for these enzymes for disabling alleles, editing alleles and gene therapy, the methods of the present invention provide an invaluable tool to screen for the most specific enzymes for any particular genome or genomic application.

Thus, the methods of the invention can also be used to analyze various zinc-finger nucleases for specificity of cutting and their effect on recombinations throughout the genome.

Agents that produce DSBs or are suspected of being capable of producing DSBs can also be TALENs.

TALENs™ are a class of sequence-specific nucleases created by the fusion of transcription activator-like effectors (TALEs) to the catalytic domain of an endonuclease. TALENs are genome customization tools that can be used for gene-specific modifications and disruptions (see, e.g., Ting Li, et al. Nucleic Acids Research, 2011, Vol. 39, No. 1 359-372; Feng Zhang, et al. Nature biotechnology Letters: published online 19 Jan. 2011).

TALEs were first discovered in the plant pathogen, Xanthomonas. TALEs specifically bind to DNA and regulate plant genes during infection by the pathogen.

Each TALE contains a central repetitive region consisting of varying numbers of repeat units of typically 33-35 amino acids. It is this repeat domain that is responsible for specific DNA sequence recognition. Each repeat is almost identical with the exception of two variable amino acids termed the repeat-variable diresidues. The mechanism of DNA recognition is based on a code where one nucleotide of the DNA target site is recognized by the repeat-variable diresidues of one repeat.

A TALEN™ is composed of a TALE DNA binding domain for sequence-specific recognition fused to the catalytic domain of an endonuclease that introduces double strand breaks (DSB). The DNA binding domain of a TALEN™ is capable of targeting with high precision a large recognition site (for instance 17 bp).

A TALEN™ is defined as a heterodimer (2 units of a TALE DNA binding domain fused to a catalytic domain) cleaving two close sequences, resulting in increased specificity.

The methods of the invention are optimal also for analysis of TALENs for specificity and recombination events throughout the genome. For example, novel TALENs can be analyzed for their sequence specificity.

One can also use the method of the present invention to identify hotspots for DSBs and recombinations as a result of a cell's exposure to a chemical agent, such as a chemotherapy agent.

Any chemical agent can be used as an agent that is "suspected of causing" DSBs in the screens of the invention. Such an analysis allows one to detect and determine the translocatome of any given cell if it is exposed to such a chemical agent.

The technical method to generate high throughput, genome-wide translocation sequencing (HTGTS) will be the same as described above when using a chemical agent. Based on the translocation pattern obtained after incubation with a DSB causing agent, it is then possible to locate DSBs hotspots induced by the agent.

One can expose the nucleus of the cell to the DSB-causing agent using any method that provides delivery of the enzyme to the nucleus or activation of an enzyme present in an inactive state in the cell, such as enzymes fused to hormone regulatory subunits such as estrogen receptor (ER) or glucocorticoid receptor (GR) or other well known hormone receptors. One method is to use a retrovirus engineered to express the agent, such as an enzyme.

Retroviruses are an efficient means to deliver single DNA expression constructs to a wide range of mammalian cell types. They are by far the easiest and fastest means to deliver genes stably to mammalian cells. Examples of retroviruses that can be used in the methods of the invention include vectors based on Moloney Murine Leukemia Virus (MMLV) which typically allows for delivery of genes to most dividing mammalian cell types. If the cell to be studied is a non-dividing cell, vectors based on lentiviruses such a feline immunodeficiency virus or human immune deficiency virus may be used.

One can also use other viruses, such as adenoviruses and adeno-associate viruses as delivery vehicles. Small molecules, including chemical agents may also be used without a specific carrier as they will pass through the membranes and reach the nucleus without particular carriers. One can also use physical exposure to gamma or UV irradiation without particular carriers.

In some embodiments, at least one agent will generate at least one DSB within 400 bp of the hybridization target of the locus-specific primer (e.g., within 400 bp of where a second DSB is expected to occur, either from natural causes or the action of a first or second agent). In some embodiments, at least one agent will generate at least one DSB on the same chromosome as the hybridization target of the locus-specific primer (e.g., on the same chromosome where a second DSB is expected to occur, either from natural causes or the action of a first or second agent).

In some embodiments, the cell can be exposed to two or more agents, e.g. two nucleases, or a nuclease and a chemotherapeutic. In some embodiments, the cell can be exposed to two agents. In some embodiments, the cell can be exposed to at least two agents, wherein one agent will generate at least one DSB on the same chromosome as a DSB generated by a second agent.

In some embodiments, the cell can be exposed to at least two agents, wherein one agent will generate at least one DSB within 400 bp of the locus-specific primer. Such an approach can permit the detection of DSBs generated elsewhere in the genome when the DSB generated within 400 bp of the locus-specific primer interacts with DSBs generated elsewhere. In some embodiments, the method can further comprise a step of inserting into a cell to be analyzed at least one target sequence for the agent, e.g., a sequence recognized by a nuclease. In some embodiments, the target sequence can be known to be absent in the genome of the cell to be analyzed.

In one aspect, described herein is a kit comprising: an agent known to cause at least one DSB in a cell; and a locus-specific primer that will anneal within 400 bp of the DSB generated by the agent. In some embodiments, the kit can further comprise an adapter, the adapter comprising: a distal portion of known DNA sequence that can be used to design PCR primers for a nested PCR amplification; a proximal portion of random nucleotides; and a 3' overhang. In some embodiments, the kit can further comprise at least one nested PCR primer. In some embodiments, the kit can further comprise a substrate comprising an affinity domain, wherein the locus-specific primer comprises an affinity tag. In some embodiments, the kit can further comprise a cell. In some embodiments, the kit can further comprise an additional agent known or suspected to cause at least one DSB in the cell.

A kit is any manufacture (e.g., a package or container) comprising at least one reagent, e.g., a locus-specific primer, the manufacture being promoted, distributed, or sold as a unit for performing the methods described herein. The kits described herein can optionally comprise additional components useful for performing the methods described herein. By way of example, the kit can comprise fluids and compositions (e.g., buffers, dNTPs, etc.) suitable for performing one or more of the reactions according to the methods described herein, an instructional material which describes performance of a method as described herein, and the like. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, "exposing" refers to directing or pointing an agent at a cell and/or contacting a cell with the agent. For example, exposing a cell to a source of radiation can comprise directing radiation towards the cell while exposing a cell to a proteinaceous agent can comprise contacting the cell with the agent. As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

In various embodiments, the methods described herein relate to performing a PCR amplification regimen with at least one primer, e.g., an oligonucleotide primer. As used herein, "primer" refers to a DNA or RNA polynucleotide molecule or an analog thereof capable of sequence-specifically annealing to a polynucleotide template and providing a 3' end that serves as a substrate for a template-dependent polymerase to produce an extension product which is complementary to the polynucleotide template. The conditions for initiation and extension usually include the presence of at least one, but more preferably all four different deoxyribonucleoside triphosphates and a polymerization-inducing agent such as DNA polymerase or reverse transcriptase, in a suitable buffer (in this context "buffer" includes solvents (generally aqueous) plus necessary cofactors and reagents which affect pH, ionic strength, etc.) and at a suitable temperature. A primer useful in the methods described herein is generally single-stranded, and a primer and its complement can anneal to form a double-stranded polynucleotide. Primers according to the methods and compositions described herein can be less than or equal to 300 nucleotides in length, e.g., less than or equal to 300, or 250, or 200, or 150, or 100, or 90, or 80, or 70, or 60, or 50, or 40, and preferably 30 or fewer, or 20 or fewer, or 15 or fewer, but at least 10 nucleotides in length.

In some embodiments, the PCR reactions described herein relate to the use of a set of primers. As used herein, the term "set of primers" refers to a group of at least two primers, including a forward primer and a reverse primer, one of which anneals to a first strand of a target nucleic acid sequence and the other of which anneals to a complement of the first strand. In some embodiments, the first primer of a primer pair subset can anneal to a first strand of the target nucleic acid sequence and the second primer of a primer pair subset (e.g., reverse primer), can anneal to the complement of that strand. The orientation of the primers when annealed to the target and/or its complement can be such that nucleic acid synthesis proceeding from primer extension of a one primer of the primer pair subset would produce a nucleic acid sequence that is complementary to at least one region of the second primer of the primer pair subset. The "first strand" of a nucleic acid target and/or sequence can be either strand of a double-stranded nucleic acid comprising the sequence of the target nucleotide and/or target site locus, but once chosen, defines its complement as the second strand. Thus, as used herein, a "forward primer" is a primer which anneals to a first strand of a nucleic acid target, while a "reverse primer" of the same set is a primer which anneals to the complement of the first strand of the nucleic acid target. As used herein, "specific" when used in the context of a primer specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

Methods of making primers are well known in the art, and numerous commercial sources offer oligonucleotide synthesis services suitable for providing primers according to the methods and compositions described herein, e.g. INVITROGEN™ Custom DNA Oligos; Life Technologies; Grand Island, N.Y. or custom DNA Oligos from IDT; Coralville, Iowa).

PCR requires the use of a nucleic acid polymerase. As used herein, the phrase "nucleic acid polymerase" refers an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and commercially available. One group of preferred nucleic acid polymerases are thermostable, i.e., they retain function after being subjected to temperatures sufficient to denature annealed strands of complementary nucleic acids, e.g. 94° C., or sometimes higher. As understood in the art, PCR can require cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. More specifically, strand separation according to the methods described herein is achieved by heating the nucleic acid sample above its Tm. Generally, for a sample containing nucleic acid molecules in buffer suitable for a nucleic acid polymerase, heating to 94° C. is sufficient to achieve strand separation. An exemplary buffer contains 50 mM KCl, 10 mM Tric-HCl (pH 8.8@25° C.), 0.5 to 3 mM MgCl2, and 0.1% BSA.

As also understood in the art, PCR requires annealing primers to template nucleic acids. As used herein, "anneal" refers to permitting two complementary or substantially complementary nucleic acids strands to hybridize, and more particularly, when used in the context of PCR, to hybridize such that a primer extension substrate for a template-dependent polymerase enzyme is formed. Conditions for primer-target nucleic acid annealing vary with the length and sequence of the primer and are based upon the calculated Tm for the primer. Generally, an annealing step in an amplification regimen involves reducing the temperature following the strand separation step to a temperature based on the calculated Tm for the primer sequence, for a time sufficient to permit such annealing. Tm can be readily predicted by one of skill in the art using any of a number of widely available algorithms (e.g., OLIGO™ (Molecular Biology Insights Inc. Colorado) primer design software and VENTRO NTI™ (Invitrogen, Inc. California) primer design software and programs available on the internet, including Primer3 and Oligo Calculator). For example, Tm's can be calculated using the NetPrimer software (Premier Biosoft; Palo Alto, Calif.; and freely available on the world wide web at http://www.premierbiosoft.com/netprimer/netprlaunch/Help/xnetprlaunch.html). The Tm of a primer can also be calculated using the following formula, which is used by NetPrimer software and is described in more detail in Frieir et al. PNAS 1986 83:9373-9377 which is incorporated by reference herein in its entirety. $Tm=\Delta H/(\Delta S+R*\ln(C/4))+16.6 \log([K+]/(1+0.7[K+]))-273.15$ wherein, $\Delta H$ is enthalpy for helix formation; $\Delta S$ is entropy for helix formation; R is molar gas constant (1.987 cal/° C.*mol); C is the nucleic acid concentration; and [K+] is salt concentration. For most amplification regimens, the annealing temperature is selected to be about 5° C. below the predicted Tm, although temperatures closer to and above the Tm (e.g., between 1° C. and 5° C. below the predicted Tm or between 1° C. and 5° C. above the predicted Tm) can be used, as can, for example, temperatures more than 5° C. below the predicted Tm (e.g., 6° C. below, 8° C. below, 10° C. below or lower). Generally, the closer the annealing temperature is to the Tm, the more specific is the annealing. The time allowed for primer annealing during a PCR amplification regimen depends largely upon the volume of the reaction, with larger volumes requiring longer times, but also depends upon primer and template concentrations, with higher relative concentrations of primer to template requiring less time than lower relative concentrations. Depending upon volume and relative primer/template concentration, primer annealing steps in an amplification regimen can be on the order of 1 second to 5 minutes, but will generally be between 10 seconds and 2 minutes, preferably on the order of 30 seconds to 2 minutes. As used herein, "substantially anneal" refers to a degree of annealing during a PCR amplification regimen which is sufficient to produce a detectable level of a specifically amplified product.

PCR also relies upon polymerase extension of annealed primers at each cycle. As used herein, the term "polymerase extension" means the template-dependent incorporation of at least one complementary nucleotide, by a nucleic acid polymerase, onto the 3' end of an annealed primer. Polymerase extension preferably adds more than one nucleotide, preferably up to and including nucleotides corresponding to the full length of the template. Conditions for polymerase extension vary with the identity of the polymerase. The temperature used for polymerase extension is generally based upon the known activity properties of the enzyme. Although, where annealing temperatures are required to be, for example, below the optimal temperatures for the enzyme, it will often be acceptable to use a lower extension temperature. In general, although the enzymes retain at least partial activity below their optimal extension temperatures, polymerase extension by the most commonly used thermostable polymerases (e.g., Taq polymerase and variants thereof) is performed at 65° C. to 75° C., e.g, 68-72° C.

Primer extension is performed under conditions that permit the extension of annealed oligonucleotide primers. As used herein, the term "conditions that permit the extension of an annealed oligonucleotide such that extension products are generated" refers to the set of conditions including, for example temperature, salt and co-factor concentrations, pH, and enzyme concentration under which a nucleic acid polymerase catalyzes primer extension. Such conditions will vary with the identity of the nucleic acid polymerase being used, but the conditions for a large number of useful polymerase enzymes are well known to those skilled in the art. One exemplary set of conditions is 50 mM KCl, 10 mM Tric-HCl (pH 8.8@25° C.), 0.5 to 3 mM MgCl2, 200 uM each dNTP, and 0.1% BSA at 72° C., under which Taq polymerase catalyzes primer extension.

As used herein, "amplified product" or "PCR product" refers to polynucleotides resulting from a PCR reaction that are copies of a portion of a particular target nucleic acid sequence and/or its complementary sequence, which correspond in nucleotide sequence to the template nucleic acid sequence and/or its complementary sequence. An amplified product can be double or single stranded.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the term "double-stranded break" or "DSB" refers to a break or cut that severs both strands of a double-stranded nucleic acid. In some embodiments, the DSB results in one or more blunt ends. In some embodimetns, the DSB results in one or more overhangs. In some embodiments, the overhangs are less than 50 bp in length. In some embodiments, the overhangs are less than 40 bp in length. In some embodiments, the overhangs are less than 30 bp in length. In some embodiments, the overhangs are less than 20 bp in length. In some embodiments, the overhangs are less than 10 bp in length.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method for high throughput, genome-wide translocation sequencing (HTGTS) and detection of double-stranded DNA break (DSB) locations, the method comprising the steps of:
a. exposing a cell to an agent known or suspected of being capable of producing at least one DSB;
b. optionally, allowing the cell to divide for at least a half cell cycle after exposure;
c. extracting genomic DNA from the cells;
d. optionally, producing a fragmented DNA sample;
e. producing a single-stranded PCR product by Linear Amplification Mediated (LAM)-PCR with a first locus-specific primer;
f. producing a ligated DNA product by ligating the single-stranded PCR product produced in step (e) to an adapter, wherein the adapter comprises:
a distal portion of known DNA sequence that can be used to design PCR primers for a nested PCR amplification;
a proximal portion of random nucleotides; and
a 3' overhang;
g. producing a nested PCR product by performing a nested-PCR with an adapter- and a locus-specific primer using the ligated DNA product thereby amplifying the nucleic acid sequence surrounding the junction around the at least one DSB;
h. optionally, digesting the ligated DNA sample with a blocking enzyme;
i. producing a sequenced nested PCR product by sequencing the nested PCR product;
j. aligning the sequenced nested PCR product against a reference sequence to identify a chromosomal location of the translocation and the chromosomal location of the at least one DSB.
2. The method of paragraph 1, wherein the first locus-specific primer comprises an affinity tag.
3. The method of paragraph 2, wherein the method further comprises isolating the PCR products produced in step (e) by affinity purification.
4. The method of any of paragraphs 2-3, wherein the affinity tag is biotin.
5. The method of paragraph 4, wherein the affinity purification comprises binding biotin with streptavidin.
6. The method of any of paragraphs 3-5, wherein the affinity purification comprises binding the PCR products produced in step (d) to a substrate.
7. The method of paragraph 6, wherein the substrate is a bead.
8. The method of any of paragraphs 1-7, wherein the primers used for the nested PCR step comprise barcode sequences;
9. The method of any of paragraphs 1-8, wherein the fragmenting is performed by sonication or restriction digest.
10. The method of any of paragraphs 1-9, wherein the fragmenting is performed by randomly shearing genomic DNA or with a frequently cutting restriction enzyme.
11. The method of any of paragraphs 1-10, wherein ligating the single-stranded PCR products to an adapter comprises contacting the PCR product with a population of adapters having the same distal portion and random proximal portion sequences.
12. The method of any of paragraphs 1-11, wherein the proximal portion of the adaptor is 3-10 nucleotides in length.
13. The method of any of paragraphs 1-12, wherein the proximal portion of the adaptor is 5-6 nucleotides in length.
14. The method of any of paragraphs 1-13, wherein the adaptor comprises barcode sequences between distal and proximal portions.
15. The method of any of paragraphs 1-14, wherein the PCR products produced in step (i) are size selected prior to sequencing.
16. The method of any of paragraphs 1-15, wherein the agent is Cas9 or a Cas9:gRNA nuclease.
17. The method of any of paragraphs 1-16 wherein the agent is selected from the group consisting of:
a nuclease; a custom nuclease; a meganuclease; a TALEN; a zinc-finger nuclease; a CRISPR; a Cpf1 CRISPR effector; an integrating virus or viral vector; an endonuclease; a chemotherapeutic; and radiation.
18. The method of any of paragraphs 1-17, wherein the agent will generate at least one DSB within 400 bp of the hybridization target of the locus-specific primer.
19. The method of any of paragraphs 1-18, wherein the agent will generate at least one DSB on the same chromosome as the hybridization target of the locus-specific primer.
20. The method of any of paragraphs 1-19, wherein the cell is exposed to two agents, wherein a first agent will generate at least one DSB on the same chromosome as a DSB generated by a second agent.
21. The method of any of paragraphs 1-20, wherein at least one agent will generate at least one DSB within 400 bp of the locus-specific primer.
22. The method of any of paragraphs 1-21, wherein the cell is exposed to two agents, wherein a first agent will generate at least one DSB on the same chromosome as a DSB generated by a second agent.
23. The method of any of paragraphs 1-22, further comprising a step of inserting into a cell to be analyzed at least one target sequence for the agent that is known to be absent in the genome of the cell to be analyzed prior to step (a) of paragraph 1.
24. The method of any of paragraphs 1-23, wherein the cells are allowed to divide for at least 12 hours.
25. The method of any of paragraphs 1-24, wherein the cells are allowed to divide for 1-5 days.
26. The method of any of paragraphs 1-25, wherein the cells are allowed to divide for 2-4 days.
27. The method of any of paragraphs 1-26, wherein the sequencing is performed using a next generation sequencing method.

28. The method of any of paragraphs 1-27, wherein the step of aligning is performed by a non-human machine.
29. The method of paragraph 28, wherein the non-human machine comprises a computer executable software.
30. The method of paragraph 29, further comprising a display module for displaying the results of the step of aligning.
31. The method of any of paragraphs 1-30, wherein the cell is a mammalian cell.
32. The method of any of paragraphs 1-31, wherein the cell is a plant cell.
33. The method of any of paragraphs 1-32, wherein the cell division step (b) is omitted.
34. The method of any of paragraphs 1-33, wherein the blocking digestion step (h) is omitted.
35. The method of any of paragraphs 1-34, wherein end repair is not performed between steps (d) and (e).
36. A kit comprising:
a. an agent known to cause at least one DSB in a cell; and
b. a locus-specific primer that will anneal within 400 bp of the DSB generated by the agent;
37. The kit of paragraph 36, further comprising an adapter, the adapter comprising: a distal portion of known DNA sequence that can be used to design PCR primers for a nested PCR amplification;
a proximal portion of random nucleotides; and
a 3' overhang.
38. The kit of any of paragraphs 36-37, further comprising at least one nested PCR primer.
39. The kit of any of paragraphs 36-38, further comprising a substrate comprising an affinity domain, wherein the locus-specific primer comprises an affinity tag.
40. The kit of any of paragraphs 36-39, further comprising a cell.
41. The kit of any of paragraphs 36-40, further comprising an additional agent known or suspected to cause at least one DSB in the cell.
42. A computer implemented method for high throughput, genome-wide translocation sequencing (HTGTS) and detection of double-stranded DNA break (DSB) locations, comprising: on a device having one or more processors and a memory storing one or more programs for execution by the one or more processors, the one or more programs including instructions for:
aligning a sequenced nested PCR product against a reference sequence to identify a chromosomal location of a translocation and the chromosomal location of at least one DSB.
43. The computer implemented method of paragraph 42, wherein the aligning step is performed by an aligning program.
44. The computer implemented method of any of paragraphs 42-43, wherein the aligning program is Bowtie2.
45. The computer implemented method of any of paragraphs 42-44, wherein the aligning step comprises a best-path search algorithm to determine prey and bait alignments.
46. The computer implemented method of any of paragraphs 42-45, wherein the aligning step comprises de-multiplexing sequence reads.
47. The computer implemented method of any of paragraphs 42-46, wherein the de-multiplexing sequence reads comprises using a fastq-multx tool.
48. The computer implemented method of any of paragraphs 42-47, wherein the aligning step comprises trimming an adapter sequence.
49. The computer implemented method of any of paragraphs 42-48, wherein the trimming the adapter sequence comprises using a SeqPrep utility.
50. The computer implemented method of any of paragraphs 42-49, wherein the aligning step comprises mapping reads to an hg19 reference genome using the Bowtie2 with the top fifty alignments reported that had an alignment score above 50, representing a perfect 25 nt local alignment.
51. The computer implemented method of any of paragraphs 42-50, wherein, on average, 94% of the demultiplexed reads per library harbored a bait sequence alignment with <10% of these reads containing an alignable prey junction.
52. The computer implemented method of any of paragraphs 42-51, wherein the aligning step comprises a best-path searching algorithm to select an optimal sequence of alignments that describe the read's composition.
53. The computer implemented method of any of paragraphs 42-52, wherein the aligning step comprises filtering.
54. The computer implemented method of paragraph 53, wherein the filtering comprises a bait alignment and a prey alignment.
55. The computer implemented method of paragraph 54, wherein the bait alignment does not extend more than 10 nucleotides beyond a targeted site.
56. The computer implemented method of any of paragraphs 42-55, wherein the aligning step comprises vector controls, off-set nicking with multiple sites, and use of a distal targeted site.
57. The computer implemented method of any of paragraphs 42-56, wherein the aligning step comprises comparing discarded alignments to a selected prey alignment.
58. The computer implemented method of paragraph 57, wherein, if any of the discarded alignments surpasses both a coverage and score threshold with respect to the prey alignment, the read is filtered due to low mapping quality.
59. The computer implemented method of any of paragraphs 42-58, wherein the aligning step comprises extending the bait alignment 10 nucleotides past the primer to remove possible mispriming events and other artifacts.
60. The computer implemented method of any of paragraphs 42-59, wherein the aligning step comprises removing potential duplicates by comparing coordinates of an end of a bait alignment and a start of a prey alignment across all reads.
61. The computer implemented method of any of paragraphs 42-60, wherein the aligning step comprises marking a read as a duplicate if it has a bait alignment off-set within 2 nt and a prey alignment offset within 2 nt of another read's bait and prey alignments.
62. The computer implemented method of any of paragraphs 42-61, wherein the aligning step comprises applying post-filter stringency to remove junctions with gaps larger than 30 nt and bait sequences shorter than 50 nt.
63. The computer implemented method of any of paragraphs 42-62, wherein the aligning step comprises removing reads with prey alignments to telomere repeat sequences.
64. The computer implemented method of any of paragraphs 42-63, wherein the aligning step comprises filtering genome mixing experiments using a combined hg19/mm9 reference or Homo sapiens/Mus musculus genome builds.
65. The computer implemented method of any of paragraphs 42-64, wherein the computer implemented method is used with a method for high throughput, genome-wide translocation sequencing (HTGTS) and detection of double-stranded DNA break (DSB) locations, the method comprising the steps of:

a. exposing a cell to an agent known or suspected of being capable of producing at least one DSB;
b. optionally, allowing the cell to divide for at least a half cell cycle after exposure;
c. extracting genomic DNA from the cells;
d. optionally, producing a fragmented DNA sample;
e. producing a single-stranded PCR product by Linear Amplification Mediated (LAM)-PCR with a first locus-specific primer;
f. producing a ligated DNA product by ligating the single-stranded PCR product produced in step (e) to an adapter, wherein the adapter comprises:
a distal portion of known DNA sequence that can be used to design PCR primers for a nested PCR amplification;
a proximal portion of random nucleotides; and
a 3' overhang;
g. producing a nested PCR product by performing a nested-PCR with an adapter- and a locus-specific primer using the ligated DNA product thereby amplifying the nucleic acid sequence surrounding the junction around the at least one DSB;
h. optionally, digesting the ligated DNA sample with a blocking enzyme;
i. producing a sequenced nested PCR product by sequencing the nested PCR product;
j. aligning the sequenced nested PCR product against the reference sequence to identify the chromosomal location of the translocation and the chromosomal location of the at least one DSB.

66. A computer system for high throughput, genome-wide translocation sequencing (HTGTS) and detection of double-stranded DNA break (DSB) locations, comprising:
one or more processors and memory to store one or more programs, the one or more programs comprising instructions for:
aligning a sequenced nested PCR product against a reference sequence to identify a chromosomal location of a translocation and the chromosomal location of at least one DSB.

67. A non-transitory computer-readable storage medium storing one or more programs for high throughput, genome-wide translocation sequencing (HTGTS) and detection of double-stranded DNA break (DSB) locations, the one or more programs for execution by one or more processors of a computer system, the one or more programs comprising instructions for: aligning a sequenced nested PCR product against a reference sequence to identify a chromosomal location of a translocation and the chromosomal location of at least one DSB.

68. The method of any of paragraphs 29-34, wherein the alignment is performed on a device having one or more processors and a memory storing one or more programs for execution by the one or more processors, comprising one or more programs including instructions for: aligning a sequenced nested PCR product against a reference sequence to identify a chromosomal location of a translocation and the chromosomal location of at least one DSB.

69. The method of paragraph 68, wherein the aligning step is performed by an aligning program.

70. The method of paragraph 69, wherein the aligning program is Bowtie2.

71. The method of any of paragraphs 68-70, wherein the aligning step comprises a best-path search algorithm to determine prey and bait alignments.

72. The method of any of paragraphs 68-71, wherein the aligning step comprises de-multiplexing sequence reads.

73. The method of any of paragraphs 68-72, wherein the de-multiplexing sequence reads comprises using a fastq-multx tool.

74. The method of any of paragraphs 68-73, wherein the aligning step comprises trimming an adapter sequence.

75. The method of any of paragraphs 68-74, wherein the trimming the adapter sequence comprises using a SeqPrep utility.

76. The method of any of paragraphs 68-75, wherein the aligning step comprises mapping reads to an hg19 reference genome using the Bowtie2 with the top fifty alignments reported that had an alignment score above 50, representing a perfect 25 nt local alignment.

77. The method of any of paragraphs 68-76, wherein, on average, 94% of the demultiplexed reads per library harbored a bait sequence alignment with <10% of these reads containing an alignable prey junction.

78. The method of any of paragraphs 68-77, wherein the aligning step comprises a best-path searching algorithm to select an optimal sequence of alignments that describe the read's composition.

79. The method of any of paragraphs 68-78, wherein the aligning step comprises filtering.

80. The method of any of paragraphs 68-79, wherein the filtering comprises a bait alignment and a prey alignment.

81. The method of any of paragraphs 68-80, wherein the bait alignment does not extend more than 10 nucleotides beyond a targeted site.

82. The method of any of paragraphs 68-81, wherein the aligning step comprises vector controls, off-set nicking with multiple sites, and use of a distal targeted site.

83. The method of any of paragraphs 68-82, wherein the aligning step comprises comparing discarded alignments to a selected prey alignment.

84. The method of paragraph 83, wherein, if any of the discarded alignments surpasses both a coverage and score threshold with respect to the prey alignment, the read is filtered due to low mapping quality.

85. The method of any of paragraphs 68-84, wherein the aligning step comprises extending the bait alignment 10 nucleotides past the primer to remove possible mispriming events and other artifacts.

86. The method of any of paragraphs 68-85, wherein the aligning step comprises removing potential duplicates by comparing coordinates of an end of a bait alignment and a start of a prey alignment across all reads.

87. The method of any of paragraphs 68-86, wherein the aligning step comprises marking a read as a duplicate if it has a bait alignment off-set within 2 nt and a prey alignment offset within 2 nt of another read's bait and prey alignments.

88. The method of any of paragraphs 68-87, wherein the aligning step comprises applying post-filter stringency to remove junctions with gaps larger than 30 nt and bait sequences shorter than 50 nt.

89. The method of any of paragraphs 68-88, wherein the aligning step comprises removing reads with prey alignments to telomere repeat sequences.

90. The method of any of paragraphs 68-89, wherein the aligning step comprises filtering genome mixing experiments using a combined hg19/mm9 reference or *Homo sapiens/Mus musculus* genome builds.

91. The method of any of paragraphs 68-90, wherein the computer implemented method is used with a method for high throughput, genome-wide translocation sequencing (HTGTS) and detection of double-stranded DNA break (DSB) locations, the method comprising the steps of:
a. exposing a cell to an agent known or suspected of being capable of producing at least one DSB;
b. optionally, allowing the cell to divide for at least a half cell cycle after exposure;
c. extracting genomic DNA from the cells;
d. optionally, producing a fragmented DNA sample;
e. producing a single-stranded PCR product by Linear Amplification Mediated (LAM)-PCR with a first locus-specific primer;
f. producing a ligated DNA product by ligating the single-stranded PCR product produced in step (e) to an adapter, wherein the adapter comprises:
a distal portion of known DNA sequence that can be used to design PCR primers for a nested PCR amplification;
a proximal portion of random nucleotides; and
a 3' overhang;
g. producing a nested PCR product by performing a nested-PCR with an adapter- and a locus-specific primer using the ligated DNA product thereby amplifying the nucleic acid sequence surrounding the junction around the at least one DSB;
h. optionally, digesting the ligated DNA sample with a blocking enzyme;
i. producing a sequenced nested PCR product by sequencing the nested PCR product;
j. aligning the sequenced nested PCR product against the reference sequence to identify the chromosomal location of the translocation and the chromosomal location of the at least one DSB.

EXAMPLES

Example 1

Described herein is a high-throughput genome-wide translocation sequencing (HTGTS) assay. The assays and methods described herein are a substantial improvement over existing methods and permit the application of Cas9: gRNA technologies. The assays and methods described herein permit the measurement of various DNA double-strand break (DSB) activities either intrinsic to the biological system or from outside agents. This improved method and redesigned sequence filtering pipeline is much cheaper, faster and more robust than the prior method, and the method described herein permits the detection and measurement of non-specific DSB activity in addition to recurrent DSB activity.

The methods and assays described herein further permit a user to directly test and compare a series of outside agents using a universal donor DSB. Contemplated herein is a universal kit to assess genome-wide DSB activities of any given outside agent (custom nuclease, chemotherapeutics, ionizing radiation, etc.). In particular, (1) the assay can have built-in control sites which are useful for troubleshooting on the user end, (2) the assay can detect recurrent joining to virtually all mappable regions in the genome, (3) the assay can also measure changes in break-site chromosome junction enrichment relating to the outside agent applied which is interpreted as non-specific DSB activity, (4) a means to further study outside agent-related recurrent DSB sites is provided by enhancing recurrent DSB site detection in cis by cloning from donor DSBs on additional chromosomes, and (5) a means is provided to optimize specific DSB activities derived from using the assay over various concentration/dose ranges of outside agent applied. Provided below is a list of advantages of the current methods and assays over existing technologies, e.g., ways in which this method is substantially different from an earlier HTGTS method (see, e.g., US Patent Publication 20140234847; which is incorporated by reference herein in its entirety)

Improved and Redesigned Methodology.

The methodology provided herein is cheaper, faster, and more robust than existing tehnologies. The HTGTS assay described herein has several advantages versus prior methods (e.g. US Patent Publication 20140234847), which make the identification of genome-wide translocations cheaper and more efficient. First, in some embodiments, genomic DNA is sheared, rather than digested by specific frequent cutter enzymes. As described herein, enzyme digest is revealed to have a tremendous bias in junction enrichment genome-wide. However, in other embodiments, fragmentation by frequent cutter enzymes is still compatible with the new HTGTS.

Second, a biotinylated locus-specific primer is used directly on the sheared DNA fragments without the need to repair the broken ends.

Third, the amplified single-strand DNA fragments are directly ligated on-bead to adapters with a 3' overhang comprised of 5-6 random nucleotides, which suppresses non-specific amplification in following PCR steps necessary for including next generation sequencing-specific nucleotides. This improved method from transfection of cells to sequence analysis takes about 1 week (2 days for cell culture, 2 days for library prep, 2 days for sequencing).

Redesigned and Improved Bioinformatics Pipeline.

A modern alignment program, Bowtie2™, is used to align to a reference genome. A best-path search algorithm is used to determine prey and bait alignments, and consequently, the currently described method permits full characterization of the breakpoints at translocation junctions. Additionally, this method now handles paired-end reads.

In greater detail, sequence reads are de-multiplexed and adapter sequence trimmed using the fastq-multx™ tool from ea-utils (available on the World Wide Web at code.google.com/p/eautils/) and the SeqPrep™ utility (available on the World Wide Web at github.com/jstjohn/SeqPrep), respectively. Reads are mapped to the hg19 reference genome using Bowtie2™ (available on the World Wide Web at bowtiebio.sourceforge.net/bowtie2/manual.shtml) with the top fifty alignments reported that had an alignment score above 50, representing a perfect 25 nt local alignment. On average, 94% of demultiplexed reads per library harbored a bait sequence alignment with <10% of these reads containing an alignable prey junction. A best-path searching algorithm was used to select the optimal sequence of alignments that describe the read's composition, typically finding the bait and prey alignments. Aligned reads were filtered on the following conditions: (1) reads must include both a bait alignment and a prey alignment and (2) the bait alignment cannot extend more than 10 nucleotides beyond the targeted site. For vector controls and off-set nicking with multiple sites, the distal targeted site was used. Discarded alignments were compared to the selected prey alignment; if any of the discarded alignments surpassed both a coverage and score threshold with respect to the prey alignment, the read was filtered due to low mapping quality. To remove possible mispriming events and other artifacts, the bait alignment must extend 10 nucleotides past the primer. Potential duplicates were removed by comparing the coordinates of the end of the bait alignment and the start of the prey alignment across all reads. A read can be marked as a duplicate if it has a bait alignment off-set within 2 nt and a prey alignment offset within 2 nt of another read's bait and prey alignments. Post-filter stringency was applied to remove junctions with gaps larger than 30 nt and bait sequences shorter than 50 nt. Reads with prey alignments to telomere repeat sequences were also removed. Genome mixing experiments were similarly filtered as described above but with using a combined hg19/mm9 reference.

Redesigned and Improved Method to Determine Hotspot Enrichment.

A peak calling system can be used to identify regions of significant enrichment. Identification of enriched regions can be performed using the MACS2™ software (Zhang et al., 2008 Genome Biology), designed for ChIP-seg™ peak calling. Junctions associated with MACS-defined peaks (FDR-adjusted p-value enrichment threshold of $10^{-9}$) can be extracted for further analysis. Hotspots can be defined as having significant focal enrichment and present in more than one biological replicate library. Off-target sites can be defined as hotspots that contain genomic sequence differing from the on-target sequence by less than or equal to ½ the targeted sequence length.

Redesigned and Improved Visualization of Genome-Wide Junctions and Hotspots.

Genome-wide translocations can be visualized using custom circos plots (Krzywinski et al., 2009 Genome Research) with central colored lines linking bait break-site to prey hotspots (e.g., dark red to yellow lines indicate high to low enrichment). The prior method used colored dots on a linear chromosome to indicate enrichment.

Cas9:gRNA and Cas9n:gRNA paired nickase systems. Targeting endogenous loci in live cells with custom nucleases designed to generate DSBs at specific endogenous sequences without the need for substrate integration permits the introduction of targeted mutations and can be applied to targeted gene therapy in humans. The recently developed Cas9 guide RNA (gRNA) endonucleases are applicable to such directed mutations. The Cas9 nuclease forms a complex with an engineered gRNA comprised of a chimeric clustered, regularly interspaced, short palindromic repeat (CRISPR) RNA and trans-activating CRISPR RNA. Cas9 gRNA sequence specificity relies on hybridization of a 20 nt targeting sequence on the 5' end of the gRNA to complementary DNA and recognition of an 'NGG' protospacer adjacent motif (PAM) on the non-complementary strand. Cas9:gRNA complexes, which again can be designed to cleave a multitude of sites across the genome, generate blunt DSB ends 3 bp into the 20 nt target sequence proximal to the PAM (Hsu et al., 2014). Cas9 D10A mutation (Cas9n), which renders the Cas9 endonuclease into a nickase that generates DSBs from off-set paired Cas9n:gRNA combinations with variable length 5' overhangs, was used to reduce the off-target activity of Cas9 endonuclease (Ran et al., 2013; Mali et al., 2013). These are novel custom nuclease systems not previously described in HTGTS methods.

Describe Off-Target Verification Methods by Cloning from Off-Target Sites as Bait.

With the new HTGTS assays and methods described herein, HTGTS libraries can be prepared from either on-target site of the candidate custom nuclease or from several of its off-target sites. Recurrent strong off-targets should be present in all the libraries independent of bait (donor) DSB position.

Assay for Recurrent and Non-Specific DSB Activity Detection.

The methods and assays described herein can identify recurrently broken sites in the genome as well as identify non-specific DSB activity which can be introduced from outside agents including but not restricted to nucleases, ionizing radiation, chemotherapeutics, and other small molecules which may impact DNA repair or may cause other DNA lesions which can lead to the formation of DSBs.

Single Characterized Bait DSB Site to Compare DSB Activities of Additional Outside Agents.

The methods and assays described herein can permit comparison of candidate agent DSB activities from a common bait DSB site provided by separate previously characterized custom nuclease. With that fixed bait site, the cutting efficiency, off-target sites, and/or non-specific activity of other candidate custom nucleases or endogenous DNA damaging factors can be determined.

Can Determine On-Target and Off-Target Translocation Saturation Curves.

The methods and assays described herein permit the preparation of libraries from tiltrated concentrations of candidate custom nuclease with fixed bait DSB induced by another kind of nuclease. The numbers of on-target and off-target hits relevant to the custom nuclease then can be normalized to the hits relevant to the fixed DSB for testing the saturation condition of the candidate custom nuclease.

Can Determine the Formation of Dicentric Chromosomes Around the Bait DSB Locus.

The methods and assays described herein can permit the examination of the formation of dicentric chromosome at the cloning bait DSB site, which distribute on the resected strand where the cloning primer binds. This requires that the targeted bait site is found on the homologous chromosome to promote the formation of dicentric chromosome joins.

Cloning Endogenously Recurrent DSBs.

The methods and assays described herein permit cloning of translocations from recurrent endogenous DSBs from biologically and/or developmentally programmed sites as described for V(D)J recombination and IgH class switch recombination.

Describe Additional Controls to Verify Specific Cutting.

Analysis of the bait sequence length in combination with the junction structure associated with the joined prey sequence can permit troubleshooting of assays which use novel bait DSBs and primers to clone translocations using the methods and assays described herein.

Example 2: Genome-Wide Detection of Specific and Non-Specific DNA DSB Activities of Custom Nucleases in Human Cells Described herein is a robust linear amplification-mediated high-throughput genome-wide translocation sequencing (HTGTS) method that identifies endogenous or ectopic "prey" DNA double-stranded breaks (DSBs) across the human genome based on their translocation to "bait" DSBs generated by custom nucleases. HTGTS with different Cas9:gRNA or TALEN-nuclease on-target baits revealed off-target hotspots for given nucleases that ranged from few or none to dozens or more, and greatly extended known off-target numbers for certain previously characterized custom nucleases. Beyond various types of nuclease off-target collateral damage, collateral damage was identified in the form of translocations between bona fide nuclease targets on homologous chromosomes. Based on frequent non-specific DSBs making any given human chromosome an HTGTS hotspot region for bait DSBs within it, it was found that HTGTS also reveals non-specific DSB-generating activities of custom nucleases. Finally, HTGTS confirmed that the Cas9D10A-nickase approach suppresses off-targets genome-wide and suggested other strategies to enhance desired nuclease activities, including titration of specific versus non-specific DSB-generating activities.

Chromosomal translocations fuse sections of two heterologous chromosomes or two separated regions on homologous chromosomes. Human cancer cells often contain recurrent translocations that activate oncogenes or delete tumor suppressor genes[1]. Cancer genomics revealed that chromosomal translocations and other related genomic rearrangements frequently result from end-joining two DNA double-stranded breaks (DSBs)[2]. Beyond oncogenic selection, mechanistic factors promote recurrent translocations[3]. Such mechanistic factors include DSB frequencies at respective translocation partner loci and the frequency at which the ends of the two DSBs are physically juxtaposed within individual cells in a population[4,5]. High-throughput genome-wide translocation sequencing (HTGTS)[6] and a related method' identifies translocations of yeast I-SceI meganuclease-generated "bait" DSBs at target sites introduced into the genome of mouse cells to other "prey" cellular DSBs genome-wide. Correspondingly, these methods also identify endogenous DSBs[6,7], including programmed antigen receptor locus DSBs generated by the RAG1/2 endonuclease during V(D)J recombination in developing B lymphocytes[7] and DSBs initiated by activation induced cytidine deaminase at the immunoglobulin heavy chain locus and at various off-target ("OT") sites during antibody class-switching in mature B cells[6-8]. These approaches also detect more general DSBs including those generated by replicative and/or transcriptional stresses[6-9], as well as ectopic DSBs generate by ionizing radiation (IR)[7]. HTGTS, which provides nucleotide-level resolution of junctions, further revealed I-SceI-generated DSB at cryptic OT sequences within the mouse genome[6].

Frequent endogenous DSBs at two loci can dominate translocation landscapes even if involved sequences are not, on average, spatially proximal in a given cell population[5,10], due to cellular heterogeneity in three-dimensional (3-D) genome organization allowing most loci to be synapsed in a subset of cells[4,5]. However, if the frequency of particular DSBs is not dominant, synapsis frequency of two broken sites may contribute more strongly to influencing their translocation frequency[4]. In this regard, treating cells with IR to generate random ectopic DSBs "normalizes" DSB frequency genome-wide, revealing influences of factors that enhance spatial proximity of DSB target sequences[5]. Indeed, in pro-B cell lines, IR-treatment turned the length of a given chromosome harboring the bait I-SeeI site in cis into a translocation hotspot region, due to much greater probability of two DSBs being proximal along the length of the same cis chromosome versus on different chromosomes including the other homologue[5]. Within the cis chromosome, translocation frequency is further enhanced between sequences within "megabase" (Mb) regions[11], due to spatial proximity influences and/or contributions of chromatin factors associated with the DSB response[4,12,12].

Targeting endogenous loci in live cells with custom nucleases designed to generate DSBs at specific endogenous sequences without the need for substrate integration has been extremely useful for introducing targeted mutations and holds great promise for targeted gene therapy in humans[14-17]. In this regard, the recently developed TALENs and Cas9 guide RNA (gRNA) endonucleases are particularly promising[18-23]. TALENs are dimeric site-specific nucleases with monomers consisting of a custom-made DNA binding domain fused to a C-terminal FokI nuclease domain[22,23]; specific TALEN activity requires the dimerization of the FokI domain from two TALEN subunits with each monomer providing half of the specific DNA recognition sequence[15]. The DNA-binding code for TALENs allows targeting of DSBs with 5' overhangs at nearly any position across different genomes[14,24,25]. For Cas9:gRNA endonucleases, the Cas9 nuclease forms a complex with an engineered gRNA comprised of a chimeric clustered, regularly interspaced, short palindromic repeat (CRISPR) RNA and trans-activating CRISPR RNA[14]. Cas9 gRNA sequence specificity relies on hybridization of a 20 nt targeting sequence on the 5' end of the gRNA to complementary DNA and recognition of an 'NGG' protospacer adjacent motif (PAM) on the non-complementary strand. Cas9:gRNA complexes, which again can be designed to cleave a multitude of sites across the genome, generate blunt DSB ends 3 bp into the 20 nt target sequence proximal to the PAM[14].

One continuing concern for employing TALENs and Cas9gRNAs for genome engineering, and for therapeutic human genome engineering in particular, is the potential for OT DSB activity at non-consensus sites within the genome for any given enzyme[13]. A variety of approaches have been developed to minimize undesired DNA cleavage activities of these enzymes[14,15]. In the latter context, robust assays for genome-wide activities of custom nucleases are critical for evaluating their potential for generating collateral damage. Current assays for OT custom nuclease activity involve cytotoxicity[26], prediction-based modeling[27-29], select screening[27,30,31], and viral vector DSB traps[32,33]. Described herein is an enhanced HTGTS approach and its application in human cells for identifying custom nuclease generated on-target and OT DSBs, as well as non-specific DSBs and collateral genomic damage such as recurrent translocations.

Results

HTGTS Libraries from Cas9-Generated DSBs at the Human RAG1 Locus.

Figure 6:
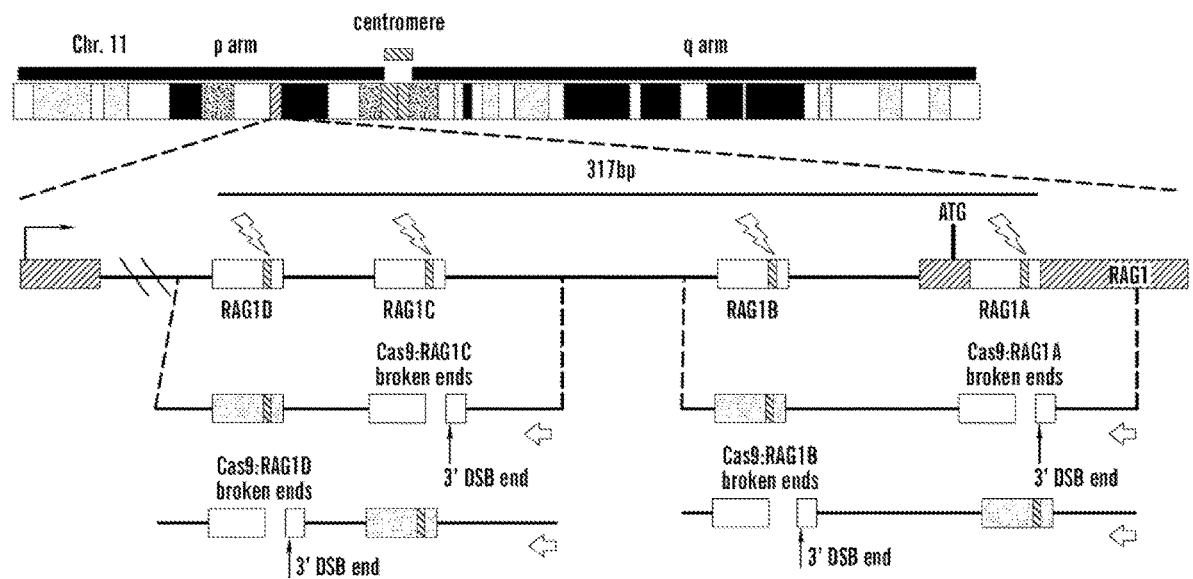
FIG. 6 depicts a schematic of the RAG1 locus indicating RAG1B, RAG1C, and RAG1D targeted sites. White arrow indicates cloning primer.
Figure 7A:
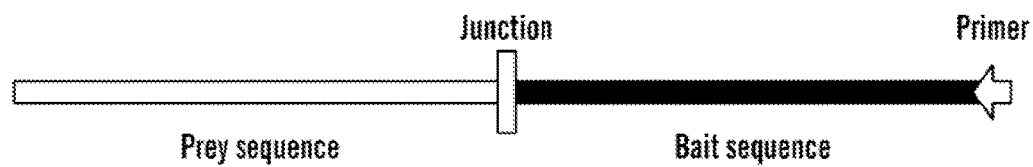
FIGS. 7A-7G depict HTGTS library junction compositions.
Figure 7B:
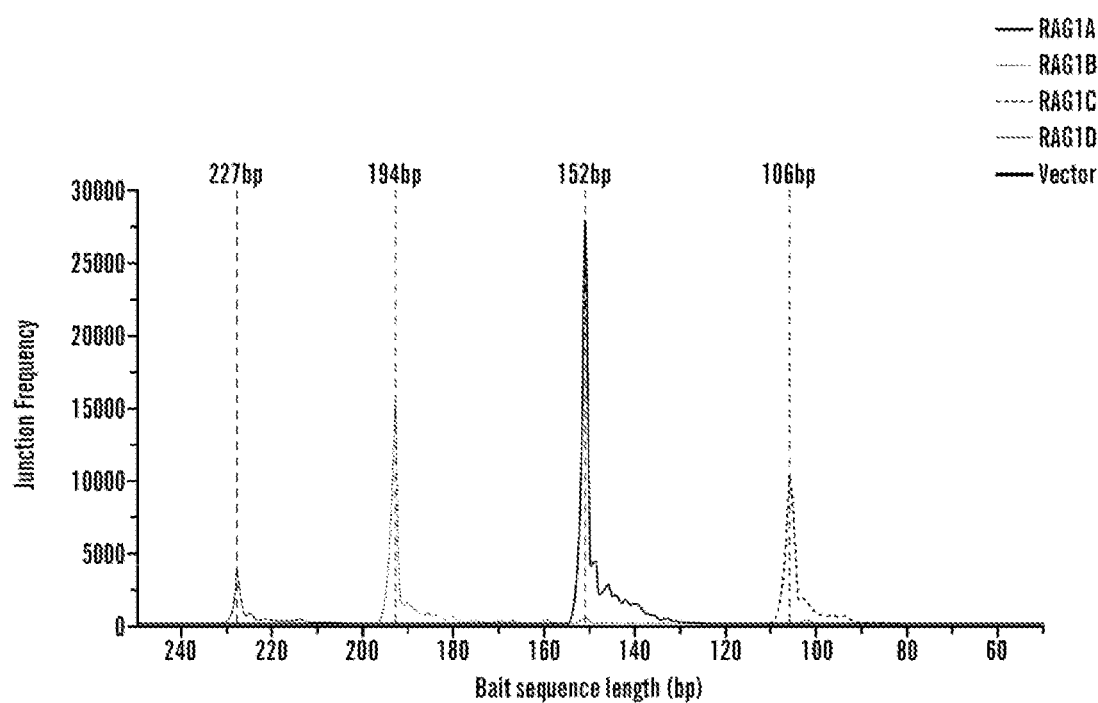
Figure 7C:
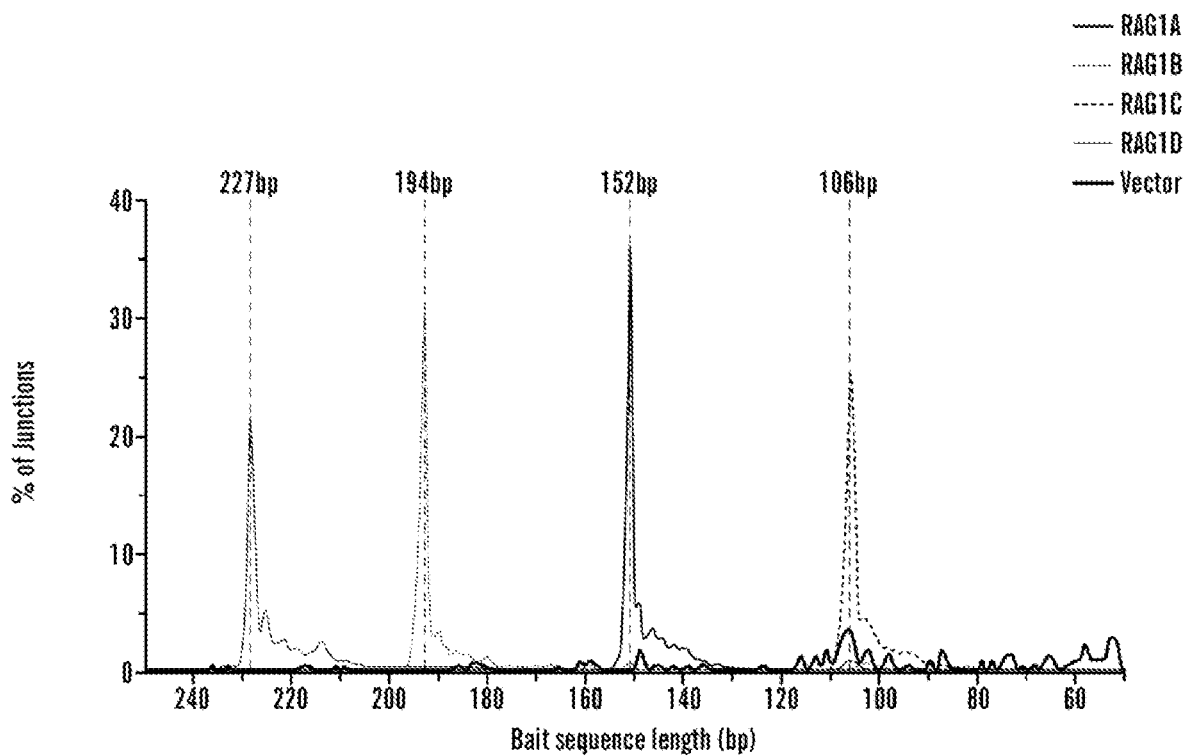
Figure 7D:
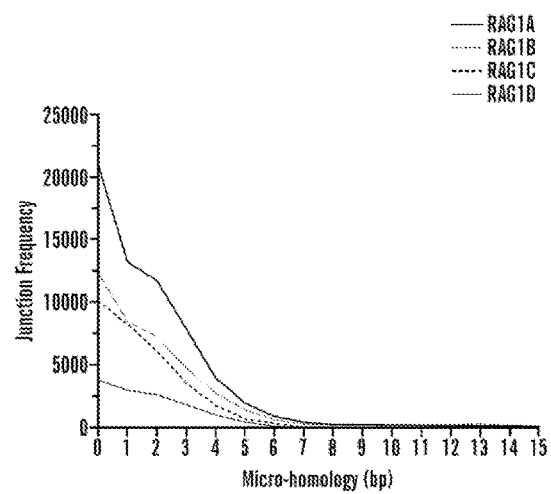
Figure 7E:
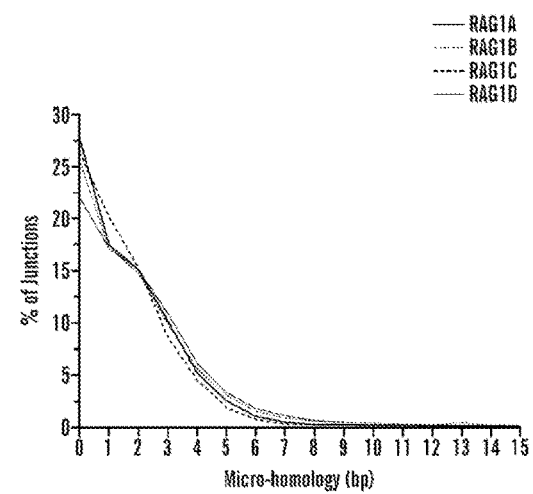
Figure 7F:
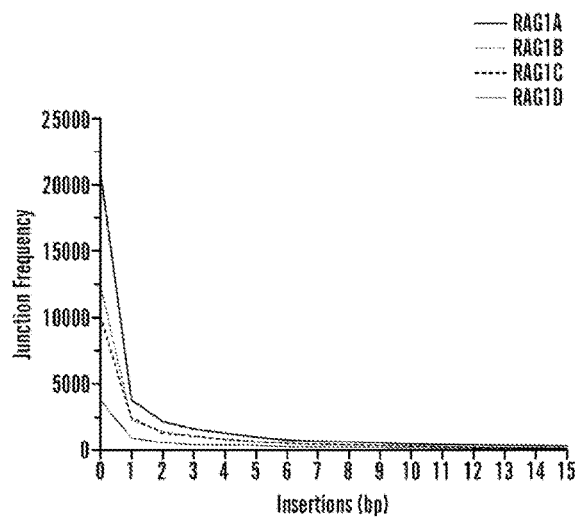
Figure 7G:
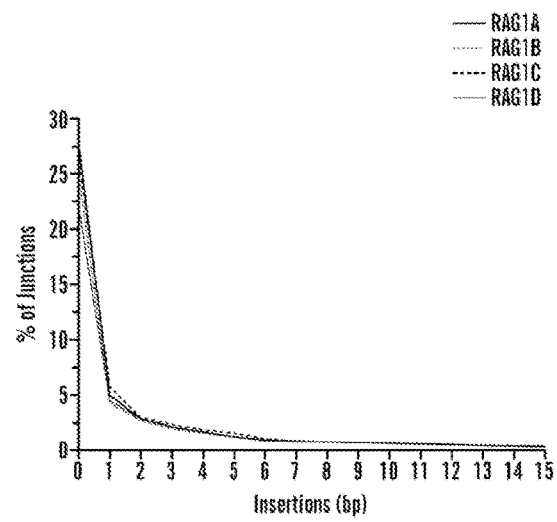

To evaluate use of HTGTS for identifying on- and off-target custom nuclease activity in human cells, HTGTS was performed using Cas9:gRNA-generated DSBs as "bait" to capture "prey" sequences genome-wide in 293T cells. For these studies, modified HTGTS approach was developed, based on linear-amplification-mediated PCR (LAM-PCR)[34] that was more robust, cost-efficient, and rapid than prior emulsion-PCR[6] HTGTS (FIG. 1A; Table 2). For initial studies, the human RAG1 gene, a proposed target for gene correction therapy[35,36], was selected. To induce RAG1 DSBs, four gRNAs that each targeted a distinct sequence within a 317 bp region spanning the beginning of RAG1 exon 2 were generated; these four Cas9:gRNA combinations are referred to herein as RAG1A, B, C, and D (FIG. 1B; FIG. 6). HTGTS was performed from the 3' DSB end (with respect to RAG1 transcriptional orientation) of a given Cas9:RAG1-generated DSBs, cloning from the A or B site via a specific primer positioned, respectively, 152 bp and 194 bp centromeric to them or from the C or D sites with a second specific primer positioned, respectively, 106 and 227 bp centromeric to them (FIG. 1B; FIG. 6). For each HTGTS library, recovered junctions fused uniquely mapped coordinates corresponding to bait sequence and genome-wide prey sequences (FIGS. 7A-7C) and were mainly direct ("blunt") or had short micro-homologies (FIGS. 7D-7G). On the bait-site side, junctions were enriched at or near the 3' DSB bait-site end with enrichment decreasing along the bait sequence length, consistent with variable resection before joining (FIGS. 7A-7C; see below).

For each set of HTGTS libraries from a particular break-site or under particular conditions, modified Circos plots of the human genome organized into individual chromosomes were used to visualize overall junction patterns and key features[37]. Translocation hotspots are indicated by lines that connect the bait-site to a given hotspot and which range in color from dark red (highest junction enrichment) to yellow (lower junction enrichment) (data not shown). HTGTS junction frequency within 5 Mb bins across all chromosomes was also denoted on the Circos plots by black bars plotted on a log scale with custom axes (see legend of FIGS. 1A-1B). For each bait site analyzed in this study, at least 3 (and usually many more) separate HTGTS libraries were generated with individual libraries ranging in size from several thousand to 80,000 independent junctions (Table 2 and detailed for each experimental figure). Independent HTGTS libraries for a given site or condition gave reproducible overall results and conclusions (FIGS. 7B-7E and Table 2 see below). HTGTS background was estimated as described[6] and found to be low (Table 2).

Figure 8D:
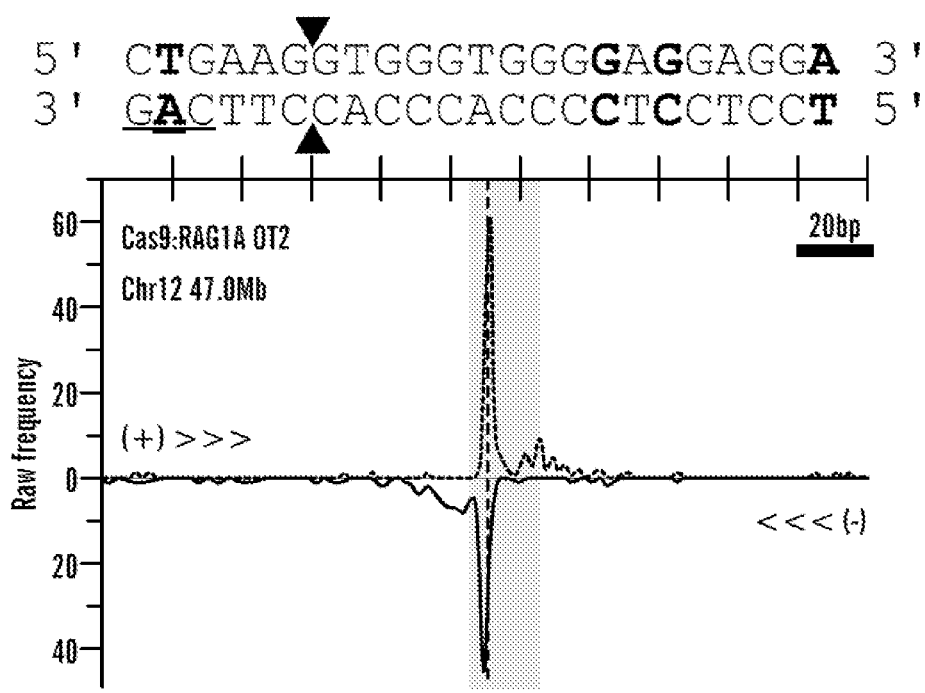
Figure 8E:
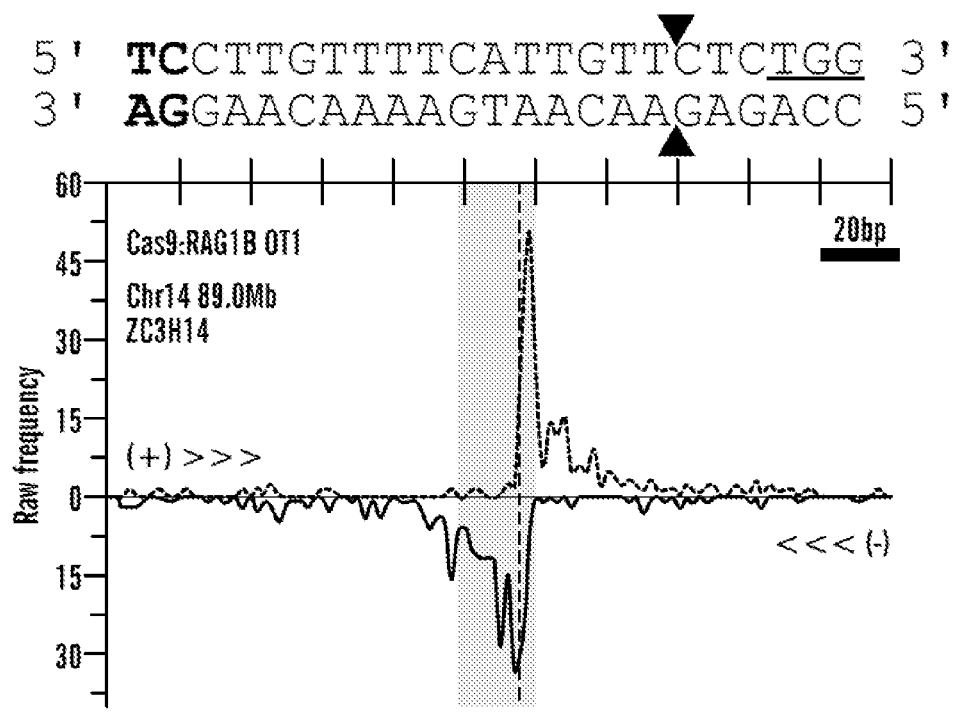

Genome-Wide Off-Target Activities of Cas9:

RAG1 gRNAs. By convention, prey sequences are joined to bait DSBs as in "+" (plus) orientation if they read from the junction in the p telomere to q telomere direction; correspondingly, junctions are in "−" (minus) orientation if in the other direction (FIG. 8A). Other than break-site junctions (see below), genome-wide Cas9:RAG1A-D HTGTS junctions occurred across the genome at similar frequencies in both orientations (data not shown). In addition, 33 highly significant, focally-enriched prey junction hotspots from RAG1A and two from RAG1B libraries were detected (Table 3). In contrast, no hotspots were detected for RAG1C and RAG1D libraries, which based on random library size normalizations would have been readily detectable if they occurred at the level of RAG1A or RAG1B OTs (data not shown). The RAG1A or RAG1B hotspot junctions showed expected characteristics for involvement of OT DSBs, peaking precisely at predicted OT break-sites based on their being highly related (with 2-7 nt mismatches) to the respective bona fide on-target sequences of these two enzymes (Table 3; FIG. 8B). All junctions were fully consistent with DSB joining, displaying approximately equal numbers of (+) and (−) orientation joins that peaked at direct prey joins (no loss of nucleotides from predicted OT break-site) and tailed off in both orientations into joins with up to 100 bp of resection (FIGS. 8C-8E). As a further test of the method, RAG1B HTGTS libraries were generated in a different human cell line (A549 lung carcinoma cells) and the same two OT hotspots were found (data not shown).

To unequivocally confirm that identified HTGTS OT sites represented DSBs and further test the ability of HTGTS to identify OT custom nuclease-generated DSBs genome-wide, HTGTS was performed using, respectively, RAG1A high level OT sites on chromosomes 12 or 19 or a RAG1A low level OT site on chromosome 7 as bait (data not shown). Strikingly, each bait produced HTGTS libraries with all characteristics expected for cloning from that specific OT RAG1A bait DSB (data not shown). Moreover, all reproducibly captured the RAG1A on-target break-site as well as the vast majority of the OT sites revealed by HTGTS from the on-target break-site. Indeed, the most highly enriched OT translocation sites recovered when bona fide RAG1A site was used as HTGTS bait were similarly highly-enriched when HTGTS was performed with each of the three OT sites as bait (FIG. 1C; Table 3). The ability of these different HTGTS bait DSBs on different chromosomes to robustly identify essentially the same set of recurrent DSBs genome-wide is consistent with prior findings on the influences of cellular heterogeneity in 3D genome organization on the translocation landscape[5]. Likewise, the major difference in frequency of translocations captured by these 4 different RAG1A HTGTS baits was the enriched recovery of prey DSB junctions that fell onto the same chromosome as the particular bait-site (Table 3), as also predicted[4,5]. Below, additional examples of such phenomena are presented in the context of exploiting them to further facilitate HTGTS assays for custom nuclease OT activity.

Break-Site Junctions Reveal a Common Type of Custom Nuclease Translocation Hotspot.

Figure 2A:
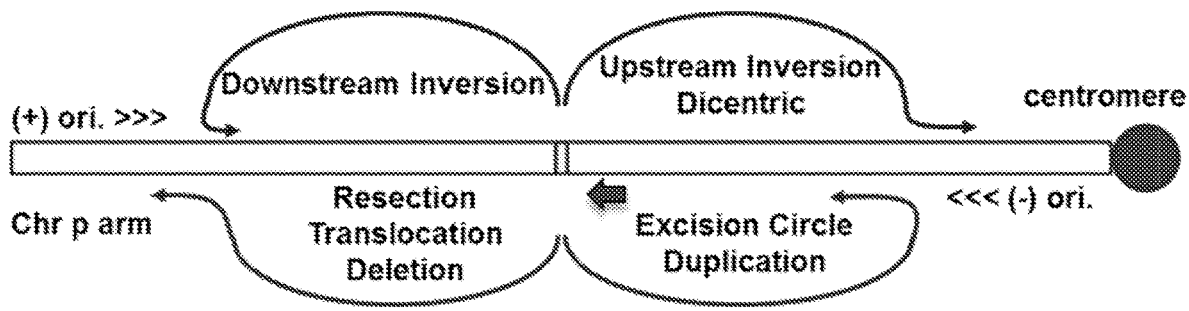
FIGS. 2A-2D demonstrate distinct prey break-site junction joining to homologous chromosomes.
Figure 2B:
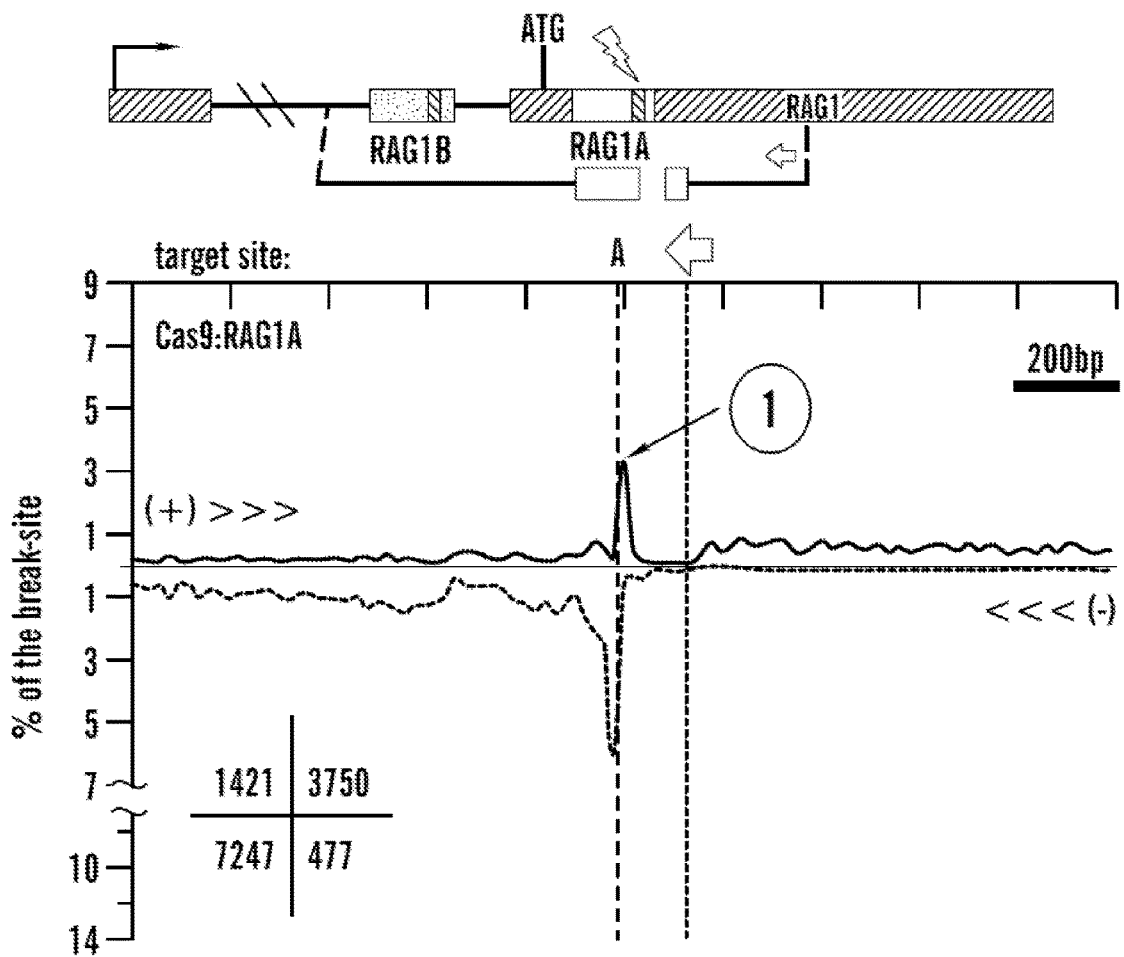
Figure 2C:
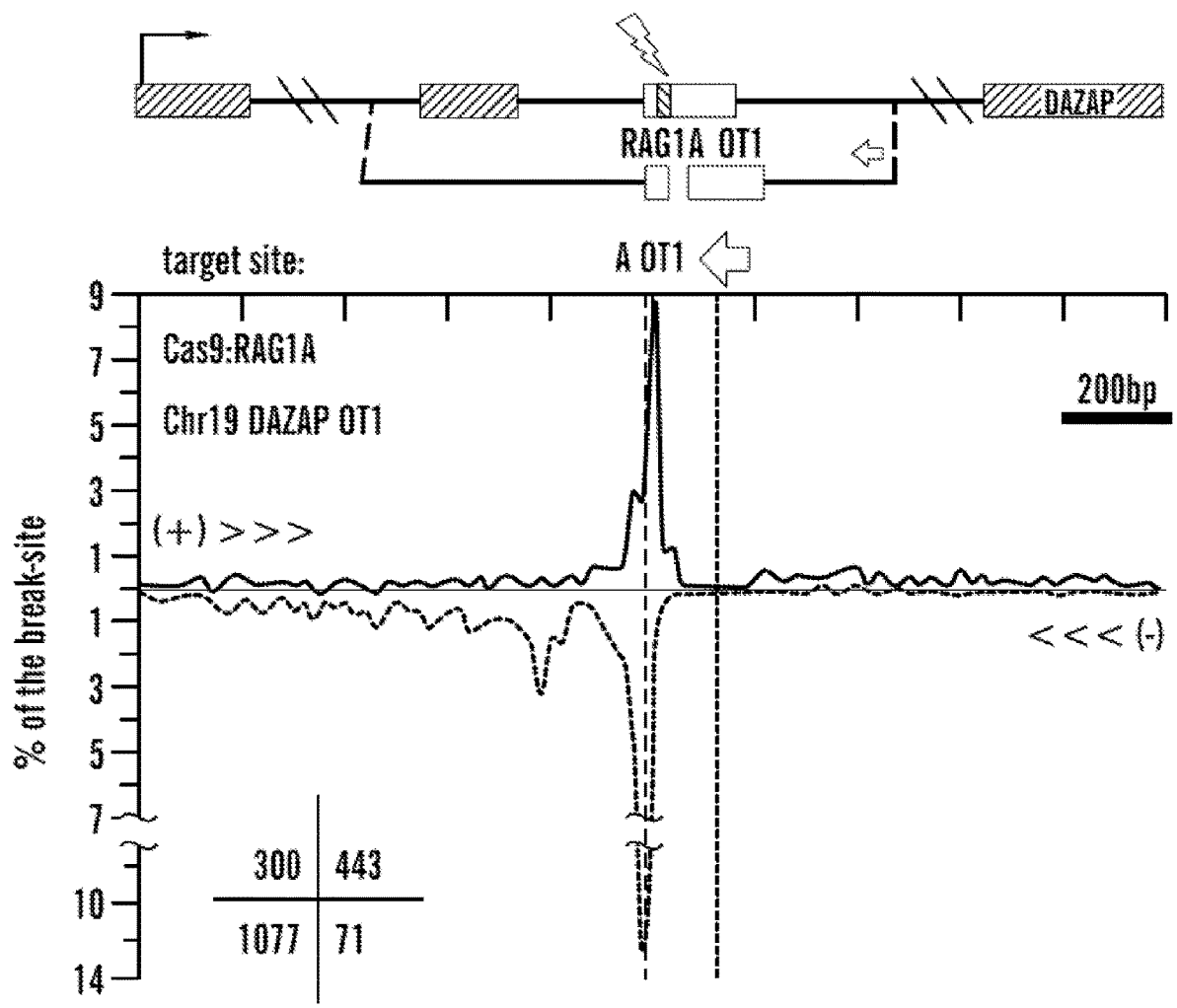
Figure 2D:
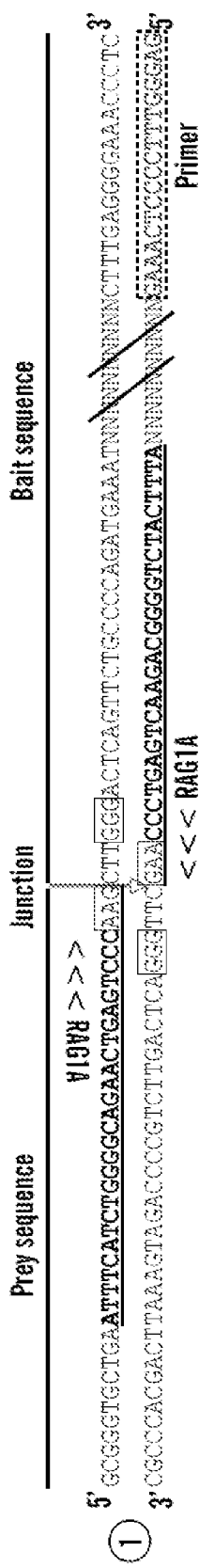
Figure 9A:
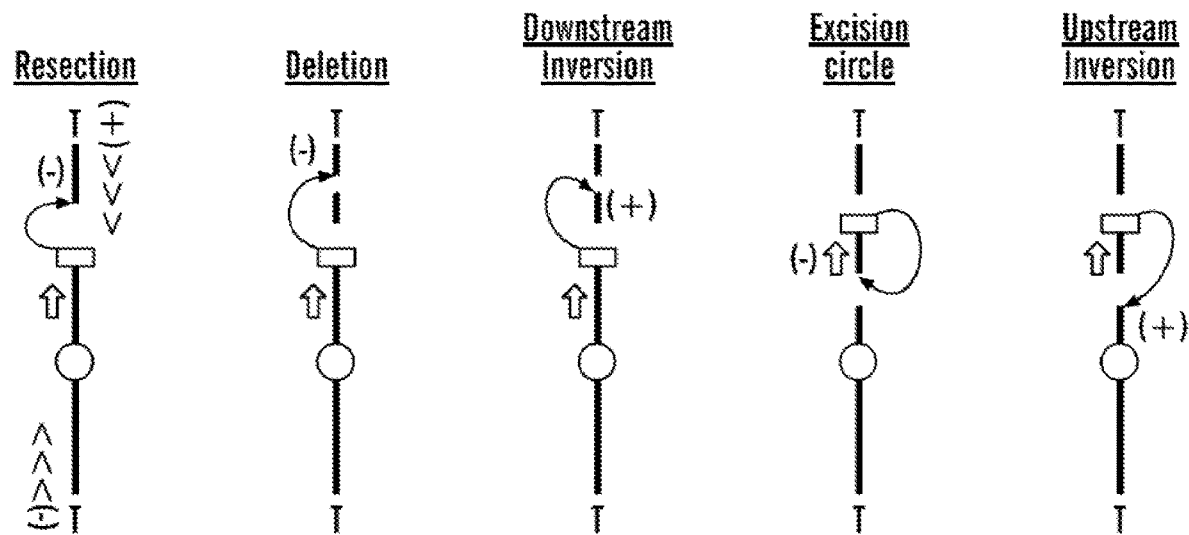
FIGS. 9A-9E demonstrate prey joining outcomes at the bait break-site.
Figure 9B:
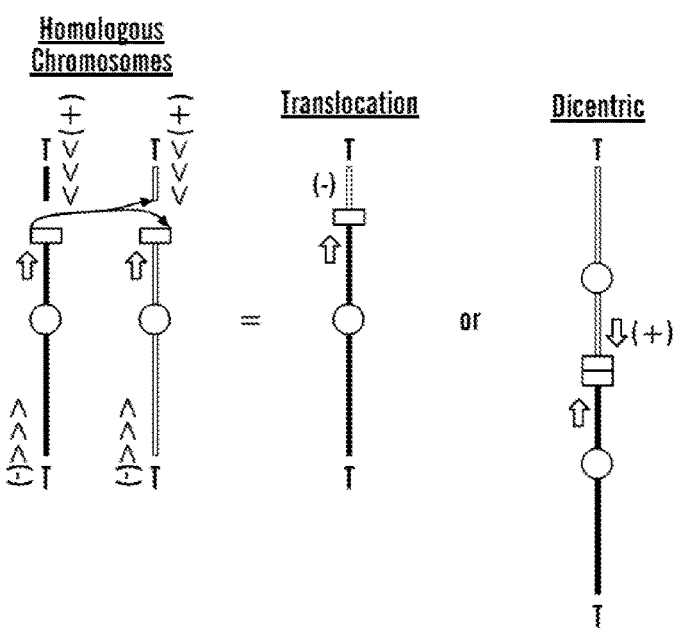
Figure 9C:
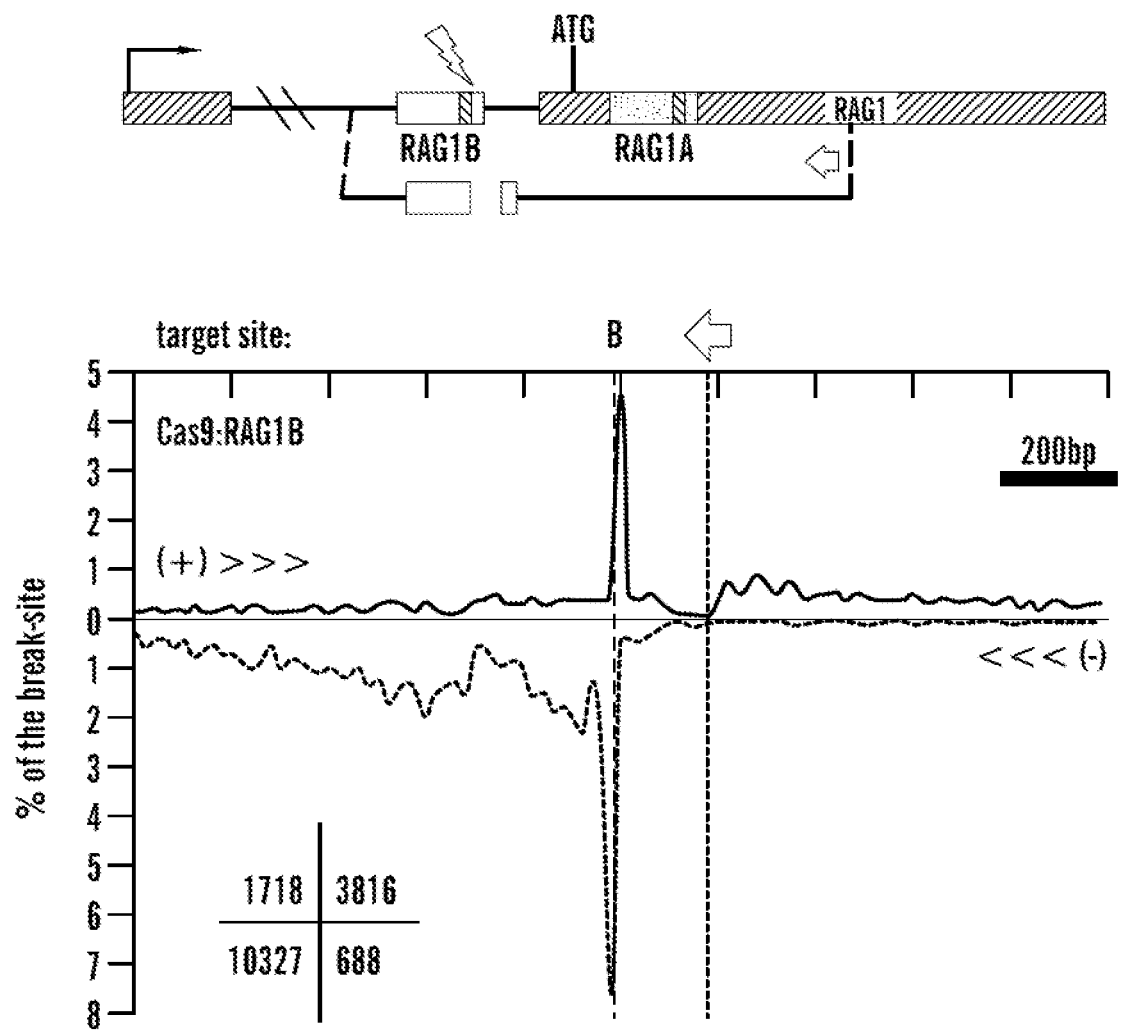
Figure 9D:
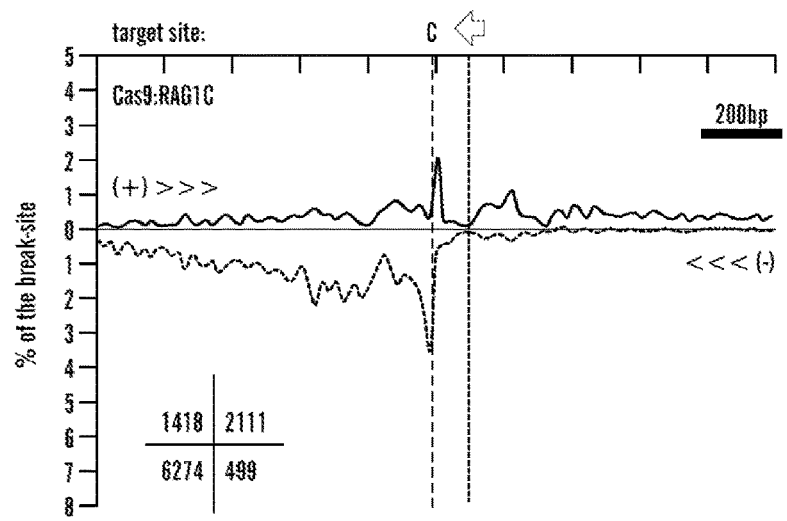
Figure 9E:
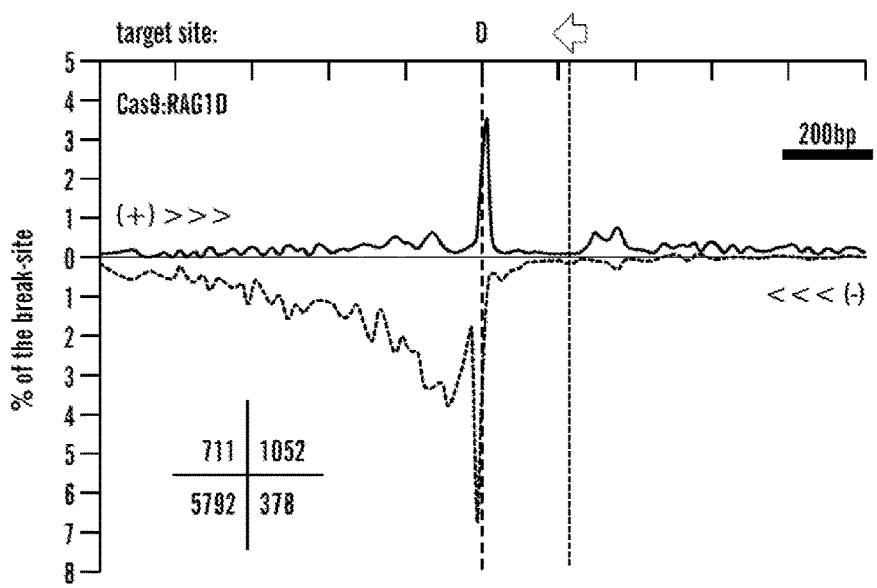

HTGTS junctions are highly-enriched in regions immediately around the break-site due to DSB rejoining following resection, as well as various types of break-site proximal translocations (deletions, inversions, and excision circles)[6] that are enhanced due to spatial proximity[4,5] (FIG. 2A; FIG. 9A). Custom endonucleases target both homologous chromosomes in diploid cells and primer sequences for detecting junctions from bait DSBs are present on both alleles (FIG. 9B). Thus, most contributions from each of the homologous chromosome bait 3' DSBs to break-site or genome-wide junctions cannot be distinguished. However, for the Cas9:RAG1A-D and RAG1A OT bait break-sites (and others, see below), a high density of prey junctions is found at or very close to the break-site in the (+) orientation quadrant that would correspond to inversional translocations that in cells would generate dicentric chromosomes (FIGS. 2B-2C; FIGS. 9C-9E). Nucleotide sequences of such junctions confirms head-to-head inversional joins of the two break-sites, including perfect direct joins of the two Cas9 3' DSB ends (FIG. 2D), with additional junctions in this inversion/dicentric quadrant extending several 100 bp or more upstream likely due to "prey" sequence resection.

Suppression of OT Activity Via Cas9 Paired Nickase-Generated Bait DSBs.

Figure 3A:
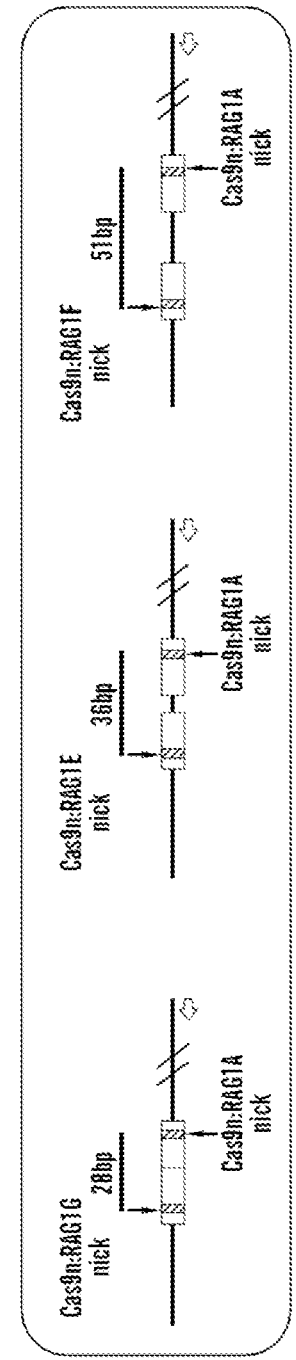
FIGS. 3A-3C demonstrate Cas9n paired nick DSB HTGTS libraries.
Figure 3B:
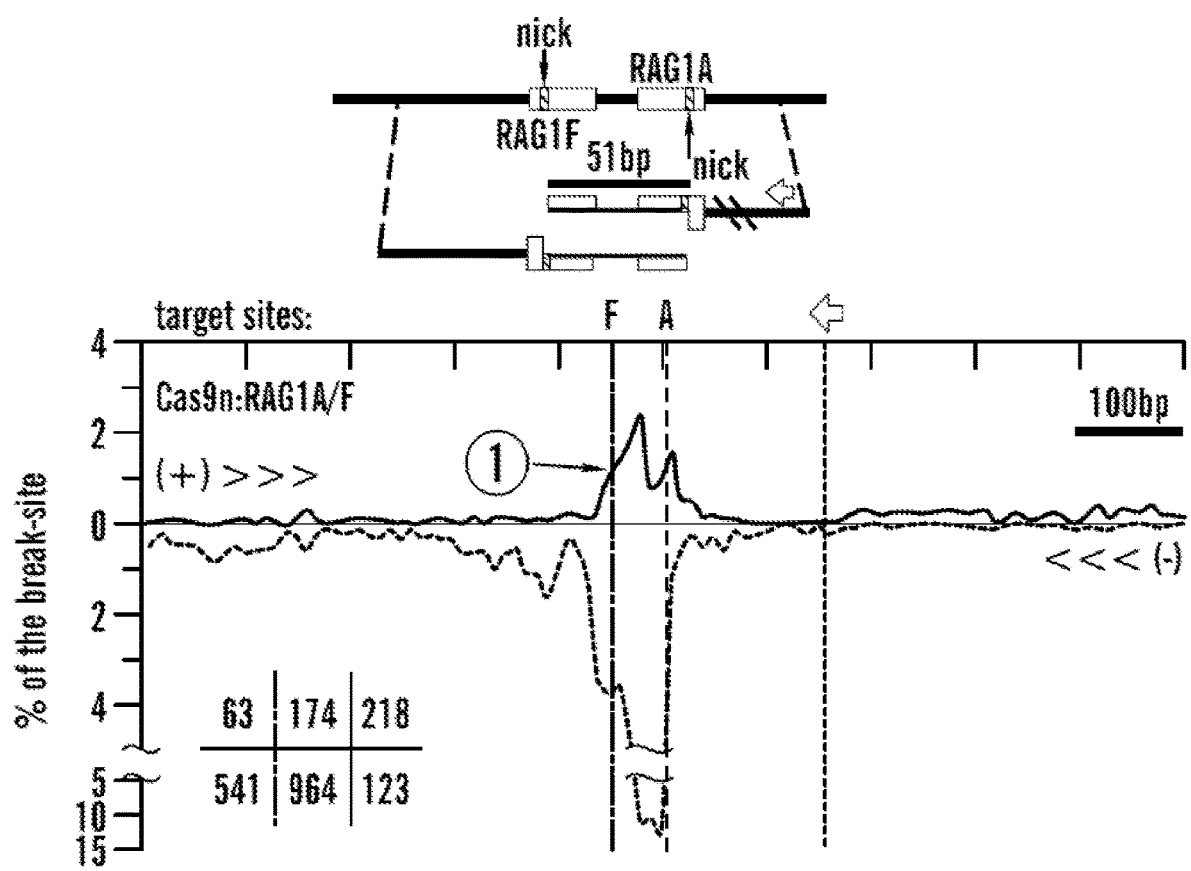
Figure 3C:
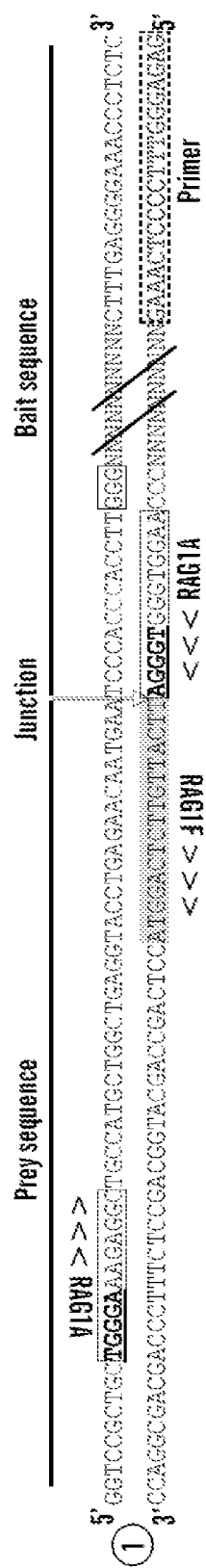
Figure 10A:
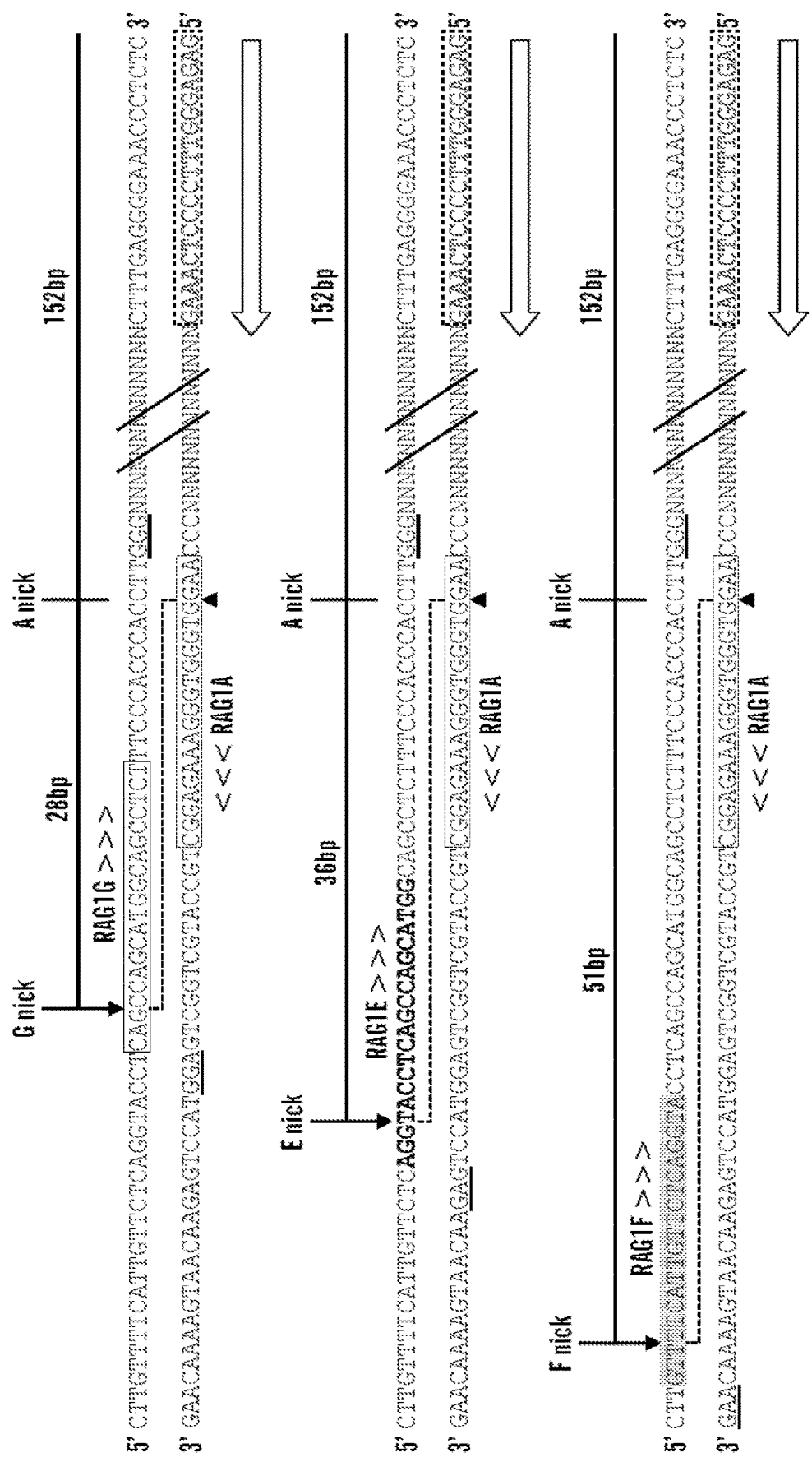
FIGS. 10A-10C demonstrate Cas9n:RAG1A/G, A/E, A/F paired nickase targets.
Figure 10B:
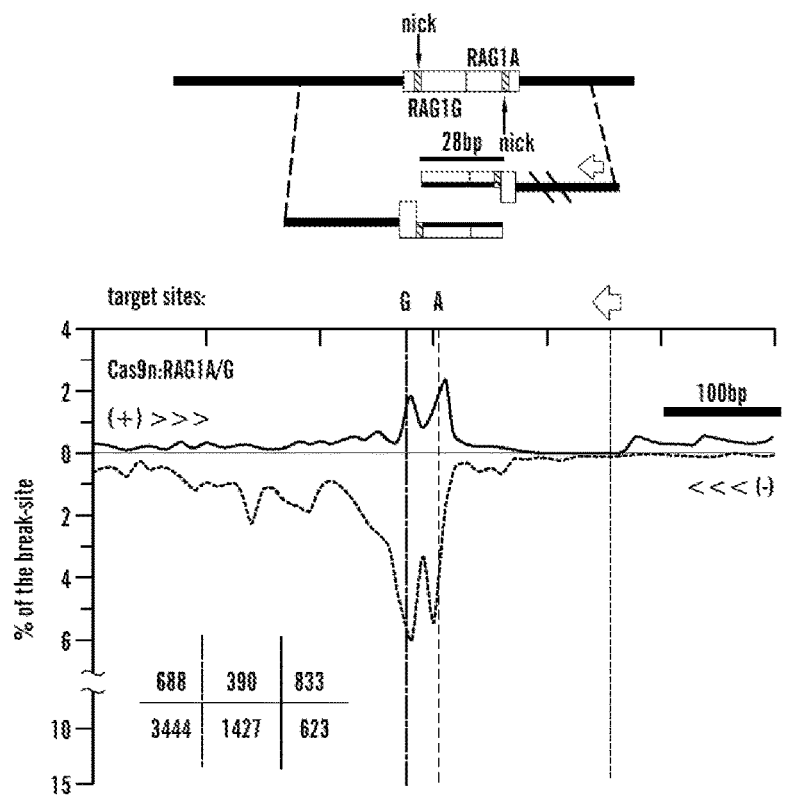
Figure 10C:
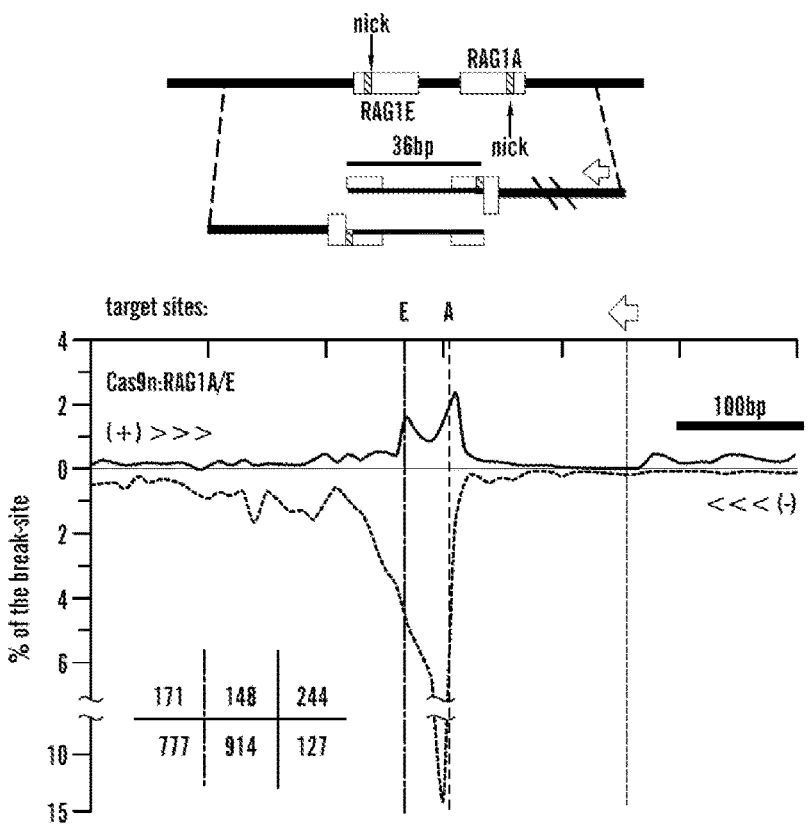
Figure 11A:
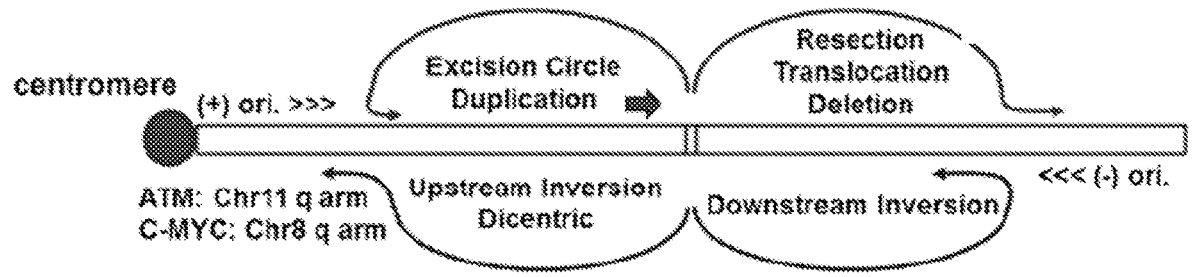
Figure 11B:
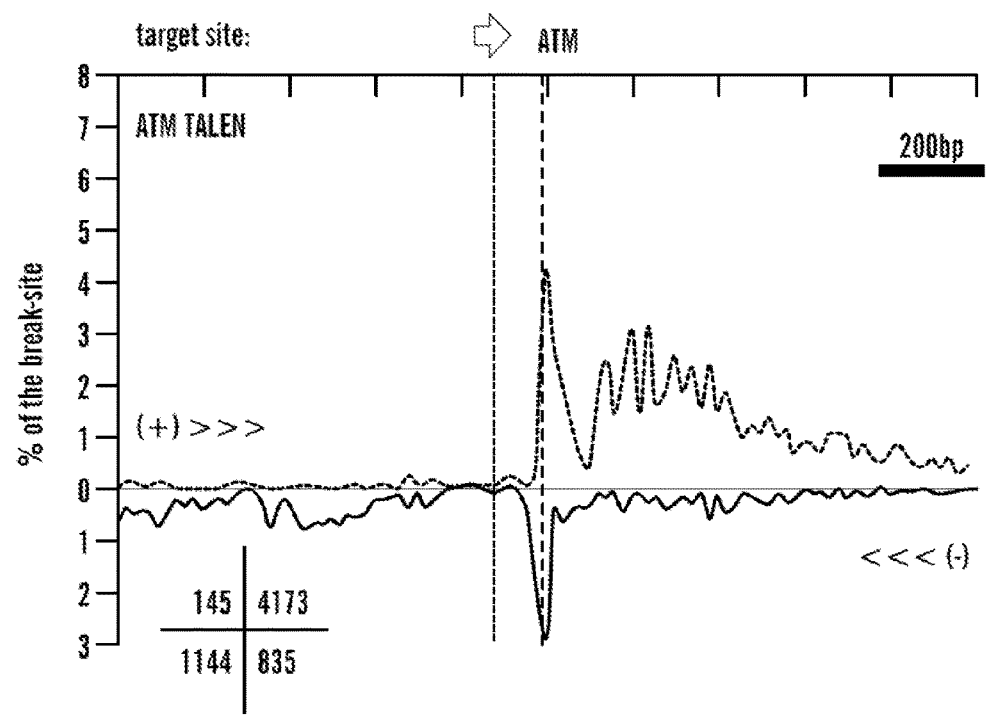
Figure 11C:
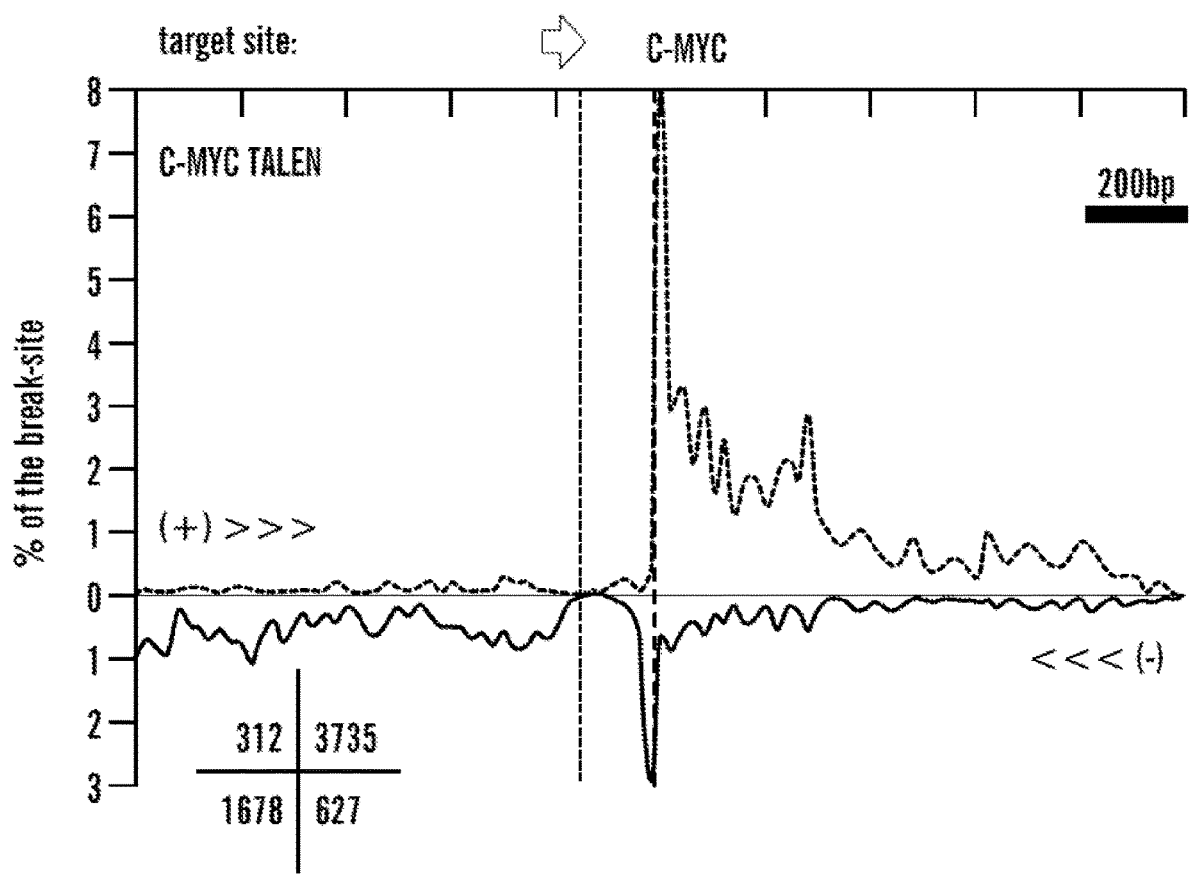

One approach to reduce Cas9:gRNA OT activity is to use Cas9 D1 0A mutation (Cas9n) which renders the endonuclease into a nickase that generates DSBs from off-set paired Cas9n:gRNA combinations with variable length 5' overhangs[38,39]. To test this approach via HTGTS, the off-target-prone RAG1A gRNA was paired with nearby downstream gRNA targets (RAG1G, E, and F), which would result in 5' overhang DSBs of 28 nt, 36 nt, and 51 nt, respectively, when used with Cas9n (FIG. 3A; FIG. 10A). Cas9n:RAG1A/G, A/E, or A/F HTGTS libraries had similar genome-wide characteristics to standard Cas9:RAG1A HTGTS libraries except that they lacked hotspots (data not shown); although occasional junctions at RAG1A OT sites were found upon inspection (Table 3). Prey junctions around the break-site also revealed expected resection and translocation patterns (FIG. 3B; FIGS. 10B, 10C), including recurrent "dicentric" (+) orientation junctions between break-sites on the two homologous chromosomes that encompassed the two off-set nick sites (FIGS. 3B-3C; FIGS. 10B-10C).

TALEN Bait HTGTS Libraries.

To test ability of HTGTS to reveal TALEN OT DSBs, two previously described TALENs[40] that, respectively, cleave the C-MYC gene on chromosome 8 or ATM gene on chromosome 11 were employed (data not shown). The ATM and C-MYC TALEN bait HTGTS libraries showed similar patterns of break-site proximal junctions as those generated with Cas9:gRNAs, including readily detectable dicentric orientation joins between the TALEN break-sites on homologous chromosomes (FIG. 11A-11D). In addition, a large number OT sites were detected for both the ATM (522 OT sites) and C-MYC (384 OT sites) TALENs of which all were lower frequency than the most robust Cas9:RAG1A OTs (FIGS. 11A-11D). Notably, many highly-enriched TALEN OTs were pseudo-palindromic sequences that corresponded to variants of the recognition site of a single TALEN monomer (FIGS. 11A-11D see Discussion). Both ATM and C-MYC TALEN bait libraries also reproducibly displayed a high enrichment of prey junctions along their respective break-site chromosomes (data not shown; see below).

Use of the RAG1B Break-Site to Detect On-Target, Off-Target, and Non-Specific DSBs.

Figure 13A:
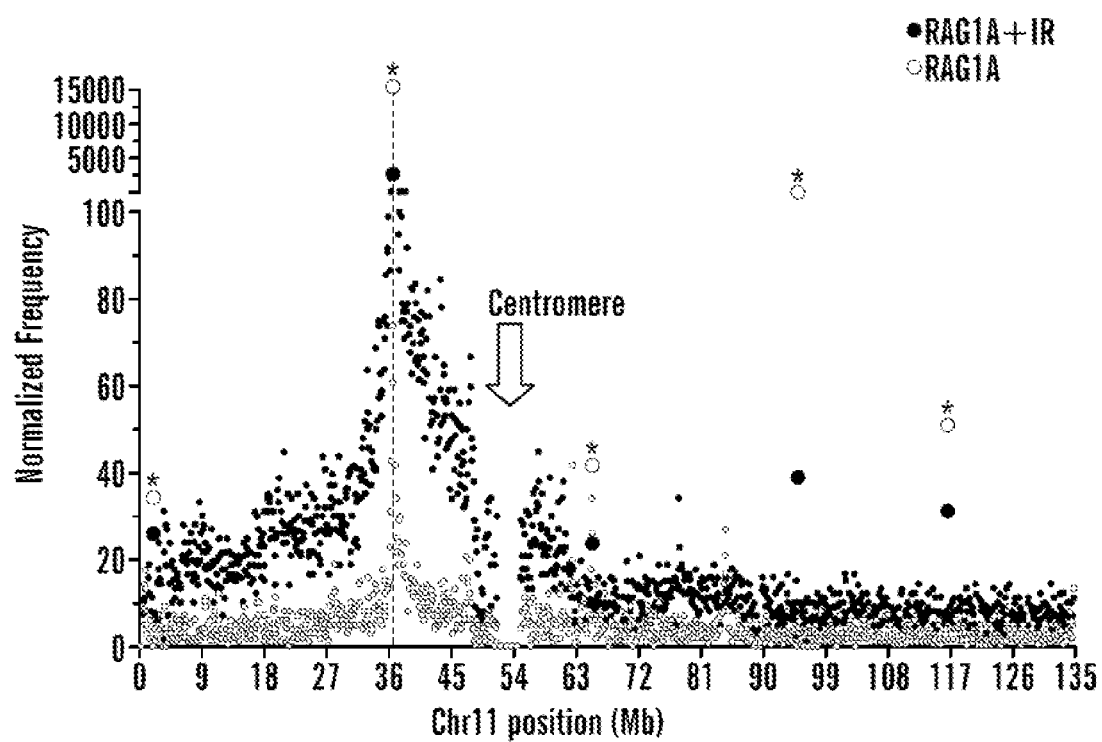
FIGS. 13A-13B demonstrate IR-treatment increases break-site chromosome junction enrichment.
Figure 13B:
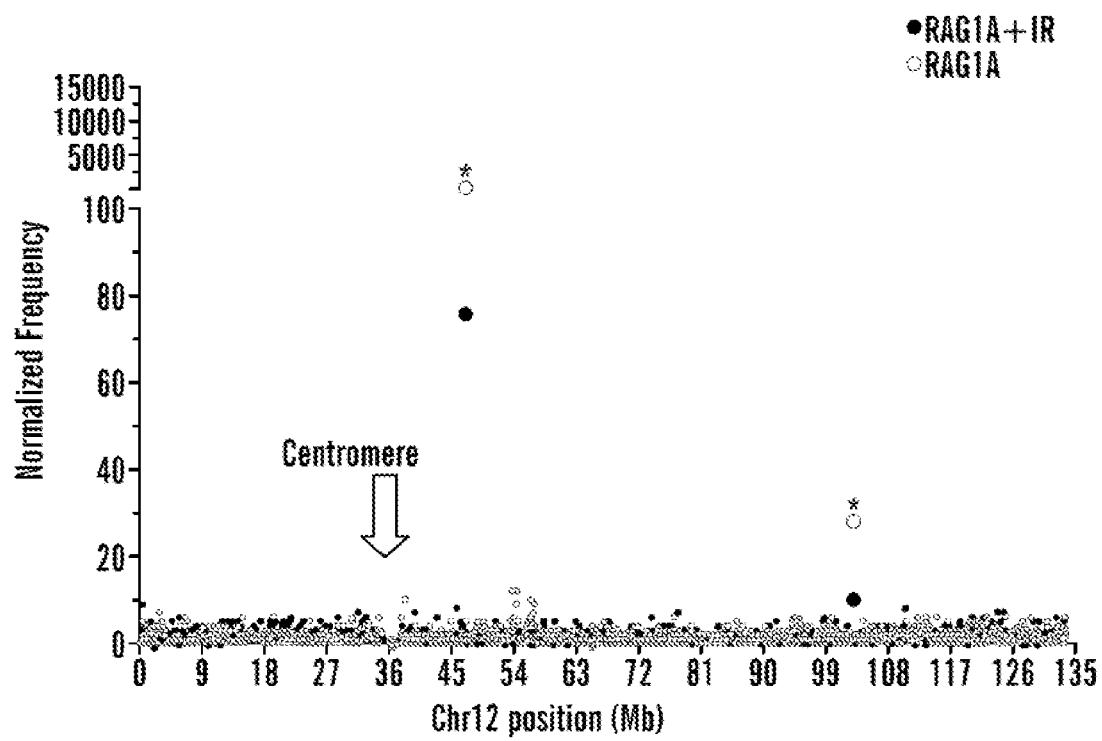

As illustrated by HTGTS from RAG1A OT sites (FIGS. 1A-1C), a fixed bait DSB from one custom nuclease can detect both on- and off-target DSBs of a second custom nuclease. To test this approach, RAG1B was co-expressed with I-SceI in 293T cells and the RAG1B bait-site used to capture I-SceI OTs. Indeed, beyond the two expected RAG1B OTs, 9 I-SceI OTs were identified with 2-4 nt mismatches from the consensus (FIG. 4A; Table 6). I-SceI OTs displayed expected characteristics of such HTGTS prey DSBs (FIGS. 12A, 12B) and were confirmed by in vitro I-SceI digestion (FIG. 12C). To test ability of the RAG1B HTGTS assay to detect random non-specific DSBs, RAG1B was introduced into 293T cells for 24 hours, then the cells were treated with 7Gy of IR (to introduce approximately 140 DSBs per cell[41]), further cultured for 24 hours and then HTGTS was performed from the RAG1B bait-site. As predicted[5], HTGTS junctions were greatly enriched across the entire RAG1B bait-site chromosome 11 with little or no increase on other chromosomes and diminished recovery of break-site and recurrent OT junctions (data not shown). Furthermore, similar IR-treatment results were obtained with RAG1A break-site bait HTGTS libraries for the on-target site on chromosome 11 and also with two tested RAG1A OT sites on chromosomes 12 and 19 (FIGS. 13A-13B). Thus, subsequent to induction of non-specific DSBs genome-wide, all chromosomes containing on-target or OT sites become hotspot regions for the targeted DSBs they harbor.

Figure 4A:
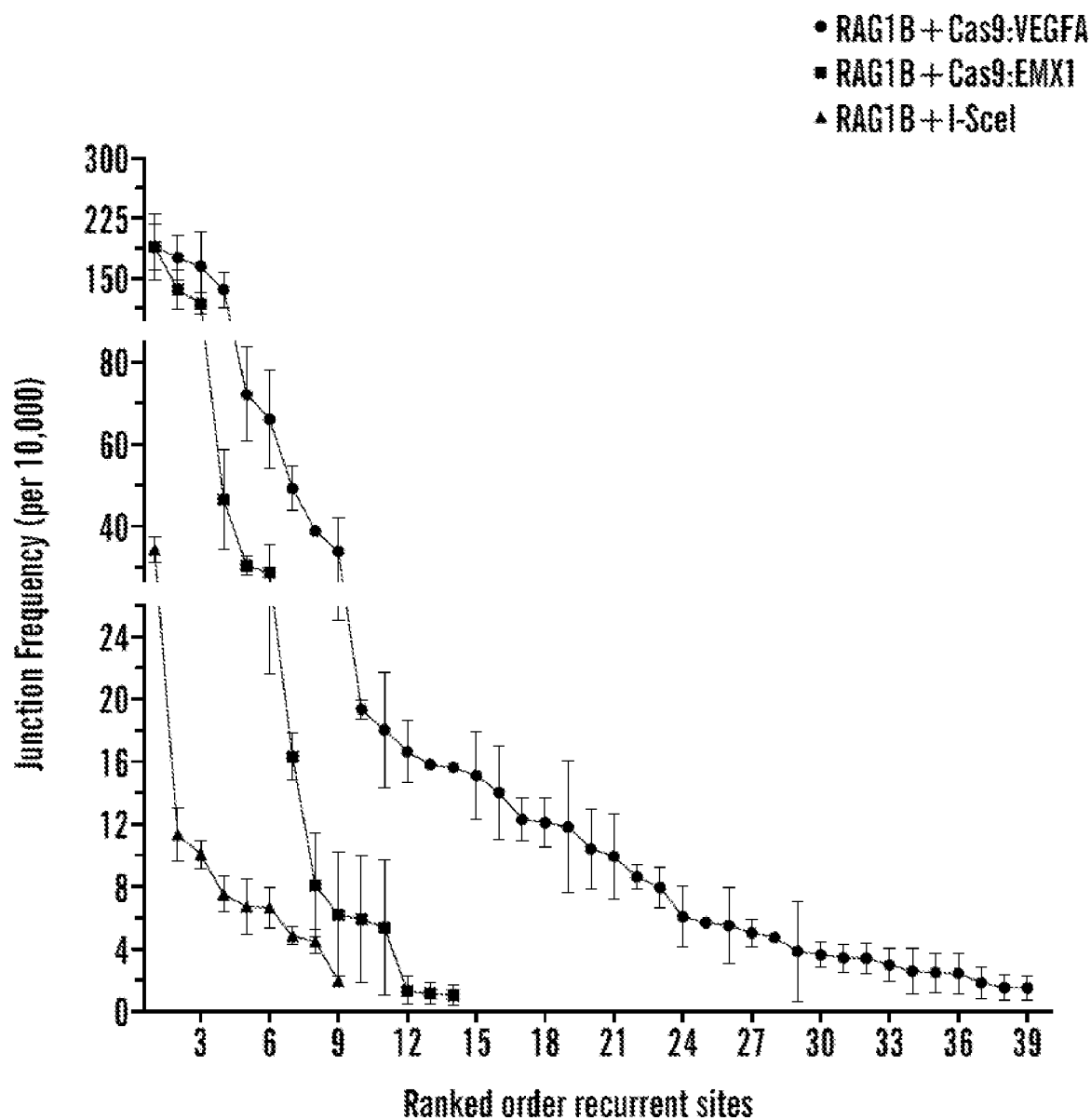
FIGS. 4A-4B demonstrate identification of OT sites from other nucleases using the fixed Cas9:RAG1B bait.
Figure 4B:
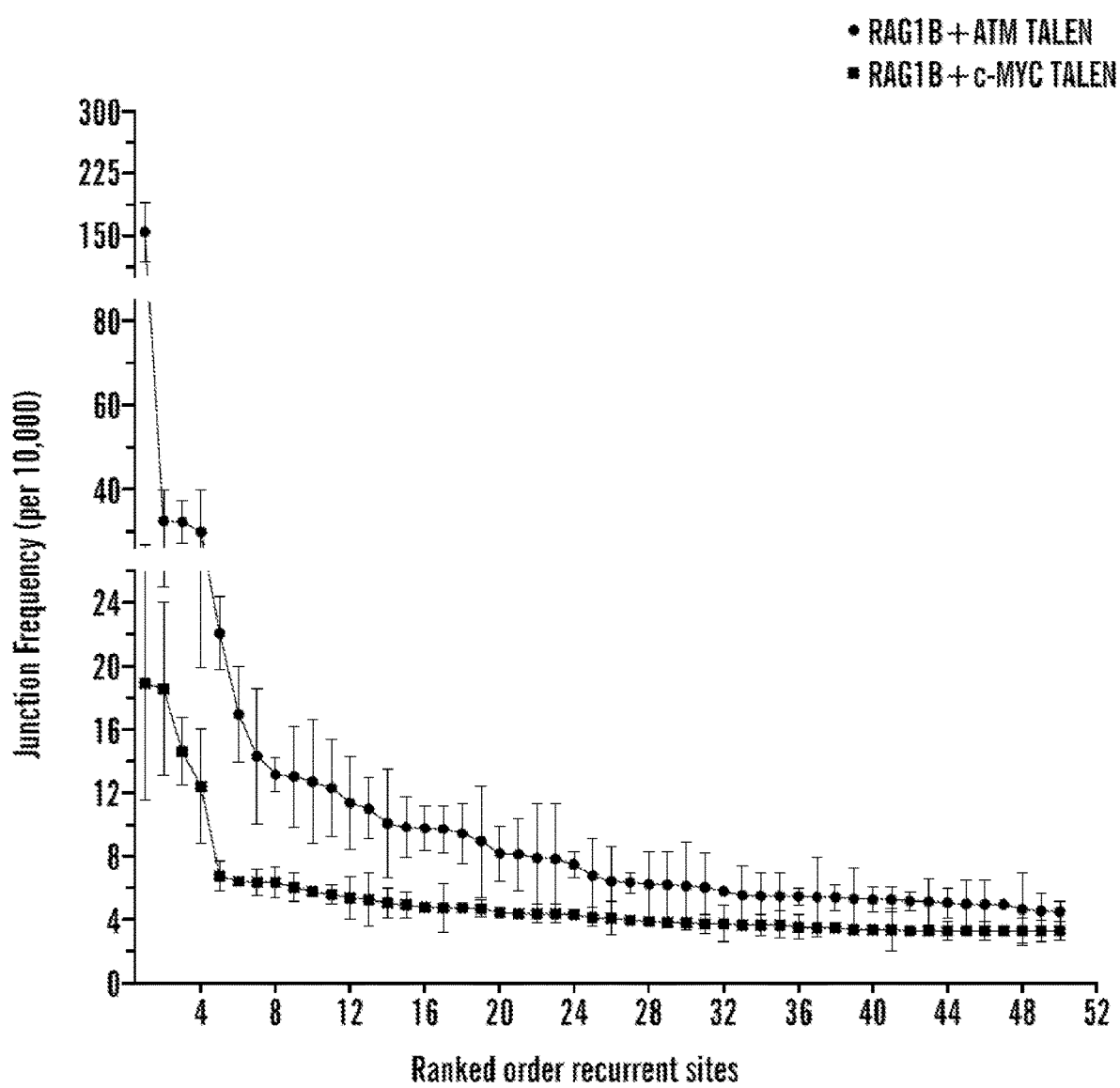
Figures 14A, 14B:
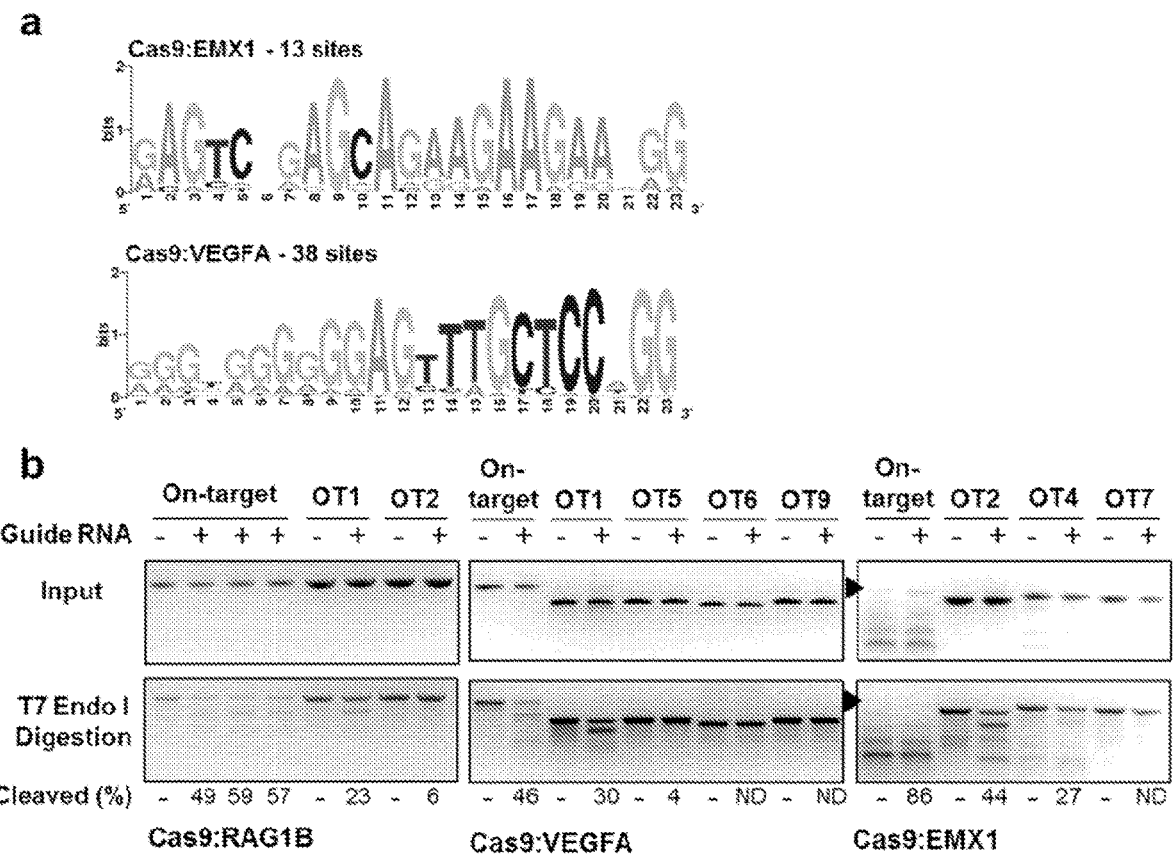
FIGS. 14A-14B demonstrate sequence analysis and in vitro cleavage assay for Cas9:EMX1 and Cas9:VEGFA.
Figure 15A:
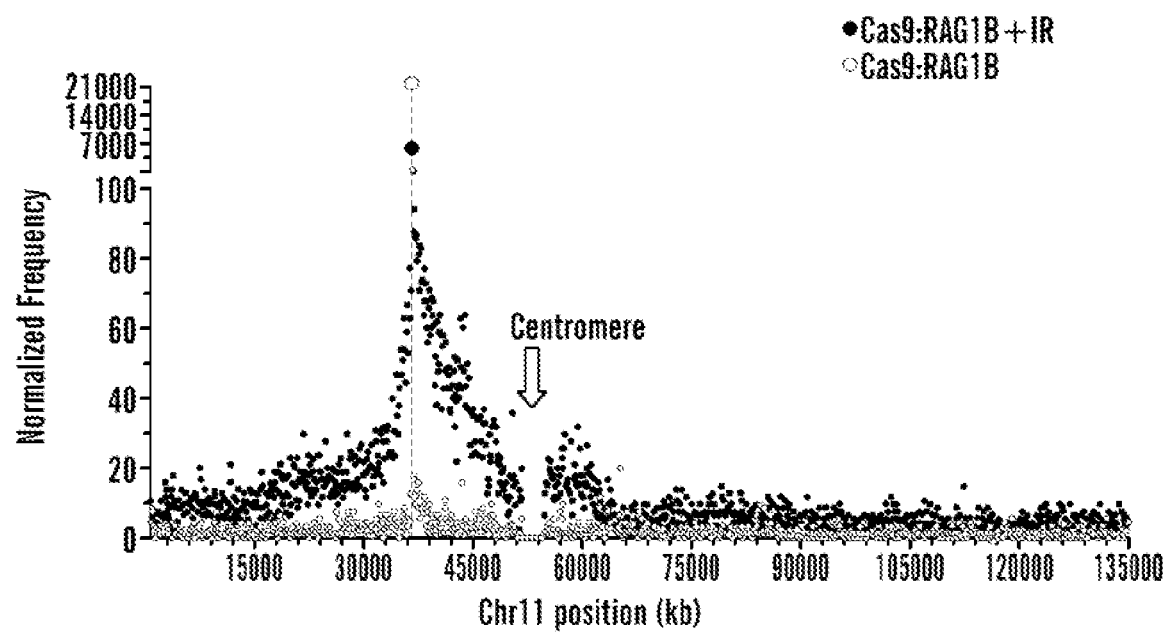
FIGS. 15A-15D demonstrate Cas9:RAG1B bait non-specific DSB activity detection assays.
Figure 15B:
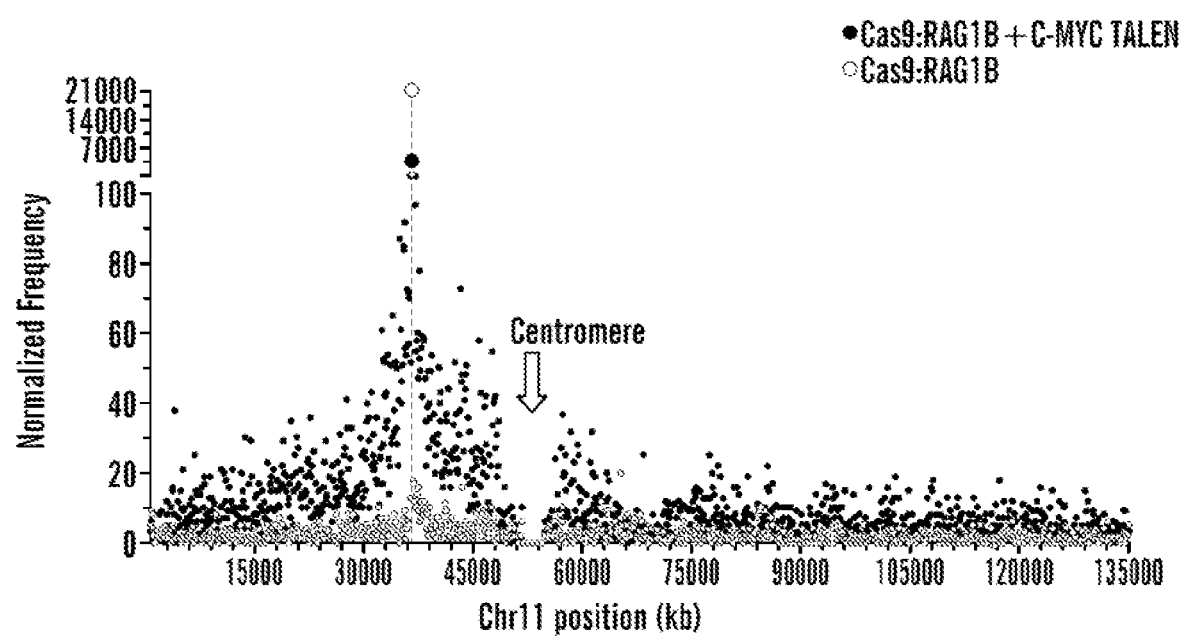
Figure 15C:
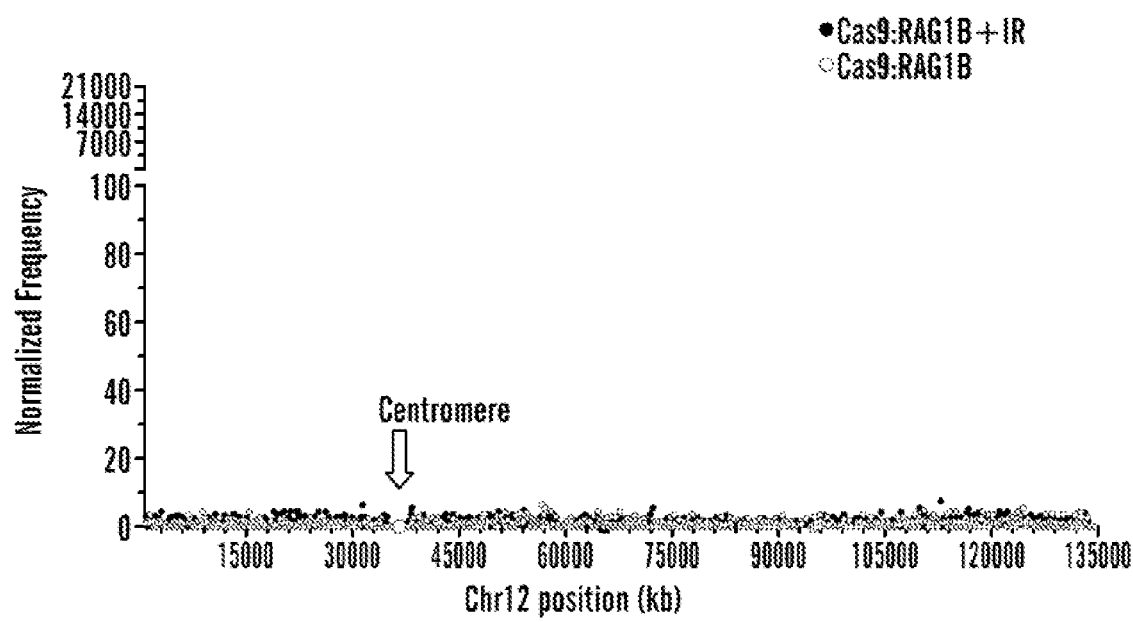
Figure 15D:
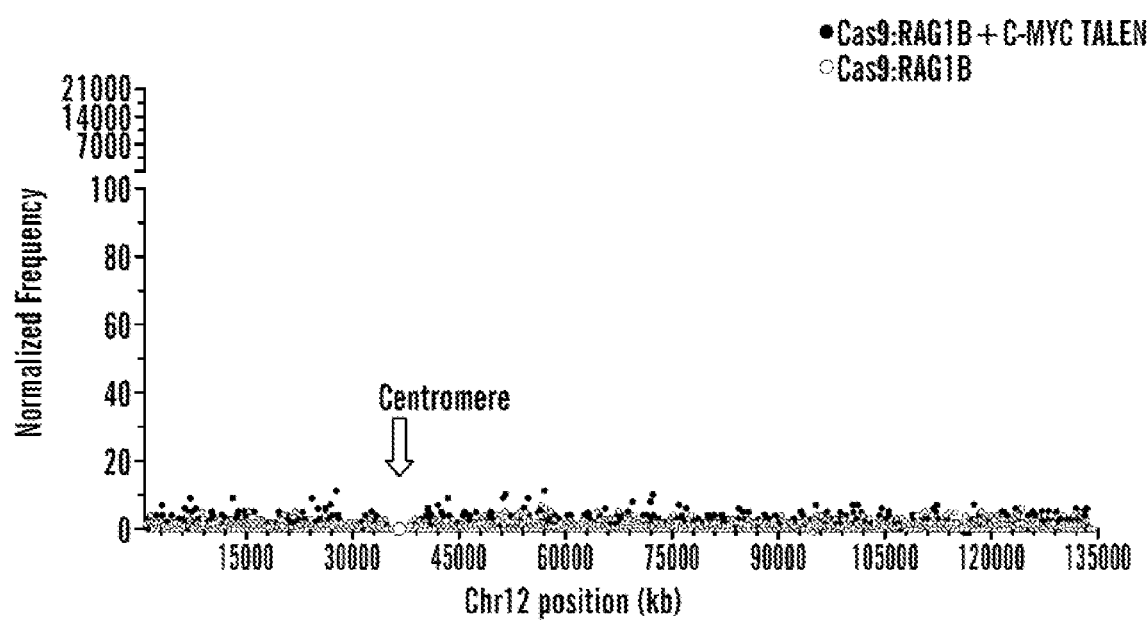

Previously described Cas9 EMX1 and VEGFA gRNAs[30] were examined using the Cas9:RAG1B co-expression HTGTS assay. For both EMX1 and VEGFA gRNA targets, RAG1B bait HTGTS identified, respectively, the single and the two OT sites previously documented by the established T7 endonuclease I (T7EI) cleavage assay[30], and also identified, respectively, an additional 12 and 34 novel OT sites (FIG. 4A). Notably, all HTGTS-detected Cas9 EMX1 or VEGFA OT sequences that were identified were related to the corresponding on-target sites and the majority were previously predicted but not confirmed (FIG. 14A; Table 7)[27,30,31,40,42]. When tested by the T7EI assay, the two on-target break-sites and three previously described OTs were detected; but only one of four tested OTs revealed by HTGTS. Consistent with these findings, a prior T7EI assay study failed to detect 24 previously predicted Cas9 EMX1 or VEGFA gRNA OT sites[30] that were clearly identified by the present unbiased HTGTS assay. The RAG1B co-expression HTGTS assays also identified a large number of ATM and C-MYC TALEN OTs including all of the approximately 100 most dominant OTs detected by HTGTS using the individual TALEN break-sites as bait (FIG. 4B; Tables 4 and 5). Cas9 EMX1 and VEGFA gRNAs did not contribute markedly to non-specific DSB background (increased junctions on bait containing chromosome) when used at the assayed concentration (data not shown; see discussion). However, the ATM and C-MYC TALENs each generated substantially increased non-specific DSB activity in RAG1B bait libraries as evidenced by substantially increased HTGTS junctions along the RAG1B break-site chromosome, reminiscent of that observed in the IR-treated RAG1B bait libraries (FIGS. 15A-15D).

Assessing Optimal Custom Nuclease Activity.

Figure 5A:
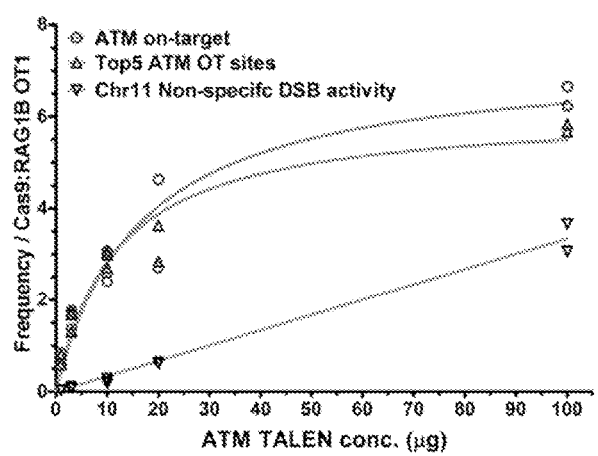
FIGS. 5A-5B demonstrate nuclease titration to measure on-target/background efficiency.
Figure 5B:
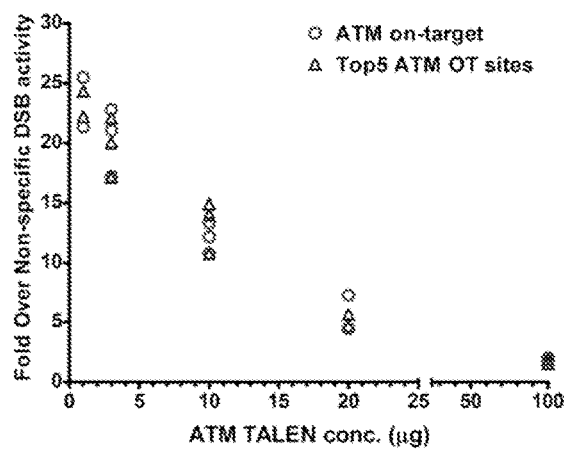
Figure 16:
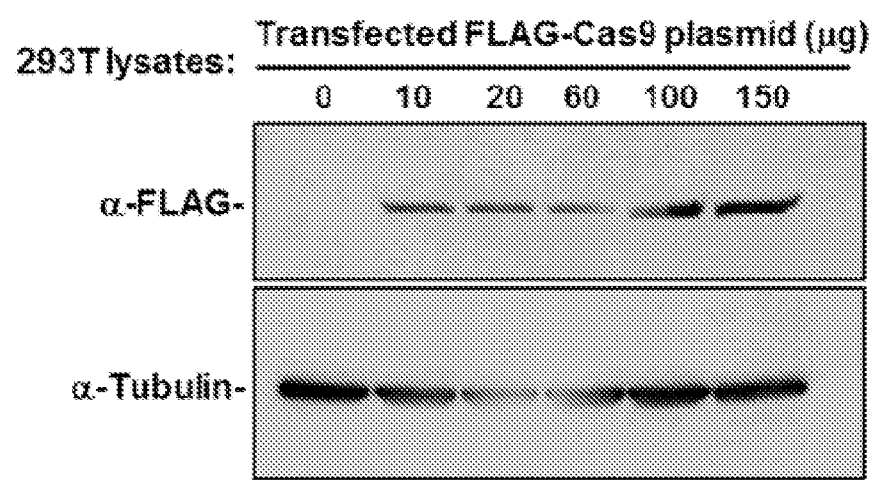
FIG. 16 depicts Western analysis probing for FLAG-tagged Cas9 and a loading control Tubulin from 293T extracts transfected with increased amounts of Cas9: RAG1B plasmid DNA.

Increasing levels of the ATM TALEN over a 10-fold range revealed additional lower level OT sites along and suggested an apparent increase in non-specific DSBs (data not shown). Assaying a single nuclease over increasing levels is not optimal for titrating specific versus non-specific activities, since both bait and prey breaks are influenced. Therefore, the RAG1B bait assay was employed to determine whether HTGTS could help assess optimal ATM TALEN nuclease levels for on-target versus OT or non-specific DSB activities. Frequencies of recovered ATM TALEN on-target versus the top 5 ATM OTs from RAG1B bait remained constant over a 100-fold tested range of ATM TALEN (FIG. 5A). As both on-target and OT sites occurred at similar relative levels even at the lowest ATM TALEN concentrations, where on-target activity is low, relative OT activities roughly corresponded to on-target activity (FIGS. 5A-5B). In contrast, the relative level of on-target and OT activity to non-specific DSB activity decreased as ATM TALEN concentration increased over the 100-fold range tested, indicating that HTGTS can be used to optimize relative levels of on-target versus non-specific DSB-inducing activity of the ATM TALEN enzyme (FIG. 5B). Increasing the amount of RAG1B Cas9:gRNA over an approximately 10-fold range did not reveal additional OT sites or increased the potentially very low level of non-specific DSB background (FIGS. 1A-1C; FIG. 16). In this regard, further testing and titrations of very low, potential non-specific DSB activity would require a bait-generating nuclease with even lower activity.

Discussion

Described herein is an LAM-PCR-based HTGTS assay employing Cas9:gRNAs, Cas9-paired nickases, or TALENs to generate bait DSBs at endogenous sequences that robustly reveals recurrent DSBs and translocations in human cells. It is demonstrated that custom nuclease-based HTGTS provides a robust assay for identifying endogenous cellular DSBs genome-wide, for studying DNA DSB repair mechanisms, and for studying mechanistic bases of recurrent genomic alterations in various cell types without potential biases imposed by inserting an exogenous DSB substrate. It is further demonstrated that this HTGTS approach provides a powerful approach for mechanistic aspects of the processing (e.g. resection) or re-joining of DSBs and a substantially unbiased and extremely robust method to evaluate OT custom endonuclease activities.

The availability of robust and accessible methods to test for OT and/or non-specific DSB inducing activities of designer nucleases is important, as this class of enzymes continues to be groomed for human therapeutic purposes[15]. The methods and assays described herein readily revealed OT sites for a series of different custom nucleases of different classes. With respect to sensitivity, the OT sites that were reproducibly detected in these studies included numerous sites predicted for previously tested custom nucleases but that had failed to be documented by existing methods, as well as a large number of OT sites that were not predicted, but which were highly specific for each tested nuclease. Beyond OT activities, it also found that HTGTS can also assay for non-specific DSB-inducing activities of some custom nucleases, an application that is useful for testing chemotherapeutic and other agents.

The LAM-PCR-based HTGTS described herein is an extremely versatile assay that goes beyond simply detecting custom nuclease OT sites by also revealing collateral damage in the form of recurrent translocations between on-target DSBs and OT DSBs, as well as translocations between different OT DSBs. While not an "off-target" event, HTGTS also revealed that a major translocation hotspot for on-target Cas9:gRNA- and TALEN-induced DSBs is the corresponding on-target DSB on the homologous chromosome, likely often leading to dicentric chromosome formation. Finally, the HTGTS findings described herein indicate that high levels of nuclease-related (or other) non-specific DSBs can make each chromosome in a cell a marked hotspot region for translocations of on-target and/or OT sites within it. HTGTS not only reveals all of these extremely complex patterns of collateral damaged generated by certain custom nucleases, but also provides an approach to estimate their relative frequency.

Consistent with cellular heterogeneity in 3D genome organization allowing dominant DSB sites across the genome to drive recurrent translocations to each other[4,5], the same large set of Cas9:RAG1A OT DSBs was identified in HTGTS assays that employed as bait, respectively, either the RAG1A on-target DSB site or three different RAG1A OT DSB sites (each on a different chromosome). Based on this finding, the HTGTS assay was further facilitated by using the RAG1B bait DSB to identify on-target, OT, and non-specific DSB activities of co-expressed custom nucleases. Indeed, this approach identified the known EMX1 and VEGFA gRNAs on-target and OT sites, as well as many additional OTs. Thus, this modification of the HTGTS assay can facilitate rapid evaluation of "on-target", OT, and non-specific DSB generating activities of candidate nucleases from fixed bait DSB sites without the need for generating and optimizing bait-site primers. It is demonstrated herein that such OT activities can be evaluated in different cell lines and even in cells that lack a known "on-target" site for the nuclease tested.

The frequency of OTs for the four RAG1 Cas9:gRNAs tested varied considerably, with two showing no detectable OT activity. If desired, HTGTS can be scaled-up for even greater sensitivity and sensitivity also can be enhanced by performing HTGTS from target sites on individual chromosomes to increase capture of OT sites on given chromosomes due to 3D proximity effects[4,5]. HTGTS confirmed that OT activity of the RAG1A gRNA was dramatically suppressed genome-wide via the Cas9 D10 nickase approach[38,39]; but also revealed that this approach does not suppress translocations involving DSBs on both bait-site chromosomes. While two tested TALENs had numerous OTs, a large fraction appeared to be generated by TALEN homodimers; thus, emerging approaches to enforce TALEN heterodimerization[43] should greatly reduce such TALEN OT activity. Finally, it is demonstrated herein that HTGTS also may be used to optimize specific versus non-specific DSB-inducing activities via "titration" of designer nuclease levels. Given the wide-ranging variations in custom nuclease OT and non-specific activities, this means for titrating the diverse on-target versus OT, non-specific and collateral activities can greatly facilitate specific custom nuclease design.

Methods

Accession Numbers: HTGTS data are available from Gene Expression Omnibus GSE57283.

REFERENCES

1. Mitelman, F., Johansson, B. & Mertens, F. The impact of translocations and gene fusions on cancer causation. *Nat. Rev. Cancer* 7, 233-245 (2007).
2. Stephens, P. J. et al. Complex landscapes of somatic rearrangement in human breast cancer genomes. *Nature* 462, 1005-1010 (2009).
3. Gostissa, M., Ranganath, S., Bianco, J. M. & Alt, F. W. Chromosomal location targets different MYC family gene members for oncogenic translocations. *Proc. Natl Acad. Sci. USA* 106, 2265-2270 (2009).
4. Alt, F. W., Zhang, Y., Meng, F. L., Guo, C. & Schwer, B. Mechanisms of programmed DNA lesions and genomic instability in the immune system. *Cell* 152, 417-429 (2013).
5. Zhang, Y. et al. Spatial organization of the mouse genome and its role in recurrent chromosomal translocations. *Cell* 148, 908-921 (2012).
6. Chiarle, R. et al. Genome-wide translocation sequencing reveals mechanisms of chromosome breaks and rearrangements in B cells. *Cell* 147, 107-119 (2011).
7. Klein, I. A. et al. Translocation-capture sequencing reveals the extent and nature of chromosomal rearrangements in B lymphocytes. *Cell* 147, 95-106 (2011).
8. Hu, J., Tepsuporn, S., Meyers, R. M., Gostissa, M. & Alt, F. W. Developmental propagation of V(D)J recombination-associated DNA breaks and translocations in mature B cells via dicentric chromosomes. *Proc. Natl Acad. Sci. USA* 111, 10269-10274 (2014).
9. Barlow, J. H. et al. Identification of early replicating fragile sites that contribute to genome instability. *Cell* 152, 620-632 (2013).
10. Hakim, O. et al. DNA damage defines sites of recurrent chromosomal translocations in B lymphocytes. *Nature* 484, 69-74 (2012).
11. Gibcus, J. H. & Dekker, J. The Hierarchy of the 3D Genome. *Mol. Cell* 49, 773-782 (2013).
12. Zarrin, A. A. et al. Antibody class switching mediated by yeast endonuclease-generated DNA breaks. *Science* 315, 377-381 (2007).
13. Gostissa, M. et al. IgH class switching exploits a general property of two DNA breaks to be joined in cis over long chromosomal distances. *Proc. Natl Acad. Sci. USA* 111, 2644-2649 (2014).
14. Sander, J. D. & Joung, J. K. CRISPR-Cas systems for editing, regulating and targeting genomes. *Nat. Biotechnol.* 32, 347-355 (2014).
15. Kim, H. & Kim, J. S. A guide to genome engineering with programmable nucleases. Nat. Rev. *Genet.* 15, 321-334 (2014).
16. Yang, H. et al. One-step generation of mice carrying reporter and conditional alleles by CRISPR/Cas-mediated genome engineering. *Cell* 154, 1370-1379 (2013).
17. Yin, H. et al. Genome editing with Cas9 in adult mice corrects a disease mutation and phenotype. *Nat. Biotechnol.* 32, 551-553 (2014).
18. Cong, L. et al. Multiplex genome engineering using CRISPR/Cas systems. *Science* 339, 819-823 (2013).
19. Jinek, M. et al. A programmable dual-RNA-guided DNA endonuclease in adaptive bacterial immunity *Science* 337, 816-821 (2012).
20. Jinek, M. et al. RNA-programmed genome editing in human cells. *eLife* 2, e00471 (2013).
21. Mali, P. et al. RNA-guided human genome engineering via Cas9. *Science* 339, 823-826 (2013).
22. Christian, M. et al. Targeting DNA double-strand breaks with TAL effector nucleases. *Genetics* 186, 757-761 (2010).
23. Miller, J. C. et al. A TALE nuclease architecture for efficient genome editing. *Nat. Biotechnol.* 29, 143-148 (2011).

24. Wood, A. J. et al. Targeted genome editing across species using ZFNs and TALENs. *Science* 333, 307 (2011).
25. Sung, Y. H. et al. Knockout mice created by TALEN-mediated gene targeting. *Nat. Biotechnol.* 31, 23-24 (2013).
26. Mussolino, C. et al. A novel TALE nuclease scaffold enables high genome editing activity in combination with low toxicity. *Nucleic Acids Res.* 39, 9283-9293 (2011).
27. Hsu, P. D. et al. DNA targeting specificity of RNA-guided Cas9 nucleases. *Nat. Biotechnol.* 31, 827-832 (2013).
28. Doyle, E. L. et al. TAL Effector-Nucleotide Targeter (TALE-NT) 2.0: tools for TAL effector design and target prediction. *Nucleic Acids Res.* 40, W117-122 (2012).
29. Xiao, A. et al. CasOT: a genome-wide Cas9/gRNA off-target searching tool. *Bioinformatics* 30, 1180-1182 (2014).
30. Fu, Y. et al. High-frequency off-target mutagenesis induced by CRISPR-Cas nucleases in human cells. *Nat. Biotechnol.* 31, 822-826 (2013).
31. Pattanayak, V. et al. High-throughput profiling of off-target DNA cleavage reveals RNA-programmed Cas9 nuclease specificity. *Nat. Biotechnol.* 31, 839-843 (2013).
32. Gabriel, R. et al. An unbiased genome-wide analysis of zinc-finger nuclease specificity. *Nat. Biotechnol.* 29, 816-823 (2011).
33. Petek, L. M., Russell, D. W. & Miller, D. G. Frequent endonuclease cleavage at off-target locations in vivo. *Mol. Ther.* 18, 983-986 (2010).
34. Schmidt, M. et al. High-resolution insertion-site analysis by linear amplification-mediated PCR (LAM-PCR). *Nat. Methods* 4, 1051-1057 (2007).
35. Lee, Y. N. et al. A systematic analysis of recombination activity and genotype-phenotype correlation in human recombination-activating gene 1 deficiency. *J. Allergy Clin. Immunol.* 133, 1099-1108 e1012 (2014).
36. Munoz, I. G. et al. Molecular basis of engineered meganuclease targeting of the endogenous human RAG1 locus. *Nucleic Acids Res.* 39, 729-743 (2011).
37. Krzywinski, M. et al. Circos: an information aesthetic for comparative genomics. *Genome Res.* 19, 1639-1645 (2009).
38. Mali, P. et al. CAS9 transcriptional activators for target specificity screening and paired nickases for cooperative genome engineering. *Nat. Biotechnol.* 31, 833-838 (2013).
39. Ran, F. A. et al. Double nicking by RNA-guided CRISPR Cas9 for enhanced genome editing specificity. *Cell* 154, 1380-1389 (2013).
40. Reyon, D. et al. FLASH assembly of TALENs for high-throughput genome editing. *Nat. Biotechnol.* 30, 460-465 (2012).
41. Asaithamby, A. & Chen, D. J. Cellular responses to DNA double-strand breaks after low-dose gamma-irradiation. *Nucleic Acids Res.* 37, 3912-3923 (2009).
42. Jiang, W., Bikard, D., Cox, D., Zhang, F. & Marraffini, L. A. RNA-guided editing of bacterial genomes using CRISPR-Cas systems. *Nat. Biotechnol.* 31, 233-239 (2013).
43. Guilinger, J. P. et al. Broad specificity profiling of TALENs results in engineered nucleases with improved DNA-cleavage specificity. *Nat. Methods* 11, 429-435 (2014).

SUPPLEMENTARY REFERENCES

47. Schueler, M. G. & Sullivan, B. A. Structural and functional dynamics of human centromeric chromatin. *Annu. Rev. Genomics Hum. Genet.* 7, 301-313 (2006).

TABLE 1

Cas9 and TALEN target sites used to generate HTGTS libraries

| Exp | Nuclease/Locus | GFP | Total DNA | Method | Library | Total Bait aligned | Filtered Junctions |
|---|---|---|---|---|---|---|---|
| Bait: Cas9 endonuclease | | | | | | | |
| #1 | Cas9:RAG1A | 81% | 100 μg | EM-PCR | 1 | 1,385,548 | 5,373 |
| #2 | Cas9:RAG1A | 45% | 100 μg | EM-PCR | 1 | 1,188,505 | 2,846 |
| #3 | Cas9:RAG1A | 76% | 100 μg | EM-PCR | 1 | 837,126 | 2,836 |
| #4 | Cas9:RAG1A | 89% | 100 μg | EM-PCR | 1 | 1,123,900 | 3,619 |
| #5 | Cas9:RAG1A | 90% | 50 μg | LAM-PCR | 1 | 1,523,373 | 33,122 |
| #6 | Cas9:RAG1A | 91% | 50 μg | LAM-PCR | 1 | 1,640,590 | 42,911 |
| | TOTAL | | 500 μg | | 6 | 7,699,042 | 90,707 |
| #1 | Cas9:RAG1A – 24 hrs | 42% | 50 μg | LAM-PCR | 1 | 1,407,635 | 2,501 |
| #2 | Cas9:RAG1A – 24 hrs | 46% | 50 μg | LAM-PCR | 1 | 646,784 | 1,898 |
| | TOTAL | | 100 μg | | 2 | 2,054,419 | 4,399 |
| #1 | Cas9:RAG1A – 96 hrs | 62% | 50 μg | LAM-PCR | 1 | 1,551,789 | 9,550 |
| #2 | Cas9:RAG1A – 96 hrs | 72% | 50 μg | LAM-PCR | 1 | 811,246 | 4,045 |
| | TOTAL | | 100 μg | | 2 | 2,363,035 | 13,595 |
| #1 | Cas9:RAG1A + IR | 86% | 50 μg | LAM-PCR | 1 | 777,941 | 62,344 |
| #2 | Cas9:RAG1A + IR | 85% | 50 μg | LAM-PCR | 1 | 949,984 | 83,302 |
| #3 | Cas9:RAG1A + IR | 86% | 50 μg | LAM-PCR | 1 | 765,342 | 60,525 |
| | TOTAL | | 150 μg | | 3 | 2,493,267 | 206,171 |
| #1 | Cas9:RAG1A OT Chr19 | 81% | 50 μg | LAM-PCR | 1 | 1,433,690 | 3,483 |
| #2 | Cas9:RAG1A OT Chr19 | 90% | 50 μg | LAM-PCR | 1 | 1,343,499 | 10,878 |

TABLE 1-continued

Cas9 and TALEN target sites used to generate HTGTS libraries

| Exp | Nuclease/Locus | GFP | Total DNA | Method | Library | Total Bait aligned | Filtered Junctions |
|---|---|---|---|---|---|---|---|
| #3 | Cas9:RAG1A OT Chr19 | 91% | 50 μg | LAM-PCR | 1 | 1,275,773 | 8,771 |
|  | TOTAL |  | 150 μg |  | 3 | 4,052,962 | 23,132 |
| #1 | Cas9:RAG1 A OT Chr19 + IR | 86% | 50 μg | LAM-PCR | 1 | 921,997 | 15,934 |
| #2 | Cas9:RAG1 A OT Chr19 + IR | 85% | 50 μg | LAM-PCR | 1 | 1,214,518 | 22,406 |
| #3 | Cas9:RAG1 A OT Chr19 + IR | 86% | 50 μg | LAM-PCR | 1 | 1,357,751 | 21,071 |
|  | TOTAL |  | 150 μg |  | 3 | 3,494,266 | 59,411 |
| #1 | Cas9:RAG1A OT Chr12 | 81% | 50 μg | LAM-PCR | 1 | 1,252,516 | 746 |
| #2 | Cas9:RAG1A OT Chr12 | 90% | 50 μg | LAM-PCR | 1 | 1,235,424 | 13,702 |
| #3 | Cas9:RAG1A OT Chr12 | 91% | 50 μg | LAM-PCR | 1 | 1,134,490 | 2,711 |
|  | TOTAL |  | 150 μg |  | 3 | 3,622,430 | 17,158 |
| #1 | Cas9:RAG1A OT Chr12 + IR | 86% | 50 μg | LAM-PCR | 1 | 1,183,240 | 25,223 |
| #2 | Cas9:RAG1A OT Chr12 + IR | 85% | 50 μg | LAM-PCR | 1 | 1,105,648 | 29,601 |
| #3 | Cas9:RAG1A OT Chr12 + IR | 86% | 50 μg | LAM-PCR | 1 | 1,358,359 | 32,528 |
|  | TOTAL |  | 150 μg |  | 3 | 3,647,247 | 87,352 |
| #1 | Cas9:RAG1A OT Chr7 | 90% | 50 μg | LAM-PCR | 1 | 1,324,361 | 3,077 |
| #2 | Cas9:RAG1A OT Chr7 | 80% | 50 μg | LAM-PCR | 1 | 581,954 | 1,389 |
| #3 | Cas9:RAG1A OT Chr7 | 87% | 50 μg | LAM-PCR | 1 | 1,422,336 | 3,777 |
|  | TOTAL |  | 150 μg |  | 3 | 3,328,651 | 8,243 |
| #1 | Cas9:RAG1B | 83% | 100 μg | EM-PCR | 1 | 1,241,696 | 4,801 |
| #2 | Cas9:RAG1B | 48% | 100 μg | EM-PCR | 1 | 1,235,718 | 2,044 |
| #3 | Cas9:RAG1B | 66% | 100 μg | EM-PCR | 1 | 798,151 | 1,693 |
| #4 | Cas9:RAG1B | 87% | 100 μg | EM-PCR | 1 | 883,814 | 1,554 |
| #5 | Cas9:RAG1B | 90% | 50 μg | LAM-PCR | 1 | 1,493,069 | 21,720 |
| #6 | Cas9:RAG1B | 90% | 50 μg | LAM-PCR | 1 | 1,478,753 | 28,036 |
|  | TOTAL |  | 500 μg |  | 6 | 7,131,201 | 59,848 |
| #1 | Cas9:RAG1B – A549 | 38% | 200 μg | LAM-PCR | 2 | 2,308,874 | 2,489 |
| #2 | Cas9:RAG1B – A549 | 51% | 100 μg | LAM-PCR | 1 | 1,351,727 | 2,540 |
|  | TOTAL |  | 300 μg |  | 3 | 3,660,601 | 5,029 |
| #1 | Cas9:RAG1B 60 μg | 68% | 50 μg | LAM-PCR | 1 | 891,902 | 11,593 |
| #2 | Cas9:RAG1B 60 μg | 66% | 50 μg | LAM-PCR | 1 | 552,083 | 4,767 |
|  | TOTAL |  | 100 μg |  | 2 | 1,443,985 | 16,360 |
| #1 | Cas9:RAG1B 100 μg | 65% | 50 μg | LAM-PCR | 1 | 895,365 | 9,819 |
| #2 | Cas9:RAG1B 100 μg | 60% | 50 μg | LAM-PCR | 1 | 1,113,910 | 5,350 |
|  | TOTAL |  | 100 μg |  | 2 | 2,009,275 | 15,169 |
| #1 | Cas9:RAG1B 150 μg | 59% | 50 μg | LAM-PCR | 1 | 1,064,148 | 14,551 |
| #2 | Cas9:RAG1B 150 μg | 52% | 50 μg | LAM-PCR | 1 | 1,104,544 | 5,840 |
|  | TOTAL |  | 100 μg |  | 2 | 2,168,692 | 20,391 |
| #1 | Cas9:RAG1B + IR | 94% | 50 μg | LAM-PCR | 1 | 1,110,892 | 47,639 |
| #2 | Cas9:RAG1B + IR | 96% | 50 μg | LAM-PCR | 1 | 1,140,162 | 39,555 |
| #3 | Cas9:RAG1B + IR | 94% | 50 μg | LAM-PCR | 1 | 1,188,273 | 46,621 |
|  | TOTAL |  | 150 μg |  | 3 | 3,439,327 | 133,815 |

TABLE 1-continued

Cas9 and TALEN target sites used to generate HTGTS libraries

| Exp | Nuclease/Locus | GFP | Total DNA | Method | Library | Total Bait aligned | Filtered Junctions |
|---|---|---|---|---|---|---|---|
| #1 | Cas9:RAG1B + ISceI | 57% | 50 μg | LAM-PCR | 1 | 988,054 | 15,978 |
| #2 | Cas9:RAG1B + ISceI | 54% | 50 μg | LAM-PCR | 1 | 1,163,969 | 10,676 |
| #3 | Cas9:RAG1B + ISceI | 58% | 50 μg | LAM-PCR | 1 | 976,679 | 9,900 |
|  | TOTAL |  | 150 μg |  | 3 | 3,128,702 | 36,554 |
| #1 | Cas9:RAG1B + Cas9:EMX1 | 92% | 50 μg | LAM-PCR | 1 | 1,358,175 | 19,474 |
| #2 | Cas9:RAG1B + Cas9:EMX1 | 87% | 50 μg | LAM-PCR | 1 | 940,919 | 16,730 |
| #3 | Cas9:RAG1B + Cas9:EMX1 | 88% | 50 μg | LAM-PCR | 1 | 699,736 | 714 |
|  | TOTAL |  | 150 μg |  | 3 | 2,998,830 | 36,918 |
| #1 | Cas9:RAG1B + Cas9:VEGFA | 88% | 50 μg | LAM-PCR | 1 | 1,265,815 | 1,996 |
| #2 | Cas9:RAG1B + Cas9:VEGFA | 92% | 50 μg | LAM-PCR | 1 | 769,647 | 14,352 |
| #3 | Cas9:RAG1B + Cas9:VEGFA | 89% | 50 μg | LAM-PCR | 1 | 712,697 | 12,103 |
|  | TOTAL |  | 150 μg |  | 3 | 2,748,159 | 28,451 |
| #1 | Cas9:RAG1B + ATM TALEN | 88% | 50 μg | LAM-PCR | 1 | 1,429,068 | 22,426 |
| #2 | Cas9:RAG1B + ATM TALEN | 77% | 50 μg | LAM-PCR | 1 | 823,007 | 24,473 |
| #3 | Cas9:RAG1B + ATM TALEN | 78% | 50 μg | LAM-PCR | 1 | 588,161 | 10,200 |
|  | TOTAL |  | 150 μg |  | 3 | 2,840,236 | 57,099 |
| #1 | Cas9:RAG1B + MYC TALEN | 88% | 50 μg | LAM-PCR | 1 | 1,723,351 | 40,995 |
| #2 | Cas9:RAG1B + MYC TALEN | 77% | 50 μg | LAM-PCR | 1 | 1,006,825 | 34,443 |
| #3 | Cas9:RAG1B + MYC TALEN | 75% | 50 μg | LAM-PCR | 1 | 1,027,535 | 35,514 |
|  | TOTAL |  | 150 μg |  | 3 | 3,757,711 | 110,952 |
| #1 | Cas9:RAG1C | 85% | 100 μg | EM-PCR | 1 | 1,434,562 | 1,878 |
| #2 | Cas9:RAG1C | 51% | 100 μg | EM-PCR | 1 | 1,238,636 | 1,512 |
| #3 | Cas9:RAG1C | 58% | 100 μg | EM-PCR | 1 | 743,963 | 407 |
| #4 | Cas9:RAG1C | 89% | 100 μg | EM-PCR | 1 | 814,688 | 644 |
| #5 | Cas9:RAG1C | 85% | 50 μg | LAM-PCR | 1 | 1,712,220 | 20,213 |
| #6 | Cas9:RAG1C | 85% | 50 μg | LAM-PCR | 1 | 1,920,004 | 25,046 |
|  | TOTAL |  | 500 μg |  | 6 | 7,864,073 | 49,700 |
| #1 | Cas9:RAG1D | 72% | 100 μg | EM-PCR | 1 | 1,498,394 | 729 |
| #2 | Cas9:RAG1D | 56% | 100 μg | EM-PCR | 1 | 1,458,917 | 784 |
| #3 | Cas9:RAG1D | 64% | 100 μg | EM-PCR | 1 | 822,563 | 132 |
| #4 | Cas9:RAG1D | 89% | 100 μg | EM-PCR | 1 | 825,052 | 184 |
| #5 | Cas9:RAG1D | 87% | 50 μg | LAM-PCR | 1 | 1,875,731 | 9,826 |
| #6 | Cas9:RAG1D | 87% | 50 μg | LAM-PCR | 1 | 1,595,863 | 9,516 |
|  | TOTAL |  | 500 μg |  | 6 | 8,076,520 | 21,171 |
| #1 | Cas9:RAG1B + ATM TALEN 100 μg | 75% | 50 μg | LAM-PCR | 1 | 1,757,242 | 54,960 |
| #2 | Cas9:RAG1B + ATM TALEN 100 μg | 77% | 50 μg | LAM-PCR | 1 | 1,685,816 | 63,678 |
|  | TOTAL |  | 100 μg |  | 2 | 3,443,058 | 118,638 |
| #1 | Cas9:RAG1B + ATM TALEN 10 μg | 96% | 50 μg | LAM-PCR | 1 | 655,488 | 20,436 |
| #2 | Cas9:RAG1B + ATM TALEN 10 μg | 86% | 50 μg | LAM-PCR | 1 | 1,476,240 | 48,912 |
|  | Cas9:RAG1B + ATM TALEN 10 μg | 87% | 50 μg | LAM-PCR | 1 | 1,485,080 | 18,331 |
|  | TOTAL |  | 150 μg |  | 3 | 3,626,808 | 87,679 |
| #1 | Cas9:RAG1B + ATM TALEN 3 μg | 94% | 50 μg | LAM-PCR | 1 | 760,330 | 8,122 |
| #2 | Cas9:RAG1B + ATM TALEN 3 μg | 87% | 50 μg | LAM-PCR | 1 | 1,461,868 | 41,457 |

TABLE 1-continued

Cas9 and TALEN target sites used to generate HTGTS libraries

| Exp | Nuclease/Locus | GFP | Total DNA | Method | Library | Total Bait aligned | Filtered Junctions |
|---|---|---|---|---|---|---|---|
|  | Cas9:RAG1B + ATM TALEN 3 μg | 83% | 50 μg | LAM-PCR | 1 | 1,293,894 | 17,930 |
|  | TOTAL |  | 150 μg |  | 3 | 3,516,092 | 67,509 |
| #1 | Cas9:RAG1B + ATM TALEN 1 μg | 92% | 50 μg | LAM-PCR | 1 | 678,188 | 7,418 |
| #2 | Cas9:RAG1B + ATM TALEN 1 μg | 77% | 50 μg | LAM-PCR | 1 | 1,399,326 | 24,120 |
|  | TOTAL |  | 100 μg |  | 2 | 2,077,514 | 31,538 |
|  | Bait: Cas9 D10A nickase |  |  |  |  |  |  |
| #1 | Cas9n:RAG1A/G | 86% | 100 μg | EM-PCR | 1 | 1,225,465 | 2,496 |
| #2 | Cas9n:RAG1A/G | 88% | 100 μg | EM-PCR | 1 | 1,489,939 | 2,018 |
| #3 | Cas9n:RAG1A/G | 86% | 100 μg | EM-PCR | 1 | 1,514,264 | 1,203 |
| #4 | Cas9n:RAG1A/G | 91% 90% | 50 μg | LAM-PCR | 1 | 1,272,060 | 13,937 |
| #5 | Cas9n:RAG1A/G | 90% | 50 μg | LAM-PCR | 1 | 1,310,951 | 13,246 |
| #6 | Cas9n:RAG1A/G | 92% | 50 μg | LAM-PCR | 1 | 1,131,288 | 12,794 |
|  | TOTAL |  | 450 μg |  | 6 | 7,943,967 | 45,694 |
| #1 | Cas9n:RAG1A/E | 89% | 100 μg | EM-PCR | 1 | 1,409,177 | 3,826 |
| #2 | Cas9n:RAG1A/E | 86% | 50 μg | LAM-PCR | 1 | 1,078,141 | 13,796 |
|  | TOTAL |  | 150 μg |  | 2 | 2,487318 | 17,622 |
| #1 | Cas9:RAG1A/F | 87% | 100 μg | EM-PCR | 1 | 1,555,687 | 1,788 |
| #2 | Cas9:RAG1A/F | 87% | 50 μg | LAM-PCR | 1 | 1,196,599 | 10,502 |
|  | TOTAL |  | 150 μg |  | 2 | 2,752,286 | 12,290 |
|  | Bait: TALEN endonuclease |  |  |  |  |  |  |
| #1 | ATM TALEN | 85% | 50 μg | LAM-PCR | 1 | 1,629,352 | 22,844 |
| #2 | ATM TALEN | 86% | 50 μg | LAM-PCR | 1 | 440,065 | 10,760 |
| #3 | ATM TALEN | 85% | 50 μg | LAM-PCR | 1 | 1,058,993 | 35,553 |
|  | TOTAL |  | 150 μg |  | 3 | 3,128,410 | 69,157 |
| #1 | c-MYC TALEN | 87% | 50 μg | LAM-PCR | 1 | 957,292 | 62,473 |
| #2 | c-MYC TALEN | 97% | 50 μg | LAM-PCR | 1 | 1,043,966 | 24,886 |
| #3 | c-MYC TALEN | 95% | 50 μg | LAM-PCR | 1 | 1,130,927 | 20,993 |
|  | TOTAL |  | 150 μg |  | 3 | 3,132,185 | 108,352 |
| #1 | ATM 1 μg + C9B:RAG1B 20 μg | 92% | 50 μg | LAM-PCR | 1 | 1,288,833 | 2,227 |
| #2 | ATM 1 μg + C9B:RAG1B 20 μg | 81% | 50 μg | LAM-PCR | 1 | 1,816,729 | 22,633 |
| #3 | ATM 1 μg + C9B:RAG1B 20 μg | 77% | 50 μg | LAM-PCR | 1 | 1,659,566 | 15,185 |
|  | TOTAL |  | 150 μg |  | 3 | 4,765,128 | 40,045 |
| #1 | ATM 3 μg + C9B:RAG1B 20 μg | 94% | 50 μg | LAM-PCR | 1 | 1,262,584 | 21,345 |
| #2 | ATM 3 μg + C9B:RAG1B 20 μg | 83% | 50 μg | LAM-PCR | 1 | 1,580,141 | 28,890 |
| #3 | ATM 3 μg + C9B:RAG1B 20 μg | 87% | 50 μg | LAM-PCR | 1 | 1,575,902 | 37,100 |
|  | TOTAL |  | 150 μg |  | 3 | 4,418,627 | 87,335 |
| #1 | ATM 10 μg + C9B:RAG1B 20 μg | 96% | 50 μg | LAM-PCR | 1 | 1,104,338 | 25,359 |
| #2 | ATM 10 μg + C9B:RAG1B 20 μg | 87% | 50 μg | LAM-PCR | 1 | 1,403,545 | 67,220 |
| #3 | ATM 10 μg + C9B:RAG1B 20 μg | 86% | 50 μg | LAM-PCR | 1 | 1,463,665 | 59,393 |
|  | TOTAL |  | 150 μg |  | 3 | 3,971,548 | 151,972 |

TABLE 2

Estimated HTGTS background for various libraries

| Target DNA | Vector control | Vector control | Cas9:RAG1A | Cas9:RAG1B | Cas9:RAG1C | Cas9:RAG1D |
|---|---|---|---|---|---|---|
| HTGTS cloning method | EM-PCR RAG1A/B | EM-PCR RAG1C/D | EM-PCR RAG1A/B | EM-PCR RAG1A/B | EM-PCR RAG1C/D | EM-PCR RAG1C/D |
| Input DNA | 100 μg | 100 μg | 100 μg | 100 μg | 100 μg | 100 μg |
| Control DNA | NA | NA | Mouse | Mouse | Mouse | Mouse |
| Target Junctions | 40 | 38 | 3,600 | 1,541 | 636 | 182 |
| Control Junctions | — | — | 23 | 19 | 5 | 5 |
| Background | NA | NA | 0.64% | 1.23% | 0.79% | 2.75% |
| HTGTS cloning method | LAM-PCR RAG1A/B | LAM-PCR RAG1C/D | LAM-PCR RAG1A/B | LAM-PCR RAG1A/B | LAM-PCR RAG1C/D | LAM-PCR RAG1C/D |
| Input DNA | 50 μg | 50 μg | 50 μg | 50 μg | 50 μg | 50 μg |
| Control DNA | NA | NA | Mouse | Mouse | Mouse | Mouse |
| Target Junctions | 2,346 | 134 | 26,508 | 16,516 | 20,247 | 7,500 |
| Control Junctions | — | — | 191 | 113 | 206 | 94 |
| Background | NA | NA | 0.72% | 0.68% | 1.02% | 1.25% |

TABLE 3

Cas9: RAG1A off-target site mismatches and translocations

| Chromosome | Nuclease/Locus | Off-target site sequence (NGG) (SEQ ID NOS 1-34, respectively, in order of appearance) | Mismatch | Cas9: RAG1A Frequency | Cas9n: RAG1A Frequency | OT1 Bait Freq. | OT2 Bait Freq. | OT17 Bait Freq. |
|---|---|---|---|---|---|---|---|---|
| Chr11 | Cas9: RAG1A | GCCTCTTTCCCACC CACCTT GGGNNN | 0 | NA | NA | 177.59 | 220.90 | 23.53 |
| Chr19 | DAZAP1 OT1 | ACCCCTTCCCCACC TACCTT GGGTCG | 4 | 77.18*** | 0.18 | NA | 89.65 | 51.47 |
| Chr12 | 47.0 Mb OT2 | TCCTCCTCCCCACC CACCTT CAGACT | 4 | 74.07*** | 0.26 | 121.84 | NA | 36.01 |
| Chr7 | 155.9 Mb OT3 | CCCTCCTTCCCCACC CACTTT GGGTGA | 3 | 40.46*** | 0.09 | 105.13 | 130.56 | 172.11 |
| Chr15 | SIN3A OT4 | TCCTCTCTCCCACC CACCTC CGGCTC | 3 | 40.19*** | 0.20 | 137.20 | 174.13 | 37.91 |
| Chr11 | 94.9 Mb OT5 | ACGTCTTCCCCACC CACCTG GGGCCT | 4 | 24.84*** | — | 7.33 | 19.21 | 13.55 |
| Chr14 | 78.5 Mb OT6 | ACTTCCTTCCCACC CACCTT CAGCCA | 4 | 23.98*** | 0.09 | 54.95 | 88.34 | 34.48 |
| Chr1 | CACHD1 OT7 | TCCTCTTCTCCACC CACCTC TGGTTT | 4 | 22.62*** | — | 33.59 | 63.81 | 25.28 |
| Chr17 | 6.8 Mb OT8 | GTCTCTTTCTCACC CACTTT GGGTTG | 3 | 19.14*** | — | 68.77 | 78.62 | 29.64 |
| Chr7 | TARP OT9 | CACCCTTTCCCATC CACCTT TGGATA | 4 | 17.57*** | — | 23.86 | 29.82 | 57.59 |
| Chr7 | 112.9 Mb OT10 | GCCTCTTCCACACC CACCCT GGGCCC | 3 | 14.90*** | — | 33.84 | 88.24 | 270.44 |
| Chr13 | RB1 OT11 | GCCTCTTTACCACC TCACCT TGGGCA | 5 | 8.03 | — | 20.78 | 39.41 | 24.20 |
| Chr4 | RBPJ OT12 | TTCTCTTCCCCACC CACCTT TGAGCT | 4 | 7.87 | — | 8.05 | 18.23 | 5.45 |

TABLE 3-continued

Cas9: RAG1A off-target site mismatches and translocations

| Chromo-some | Nuclease/Locus | Off-target site sequence (NGG) (SEQ ID NOS 1-34, respectively, in order of appearance) | Mis-match | Cas9: RAG1A Frequency | Cas9n: RAG1A Frequency | OT1 Bait Freq. | OT2 Bait Freq. | OT17 Bait Freq. |
|---|---|---|---|---|---|---|---|---|
| Chr11 | 116.5 Mb OT13 | ICCTCTTCTCCACC CACCAT AGGGTG | 4 | 7.69 | — | 11.99 | 6.36 | 13.53 |
| Chr20 | ATRN OT14 | GTCTCTTTCCCATC CACCTT TGATAA | 3 | 6.01 | — | 12.18 | 20.92 | 20.96 |
| Chr11 | PCNXL3 OT15 | GCCCCTACCCCACC CACCTG GGTGGA | 5 | 5.62 | — | 5.76 | 1.46 | 0.88 |
| Chr17 | FBXL20 OT16 | ACCTCTTATCCACC CACCTT GGCCTC | 4 | 4.49 | 0.09 | 38.21 | 44.59 | 28.79 |
| Chr7 | 103.6 Mb OT17 | GCCTCTCCCCACCC ACCCTT GGCTTG | 7 | 4.25 | — | 7.68 | 4.41 | NA |
| Chr8 | 143.6 Mb OT18 | ACCTCCTTCCCGCC CACCTG GGGCTC | 4 | 3.43 | — | 39.66 | 34.66 | 39.52 |
| Chr7 | AGK OT19 | ACCCCTTCCCCACT CACCTC CGGGAT | 5 | 3.12 | — | 0.69 | 1.95 | 12.90 |
| Chr12 | 103.2 Mb OT20 | GCTTCTTCCCCACC CACACT TGGTGG | 4 | 2.82 | 0.1 | 3.90 | 26.07 | 21.15 |
| Chr1 | SLC35F3 OT21 | CACCCTTCCCCACC CACCCT GGGACC | 5 | 2.27 | — | 4.51 | 3.43 | 7.65 |
| Chr11 | 2.2 Mb OT22 | GCCCCTCCCCCACC CACCCT GGGGGA | 4 | 1.95 | — | 4.19 | 10.35 | 12.90 |
| Chr22 | SUN2/ DNAL3 OT23 | TGCTCTTCCCCACC CACCCA AGGCCT | 5 | 1.82 | — | 8.13 | 4.42 | 4.37 |
| Chr1 | 33.6 Mb OT24 | ACCTCCATCCTCCC CACCTT GGGTCT | 5 | 1.54 | — | 1.37 | 0.73 | 1.08 |
| Chr14 | XRCC3 OT25 | GGCTCCTCCTCACC CACCTC TGGGTC | 5 | 1.43 | 0.09 | 11.80 | 3.43 | 5.88 |
| Chr17 | LOC284009 OT26 | GACTCTTTTCCACC CACCCT AGGGGA | 3 | 1.40 | — | 24.14 | 14.50 | 9.58 |
| Chr3 | 0.4 Mb OT27 | ACCTCTTCCCTCCC CACCTT TGGAGG | 4 | 1.33 | — | 0.69 | 1.72 | 8.50 |
| Chr4 | 181.5 Mb OT28 | ACCTCTTTCCATCC CACCTT GGGAAA | 3 | 1.14 | — | 2.67 | 1.72 | 7.85 |
| Chr6 | 40.0 Mb OT29 | GTGTATTCCCCACC CACCTT GGGAAG | 4 | 0.77 | — | — | — | — |
| Chr16 | FBX031 OT30 | GCCCCTTCCCCACC CACCCT GTGGAA | 4 | 0.74 | — | 7.49 | 6.91 | 6.33 |
| Chr19 | CYTH2 OT31 | ACCTTGTCCCCACC CACCAG GGGATC | 6 | 0.61 | — | 8.75 | 1.47 | — |
| Chr22 | CECR5 OT32 | GCCCCTTACCCATC CACCCT GGGTGC | 4 | 0.60 | — | 0.61 | 3.92 | 1.97 |
| Chr7 | VIPR2 OT33 | GCCCCTGCCCCACC CACCTG TGGAGC | 4 | 0.55 | — | 1.99 | 1.72 | 11.35 |

Mismatches to targeted Cas9: RAG1A and PAM are listed in underlined text. Average junction frequencies (per 10,000 unique junctions) for off-target sites are listed for the Cas9: RAG1A (N = 6) and the Cas9n: RAG1 combinations (total N = 10; A/G (N = 6), A/E (N = 2), A/F (N = 2)). Two-way ANOVA indicates an extremely significant interaction between Cas9 and Cas9n: RAG1 A/G, A/E, A/F with the off-targets listed (p<0.0001). Post-tests indicate significance for each site (p<0.001 = ***). Additional Cas9: RAG1A OT bait site libraries with average on-target and OT junction frequencies also listed (N = 3 each).

TABLE 4

ATM TALEN off-target site sequences

| Chromosome | Nuclease/ Locus | Left half-site (SEQ ID NOS 35-93, respectively, in order of appearance) | Spacer | Right half-site (SEQ ID NOS 94-96, respectively, in order of appearance) | Mis-match | RAG1B Bait Freq. | ATM Bait Freq. |
|---|---|---|---|---|---|---|---|
| Chr11 | ATM TALEN | TGAATTGGGATGCTG TTT (+) TGGATAGGGATGATG TGC (+) | 18 | TTTATTTTACTGTCTTT A (+) | NA | 189.32 | NA |
| Chr16 | HYDIN OT | TGAATAGAACTGCTT TTC (-) | 17 | — | 5, 7 | 43.83 | 61.03 |
| Chr1 | JAK1 OT | TAAATAGGGATTCTG AGC (+) TGAAATGGGGTTTTG ATT (-) | 15 | — | 6, 5 | 43.25 | 100.42 |
| Chr21 | BRWD1-AS1 OT | TGAATAGGAACAAAG ATT (+) CGAATCGGGAAGATA TTC (-) | 14 | — | 7, 6 | 38.43 | 31.99 |
| Chr15 | FRMD5 OT | TCAATTGAAAAGCTG AGG (+) CGAATAGGAATGCTC TGC (-) | 17 | — | 7, 6 | 17.88 | 27.53 |
| Chr21 | MIR5009 OT | TGAATAGAAATGCTG TCA (+) AAAATTGGGATGATT TTC (-) | 14 | — | 5, 5 | 14.52 | 11.22 |
| Chr10 | 65.5 Mb OT | TTGAATAGAATGATG TAT (+) TGAATGAGAATGCTC ATT (-) | 18 | — | 7, 5 | 12.48 | 15.25 |
| Chr6 | TSPYL4 OT | TGAACAAGGATGCTG CAT (+) TCACTTAAAATACTG TTT (-) | 18 | — | 5, 6 | 12.32 | 26.15 |
| Chr3 | 176.1 Mb OT | TAGATAGTGATACTG TTT (+) TAAATAGTGATGCTG TGG (-) | 15 | — | 5, 5 | 11.75 | 19.26 |
| Chr9 | 7.7 Mb OT | TAAATTAGGAAGCTG AGG (+) TGAATCAGGAAACTG TCC (-) | 23 | — | 6, 6 | 12.25 | 13.29 |
| Chr9 | 13.4 Mb OT | TGACTTCAGATGCTG CCT (+) TGAATTGGAAAGCAG TAG (-) | 15 | — | 5, 5 | 10.17 | 14.19 |
| Chr15 | 37.9 Mb OT | TGGACTAGAGTGCTG GTT (+) TTAGTTGGGATACTG CTT (-) | 18 | — | 5, 4 | 8.25 | 14.38 |
| Chr1 | 22.9 Mb OT | GGAATCAGGATACTC CTC (+) TGGATTAGAATGATC TAC (-) | 17 | — | 7, 7 | 7.70 | 11.68 |
| Chr1 | 180.0 Mb OT | TGAATGGAGATGATT ACA (+) TGAATAGGCACGCTG TTC (-) | 16 | — | 7, 4 | 8.18 | 15.30 |
| Chr6 | LRFN2 OT | TGATTTGAGATGCTC TTA (+) TGCATAGGGGAGATG TTT (-) | 14 | — | 4, 5 | 6.10 | 12.37 |

TABLE 4-continued

ATM TALEN off-target site sequences

| Chromosome | Nuclease/ Locus | Left half-site (SEQ ID NOS 35-93, respectively, in order of appearance) | Spacer | Right half-site (SEQ ID NOS 94-96, respectively, in order of appearance) | Mis-match | RAG1B Bait Freq. | ATM Bait Freq. |
|---|---|---|---|---|---|---|---|
| Chr6 | 160.5 Mb OT | TGAAGCAGGATACTG CAT (+) TGCATAAAGATGCTA TTG (-) | 18 | — | 6, 6 | 6.49 | 12.42 |
| Chr2 | 40.0 Mb OT | TGCATAGTGAAGCTG CTT (+) TGAATAGGGAACCTA TAG (-) | 17 | — | 5, 6 | 6.53 | 7.65 |
| Chr15 | FBN1 OT | TGAGTGAGGGTTCTA GTT (-) | 16 | ACTATTTTACTGTCTTT C (-) | 7, 3 | 6.08 | 3.11 |
| Chr13 | PCDH9 OT | TGAGATGAGAGACTC ACT (+) TGAATTAAGATACTG TTT (-) | 16 | — | 8, 3 | 6.37 | 4.28 |
| Chr18 | 20.3 Mb OT | TGCATTGAAAAACTA TCT (+) TAAATAAGAAAGCTT TCT (-) | 17 | — | 7, 7 | 6.41 | 4.24 |
| Chr14 | GMFB OT | TGAAAGGAAATACTG TCT (+) TGAAATAGGATATTA TAT (-) | 15 | — | 6, 6 | 4.82 | 4.72 |
| Chr2 | 55.8 Mb OT | TAAATTGAAAGGCTG TTG (+) GGCATTGCGTTGAAT TGT (-) | 17 | — | 5, 8 | 4.63 | 3.87 |
| Chr10 | SH3PXD2A OT | GGAAATGGAAACCTG TTT (+) TGAAATGAGATGATT TAT (-) | 13 | — | 5, 5 | 6.28 | 18.27 |
| Chr12 | MLXIP OT | TGAAGTGGGGTGCTG CCT (+) TTGATTGGGATTATG TTT (-) | 17 | — | 4, 4 | 5.24 | 8.65 |
| Chr19 | ZNF814 OT | TGAATGAGGCTGCTC TTT (+) TGAATGTGGAGAATG TGG (-) | 15 | — | 4, 7 | 4.93 | 8.47 |
| Chr3 | WNT7A OT | TGAACAGGGATGCTT TGT (+) TAAATTGAGATATTG CTT (-) | 15 | — | 4, 5 | 3.71 | 7.96 |
| Chr12 | FBXO21 OT | TACATTAGAATGATG TCC (+) TGAATGTGAATGCTA ATG (-) | 17 | — | 7, 6 | 4.26 | 4.31 |
| Chr15 | TCF12 OT | TTAATTGGGACCCTG CCT (+) TGCATCTGGCTAATG TTT (-) | 17 | — | 5, 6 | 4.50 | 5.06 |
| Chr22 | PI4KA OT | TAAATGAAGCAACTG TTT (+) | 18 | GACACTCTACTGTCTTC A (+) | 7, 6 | 4.41 | 5.21 |
| Chr7 | ABCB1 OT | TGAATATGTATACTG CTT (+) TGAATTGGAAGACTA TTG (-) | 21 | — | 5, 5 | 4.50 | 7.10 |

TABLE 4-continued

ATM TALEN off-target site sequences

| Chromosome | Nuclease/Locus | Left half-site (SEQ ID NOS 35-93, respectively, in order of appearance) | Spacer | Right half-site (SEQ ID NOS 94-96, respectively, in order of appearance) | Mis-match | RAG1B Bait Freq. | ATM Bait Freq. |
|---|---|---|---|---|---|---|---|
| Chr15 | 82.1 Mb OT | AGAATGCTGTTGCTC TTT (+) CCAATGGGGAGAATG TTT (−) | 16 | — | 6, 6 | 3.97 | 6.49 |

Left and Right TALEN half-sites are reported in the same chromosomal orientation except for loci displaying the same half-site for both sides with the 2$^{nd}$ site reported in the (−) orientation. Average frequencies (per 10,000) are listed for RAG1B and ATM bait libraries.

TABLE 5

C-MYC TALEN off-target site sequences

| Chromosome | Nuclease/Locus | Left half-site (SEQ ID NOS 97-124 respectively, in order of appearance) | Spacer | Right half-site (SEQ ID NOS 125-158, respectively, in order of appearance) | Mismatch | RAB1B Bait Freq. | C-MYC Bait Freq. |
|---|---|---|---|---|---|---|---|
| Chr8 | C-MYC TALEN | TGCTTAGACGCTGG ATTT (+) | 16 | AACCAGGTAAGCACCGA A (+) | NA | 26.10 | NA |
| Chr19 | TIMM44 OT | TACTTAGAACCTGG GTTT (−) | 18 | GGCCAGGGTGGCATCTG A (−) | 5, 8 | 17.23 | 25.11 |
| Chr11 | CUL5 OT | — | 16 | TATTAGTTAAGTACTTG T (+) CCACAGGTAAGTACTTA A (−) | 9, 6 | 23.12 | 3.60 |
| Chr3 | SEMA5b OT | — | 20 | ACCCAGGCACACACAGA A (+) CCTCAGGTATGCATTGA A (−) | 5, 6 | 9.23 | 13.27 |
| Chr14 | SLC35F4 OT | TACTCAGAAAATGA ATTA (−) | 17 | AACCAGGTAATCTTTGT A (−) | 7, 5 | 8.41 | 22.76 |
| Chr19 | 4.5 Mb OT | — | 22 | TTACAGGAGTGCACTGC C (+) AACACGAGAATCGCTTG A (−) | 9, 8 | 8.07 | 20.79 |
| Chr21 | 25.3 Mb OT | TCCCGAGAAGCTGG AATT (−) | 18 | AACCAGGTAATTTTTGT A (−) | 5, 6 | 4.52 | 2.40 |
| Chr8 | 1.6 Mb OT | TGATTAAACCCTGA TTCT (+) TCCTTGAACACTGG CTTT (−) | 16 | — | 7, 5 | 5.34 | 33.84 |
| Chr1 | PHC2 OT | — | 15 | AAGCAGGTAAGGACCTT A (+) AACCAGGGAAGTATCCA A (−) | 4, 4 | 4.01 | 6.26 |
| Chr3 | CCDC14 OT | — | 15 | GATCAGGTAGGCATTCA A (+) AGTCAGGTAAGCACACC A (−) | 6, 5 | 6.90 | 5.84 |
| Chr8 | LRRC6 9 OT | TCCCAAGAAGCTGG GATT (−) | 18 | AACCAGGTAATTTTTGT A (−) | 6, 7 | 5.81 | 66.63 |
| Chr5 | RhoBT B3 OT | — | 18 | CATCTGGTGAGTGCTGA A (+) AATGAGGCAGGCACATA A (−) | 7, 6 | 4.34 | 3.09 |
| Chr13 | 39.6 Mb OT | TACTAAAAGACAAG GTTT (−) | 17 | AACCAGGTAGGGAACTA T (−) | 8, 5 | 3.09 | 7.99 |

TABLE 5-continued

C-MYC TALEN off-target site sequences

| Chromosome | Nuclease/ Locus | Left half-site (SEQ ID NOS 97-124 respectively, in order of appearance) | Spacer | Right half-site (SEQ ID NOS 125-158, respectively, in order of appearance) | Mismatch | RAB1B Bait Freq. | C-MYC Bait Freq. |
|---|---|---|---|---|---|---|---|
| Chr4 | 43.3 Mb OT | — | 10 | ATGCTTGTAATCCCAGCA (+) | 7, 5 | 3.78 | 4.04 |
| Chr17 | 14.6 Mb OT | TACTCATGAGCTAAATAT (−) | 17 | AACCAGGTACTTTCTTAA (−) TACCAGGTATGTCTTGAA (−) | 8, 6 | 4.29 | 5.72 |
| Chr13 | 74.7 Mb OT | — | 17 | GCCCAAGTAAGCATCCAA (+) GCGCAGGTAAGCATCTAA (−) | 5, 5 | 3.71 | 6.58 |
| Chr3 | 165.2Mb OT | TGCTAAGAAGCTGGACTC (+) TGCTTAGAAGCAGGTCTT (−) | 15 | — | 4, 4 | 3.56 | 14.73 |
| Chr10 | FAM171A OT | TACATAAAAGCAAGATTC (+) | 17 | GGGAAGGTAAACATTGAA (+) | 7, 7 | 3.09 | 5.43 |
| Chr8 | PBK OT | TAATAAGACACAAGATAC (+) TGCTTCTCTGCTGAATTA (−) | 16 | — | 8, 6 | 4.07 | 31.67 |
| Chr5 | 108.7Mb OT | TAAATAGAAGAAGGCTTG (+) TGATTAGAACATAGATCC (−) | 14 | — | 8, 7 | 3.42 | 11.77 |
| Chr5 | SH3PXD2B OT | TCCATAGACACTGCATCT (+) | 16 | AACCAGTCAAGCACTTTT (+) | 5, 6 | 3.19 | 10.95 |
| Chr10 | 101.5Mb OT | TCCTGAGTAGCTGGATTA (+) | 17 | GCCCAGGTAATTTTTGTA (+) | 5, 8 | 3.64 | 5.83 |
| Chr18 | SS18 OT | TACCTAGAAAAGAATGT (−) | 17 | CAGCAAGTATGCACTGGA (−) | 8, 7 | 3.64 | 3.60 |
| Chr21 | 30.3 Mb OT | TGTATAGAAGCTGGGTGT (+) TCCCAAAGCACTAGGATT (−) | 16 | — | 5, 9 | 3.12 | 4.58 |
| Chr3 | FAM208A OT | TAATGAAGCCCTGAACAT (+) | 13 | GTCCAGTTAAGCTCTTTA (−) | 9, 7 | 3.73 | 13.00 |
| Chr10 | DNA2 OT | TCCCAAGAAGCTGGGTTT (−) | 18 | ACCCAGCTAATTTTTGTA (−) | 5, 8 | 2.82 | 3.76 |
| Chr3 | MRPS22 OT | TAATGAAGCCCTGAACAT (+) | 14 | GTCCAGTTAAGCTCTTTA (+) | 9, 7 | 2.63 | 4.55 |
| Chr17 | 69.9 Mb OT | — | 22 | AATATGGTAAACTTTGAA (+) AATCAGGTAAGTATTTCA (−) | 7, 6 | 4.21 | 4.66 |
| ChrX | PGK1 OT | TGCTTAAAAAAGAATAT (+) TACCTAGAAGCTGATGGA (−) | 16 | — | 7, 8 | 2.96 | 14.29 |
| ChrX | 122.9 Mb OT | TGCTTTGGCCCTGTGAGT (−) | 21 | GAGATAGGAAGCACTTAA (−) | 7, 8 | 2.85 | 5.19 |
| Chr17 | HS3ST3A1 OT | TCTCGAGAAGCTGAAATT (+) | 20 | GCCCAGGTAATTTTTGTA (+) | 6, 8 | 3.37 | 4.85 |

Left and Right TALEN half-sites are reported in the same chromosomal orientation except for loci displaying the same half-site for both sides with the 2$^{nd}$ site reported in the (−) orientation. Average frequencies (per 10,000) are listed for RAG1B and C-MYC bait libraries.

TABLE 6

Cas9: EMX1 and Cas9: VEGFA off-target site mismatches and translocations

| Bait | Chromosome | Nuclease/Locus | Off-target site sequence (SEQ ID NOS 159-211, respectively, in order of appearance) | Mismatch | Frequency (per 10,000) |
|---|---|---|---|---|---|
| Cas9:Chr2 RAG1B | Cas9: EMX1 | | GAGTCCGAGCAGAAGAAGAA GGGNNN | 0 | 136.25 |
| Cas9:Chr15 RAG1B | MFAP1 OT1 | | GAGTCTAAGCAGAAGAAGAA GAGAGC | 3 | 189.39 |
| Cas9:Chr5 RAG1B | HCN1 OT2** | | GAGTTAGAGCAGAAGAAGAA AGGCAT | 2 | 120.13 |
| Cas9:Chr5 RAG1B | SEMA5A OT3 | | AAGTCTGAGCACAAGAAGAA TGGTGA | 3 | 46.42 |
| Cas9:Chr2 RAG1B | 219.8 Mb OT4 | | GAGGCCGAGCAGAAGAAAGA CGGCGA | 3 | 30.31 |
| Cas9:Chr11 RAG1B | HSD17B12 OT5 | | AAGCCCGAGCAAAGGAAGAA AGGAGA | 4 | 28.48 |
| Cas9:Chr8 RAG1B | 128.8 Mb OT6 | | GAGTCCTAGCAGGAGAAGAA GAGGCA | 3 | 16.35 |
| Cas9:ChrX RAG1B | 53.4 Mb OT7 | | GAGTCCGGGAAGGAGAAGAA AGGCTC | 3 | 8.11 |
| Cas9:Chr5 RAG1B | DPYSL3 OT8 | | GAGCCGGAGCAGAAGAAGGA GGGAGG | 3 | 6.21 |
| Cas9:Chr11 RAG1B | MTA2 OT9 | | GAATCCAAGCAGAAGAAGAG AAGGAG | 4 | 5.95 |
| Cas9:Chr6 RAG1B | WASF1 OT10 | | AAGTCAGAGCAGAAAAAGAG AGGACA | 4 | 5.41 |
| Cas9:Chr6 RAG1B | 9.1 Mb OT11 | | ACGTCTGAGCAGAAGAAGAA TGGACA | 3 | 1.34 |
| Cas9:Chr1 RAG1B | TCEA3 OT12 | | AAGTCCGAGGAGAGGAAGAA AGGGTT | 3 | 1.14 |
| Cas9:Chr13 RAG1B | 27.7 Mb OT13 | | GAGTAGGAGCAGGAGAAGAA GGAGGA | 4 | 1.08 |
| Cas9:Chr6 RAG1B | Cas9: VEGFA | | GGGTGGGGGGAGTTTGCTCC TGGNNN | 0 | 190.26 |
| Cas9:Chr15 RAG1B | IGDCC3 OT1** | | GGATGGAGGGAGTTTGCTCC TGGGGT | 2 | 176.22 |
| Cas9:Chr17 RAG1B | KRT42P OT2 | | TAGTGGAGGGAGCTTGCTCC TGGCTG | 4 | 165.88 |
| Cas9:Chr1 RAG1B | 99.3 Mb OT3** | | GGGGAGGGGAAGTTTGCTCC TGGCAT | 3 | 136.19 |
| Cas9:Chr12 RAG1B | LINC01257 OT4** | | GGGAGGGTGGAGTTTGCTCC TGGGA | 3 | 72.27 |
| Cas9:Chr12 RAG1B | CACNA2D4 OT5** | | CGGGGAGGGAGTTTGCTCC TGGGA | 3 | 66.03 |
| Cas9:Chr22 RAG1B | PVALB OT6 | | GGGTGGGGGAGTTTGCCCC AGGCCA | 1 | 49.04 |
| Cas9:Chr6 RAG1B | 14.3 Mb OT7 | | GTGGGGGTAGAGTTTGCTCC AGGTGT | 4 | 38.70 |
| Cas9:Chr22 RAG1B | 19.6 Mb OT8 | | GAGGGGGAGCAGTTTGCTCC AGGTGA | 4 | 33.47 |
| Cas9:Chr5 RAG1B | 32.9 Mb OT9 | | GCGTGGGGGGTGTTTGCTCC CGGGCA | 2 | 19.33 |

TABLE 6-continued

Cas9: EMX1 and Cas9: VEGFA off-target site mismatches and translocations

| Bait | Nuclease/ Chromosome | Locus | Off-target site sequence (SEQ ID NOS 159-211, respectively, in order of appearance) | Mismatch | Frequency (per 10,000) |
|---|---|---|---|---|---|
| Cas9: RAG1B | Chr17 | 47.3 Mb OT10 | CTGGTGGGGGAGCTTGCTCC AGGGAA | 5 | 18.04 |
| Cas9: RAG1B | Chr11 | 67.5 Mb OT11 | AGGAAGGAGGAGTTAGCTCC TGGGGG | 5 | 16.66 |
| Cas9: RAG1B | Chr5 | MAP3K1 OT12 | GGTGGGGGTGGGTTTGCTCC TGGTAT | 4 | 15.86 |
| Cas9: RAG1B | Chr11 | DSCAML1 OT13 | GGGCAAGGGGAGGTTGCTCC TGGAGA | 4 | 15.63 |
| Cas9: RAG1B | Chr3 | 128.2 Mb OT14 | AGGTGGTGGGAGCTTGTTCC TGGCTT | 4 | 15.12 |
| Cas9: RAG1B | Chr1 | PCNXL2 OT15 | GGAGGAGGGGAGTCTGCTCC AGGTTT | 4 | 14.02 |
| Cas9: RAG1B | Chr11 | KIAA1549L OT16 | AGCTGAGGGGAGCTTGCTCT GGGCTG | 5 | 12.31 |
| Cas9: RAG1B | Chr4 | TRMT44 OT17 | GAGTGGGTGGAGTTTGCTAC AGGCAG | 3 | 12.12 |
| Cas9: RAG1B | Chr13 | ATP8A2 OT18 | GGTTGAGGGGAGTCTGCTCC AGGCTT | 3 | 11.80 |
| Cas9: RAG1B | Chr1 | TRIM62 OT19 | GGGTGGGTGGAGTTTGCTAC TGGCAT | 2 | 10.41 |
| Cas9: RAG1B | Chr20 | 56.1 Mb OT20 | AGGGAGGAGGAATTTGCTCC AGGAGT | 5 | 9.96 |
| Cas9: RAG1B | Chr17 | 32.9 Mb OT21 | GGGGGTGGGACTTTGCTCC AGGGCC | 3 | 8.65 |
| Cas9: RAG1B | Chr22 | SUN2 OT22 | GGGCAGAGGGAGTTAGCACC GGGCGT | 5 | 7.95 |
| Cas9: RAG1B | Chr16 | 8.7 Mb OT23 | AAGTAAGGGAAGTTTGCTCC TGGTCC | 5 | 6.11 |
| Cas9: RAG1B | Chr11 | 3.4 Mb OT24 | AGGAAGGAGGAGTTAGCTCC TGGGGG | 5 | 5.69 |
| Cas9: RAG1B | Chr11 | 71.4 Mb OT25 | AGGAAGGAGGAGTTAGCTCC TGGGGG | 5 | 5.52 |
| Cas9: RAG1B | Chr10 | 124.7 Mb OT26 | AGCTGGAGGGAGTTTGCCCC AGGTGA | 4 | 5.03 |
| Cas9: RAG1B | Chr5 | 7.0 Mb OT27 | GAGGGTGGGAGTTTACTCC TGGAAG | 4 | 4.72 |
| Cas9: RAG1B | Chr20 | C20orf62 OT28 | GGGTGAGGGGAATAAACTCC AGGGTG | 5 | 3.80 |
| Cas9: RAG1B | Chr22 | 38.2 Mb OT29 | AGGTCGGGGGAGTTAGATCC CGGGGT | 4 | 3.66 |
| Cas9: RAG1B | Chr11 | 47.2 Mb OT30 | GGGGAGGGGAGGGTGCTCC AGGCAG | 3 | 3.47 |
| Cas9: RAG1B | ChrX | 19.1 Mb OT31 | GGGAGGGAGAGTTTGTTCC AGGAAA | 3 | 3.38 |
| Cas9: RAG1B | Chr21 | RUNX1 OT32 | AAGTGGGAAGAGTTTGTTCC AGGCTC | 5 | 2.96 |
| Cas9: RAG1B | Chr12 | C12orf39 OT33 | GGGAGGGGCAGGTTGCTCC AGGATA | 3 | 2.58 |

TABLE 6-continued

Cas9: EMX1 and Cas9: VEGFA off-target site mismatches and translocations

| Bait | Nuclease/Chromosome | Locus | Off-target site sequence (SEQ ID NOS 159-211, respectively, in order of appearance) | Mismatch | Frequency (per 10,000) |
|---|---|---|---|---|---|
| Cas9:Chr11 RAG1B | NAV2 | OT34 | AGGTAGGAGAAGCTTGCTCC TGAGAT | 6 | 2.45 |
| Cas9:Chr3 RAG1B | LINC00885 | OT35 | GGTGGGGGAGAGCTAGCTCC GGGAGG | 5 | 2.41 |
| Cas9:Chr8 RAG1B | 28.4 Mb | OT36 | AAGTGGGAGGAGACTGCTCC AGGTAG | 5 | 1.80 |
| Cas9:Chr10 RAG1B | 6.7 Mb | OT37 | AAATGGGGGAGTTTGCCCC CCGGAG | 5 | 1.52 |
| Cas9:Chr19 RAG1B | 18.5 Mb | OT38 | GGGGGCGGGGAGGTTGCCCC GGGGAA | 4 | 1.52 |

Mismatches to target sequences are listed in underlined text. Average frequencies are listed (Cas9: EMX1 N = 3; Cas9: VEGFA N = 3). Double Asterisks (**) represent sites previously identified[20].

TABLE 7

Translocation cloning and off-target oligos

| Name | Sequence 5'→3' ** (SEQ ID NOS 212-275, respectively, in order of appearance) | Purpose |
|---|---|---|
| *I-SceI off-target (OT) oligos* | | |
| Chr11_18.7 Mb_F | AGC CCC GTC TTC TCT GAA TG | 1 kb amplicon; OT site 800 bp / 200 bp |
| Chr11_18.7 Mb_R | CGT TGA GCT GCT TTT TCC TC | |
| Chr8_31.4 Mb_F | GCA ACA CGG TGT GGT ATT TC | 980 bp amplicon OT site 600 bp / 380 bp |
| Chr8_31.4 Mb_R | TGA ACC AAT CCT GAC ATT GC | |
| Chr11_29.5 Mb_F | TTT GGA AAC AAG CCC AGT TG | 1,419 bp amplicon; 2 OT sites 250 bp / 800 bp / 350 bp |
| Chr11_29.5 Mb_R | TGA CCC AGA ATT CCT TCT TC | |
| CACNA1E_F | GGT GGT TCC TGA GTG TTT CC | 995 bp amplicon; OT site 300 bp / 695 bp |
| CACNA1E_R | TGG CCA AAA GTC ATG AAG TG | |
| Chr20_11.4 Mb_F | GGT TGC CAT TGT GAT TCC TC | 1 kb amplicon; OT site 700 bp / 300 bp |
| Chr20_11.4 Mb_R | GGC ATA AAC CCA CAA AAA GG | |
| GLYAT_F | CCT TAG CCC ATG GAT TCT ACC | 964 bp amplicon; OT site 220 bp / 744 bp |
| GLYAT_R | TCA GTT TAC CCC AAC CAA GC | |
| Chr2_119.9 Mb_F | TGC TGT GGC TTG AAT GTC TC | 900 bp amplicon; OT site 800 bp / 100 bp |
| Chr2_119.9 Mb_R | ACT TCT GAG GGG CCT TTG TC | |
| *Oligos for T7 Endo I* | | |
| RAG1_F | CCC CCT GGA AGA CTG CTT TA | 690 bp amplicon; 470 bp / 220 bp Cas9: RAG1B site |

TABLE 7-continued

Translocation cloning and off-target oligos

| Name | Sequence 5'→3' ** (SEQ ID NOS 212-275, respectively, in order of appearance) | Purpose |
|---|---|---|
| RAG1_R | AGG ACT GCT GGA GAT TGC TC | |
| RAG1B_OT1_F | TTG GTT GCC CAT CTT ATT CC | 700 bp amplicon; OT site 220 bp / 480 bp |
| RAG1B_OT1_R | AGC TAA ACC TGC CTG CAG AA | |
| RAG1B_OT2_F | AAT AAC TTG CAG CCA TTC CA | 700 bp amplicon; OT site 180 bp / 520 bp |
| RAG1B_OT2_R | TAA ATT GCC CAT GAT TGC AC | |

EM-PCR adapter oligos

| Name | Sequence | Purpose |
|---|---|---|
| Universal oligo | /5phos/ TAA CCA GCC C /3InvdT/ | Suppress adapter-ended amplification |
| Priming oligo | GTA ATA CGA CTC ACT ATA GGG CAC GCG TGG TCG ACG GCC CGG GCT GGT TAT | Contains adapter primer |

RAG1 A/B

| Name | Sequence | Purpose |
|---|---|---|
| Bio RAG1A/B - F1 | /5BiosG/ AGG ACT GCT GGA GAT TGC TC | Bio-PCRI |
| RAG1A/B - F2 I5 M00B | TAC ACT CTT TCCCTA CAC GACGCT CTT CCG ATC TGA GAG GGT TTC CCC TCA AAG | Miseq tail |
| RAG1A/B - F2 I5 M02B | TAC ACT CTTTCC CTA CACGAC GCT CTT CCG ATC TTG GAG AGG GTT TCC CCT CAA AG | Miseq tail multiplex |
| RAG1A/B - F2 I5 M03B | TAC ACT CTTTCC CTA CACGAC GCT CTT CCG ATC TCA TGA GAG GGT TTC CCC TCA AAG | Miseq tail multiplex |
| RAG1A/B - F2 I5 M04B | TAC ACT CTTTCC CTA CACGAC GCT CTT CCG ATC TGC TCG AGA GGG TTT CCC CTC AAA G | Miseq tail multiplex |
| RAG1A/B - F2 I5 M05B | TAC ACT CTTTCC CTA CACGAC GCT CTT CCG ATC TGC CAT GAG AGG GTT TCC CCT CAA AG | Miseq tail multiplex |
| RAG1A/B - F2 I5 M06B | TAC ACT CTTTCC CTA CACGAC GCT CTT CCG ATC TAT ATC GGA GAG GGT TTC CCC TCA AAG | Miseq tail multiplex |
| AP2 17 | TCT CGG CATTCC TGC TGAACC GCT CTT CCG ATC TAC TAT AGG CAC GCG TGG T | Adapter primer; Miseq tail reverse complement |
| P5 | AAT GAT ACGGCG ACCACC GAG ATC TAC ACT CTTTCC CTACAC GAC GCT | Miseq tail PCRIII |
| P7 | CAA GCA GAAGAC GGCATA CGA GAT CGG TCT CGGCAT TCCTGC TGA ACC | Miseq tail PCRIII reverse |

RAG1 C/D

| Name | Sequence | Purpose |
|---|---|---|
| Bio RAG1C/D - F1 | /5BiosG/ CCT GAG AAC AAT GAA AAC AAG TC | Bio-PCRI |
| RAG1C/D - F2 I5 M00C | TAC ACT CTTTCC CTACAC GAC GCTCTT CCG ATC TAC CAA TAT CAA TAT CCC ACT GAT G | Miseq tail |

TABLE 7-continued

Translocation cloning and off-target oligos

| Name | Sequence 5'→3' ** (SEQ ID NOS 212-275, respectively, in order of appearance) | Purpose |
|---|---|---|
| RAG1C/D - F2 I5 M02C | *TAC ACT CTT TCCCTA CAC GAC GCT CTT CCG ATC T*CG ACC AAT ATC AAT ATC CCA CTG ATG | Miseq tail multiplex |
| RAG1C/D - F2 I5 M04C | *TAC ACT CTTTCC CTA CACGAC GCT CTT CCG ATC T*CA CGA CCA ATA TCA ATA TCC CAC TGA TG | Miseq tail multiplex |
| RAG1C/D - F2 I5 M06C | *TAC ACT CTTTCC CTA CACGAC GCT CTT CCG ATC T*GA CTC GAC CAA TAT CAA TAT CCC ACT GAT G | Miseq tail multiplex |

Bridge adapter oligos (LAM-PCR)

| Name | Sequence 5'→3' | Purpose |
|---|---|---|
| ssA-upper-TN | GCG ACT ATA GGG CAC GCG TGG TNN NNN-/3AmMO/ | Common bridge oligo |
| ssA-lower | /5Phos/ CCA CGC GTG CCC TAT AGT CGC-/3AmMO/ | To link A-tailed DNA |
| ssA-lower-A | /5Phos/ ACC ACG CGT GCC CTA TAG TCG C-/3AmMO/ | To link G-, C-, T-tailed or blunt DNA |

Cas9: RAG1A - OT

| Name | Sequence 5'→3' | Purpose |
|---|---|---|
| Bio DAZAP - F1A | /5BiosG/ TTC CCT GTA ACT TGG GAT GG | Bio-PCRI |
| DAZAP - F2A I5 M00F | *TAC ACT CTTTCC CTA CACGAC GCT CTT CCG ATC T*TG CCC AGA AAT CAG AAC AAC | Miseq tail |
| DAZAP - F2A I5 M02F | *TAC ACT CTTTCC CTA CACGAC GCT CTT CCG ATC T*AG TGC CCA GAA ATC AGA ACA AC | Miseq tail multiplex |
| DAZAP - F2A I5 M03F | *TAC ACT CTTTCC CTA CACGAC GCT CTT CCG ATC T*TC ATG CCC AGA AAT CAG AAC AAC | Miseq tail multiplex |
| DAZAP - F2A I5 M04F | *TAC ACT CTTTCC CTA CACGAC GCT CTT CCG ATC T*GA TCT GCC CAG AAA TCA GAA CAA C | Miseq tail multiplex |
| DAZAP - F2A I5 M05F | *TAC ACT CTTTCC CTA CACGAC GCT CTT CCG ATC T*CT GAA TGC CCA GAA ATC AGA ACA AC | Miseq tail multiplex |
| Bio 12_47 + F1 | /5BiosG/ GGA CAA CAA CCC CCA GTT AG | Bio-PCRI |
| 12_47 + F2A I5 M00G | *TAC ACT CTTTCC CTA CACGAC GCT CTT CCG ATC T*TG TGG TAA AGG AGA CAA TGC T | Miseq tail |
| 12_47 + F2A I5 M02G | *TAC ACT CTT TCCCTA CAC GACGCT CTT CCG ATC T*CT TGT GGT AAA GGA GAC AAT GCT | Miseq tail multiplex |
| 12_47 + F2A I5 M03G | *TAC ACT CTTTCC CTA CACGAC GCT CTT CCG ATC T*GA CTG TGG TAA AGG AGA CAA TGC T | Miseq tail multiplex |
| 12_47 + F2A I5 M04G | *TAC ACT CTTTCC CTA CACGAC GCT CTT CCG ATC T*AC GTT GTG GTA AAG GAG ACA ATG CT | Miseq tail multiplex |
| 12_47 + F2A I5 M05G | *TAC ACT CTTTCC CTA CACGAC GCT CTT CCG ATC T*TG ACA TGT GGT AAA GGA GAC AAT GCT | Miseq tail multiplex |

TABLE 7-continued

Translocation cloning and off-target oligos

| Name | Sequence 5'→3' ** (SEQ ID NOS 212-275, respectively, in order of appearance) | Purpose |
|---|---|---|
| TALEN sites | | |
| Bio ATM + F1 | /5BiosG/ CTG CTG CCG TCA ACT AGA AC | Bio-PCRI |
| ATM + F2 I5 M00H | <u>*TAC ACT CTT*</u>*TCC CTA CACGAC GCT CTT CCG ATC T*AT TTA AGC GCC TGA TTC GAG | Miseq tail multiplex |
| ATM + F2 I5 M02H | <u>*TAC ACT CTT*</u>*TCC CTA CACGAC GCT CTT CCG ATC T*CG ATT TAA GCG CCT GAT TCG AG | Miseq tail multiplex |
| ATM + F2 I5 M03H | <u>*TAC ACT CTT*</u>*TCC CTA CACGAC GCT CTT CCG ATC T*TC AAT TTA AGC GCC TGA TTC GAG | Miseq tail multiplex |
| ATM + F2 I5 M04H | <u>*TAC ACT CTT*</u>*TCC CTA CACGAC GCT CTT CCG ATC T*AT CTA TTT AAG CGC CTG CGA G | Miseq tail multiplex |
| ATM + F2 I5 M05H | <u>*TAC ACT CTT*</u>*TCC CTA CACGAC GCT CTT CCG ATC T*CC GCG ATT TAA GCG CCT GAT TCG AG | Miseq tail multiplex |
| ATM + F2 I5 M05H2 | <u>*TAC ACT CTT*</u>*TCC CTA CACGAC GCT CTT CCG ATC T*TG TAC ATT TAA GCG CCT GAT TCG AG | Miseq tail multiplex |
| Bio MYC + F1 | /5BiosG/ CGA AAC TTT GCC CAT AGC AG | Bio-PCRI |
| MYC + F2 I5 M00I | <u>*TAC ACT CTT*</u>*TCC CTA CACGAC GCT CTT CCG ATC T*CT TAC AAC ACC CGA GCA AGG | Miseq tail multiplex |
| MYC + F2 I5 M03I | <u>*TAC ACT CTT*</u>*TCC CTA CACGAC GCT CTT CCG ATC T*AG CCT TAC AAC ACC CGA GCA AGG | Miseq tail multiplex |
| MYC + F2 I5 M041I | <u>*TAC ACT CTT*</u>*TCC CTA CACGAC GCT CTT CCG ATC T*CT CGC TTA CAA CAC CCG AGC AAG G | Miseq tail multiplex |
| MYC +F2 I5 M05I | <u>*TAC ACT CTT*</u>*TCC CTACAC GACGCT CTT CCG ATC T*TG TAT CTT ACA ACA GAG CAA GG | Miseq tail multiplex |

**Color code: Underlined = adapter sequence complementarity; non-bolded = multiplex sequence; italicized and underlined = Terminal ends for MiSeq; italicized and not underlined = Internal MiSeq priming sequence; /5phos/ = 5' phosphorylation; /3InvdT/ = 3' inverted dT; /5BiosG/ = 5' Biotin; /3AmMO/ = 3' Amino modified.

TABLE 8

Cas9: RAG1B and I-SceI off-target site mismatches and translocations

| Bait | Nuclease/ Chromosome | Locus | Off-target site sequence (SEQ ID NOS 276-288, respectively, in order of appearance) | Mismatch | Frequency (per 10,000) |
|---|---|---|---|---|---|
| Cas9: RAG1B | Chr11 | Cas9: RAG1B | GACTTGTTTTCATTGTTCTC AGGNNN | 0 | NA |
| Cas9: RAG1B | Chr14 | ZC3H14 OT1 | TCCTTGTTTTCATTGTTCTC TGGTGG | 2 | 289.64 |
| Cas9: RAG1B | Chr4 | 120.5 Mb OT2 | CATTTGTTTTCATTGTTCTC TGGCTG | 2 | 37.42 |
| Cas9: RAG1B | NA | I-SceI | NNN TAGGGATAACAGGGTAAT NNN | 0 | NA |

TABLE 8-continued

Cas9: RAG1B and I-SceI off-target site mismatches and translocations

| Bait | Nuclease/ChromosomeLocus | | Off-target site sequence (SEQ ID NOS 276-288, respectively, in order of appearance) | Mismatch | Frequency (per 10,000) |
|---|---|---|---|---|---|
| Cas9: RAG1B | Chr11 | 18.7 Mb OT1 | GTC TTGGGATAACAGGGCAAA GCA | 3 | 28.85 |
| Cas9: RAG1B | Chr8 | 31.4 Mb OT2 | ATT TTGGGATAACAGGGCAAT ACT | 2 | 8.45 |
| Cas9: RAG1B | Chr11 | 29.5 Mb OT3* | TTG TAGGGATACCAGGTTTAT TTC | 3 | 6.97 |
| Cas9: RAG1B | Chr1 | CACNA1E OT4 | GGC TAGGGATACCAGGTCAAA CAA | 4 | 5.20 |
| Cas9: RAG1B | Chr11 | GLYAT OT5 | CAC TAGGGATAACAGGCTATT CGG | 2 | 5.17 |
| Cas9: RAG1B | Chr20 | 11.4 Mb OT6 | TAC TAGGGATACCAGGGTCAT TCA | 2 | 4.86 |
| Cas9: RAG1B | Chr9 | 24.8 Mb OT7 | TGC TAGGGATAACAGGTTGAA GGT | 3 | 3.64 |
| Cas9: RAG1B | Chr6 | CCND3 OT8 | CAG TAGGGATAACAGGGCTGT TGA | 3 | 3.54 |
| Cas9: RAG1B | Chr2 | 119.9 Mb OT9 | CAC TAGGGATGCCAGGGTGAA CAA | 4 | 1.4 |

Mismatches to target sequences are listed in underlined text. Average frequencies are listed (Cas9: RAG1B N = 6; I-SceI N = 3). Asterisk (*) indicates locus with 2 identical off-target sequences.

Example 3: Detecting DNA Double-Stranded Breaks in Mammalian Genomes by Linear Amplification-Mediated High-Throughput Genome-Wide Translocation Sequencing Unbiased, high-throughput assays to detect and quantify DNA double-stranded breaks (DSBs) genome-wide in mammalian cells will be of great value to both basic studies of mechanisms that generate and repair endogenous DSBs and to more applied studies, such as evaluating on- and off-target activities of designer nucleases. Here we describe a linear amplification-mediated high-throughput genome-wide sequencing (LAM-HTGTS) method for detecting genome-wide "prey" DSBs via their translocation in cells to a fixed "bait" DSB. A custom bioinformatic pipeline identifies prey sequences that contribute to junctions and maps them across the genome. LAM-HTGTS differs from related approaches that have been described in that it detects diverse broken end structures with nucleotide level resolution. Expertise in nucleic acid methods and next-generation sequencing analysis are necessary for library generation and data interpretation. LAM-HTGTS assays are sensitive, reproducible, relatively inexpensive, scalable, and straightforward to implement with a turnaround time of less than one week.

Introduction.

In somatic mammalian cells, a large proportion of DNA double-stranded breaks (DSBs) are rejoined by the classical non-homologous DNA end-joining pathway[1]. Such rejoining often may be accompanied by end-processing including resections that can lead to deletion of sequences on either side of the break-site[2]. A small fraction of DSBs can participate in chromosomal translocations, which frequently result from end joining of two distinct DSBs[3]. In this regard, we consider all events in which two separate DSBs are fused as translocations, including those that result in joining two closely linked DSBs in the same chromosome to generate intra-chromosomal deletions[3]. The frequency of translocations between two sites in the genome is a function of the frequency at which DSB ends at the two sites are available to be translocated and the frequency at which they are physically juxtaposed[3]. The frequency at which DSBs are available is influenced both by their rate of generation and by how long they persist before being rejoined[3]. DSBs are intrinsic to various biological processes such as transcription, are programmed to generate antigen receptor diversification in lymphocytes, and are key substrates for translocations, deletions and amplifications associated with various cancers[3,4]. There is also great interest currently in defining the range of DSBs across the genome generated by engineered nucleases used for gene editing[5].

There have been many methods employed to locate genomic DSBs over the years. Among those developed and applied more recently are chromatin immunoprecipitation and sequencing (ChIP-seq) approaches to detect DSB-associated proteins that are enriched in regions spanning DSBs[6-8], DSB-seq[9] and direct in situ breaks labeling, enrichment on streptavidin and next generation sequencing (BLESS[10]) methods to tag broken ends in vitro or in situ. In addition, high-throughput genome-wide translocation sequencing (HTGTS[11]) and translocation-capture sequencing (TC-seq[12]) were developed as in vivo translocation-based methods to detect translocations genome-wide. Two additional in vivo DSB tagging methods including integrase-deficient lentiviral vectors (IDLV[13,14]) and genome-wide, unbiased identification of DSBs enabled by sequencing (GUIDE-seq[15]) have been described in the context of identifying off-target DSBs of CRISPR/Cas9 nucleases. As described herein, we have developed a greatly improved HTGTS method termed linear amplification-mediated HTGTS (LAM-HTGTS[16]) and described its application for detecting off-target activities of various types of engineered nucleases and also for a wide-range of other classes of cellular DSBs[16-19]. Here, we describe in depth the LAM-HTGTS protocol and also discuss applications and comparisons to the other DSB detection approaches.

Development of HTGTS.

Figure 18A:
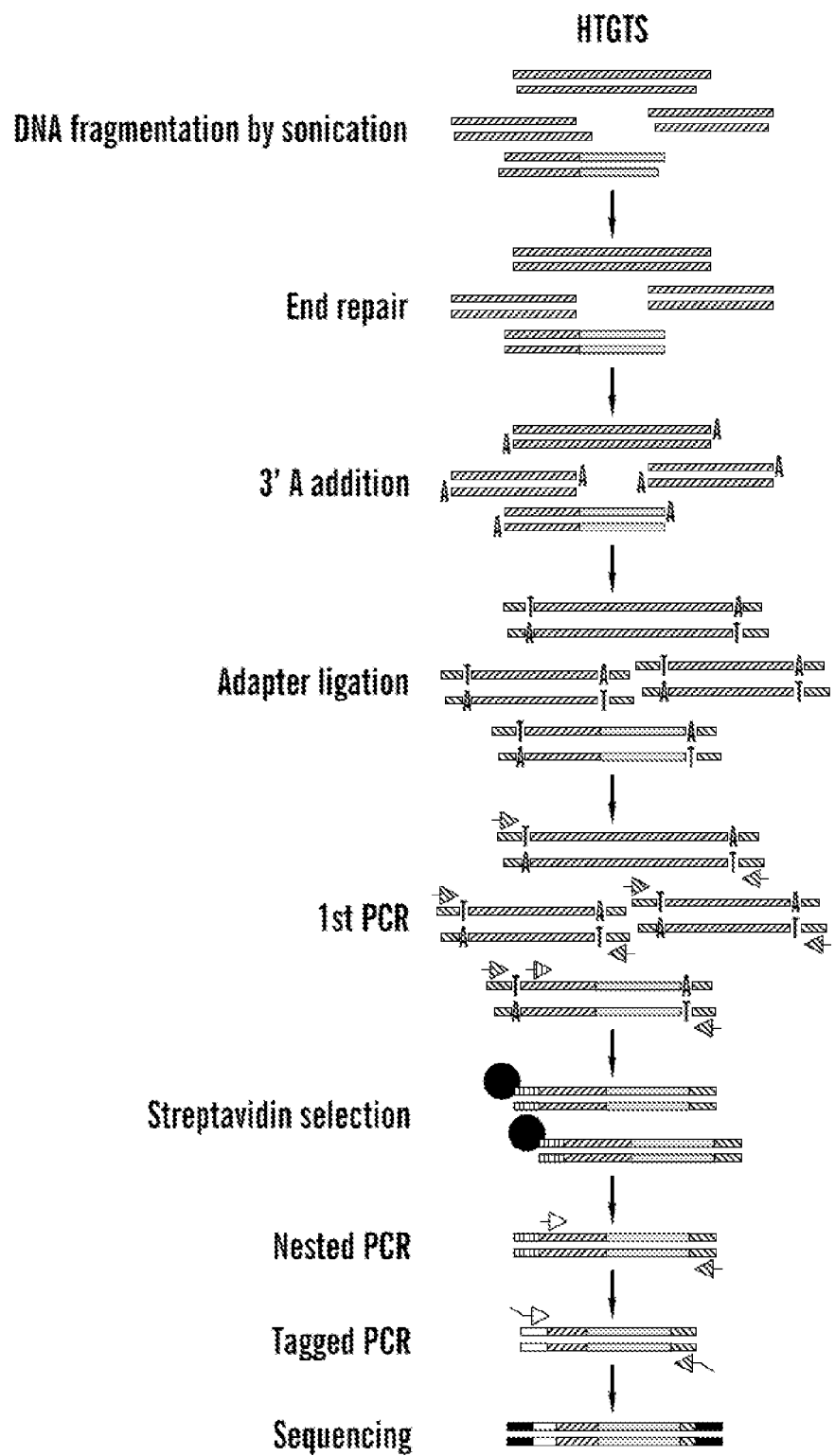
FIGS. 18A-18C depict a step-by-step overview of HTGTS methods.

Based on our studies of the frequent joining of two DSBs at target sites 100 kb apart in the mouse immunoglobulin heavy chain (IgH) locus[20], we developed HTGTS to identify DSBs genome-wide based on their ability to translocate to a fixed "bait" DSB generated by the yeast I-SceI nuclease at its 18-bp recognition site inserted at a desired location in the mouse genome[11]. This method leveraged aspects of whole-genome library construction and next generation sequencing[21,22] for high-throughput junction cloning[11,23,24]. HTGTS provides nucleotide-level resolution of translocation junctions that fuse the broken ends of the genome-wide "prey" DSBs to the bait I-SceI DSBs (FIG. 18A). Prey DSBs can represent any other DSB in the cell that is not the targeted bait DSB. Numerous control studies demonstrated that the HTGTS background was very low[11]. HTGTS not only allows sensitive detection of DSBs genome-wide, but also allows in depth studies of mechanisms by which these prey DSBs translocate to bait DSBs. At the time of the initial HTGTS studies, it was generally considered that there were no I-SceI targets in the mammalian genome. The utility of the original approach to detect recurrent DSBs genome-wide was evidenced by the ability of HTGTS to precisely identify multiple "off-target" I-SceI DSB hotspots across the mouse genome, many of which were quite divergent from the I-SceI consensus sequence, but all of which could be cleaved by I-SceI in vitro[11]. The approach also detected DSBs generated by the activation-induced cytidine deaminase (AID) in IgH switch (S) regions during class switch recombination (CSR)[11] or those generated by the RAG-endonuclease in antigen receptor loci during V(D)J recombination[23], as well as general classes of DSBs such as those associated with active transcription start sites[11]

Development of LAM-HTGTS.

Figure 1B:
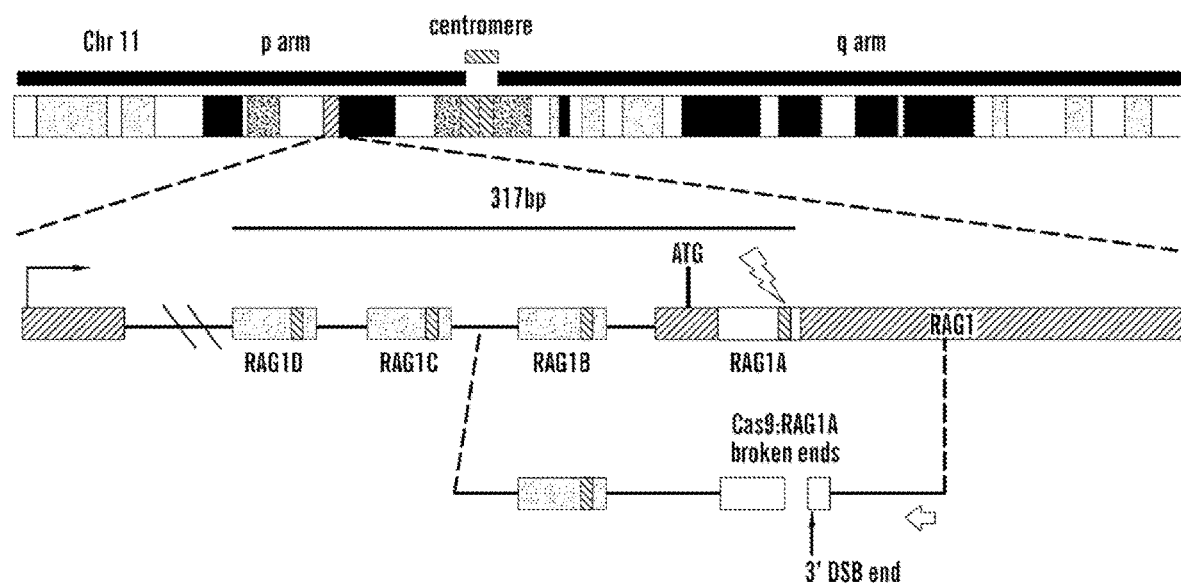
Figure 1C:
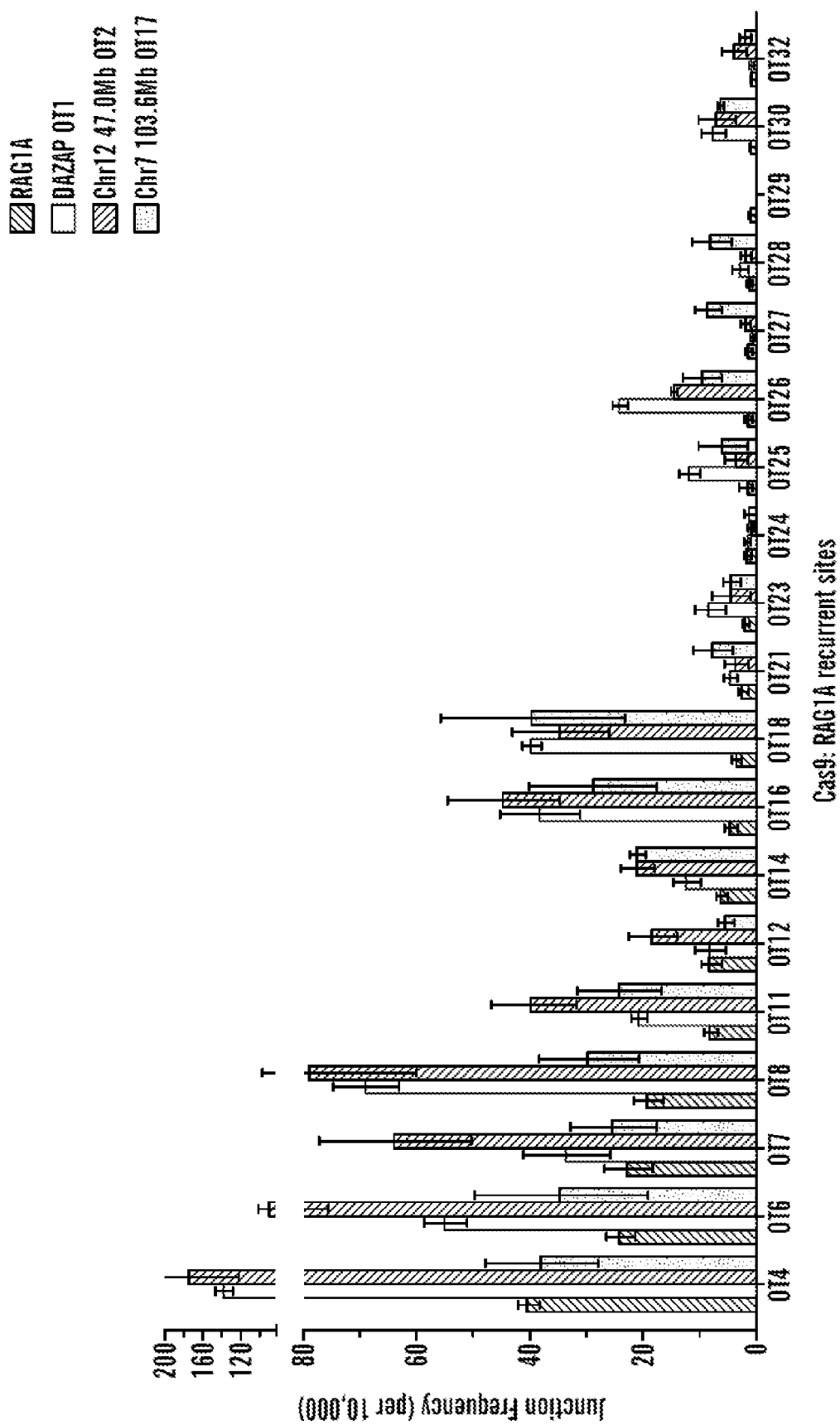

Our original HTGTS method was not optimal because the construction of whole-genome libraries preceded enrichment of target DNA fragments (FIG. 18A). To significantly improve the efficiency and reduce cost, time, and effort, we developed an improved method in which target DNA fragments were enriched first, thereby greatly reduce the amount of unnecessary DNA for adapter ligation. To achieve this, we introduced LAM-PCR[25,26], bridge adapter ligation[7], and major modifications to the HTGTS pipeline, to develop the current LAM-HTGTS method[16] (FIG. 1B). LAM-HTGTS increases junction yields 10-50-fold over the original HTGTS method[16]. In recent studies, we have extensively documented the ability of LAM-HTGTS to map endogenous and ectopic DSBs across mouse and human genomes[16,17] and the utility of this approach for studying mechanisms of DSB generation and repair in the context of various physiological processes, including, for example, in the context of mechanisms of IgH V(D)J recombination, IgH CSR, and translocations associated with these processes[17-19,24,27]. In this regard, we also showed that, beyond the I-SceI nuclease, we could employ LAM-HTGTS bait DSBs generated via engineered nucleases such as Cas9 guide RNA (Cas9: gRNA) nucleases or TALENs[16]. Moreover, we also could sensitively employ endogenous DSBs generated by the RAG endonuclease during V(D)J recombination in developing lymphocytes[18] or IgH CSR DSBs initiated by the AID in activated B lymphocytes[19] as LAM-HTGTS bait DSBs.

To our knowledge, no method, including LAM-HTGTS, is capable of detecting all DSBs that occur in a population of cells over a period of time. In this regard, LAM-HTGTS detects those DSBs genome-wide that translocate to the bait DSB. That being said, our studies have shown that LAM-HTGTS can detect all known classes of recurrent DSBs across the genome, including DSBs introduced by on- or off-target activities of antigen receptor diversification enzymes[17,18] or by on- and off-target activities of engineered nucleases[16]. The assay also detects DSBs that occur at lower frequency individually but are associated with specific cellular process across the genome, such as active transcription start sites[17]. Finally, the assay also detects low-level widespread breaks, such as those generated by ionizing radiation[16].

The versatility of the LAM-HTGTS assay in detecting DSBs genome-wide derives from general principles of translocation, which were revealed in part by the assay itself. Thus, one key to the success of LAM-HTGTS in identifying DSBs genome-wide was the finding that recurrent DSBs can dominate translocation landscapes in mouse and human cells genome-wide regardless of chromosomal location due to cellular heterogeneity in 3-D genome organization[3,16,23]. Another key for various aspects of the application of LAM-HTGTS was the finding that, in the absence of recurrent prey DSBs, relative proximity of bait and prey DSBs becomes a more dominant influence in the frequency at which they translocate[16]. Thus, treating mouse or human cells with γ-irradiation to generate wide spread random DSBs across all chromosomes leads the length of each chromosome to become a translocation "hotspot" for the joining of DSBs generated within it due to proximity effects of sequences within a cis chromosome[3,16,23]. Within a cis chromosome, translocation frequency is further enhanced between sequences within "megabase" or sub-megabase topologically-associated domains (TADs) due to further increased interaction frequencies[3,23,24]. These latter properties allow the sensitivity of LAM-HTGTS DSB detection to be extended by employing bait DSBs on different chromosomes or regions of chromosomes to detect DSBs in proximal regions in cis with increased sensitivity[16].

Overview of the LAM-HTGTS Method.

Figure 18B:
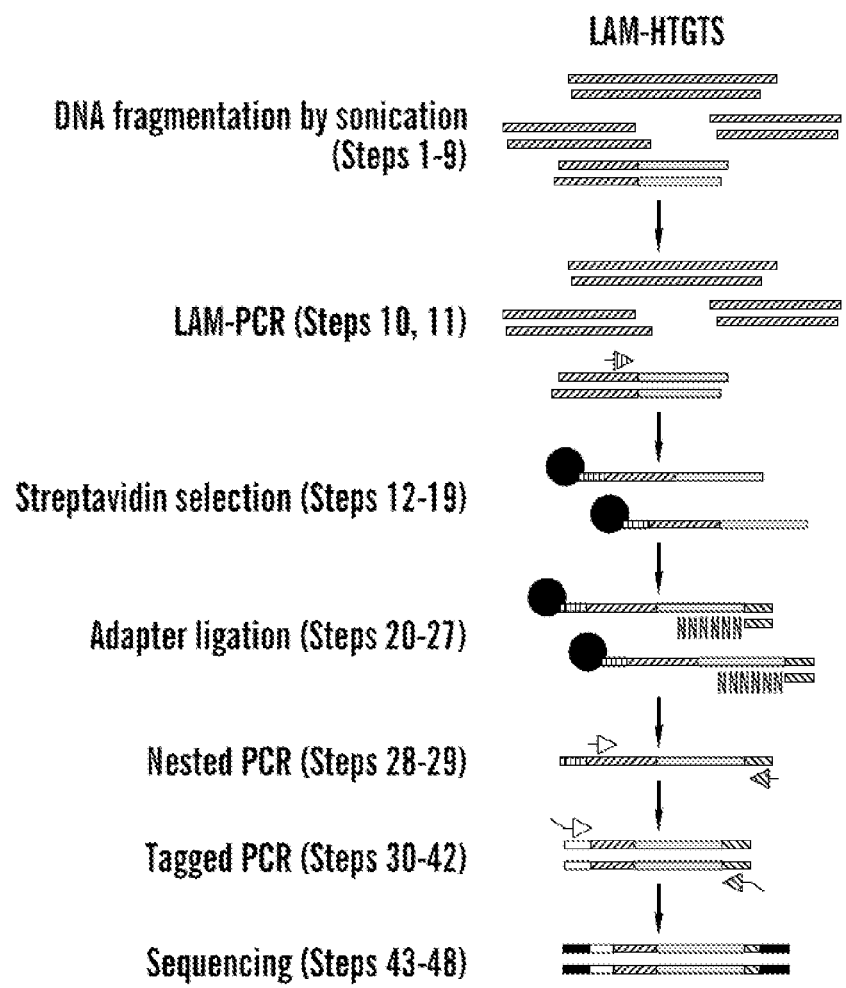
Figure 21:
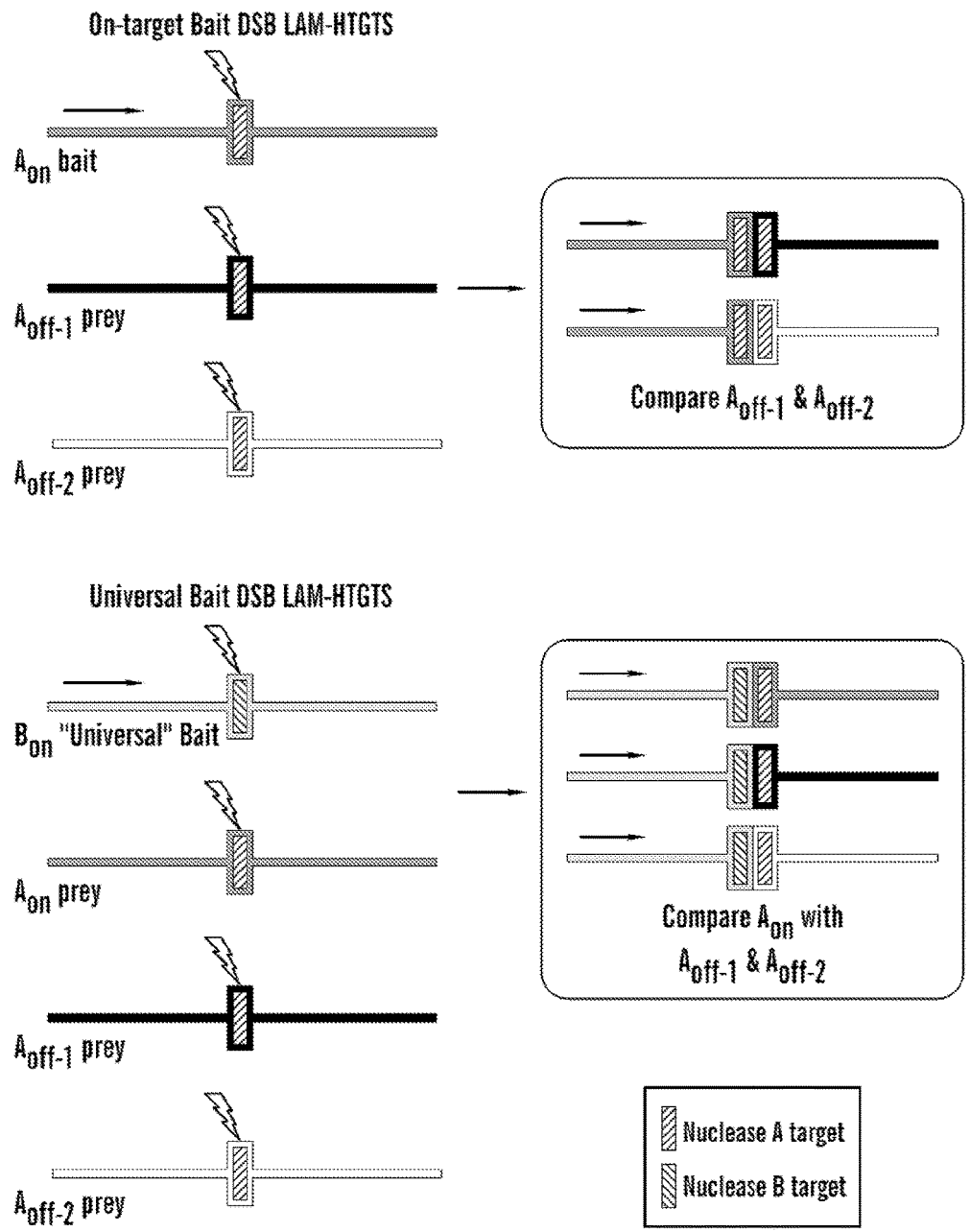
FIG. 21 depicts schematics of the methods described herein. Recurrent off-target activity can be detected either by directly cloning from the on-target DSB to the off-target prey DSBs or by co-expressing a second previously established nuclease which can provide the donor bait DSB necessary to compare the joining rates of the on-target and off-target prey DSBs of the candidate nuclease. Direct bait DSB cloning presents joining events with respect to the on-target site, but suffers from the inability to accurately compare its own on-target activity relative to potential off-target activity. Universal bait DSB cloning provides a tertiary bait DSB that can compare the relative joining rates between predicted on-target sites and empirically derived off-target sites of the candidate nuclease. Furthermore, the off-target sites of the defined universal bait nuclease can also be used as bait DSBs to control for off-target detection frequencies on the initial on-target universal bait chromosome.

After a limited duration of cell culturing to allow for nuclease expression to induce cleavage of the bait break-site and translocation of bait broken ends to other DSBs generated by endogenous (e.g. AID or RAG cleavage sites, transcriptional start sites, etc.) or ectopic mechanisms (e.g. nuclease-generated DSBs), DNA is isolated by a standard proteinase K digestion method. Junctions to bait broken ends (see FIG. 21) are amplified, with directional primers lying on one or the other side(s) of the break-site (or sites) from sheared genomic DNA using LAM-PCR[25]. LAM-PCR with a single 5' biotinylated primer amplifies across the bait sequence into the unknown prey sequence. Junctions-containing single-stranded DNA (ssDNA) are enriched via binding to streptavidin-coated magnetic beads. After washing, bound ssDNA is uni-directionally ligated to a bridge adapter[7]. Adapter-ligated, bead-bound ssDNA fragments are then subjected to a nested PCR step which adds a barcode sequence necessary for de-multiplexing, followed by an optional blocking digest to suppress the potentially large number of uncut and/or perfectly rejoined/minimally-modified bait sequences (see FIGS. 18B, 18C and FIG. 21), and a final PCR step to incorporate Illumina Miseq adapter sequences. Samples are then separated on an agarose gel, and a resulting population of 0.5-1 kb fragments (FIG. 19) are collected and quantified prior to Miseq sequencing.

We also generated a custom pipeline which can be used to characterize the bait-prey junctions from the library of sequence reads and should be sufficient for most LAM- HTGTS applications using long paired-end sequence reads (Illumina) It consists of both third-party stand-alone tools (e.g. aligners) as well as custom programs built in Perl and R, enabling the processing of sequence reads directly off the sequencer into fully annotated translocation junctions in as few as two commands (Table 9). Briefly, library pre-processing steps consist of deconvoluting the barcoded libraries and trimming Illumina primers. The main processing pipeline is made up of three major steps: 1) local read alignment, 2) junction detecting, and 3) results filtering. We use bowtie 2 to perform read alignments[28]. The junction detection algorithm is based on the Optimal Query Coverage (OQC) algorithm from the YAHA read aligner and breakpoint detector[29]. The OQC attempts to achieve the following objective: to optimally infer the full paired-end query sequence from one or more alignments to a reference sequence. The optimal set is determined by using a best-path search algorithm, which enables the detection of not only simple bait-prey junction reads, but also un-joined bait sequences, as well as reads harboring multiple consecutive junctions. The algorithm allows for overlapping alignments which is required for micro-homology analyses and naturally extends to paired-end reads. The final characterization is an ordered set of alignments termed the Optimal Coverage Set (OCS). The library of resulting OCSs is subjected to a number of filters. The precise set of filters and filter parameters used depends largely on the application.

wide range of off-target nuclease-specific DSB activities, including many predicted by cutting algorithms and not found previously and many that were not previously predicted[16]. Other aspects that demonstrate the utility of LAM-HTGTS for such off-target nuclease assays, that have been noted[16,39], and include the following:

1. LAM-HTGTS can be adapted to employ an independent, well-defined engineered nuclease DSB as a universal donor bait DSB that can detect the genome-wide DSB activities of a co-expressed "uncharacterized" engineered nuclease (FIG. 21)[16]. Given that target DSB frequencies of uncharacterized nucleases can be normalized to universal baits, this assay is capable of comparing on-target cutting efficiencies of different nucleases, which is useful for choosing an appropriate nuclease for targeting a desired locus or particular application.
2. DSB detection by LAM-HTGTS can be made even more sensitive. In this regard, due to spatial proximity effects mentioned above, off-target breaks on the same chromosome as the bait DSB have a higher chance to be captured by LAM-HTGTS[3,16,23]. Thus, the sensitivity of LAM-HTGTS can be further enhanced (by 5 fold or more) by placing bait DSBs in or along each chromosome to look for off-targets in cis within the chromosome.

TABLE 9

List of identified off-targets of SeC9-2 or VEGFA with Cas9: SeC9-2 bait in v-Abl pro-B cells

| Bait | Chromosome | Nuclease/Locus | Off-target site sequence (SEQ ID NOS 300-307, respectively, in order of appearance) | Frequency (per 10,000) |
| --- | --- | --- | --- | --- |
| SeC9-2 | Chr 12 | SeC9-2 | GCCCTAACACCCAGGAACAG GGG | — |
| SeC9-2 | Chr 12 | SeC9-2 off-target 1 | GCCCTAACATCCAGAAACAG GGG | 177 |
| SeC9-2 | Chr 14 | SeC9-2 off target 2 | ACCCTTACATCCAGGAACAG CGG | 13 |
| SeC9-2 | ChrX | SeC9-2 off-target 3 | ACCCTACCACTCAGGAACAG AGG | 7 |
| SeC9-2 | — | VEGFA* | GGGTGGGGGGAGTTTGCTCC TGG | — |
| SeC9-2 | Chr3 | VEGFA off-target 1 | AGGAGGGAGGGGTTTGCTCC CGG | 42 |
| SeC9-2 | Chr2 | VEGFA off-target 2 | AGTGGGGGGAGTTTGCCCC GGG | 11 |
| SeC9-2 | Chr6 | VEGFA off-target 3 | ACGTGAGGGAGCTTGCTCC AGG | 7 | a. SeC9-2 off-targets are listed in the upper rows with mismatches to target sequence in underlinded text.
b. VEGFA off-targets are listed in the lower rows with mismatches in underlined text.
c. Asterisk (*) indicates that VEGFA gRNA is designed based on human genome, thus has no on-target site in mouse genome.

HTGTS Applications to Detection of Engineered Nuclease Off-Target Activity.

Recently developed engineered nucleases—including meganucleases[30], zinc finger nucleases[31,32], TALENs[33,34], and Cas9:gRNA nucleases[35-38]—require precise targeting of specific DNA sequences and have substantially improved their ability to target virtually any desired genomic location, but comprehensive analyses of the collateral damage associated with these nuclease activities had been lacking[5]. We demonstrated the ability of LAM-HTGTS to reproducibly 3. LAM-HTGTS is able to detect low-level wide-spread breaks generated by a particular designer nuclease or by other agents such as ionizing radiation[16], which provides an important feature not provided by other currently described assays such as GUIDE-seq[15] or IDLV[13]. In this context, universal bait LAM-HTGTS revealed that introducing certain TALENs generated an effect reminiscent of treating cells with ionizing radiation[16].

4. Collateral damage is a key problem for nuclease off-target activities which includes more than just relative frequencies of on- vs off-target DSBs but also the frequency of deletions and translocations between on-target and off-targets and also between off-targets with other off-targets. LAM-HTGTS gives an estimate of such events which, given equal DSB frequencies, occur more frequently for different DSBs that occur on the cis chromosome. Other reported assays, GUIDE-seq[15] or IDLV[13], have not thus far been reported to have been used for this purpose in depth.

5. A unique feature of LAM-HTGTS is that it detects a wide range of broken ends that can be generated by various classes of nucleases, including blunt ends for Cas9:gRNA nucleases, nucleotide overhangs for meganucleases, FokI-domain containing nucleases, paired nickases, and also hairpin-sealed ends from RAG-mediated cleavage[11,16,18,23]. In this context, LAM-HTGTS detected hundreds of off-targets for two tested TALENs as well as robust low-level wide-spread DSB activity[5] and further showed that the vast majority of the many TALEN off-targets resulted from homodimers recognizing a palindromic cleavage site, as opposed to desired heterodimers recognizing two different sites[16]. The versatility of LAM-HTGTS DSB detection, thus, should allow characterization of new classes of designer nucleases such as the recently described Cpf1 CRISPR effector family[40].

6. A key feature reported for LAM-HTGTS but thus far not for other nuclease off-target assays is the ability to readily detect a major class of off-targets that result from targeting of the same site on homologous chromosomes. This point is not trivial because these events can lead to dicentric chromosomes that could promote additional DSBs, translocations, and potentially oncogene amplifications via breakage-fusion-bridge mechanisms[16].

HTGTS Applications to Endogenous DSB Detection and Joining.

Beyond engineered nuclease DSB activities, both original HTGTS and LAM-HTGTS methods can also be used to detect DSBs generated from the cellular environment (e.g. ionizing radiation, chemotherapeutics, viral integration, etc.)[16,18,23]. Both methods also detect DSBs generated via endogenous sources such as transcription-associated DSBs[11,17], programmed DSB-inducing activities in lymphoid cells[11,17-19,23,24,27], and likely could be applied to detect endogenous DSBs that arise from other sources such as oxidative DNA damage or replication stress. More generally, LAM-HTGTS reveals the various classes of DSBs across the genome that can contribute to inter- or intra-chromosomal translocations and deletions, including sources of DSBs that contribute to known oncogenic translocations[17,18].

LAM-HTGTS based studies employed endogenous AID-initiated DSBs in endogenous S regions as bait in B cells activated for IgH CSR[19]. The design of these studies allowed the fate of 14 different AID-target DSBs within a 150 bp region to be followed via a single bait-site LAM-HTGTS primer; these bait-site DSBs joined mainly to targeted S regions 100-200 kb downstream[19]. S regions are long (up to 10 kb) and highly repetitive which limited prior CSR junction studies to standard PCR-based assays that generally yielded only dozens of junctions, all of which occurred at the S region borders but were not fully representative of the dominant core S region driven CSR[41]. However, the LAM-HTGTS assays provide tens of thousands of junctions spreading over the entire length of the repetitive S region, offering hugely expanded data sets and far more mechanistic detail than previously could be generated and was done so by employing this substantially less expensive and time-consuming assay[19]. The CSR studies also revealed how LAM-HTGTS could be used for a sensitive joining and end-resection assay with respect to rejoining of single DSBs, revealing differential effects of a broad range of DNA damage response factors on the resection process[19].

Most recently, LAM-HTGTS has been applied to study the on-target and off-target activities of the RAG V(D)J recombination specific endonuclease using endogenous RAG-generated DSBs as bait[18]. While prior studies detected only a handful of off-target RAG generated DSBs[42], the LAM-HTGTS studies identified thousands of RAG off-target sites, which are tightly restricted within chromosomal loop domains, strongly suggesting a linear tracking model to explain the generation of most RAG off-target events[18].

Comparison of HTGTS with Other Related Methods.

Several other DSB detection assays were developed about the same time as the original HTGTS method[11] or LAM-HTGTS[16] that either leveraged chromosomal translocation cloning or in vivo tagging of broken ends[12,13,15]. Such methods provide higher resolution than ChIP-seq[6-8] and lower background than DSB-seq[9] and BLESS[10]. Thus, we limit comparison below to these more recently developed translocation-based or in vivo tagging-based methods. However, we do note that a recent report indicates the application of BLESS for Cas9 off-target detection using strict custom optimization to address the background[43].

TC-seq[12] has many overlapping features and applications with the original HTGTS method[11], including the use of an I-SceI bait DSB approach to detect prey DSBs. However, the TC-Seq method as described did not allow junction structures to be defined at nucleotide resolution, and thus did not allow precise mapping of I-SceI off-targets[12]. Also, TC-seq studies reported thus far have not employed endogenous DSBs or engineered nuclease-generated DSBs as bait. However, it seems likely that TC-seq method could be readily adapted for use in the various contexts outlined above.

The GUIDE-seq[15] method tags engineered nuclease-induced DSBs with blunt-ended, 5' and 3' end-phosphorothioated, double-stranded DNA (dsDNA) oligos via end-joining; tagged DSBs are then amplified from the inserted dsDNA fragment and mapped genome-wide. GUIDE-seq is very similar to the IDLV DSB detection assayl[13,14] but with higher efficiency than IDLV for DSB detection. In its published form, GUIDE-seq DSB detection was dependent on in vivo blunt end joining mechanisms due to the type of dsDNA oligo tags employed and, thus, would be limited in detecting such broken end structures in the cell. In this regard, detection of DSBs from other types of engineered nucleases or endogenous DSBs with 5' or 3' overhangs may not be readily detected by GUIDE-seq. Despite this blunt end-joining limitation, GUIDE-seq is capable of identifying recurrent Cas9 DSBs throughout the genome. Indeed, GUIDE-seq identified the same major off-targets as LAM-HTGTS for the 2 common guides tested. However, LAM-HTGTS and GUIDE-seq also identified some of the same lower level off-targets, there were also low off-targets uniquely identified by each method. Those differences could be attributable to the different cell lines tested, but could reflect differences in the two assays to detect certain DSBs. LAM-HTGTS could be scaled up to much greater sensitivity, using more material and by using baits on different chromosomes to test these if it were of interest. Finally, the background of GUIDE-seq relative to off-target detection has not be described and, thus, it remains unknown whether this assay could be further scaled up and applied more generally for other types of recurrent DSB detection.

To clone tagged DSBs for GUIDE-seq, sheared input genomic DNA must undergo end-processing and adapter ligation prior to cloning out the <0.001% dsDNA oligo-containing sequences[15]; such an approach was employed for the originally described HTGTS and TC-Seq methods and, at least for HTGTS, was found to present significant financial burden[11,12] (FIG. 18A). LAM-HTGTS directly amplifies relevant sequences from sheared genomic DNA without prior end-modification, A-tailing, and adapter-ligation, averaging an estimated cost of $150/library, about half of which includes in-house Miseq sequencing cost. In this regard, LAM-HTGTS is approximately 5 times less expensive than the original HTGTS method.

Although LAM-HTGTS can compare relative recurrent DSB frequencies, LAM-HTGTS and all other related assays currently cannot readily quantify absolute cutting rates due to inability to differentiate uncut sequences from cut and perfectly rejoined sequences or bait sequence that undergoes rejoining with very limited diversity close to the break site[19]. LAM-HTGTS requires joining of prey DSBs to a known bait DSB and, therefore, cannot be employed from isolated genomic DNA unless those cells generate known recurrent DSBs to serve as bait, such as AID-initiated or RAG initiated DSBs in B lymphocytes[18,19]. Also, LAM-HTGTS only reveals information about the genomic DSBs that join to bait DSBs and does not reveal information about DSBs that are rejoined or just persist as DSBs, although studies based on employing γ-H2AX and 53BP1 foci as a marker for DSBs indicate that most are resolved well within our recommended culture times[44] (see below). Given that translocations between two I-SceI-generated DSBs are approximately 1 per 300 DSB-generated mouse cells upon 24-hour induction by live cell microscopy[45] and 1 per 200-1000 bait DSB-generated cells from our libraries of I-SceI-, Cas9: gRNA-, or TALENs-generated bait DSBs[16,17], at least 200,000 bait DSB-generated cells (~1 µg DNA) are required to identify 1000 translocation junctions, which limits the use of LAM-HTGTS in certain contexts that might provide very little starting material. Recurrent DSBs in highly repetitive regions might also be misrepresented due to mapping difficulties and the potential for mis-priming; such problems are universal for any amplification-based high-throughput sequencing method. Notably, however, LAM-HTGTS has, for example in the case of IgH CSR, been useful for solving such potentially confounding issues[19].

Experimental Design

Samples and Controls.

To prepare samples, sufficient time should be reserved after induction of the recurrent DSBs to facilitate the formation of translocation. In our experiments with regard to different nucleases, we typically culture cells for 48-72 hours after nuclease transfection or induction. Generally, DSBs can be efficiently repaired within 8 hours based on γ-H2AX and 53BP1 foci[44], thus 48-72 hrs should be sufficient for DSBs to be induced and repaired, partially as translocations. Genomic DNA isolation is compatible with various published methods as long as the DNA is fully dissolved and the absorbance 260/280 ratio of genomic DNA is higher than 1.8. With regard to different experimental purposes, one should evaluate the requisite starting material sufficient for generating robust HTGTS libraries. For initial LAM-HTGTS studies, 20-100 mg genomic DNA sampling 0.5-1×10$^6$ Miseq sequence reads are recommended, which should identify thousands of translocations in the context of efficient DSB generation based on our findings with bait DSBs generated by I-SceI, Cas9:gRNA, or TALENs[16,17]. However, the final yield of identified junctions may vary considerably depending on the context of the experiment, genetic backgrounds (e.g. between repair deficient versus wild-type), and most notably, ability to generate sufficient bait DSBs in certain cell types. We generally perform preliminary libraries to confirm that our HTGTS junction yields for a given experimental setting will be sufficient to achieve the goals of the experiment. Means to increase the "junction per amount of DNA" can include increasing expression of the bait DSB, longer culturing periods (though potentially at the cost of affecting junction bias due to selective forces), and deeper sequencing of the library. Artifactual background effects can vary depending on the position and priming strategy of the bait DSB site (see FIG. 21); therefore, proper controls should be included to fully interpret the data. In this regard, generating libraries with the genomic DNA of untreated cells (i.e. no bait DSB) will be a necessary control to help evaluate the primers and level of artifactual background. Generally, libraries with at least 10-fold more junctions than the uncut control libraries with the same set of primers are expected.

Choice of Bait DSB Region.

Each bait DSB provides two broken ends and, thus, two potential bait DSB strategies: either a (+) or (−) chromosomal orientation. Bait sequence within lkb of the targeted DSB should be analyzed to avoid potential repeat sequences as determined by repeat masker (available on the world wide web at repeatmasker.org) which can be prone to junction artifacts due to mispriming. It is recommended to clone the bait sequence region from the target cells of interest and sequence for potential polymorphisms which could disrupt nuclease cutting or priming Finally, it is also suggested, but not required, to identify a rare restriction enzyme site downstream of the bait DSB to suppress germline sequence and to enhance translocations (see below).

Primer Design.

Bait sequence length leading up to the bait DSB can be varied but constrained by the position of primers used and sequencing length limitations. HTGTS uses a nested priming strategy with extension times to cover lkb of sequence per cycle. For 2×250 bp Illumina Miseq, the outer biotinylated locus primer can be positioned up to 400 bp away from the bait DSB, whereas the nested locus primer (nested primer) must be placed within 200 bp (ideally 80-150 bp) of the bait DSB to allow for optimal contiguous junction mapping across bait and prey sequences. Shorter bait sequences limit the amount of junctions identified due to resection of the bait sequence beyond the sequencing primer. Longer bait sequences limit the available sequence on the forward paired read to be uniquely mapped as a translocation partner. This limitation may be partially mitigated if the alignment extends to the reverse paired read. The length of primers range from 20-25 bp, with the intended melting temperature around 58° C. and 60° C. for bio-primer and nested primer, respectively. To multiplex LAM-HTGTS libraries from the same bait we typically include a user-defined barcode sequence (0-10 bp) positioned between the nested primer sequence on the 3' end and a portion of the Illumina-specific sequence on the 5' end of the primer.

Blocking Enzyme (Optional).

Translocations are rare cellular events compared to uncut (germ-line) or local processing of the bait DSB. Thus, to enhance detection of genome-wide DSBs when the bait DSB positive cell population and/or cutting levels at the bait DSBs are low, it is suggested to block the amplification of germ-line sequence by using rare restriction enzymes that will cleave downstream of the bait DSB. To minimize junction loss at the break-site, the blocking enzyme site should be located as close as possible to the downstream side of the bait DSB. Since restriction enzymes have wide-ranging numbers of substrate sites genome-wide, primarily determined by the length of their recognition sequences, enzymes with six or greater base pair recognition are required. Since the blocking step uses PCR amplified DNA, virtually any rare cutting restriction enzyme that has been employed previously for molecular cloning or Southern can be used. Blocking will only suppress but not eliminate all of the germ-line fragments and some germ-line sequences would still be observed. It should be noted that the choice of blocking enzyme should not conflict with nested primers and the bait sequence leading up to and including the break-site. The particular blocking enzyme used will reduce the number of prey junctions harboring the same enzymatic site; blocking germ-line amplification can be omitted in circumstances where the majority of cells are efficiently cutting at their on-target site. Moreover, deeper sequencing can compensate for the omission of enzyme blocking particularly for lower cutting at bait DSBs.

DNA Polymerase.

Any thermo-stable DNA polymerase engineered for PCR should fit the purpose of LAM-HTGTS. We tested both Taq (Qiagen) and Phusion (Thermo Scientific) to prepare LAM-HTGTS libraries, and they showed similar genome-wide profiles. Taq is economical, but its short half-life requires supplementing more polymerase half-way to finish the 100-cycle PCR[16,25,26]. The proofreading activity of Phusion enhances the amount of amplified DNA fragments and can increase fidelity though secondary DNA structures. Nonetheless, the proofreading activity also can degrade primers and single-stranded DNA products in the LAM-PCR step. To minimize this, a higher concentration of dNTPs are used (3-fold higher than with Taq), and back-to back comparison showed no major difference between the HTGTS libraries generated by these two thermal polymerases.

DNA Fragmentation.

Isolated genomic DNA can be used for LAM-PCR directly, but the elongation time is very limited to suppress the formation of very long amplicons (5 seconds[26]). Furthermore, the accessibility of the biotinylated primer to anneal to the denatured long filaments of genomic DNA also reduces the efficiency of LAM-PCR. Shearing DNA into ~1 kb fragments greatly solves the accessibility problem, and an extended elongation time (1.5 min in this protocol) suppresses PCR-mediated recombination[46]. Sonicating genomic DNA is preferred as the fragmentation method over enzymatic digestion, which requires the presence of a nearby restriction site to capture any given translocation. With sonication, coverage across the genome is less biased leading to more comprehensive genome-wide coverage of potential recurrent DSBs.

Bridge Adapter.

Standard library preparation protocols for genome-wide sequencing typically require end-polishing and 3' A-tailing of dsDNA[11]. To ligate adapters to the ssDNA generated in the LAM-PCR, we perform the bridge-adapter ligation strategy[7], which introduces a single-stranded "bridge" oligo to stabilize both the adapter and the 3' end of the unknown prey sequence and improve ligation efficiency; the 3' ends of the adapter and bridge oligo are amino-modified to suppress adapter-to-adapter ligation. Compared with T4 RNA ligase, the T4 DNA ligase-mediated bridge ligation for ssDNA has higher efficiency, less bias, and lower background[7,47].

Sequencing and Pre-Processing.

Figure 18C:
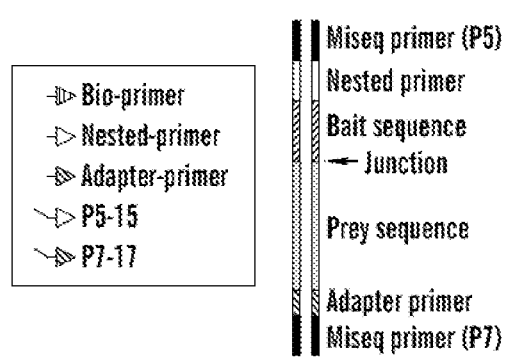
Figure 19:
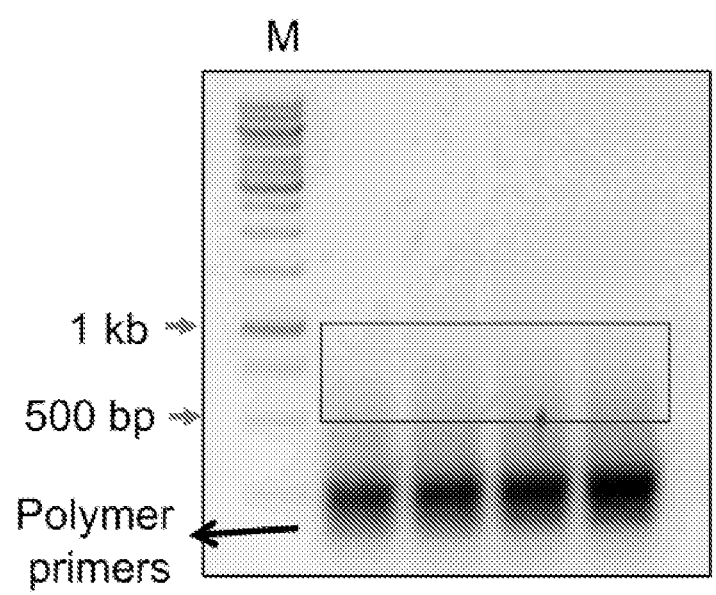
FIG. 19 depicts a representative smear of amplified and Illumina sequence tagged products. Sequences harboring Bait/Prey components can vary in size due to the combination of stochastic shearing of genomic DNA and the juxtaposition of Bait/Prey sequences. Products ranging from 500 bp-1 kb are excised and purified for Miseq sequencing. Smaller products may also contain sequences with relevant junction information but co-migrate with various artifactual poly-priming intermediates. M=Molecular weight ladder.
Figure 20:
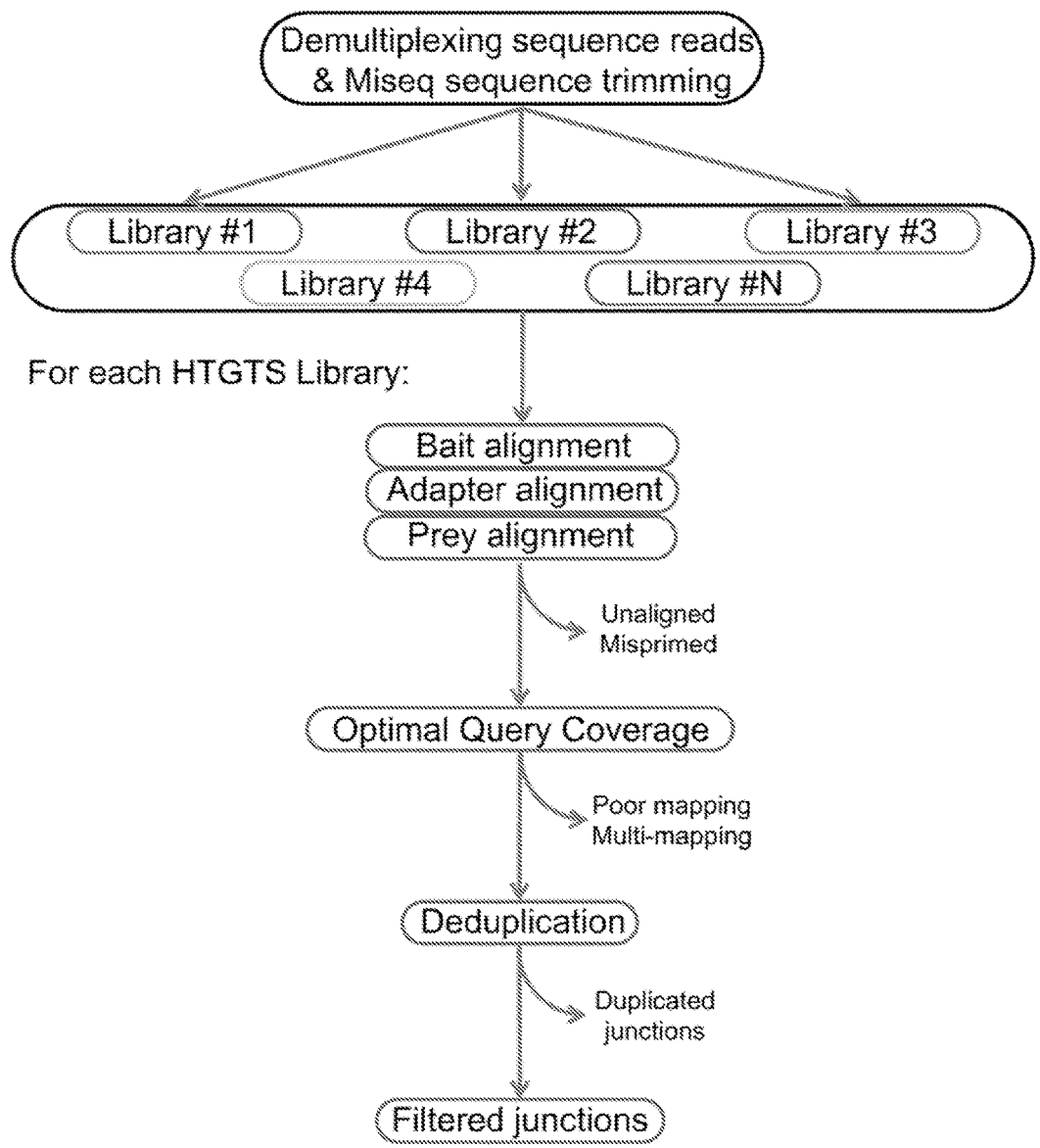
FIG. 20 depicts a flow chart of bioinformatic pipeline for translocation junction identification. Multiple HTGTS libraries with different barcodes can be sequenced in the same Miseq flow cell. De-multiplexing separates Miseq sequencing reads for each library, and then unique junctions for each library can be identified independently following the sequential steps (from adapter trimming).

HTGTS libraries are prepared such that the barcode and bait sequence are always sequenced on read 1 (P5 Illumina adapter) and the adapter end sequenced on read 2 (P7 Illumina adapter) (FIG. 18C). HTGTS libraries are pooled by varying numbers, depending on the desired number of sequence reads per library, before loading on the flow cell. Pre-processing parameters should be selected depending on the length and uniqueness of the library barcodes.

Alignment and OQC.

Reads are aligned to the full reference genome, the bait sequence (if non-endogenous, such as an I-SceI site), and the adapter sequence. Read 1 (R1) and read 2 (R2) are aligned independently and the top scoring alignments from each are passed to the junction detection algorithm. For OCS determination, all R1 and R2 alignments, as well as R1/R2 properly-aligned pairs, are conceptualized as nodes on a directed acyclic graph. The graph may be initialized and guaranteed acyclic by ordering nodes with their query start coordinate and using the following edge rules: an R1 node may only follow other R1 nodes with a smaller query start coordinate; an R1/R2 properly-aligned pair may only follow R1 nodes with smaller query start coordinate; an R2 node may only follow R1/R2 nodes or R2 nodes with a smaller query coordinate. Importantly, an R2 node may not immediately follow an R1 node as this would indicate the junction occurs between the reads. This event may occur, but cannot be fully characterized and inspected as an artifact, and thus is not considered. For each node, the scores of its edges to previous nodes explored are calculated, and the edge with the highest score is retained. Edges are scored by summing the alignment score of the new node with the previous node's score and subtracting any penalties. The OCS is the set of nodes that give the highest scoring path through the graph.

OCSs with large gaps between bait and prey alignments should be removed since they represent unverifiable (artifactual or biological) events. Bait alignments that minimally extend past the priming site should be removed as these represent potential mispriming events. The prey alignment must have a uniquely high alignment score relative to other overlapping alignments. The pipeline allows duplicate junction detection and filtering, since they may arise from either cellular or PCR replication and not independent events. Duplicate junctions may also arise independently, however, particularly in very dense clusters of junctions. Therefore, in the case of apparently low diversity libraries (i.e. many reads contain identical bait-prey junctions) interpretation needs to take into account both biological (e.g. predicted) and technical (e.g. amplification bias/artifactual) sources of the assay.

Materials

Reagents:

Mammalian cells of interest (transfected or induced cells to generate DSBs, untreated cells should be included as control)

Nuclease-free Milli-Q water ($H_2O$, 0.22 μm filter, autoclaved)

10% SDS solution (w/v, Thermo Scientific, cat. no. 24730-020)

CAUTION: SDS is toxic. Wear gloves and avoid inhalation.

Proteinase K (Thermo Scientific, cat. no. 25530-031)

Isopropanol (Fisher Scientific, BP26184)

Ethanol (Pharmco-AAPER, cat. no. 111000200)

Hydrochloric acid (HCl, Fisher Scientific, cat. no. A144-500LB)

2.5-N Sodium hydroxide solution (NaOH, Fisher Scientific, SS414-1)

Phusion High-Fidelity DNA Polymerase (Thermo Scientific, cat. no. F530)

5× Phusion HF buffer (Thermo Scientific, cat. no. F518)

dNTPs (Fisher Scientific, cat. no. 28406522, 2840502, 2840532, 2840512), four dNTPs are mixed equally and diluted with $H_2O$ to 2.5 mM each, stored at −20° C.

Oligos and primers (synthesized by Integrated DNA Technologies, check Table 1 for sequences), modified primers are synthesized at 100 nmol scale with standard desalting NaCl (American Bioanalytical, cat. no. AB01915)

EDTA (Sigma Life Sciences, cat. no. E5134)

Tris base (Roche, cat. no. 11814273001)

Dynabeads MyONE C1 streptavidin beads (Life Technologies, cat. no. 65002)

T4 DNA ligase (Promega, cat. no. M1808)

10× T4 DNA ligase buffer (Promega, cat. no. C126A)

Hexammine cobalt (III) chloride (Sigma Life Sciences, cat. no. H7891)

PEG8000 (Sigma Life Sciences, cat. no. P2139)

Agarose (Lonza, cat. no. 50004)

1-kb DNA ladder (Thermo Scientific, cat. no. SM0311)

6×DNA loading buffer (Thermo Scientific, cat. no. R0611)

50×TAE buffer (Thermo Scientific, cat. no. B49), diluted to 1× (40 mM Tris, 20 mM acetic acid, 1 mM EDTA) before use.

Miseq 500V2 kit (Illumina, cat. no. MS-102-2003)

Ethidium bromide (Life Technologies, cat. no. 15585011)
CAUTION: Ethidium bromide is toxic. Wear gloves.

QIAquick Gel Extraction kit (Qiagen, cat. no. 28706), including buffer QG and PE Equipment:

Bioruptor (Diagenode, cat. no. B01010002), including 1.5-ml tube holder

Vortex-Genie 2 (VWR Scientific)

Precision barrier tips (Denville Scientific, cat. no. P1126, P1122, P1096-FR)

1.5-ml TPX microtubes (Diagenode, cat. no. C30010010)

1.5-ml microtubes (Sarstedt, cat. no. 72.690)

0.2-ml PCR tubes (Thermo Scientific, cat. no. AB-045)

Gel image acquisition system (Alpha Innotech, FluorChem SP)

Magnet stand (Life Technologies, cat. no. 12321D)

PCR machine (MJ Research, cat. no. PTC-200)

Rotary mixer (Labindustries, cat. no. 400-110)

Water Bath (Fisher Scientific, cat. no. 15-462-15Q)

Miseq sequencer (Illumina)

Centrifuge (Eppendorf, cat. no. 5415D)

NanoDrop 2000 spectrophotometer (Thermo Scientific)

Electrophoresis system (Fisher Scientific, cat. no. FB-SBR-2025)

0.22 µm Syringe filter (Fisher Scientific, cat. no. SLGP033RB)

Bioinformatics Tools and Source Codes

Standard PC with at least 8 Gb RAM

Translocation pipeline source code: github.com/robinmeyers/translocpipeline ea-utils package: code.google.com/p/ea-utils/

SeqPrep package: github.com/jstjohn/SeqPrep

Bowtie2 package: sourceforge.net/projects/bowtie-bio/files/bowtie2/

Samtools: samtools.sourceforge.net/

Exemplary Reagents Setup:

Proteinase K stock: dissolve Ig proteinase K powder in 50 ml $H_2O$ to make 20 mg/ml stock, aliquot into 0.5 ml per tube and store at −20° C.
CAUTION: Proteinase K is toxic. Wear gloves.

5-M NaCl: dissolve 292.5 g NaCl in $H_2O$, adjust the total volume to 1 L. Autoclave and store at room temperature (RT; 20-25° C.).

0.5-M EDTA (pH 8.0): dissolve 186.12 g EDTA-$Na_2$-$2H_2O$ in $H_2O$, adjust the pH to 8.0 using 2.5-N NaOH and then the total volume into 1 L. Autoclave and store at RT.

1-M Tris-HCl (pH 7.4): dissolve 121.14 g Tris base in $H_2O$, adjust the pH to 7.4 using HCl and then the total volume into 1 L. Autoclave and store at RT.

Cell lysis buffer: 200-mM NaCl, 10 mM Tris-HCl (pH 7.4), 2 mM EDTA (pH 8.0), and 0.2% SDS; store at RT; proteinase K is added (final concentration at 200 ng/ml) before use.
CRITICAL: Prepare aliquot with fresh proteinase K every time before use.

TE buffer: 10 mM Tris-HCl (pH 7.4), 0.5 mM EDTA (pH 8.0); store at RT.

50% (w/v) PEG8000: dissolve 5 g PEG8000 in H2O at 56° C., adjust the total volume to 10 ml. Filter through 0.22 µm syringe filter, aliquot into 1 ml per tube and store at −20° C.

20-mM hexammine cobalt (III) chloride: dissolve 0.53 g hexammine cobalt (III) chloride in $H_2O$, adjust the total volume to 100 ml. Store at RT.

2× B&W buffer: 2-M NaCl, 10 mM Tris-HCl (pH 7.4), 1 mM EDTA (pH 8.0). Dilute with $H_2O$ to make 1× B&W buffer. Store at RT.

Annealing buffer: 25-mM NaCl, 10 mM Tris-HCl (pH 7.4), 0.5 mM EDTA (pH 8.0). Store at RT.

50 µM bridge adapter: dissolve the two DNA oligos (see Table 10) into annealing buffer to make the final concentration 400 µM. Mix equal volumes of the two dissolved oligos in a new 1.5-ml microtube, put the tube in 1 L boiling water with a foam floating tube rack, boil for 5 min, then cool down slowly in water to ~30° C. on the bench (adapter concentration is 200 µM). Alternatively, the oligos can be annealed on a PCR thermoblock[48]. Dilute by 4-fold (concentration is 50 µM) with $H_2O$, aliquot to 100 µl per tube and store at −20° C.

CRITICAL: Thaw the adapter on ice before use.

Exemplary Procedures:

Genomic DNA Isolation (Timing: 1 clay)

1. Resuspend 10×10⁶ mammalian cells (treated or untreated) in 500 µl of cell lysis buffer and incubate at 56° C. overnight (10-16 hours).
2. Add 500 µl isopropanol into the microtube directly, mix immediately by inverting the microtube until the genomic DNA pelleting together.
3. Pick up the DNA pellet into a new microtube with 1 ml 70% ethanol by pipette, spin at 13,000×g for 5 mins at 4° C.
4. Discard the supernatant completely; dissolve the pellet in 200 µl TE at 56° C. for at least 2 hours.
5. Take 1 µl to check the concentration with NanoDrop and A260/280 should be above 1.8.

Sonication (Timing: 1 hr)

6. Take 20-100 µg genomic DNA into a 1.5-ml TPX microtube, adjust the final volume to 200 µl with $H_2O$, mix by vortexing and then incubate on ice for 5 min.

CRITICAL STEP: Make sure the DNA is dissolved completely before sonication.
7. Fix the tube in 1.5-ml Bioruptor tube holder, fill in empty spaces of the holder with 1.5-ml TPX microtubes containing 200 µl H$_2$O each.
8. Turn on the water bath to cool the Bioruptor system to 4° C., then set the Bioruptor as below to fragment the genomic DNA:

| Setting | Value |
|---|---|
| Energy output | Low |
| Working time | 25 seconds |
| Resting time | 60 seconds |
| Sonication cycles | 2 cycles |

9. After sonication, take 1 µl fragmented DNA to run on a 1% agarose gel (w/v) in 1× TAE buffer; the DNA smear should range from 0.2-2 kb with a peak at approximate 750 bp.
PAUSE POINT: Fragmented DNA can be stored at −20° C. for months or 4° C. for one week.
CRITICAL STEP: Insufficient sonication of genomic DNA results in lower yield.
LAM-PCR (Timing: 6 hr)
10. Set up eight 50-µl LAM-PCR reactions for each sample as below:

| Reagents | Volume (µl) | Final |
|---|---|---|
| 5× Phusion HF buffer | 10 | — |
| dNTPs (2.5 mM each) | 1.5 | 75 µM |
| Bio-primer (1 µM) | 0.5 | 10 nM |
| Phusion polymerase (2 U/µl) | 0.5 | 1 U |
| sonicated DNA | 25 | 20-100 µg |
| H$_2$O | 12.5 | — |
| Total | 50 | |

CRITICAL STEP: the amount of fragmented DNA for each 50-µl LAM-PCR reaction should be 1-10 µg, optimally around 5 µg.
11. Set the PCR machine to amplify the DNA fragments as below:

| Cycle number | Denature | Anneal | Extend |
|---|---|---|---|
| 1 | 98° C., 2 min | | |
| 2-81 | 95° C., 30 s | 58° C., 30 s | 72° C., 90 s |
| 82 | | | 72° C., 2 min |

PAUSE POINT: Storing amplified single-stranded DNA fragments for longer than one week at −20° C. is not recommended.
CRITICAL STEP: do not leave PCR products in the PCR machine for too long (>4 hours) after the PCR amplification is done since Phusion may resect the 3' ends of the ssDNA products.
Streptavidin Purification (Timing: 3 hr)
12. Pool the PCR products together in a new 1.5-ml microtube, add 100 µl 5-M NaCl (1 M final) and 5 µl 0.5-M EDTA (pH 8.0; 5 mM final).
13. Take 40 µl Dynabeads Cl streptavidin beads (400 µg) into another new 1.5-ml microtube, add 600 µl 1× B&W buffer and mix by pipetting.
CRITICAL STEP: Before pipetting streptavidin beads, fully resuspend the beads by vortexing for at least 30 seconds.
14. Capture the beads on a magnet stand for 1 min, and discard the supernatant.
15. Resuspend the beads with 600 µl 1× B&W buffer, capture the beads on the magnet stand for 1 min, discard the supernatant.
16. Resuspend the beads with pooled PCR products from step 12, incubate the mixture on a rotary mixer at RT for at least 2 hours;
CRITICAL STEP: 2 hours are sufficient for the beads to capture most of the biotinylated PCR products, however, 4-hour incubation time is recommended.
PAUSE POINT: binding mixture can be incubated at RT overnight.
17. Capture the DNA-beads complex on the magnet stand and wash the DNA-beads complex with 600 µl 1× B&W buffer (as step 15) three times;
18. Resuspend the beads with 1 ml H$_2$O, capture the beads on the magnet stand for 1 min, discard the supernatant.
19. Resuspend the beads in 45 µl H$_2$O.
On-Beads Ligation (Timing: 5 hr)
20. Set up a 100-µl ligation reaction as below:

| Reagents | Volume (µl) | Final |
|---|---|---|
| DNA-beads complex | 45 | — |
| 10× T4 ligation buffer | 10 | — |
| hexammine cobalt (III) chloride (20 mM) | 5 | 1 mM |
| Bridge adapter (50 µM) | 5 | 2.5 µM |
| T4 DNA ligase (3 U/µl) | 5 | 15 U |
| 50% PEG8000 | 30 | 15% |
| Total | 100 | |

CRITICAL STEP: thaw the bridge adapter on ice; mix all the reagents except 50% PEG8000 well first, then add 30 µl 50% PEG8000 with cut tips to more accurately pipet the viscous solution, mix thoroughly by pipetting.
21. Aliquot ligation mixture evenly into two PCR tubes (50 µl each).
22. Set PCR machine as below using a heated lid to incubate the ligation for 4 hours:

| Temperature | Time |
|---|---|
| 25° C. | 1 hour |
| 22° C. | 2 hours |
| 16° C. | 1 hour |

PAUSE POINT: ligation can be optionally incubated at 16° C. for overnight instead of 1 hour.
CRITICAL STEP: To improve the ligation efficiency, resuspend the mixture 2 hours after incubation. Do not spin the mixture before incubation.
23. Add 50 µl 2× B&W buffer into each PCR tube, transfer and combine the mixture in a new 1.5-ml microtube.
24. Add 50 µl 1× B&W buffer into each PCR tube to collect residual ligation products, transfer the residual ligation products into the new microtube from step 23.
25. Capture the on-beads ligation products on the magnet and wash the DNA-beads complex with 600 µl 1× B&W buffer (as step 15) twice;
26. Resuspend the on-beads ligation products with 1 ml H$_2$O, capture the beads on the magnet stand for 1 min, discard the supernatant.
27. Resuspend the on-beads ligation products in 200 µl H$_2$O.

PAUSE POINT: Storing on-beads single-stranded DNA for more than one week at −20° C. is not recommended.

Nested PCR (Timing: 1 hr 30 mins)

28. Set up eight 50-µl PCR reactions for each DNA sample as below:

| Reagents | Volume (µl) | Final |
|---|---|---|
| 5x Phusion HF buffer | 10 | — |
| dNTPs (2.5 mM each) | 4 | 200 µM |
| I5-nested (10 µ M) | 2 | 400 nM |
| I7-blue (10 µM) | 2 | 400 nM |
| Phusion polymerase (2 U/µl) | 0.5 | 1 U |
| DNA-beads complex | 25 | — |
| H₂O | 6.5 | — |
| Total | 50 | |

29. Set the PCR machine to amplify the DNA fragments as below:

| Cycle number | Denature | Anneal | Extend |
|---|---|---|---|
| 1 | 95° C., 5 min | | |
| 2-16 | 95° C., 60 s | 60° C., 30 s | 72° C., 60 s |
| 17 | | | 72° C., 6 min |

PAUSE POINT: Amplified DNA products can be stored at −20° C. for months.

CRITICAL STEP: do not spin the PCR mixture before amplification.

Enzyme Blocking (Optional; Timing: 2 hr)

30. Pool the samples together in a new 1.5-ml microtube, spin at 15,000×g for 5 min at RT.
31. Transfer the supernatant to a new 1.5-ml microtube, add 1.2 ml buffer QG.
32. Spin the mixture through a QIAquick Gel Extraction column at 15,000×g for 1 min at RT, discard the flow through.
33. Add 800 µl buffer PE into the column, spin at 15,000×g for 1 min at RT, discard the flow through.
34. Spin the column at 15,000×g for 2 min at RT, transfer the column to a new 1.5-ml microtube.
35. Add 30 µl H₂O to the column, spin at 15,000×g for 1 min at RT. Repeat this step once.
36. Take 1 µl of the eluted DNA products to check the concentration by NanoDrop.
37. Set up a 100-µl blocking reaction as below:

| Reagents | Amount |
|---|---|
| DNA products | 60 µl |
| 10x enzyme buffer | 10 µl |
| Blocking enzyme | 5 U |
| H₂O | 30 µl |

38. Aliquot blocking mixture equally into two PCR tubes (50 µl each), incubate at recommended temperature by enzyme manufacturer in water bath for 1 hour.

PAUSE POINT: Blocked DNA products can be stored at −20° C. for months after heat inactivation of the blocking enzyme.

39. Add 300 µl buffer QG into the blocking mixture, recover the blocked DNA products with a Qiagen column as steps 32-35, elute the products with 60 µH₂O as in step 35.

40. Take 1 µl of the eluted DNA products to check the concentration by NanoDrop.

PAUSE POINT: Purified DNA products can be stored at −20° C. for months.

Tagged-PCR (Timing: 1 hr)

41. Set up four 50-µl PCR reactions for each DNA sample as below:

| Reagents | Volume (µl) | Final |
|---|---|---|
| 5x Phusion HF buffer | 10 | — |
| dNTPs (2.5 mM each) | 4 | 200 µM |
| P5-I5 (10 µM) | 2 | 400 nM |
| P7-I7 (10 µM) | 2 | 400 nM |
| Phusion polymerase (2 U/µl) | 0.5 | 1 U |
| Blocked DNA products | 15 | — |
| H₂O | 16.5 | — |
| Total | 50 | |

42. Set the PCR machine as below to amplify the DNA fragments:

| Cycle number | Denature | Anneal | Extend |
|---|---|---|---|
| 1 | 95° C., 3 min | | |
| 2 – n | 95° C., 30 s | 62° C., 30 s | 72° C., 60 s |
| N + 1 | | | 72° C., 6 min |

"n" can be 12 to 16, depending on the amount of template DNA

PAUSE POINT: Amplified DNA products can be stored at −20° C. for months.

CRITICAL STEP: the cycle number of PCR amplification depends on the concentration determined at step 40. The cycle number can be generally calculated as below:

| Concentration (ng/µl) | Cycles |
|---|---|
| >10 | 10 |
| 7-10 | 11-12 |
| <7 | 13-15 |

Library Purification (Timing: 1 hr)

43. Pool the samples together, run all the amplified DNA products on a 1% agarose gel in 1×TAE buffer.
44. Cut the DNA fragments between 500-1000 bp (see FIG. 2).
45. Purify each library with one Qiagen column similarly as performed in steps 31-35, elute with 30 µl H₂O
46. Take 1 µl of library DNA to check the concentration by NanoDrop.

High-Throughput Sequencing (Timing: 2 clays)

47. Sequence the library by Miseq sequencer using the 500 cycle V2 kit following the manufacturer's instruction.
48. Process sequence reads using translocation pipeline according to program documentation. Some detail is given below.

Sequence Read Preprocessing (Timing: <1 hour)

49. Create a metadata file for the MiSeq run according to pipeline documentation.

CRITICAL STEP: The metadata file will contain minimum information necessary to process sequence reads of a particular library. Incorrect information will result in errors at specific stages of the pipeline.

50. Execute the pre-processing command included with the pipeline.
51. The pipeline will expect a unique barcode for each library by combining the nested primer barcode with the nested primer sequence.
52. The pipeline will call the fastq-multx utility, sort R1 and paired R2 sequences into separate fastq (.fq) files based on unique barcode sequence.
53. The pipeline will call the SeqPrep utility and trim Illumina adapters from both R1 and R2 of the demultiplexed libraries.
    PAUSE POINT: paired-end sequences are demultiplexed and adapter trimmed Each library now has its own set of sequence files. They may be processed individually or in batch.

Local Alignment (Timing: 1-2 hours)
54. Verify the location on disk of both the fasta file and bowtie2 index of the target genome. A custom script for modifying an existing genome is included in the pipeline.
55. Execute the main processing command included with the pipeline.
56. The pipeline will read in the metadata file and call bowtie2 to align the forward and reverse reads against the genome build, as well as the bridge adapter and bait sequence if included (non-endogenous cut site).

Optimal Query Coverage (Timing: 1-5 hours)
57. The pipeline will pool all three alignments for each paired-end read to run through the OQC algorithm.
58. The pipeline will return for each read the OCS defined by the set of alignments that optimally cover the query paired-end sequences. See the pipeline documentation for the parameters that control this process.

Optimal Coverage Set Filtering (Timing: 1-2 hours)
59. The pipeline will filter OCS-defined reads that do not satisfy certain conditions. For example: reads with insufficient bait sequence length (associated with mispriming events), reads with a bait sequence that extends past the cut site, reads that do not contain a prey junction, or reads with a large gap between bait and prey alignments.
60. The pipeline will filter out reads with a strong competing prey alignment, indicating that the translocation cannot be uniquely mapped.
61. The pipeline will identify and filter duplicate junctions.
62. Using program included in pipeline, refilter reads depending on nature of experiment (e.g. keep unjoined bait sequences, keep duplicate junctions, etc).

Timing
Steps 1-5, genomic DNA isolation: 1 day
Steps 6-9, sonication: 1 hr
Steps 10-11, LAM-PCR: 6 hours
Steps 12-19, streptavidin purification: 3 hours
Steps 20-27, on-beads ligation: 5 hours
Steps 28-29, nested PCR: 1 hour 30 minutes
Steps 30-40, enzyme blocking: 2 hours
Steps 41-42, tagged PCR: 1 hour
Steps 43-46, library purification: 1 hour
Step 47-48, high-throughput sequencing: 2 days
Steps 49-53, sequence read pre-processing: <1 hour
Steps 54-62, sequence read main processing: 2-8 hours Anticipated Results The junction yield is influenced by the level of bait DSB cutting in the cells assayed and the amount of input genomic DNA used for HTGTS; increasing junction yields are more susceptible to saturation bias and optimization of user-defined conditions may be needed. To monitor the library preparation process, we quantify DNA products at steps 36 and 40. For our libraries with bait DSBs generated by I-SceI[17], Cas9:gRNA[16], TALENs[16], AID[19], or RAG[18], concentrations ranged from 8-20 ng/µl for step 36 and 5-15 ng/µl for step 40 using 20-100 µg total input genomic DNA, respectively. It is important to optimize the cycle number for the Tagged-PCR to control for over-amplification bias, and generally, the final library DNA concentration should be within 20-40 ng/µl. For control libraries (i.e. no bait DSB), similar, but not lower, concentrations are expected for steps 36 and 40; however, they result in very few junctions. Experimental libraries with unique junctions>10-fold more than control libraries should be considered for analysis. If primers anneal to many sites in the genome, or the bait region contains repetitive sequences, very high concentrations are expected in steps 36 and 40 (i.e. >50 ng/µl final) with filtered junctions typically containing a high background. In this case, we recommend choosing another bait DSB site/strategy, or reduce the amount of amplified DNA in the above steps if choice of bait site is limited. Repeat masked reference genomes can be used for alignment. However, junctions in such masked regions, especially telomere, ribosomal, and LINE repeats, are good indicators for the quality of the libraries. Libraries may need to be generated again if repetitive region junctions comprise more than 20% of the total, indicating relevant junctions are likely under-amplified and may negatively impact downstream analyses. Example HTGTS libraries are provided for Abelson virus-transformed murine (v-Abl) pro-B cells co-expressing the universal bait Cas9:SeC9-2 gRNA located in the IgH locus (at the end of chromosome 12) and an additional VEGFA gRNA that would target the human VEGFA locus with a relatively large number of additional off-targets in the human genome (FIG. 4a)[16]. The SeC9-2 universal bait identified 3 SeC9-2 off-targets (1 very close to the bait). Even though VEGFA has no on-target site in mouse genome, 3 VEGFA off-targets were identified with this universal bait assay (FIG. 4a,b).

TABLE 10

Primers for HTGTS

| Usage | Name | Sequences (SEQ ID NOS 308-313, respectively, in order of appearance) |
|---|---|---|
| Bridge adapter | Adapter-upper* | GCGACTATAGGGCACGCGTGG-NH$_2$ |
| | Adapter-lower* | /5-Phosphorylation/CCACGCGTGCCCTATAGTCGC-NH$_2$ |

TABLE 10-continued

Primers for HTGTS

| Usage | Name | Sequences (SEQ ID NOS 308-313, respectively, in order of appearance) |
|---|---|---|
| Nested PCR | I5-Nested** | ACACTCTTTCCCTACACGACGCTCTTCCGATCTBARCODENESTEDPRIMER |
|  | I7-Blue | CTCGGCATTCCTGCTGAACCGCTCTTCCGATCTGACTATAGGGCACGCGTGG |
| Tagged PCR | P5-I5 | AATGATACGGCGACCACCGAGATCTACACTCTTTCCCTACACGACGCTCTTCCGATCT |
|  | P7-I7 | CAAGCAGAAGACGGCATACGAGATCGGTCTCGGCATTCCTGCTGAACCGCTCTTC |

1. * End modifications can be produced by Integrated DNA Technologies, the synthesis code for "/5-Phosphorylation/" is "/5Phos/", for "-NH$_2$" is "/3AmMO/", and for "/5-biotin/" is "/5BiosG/", "N" means random nucleotide.
2. ** "Nested primer" is the locus-specific nested primer, and "barcode" means the DNA sequence to differentiate samples with the same locus-specific nested primer, thus these samples can be sequenced in the same Miseq run. Barcodes can be any non-tandem DNA sequences between 0 and 10 bp, or use the Miseq index following the manufacturer's instructions.
3. Sequences from the Miseq primers are marked in underlined text. Note that I5 and I7 primers share 14-bp homologies at the 3' end (compared the orange sequences of I5-nested to that of I7-Blue), thus the $T_m$ in step 42 is 62° C. to reduce cross-template amplification. Alternatively, P5-I5 can be further shortened from the 3' end to avoid annealing to the 3' region of I7 with same sequences.

TABLE 11

Troubleshooting

| Steps | Problem | Possible reason | Possible solution |
|---|---|---|---|
| 5 | A260/280 is low | Proteinase K digestion is not sufficient | Extract the DNA with Phenol-Chloroform twice |
| 9 | Average size of DNA smear is too large | Insufficient sonication or incompletely dissolved genomic DNA | Perform 1-2 more sonication cycles. |
| 36 | Very low concentration (<3 ng/µl) | Melting temperature (Tm) is not optimal for steps 11, 29 | Test the primer by gradient PCR and choose the right Tm |
|  |  | Wrong primer and/or dNTP concentrations for step 10 | Use correct concentrations for step 10 |
|  |  | Wrong pair of primers for steps 11, 29 | Check the sequences of the primers and make sure the nested primer corresponds with the bio primer |
|  |  | Bait DSB site is not cutting | Check amplified region to ensure target sequence is present; test another nearby target site |
|  |  | The bridge adapter is thawed and frozen too many times | Use fresh aliquot of bridge adapter |
|  |  | Spin the beads to bottom before ligation or nested PCR at steps 22, 29 | Do not spin the mixture before PCR |
|  |  | Operation error in some step | Re-do on-bead PCR or start over |
|  | Too high concentration (>50 ng/µl) | Unspecific priming | Design new primers/Test background in an untreated (uncut bait DSB) library |
| 40 | Very low concentration (<2 ng/µl) | Blocking enzyme sites on the bait region or the I7-Blue primer | Change blocking enzyme |
|  |  | Operation error in some step | Re-do on-bead PCR or start over |
| 43 | Very short DNA smear tail | Too few PCR cycles | Increase the PCR cycles |
|  | Very long DNA smear tail | Too many PCR cycles | Reduce the input DNA amount for step 41 or decrease PCR cycles |
| 50, 55 | Pipeline does not execute | Incorrect metadata file | Check to make sure primer sequences match specified coordinates |

TABLE 11-continued

Troubleshooting

| Steps | Problem | Possible reason | Possible solution |
|---|---|---|---|
| 53 | No reads | Wrong barcode sequence | Check the sequences of the barcode and primer |
| | | Multiple samples with identical barcode and primer sequence at step 427 | Run identical barcode/primer samples on separate Miseq runs |
| | | Operation error for step 41 | Re-do step 41 |
| 61 | Very few junctions | Poor cutting at the bait DSB | Verify sufficient cutting at bait DSB |
| | | Primers are not annealing properly | Check amplified region to ensure primers do not overlap with a polymorphic site |
| | Too high background | Cells are not healthy or dying | Make sure the treatment doesn't cause too much DNA damages to the cells |
| | Many junctions in uncut-cell control | Repetitive sequence in bait region | Design a new bait DSB site |

REFERENCES

1. Boboila, C., Alt, F. W. & Schwer, B. Classical and alternative end-joining pathways for repair of lymphocyte-specific and general DNA double-strand breaks. *Adv. Immunol.* 116, 1-49 (2012).
2. Symington, L. S. & Gautier, J. Double-strand break end resection and repair pathway choice. *Annu. Rev. Genet.* 45, 247-271 (2011).
3. Alt, F. W., Zhang, Y., Meng, F.-L., Guo, C. & Schwer, B. Mechanisms of programmed DNA lesions and genomic instability in the immune system. *Cell* 152, 417-429 (2013).
4. Nussenzweig, A. & Nussenzweig, M. C. Origin of Chromosomal Translocations in Lymphoid Cancer. *Cell* 141, 27-38 (2010).
5. Hendel, A., Fine, E. J., Bao, G. & Porteus, M. H. Quantifying on- and off-target genome editing. *Trends Biotechnol.* 33, 132-140 (2015).
6. Barlow, J. H. et al. Identification of Early Replicating Fragile Sites that Contribute to Genome Instability. *Cell* 152, 620-632 (2013).
7. Zhou, Z.-X. et al. Mapping genomic hotspots of DNA damage by a single-strand-DNA-compatible and strand-specific ChIP-seq method. *Genome Res.* 23, 705-715 (2013).
8. Khair, L., Baker, R. E., Linehan, E. K., Schrader, C. E. & Stavnezer, J. Nbs1 ChIP-Seq Identifies Off-Target DNA Double-Strand Breaks Induced by AID in Activated Splenic B Cells. *PLoS Genet.* 11, e1005438 (2015).
9. Baranello, L. et al. DNA Break Mapping Reveals Topoisomerase II Activity Genome-Wide. *Int. J. Mol. Sci.* 2014, 15, 13111-13122 (2014).
10. Crosetto, N. et al. Nucleotide-resolution DNA double-strand break mapping by next-generation sequencing. *Nat. Meth.* 10, 361-365 (2013).
11. Chiarle, R. et al. Genome-wide translocation sequencing reveals mechanisms of chromosome breaks and rearrangements in B cells. *Cell* 147, 107-119 (2011).
12. Klein, I. A. et al. Translocation-capture sequencing reveals the extent and nature of chromosomal rearrangements in B lymphocytes. *Cell* 147, 95-106 (2011).
13. Wang, X. et al. Unbiased detection of off-target cleavage by CRISPR-Cas9 and TALENs using integrase-defective lentiviral vectors. *Nat. Biotechnol.* 33, 175-178 (2015).
14. Gabriel, R. et al. An unbiased genome-wide analysis of zinc-finger nuclease specificity. *Nat. Biotechnol.* 29, 816-823 (2011).
15. Tsai, S. Q. et al. GUIDE-seq enables genome-wide profiling of off-target cleavage by CRISPR-Cas nucleases. *Nat. Biotechnol.* 33, 187-197 (2015).
16. Frock, R. L. et al. Genome-wide detection of DNA double-stranded breaks induced by engineered nucleases. *Nat. Biotechnol.* 33, 179-186 (2015).
17. Meng, F.-L. et al. Convergent transcription at intragenic super-enhancers targets AID-initiated genomic instability. *Cell* 159, 1538-1548 (2014).
18. Hu, J. et al. Chromosomal Loop Domains Direct the Recombination of Antigen Receptor Genes. *Cell* (2015). doi:10.1016/j.cell.2015.10.016.
19. Dong, J. et al. Orientation-specific joining of AID-initiated DNA breaks promotes antibody class switching. Nature 525, 134-139 (2015).
20. Zarrin, A. A. et al. Antibody class switching mediated by yeast endonuclease-generated DNA breaks. *Science* 315, 377-381 (2007).
21. O'Malley, R. C., Alonso, J. M., Kim, C. J., Leisse, T. J. & Ecker, J. R. An adapter ligation-mediated PCR method for high-throughput mapping of T-DNA inserts in the Arabidopsis genome. *Nat. Protoc.* 2, 2910-2917 (2007).
22. Williams, R. et al. Amplification of complex gene libraries by emulsion PCR. *Nat. Meth.* 3, 545-550 (2006).
23. Zhang, Y. et al. Spatial organization of the mouse genome and its role in recurrent chromosomal translocations. *Cell* 148, 908-921 (2012).
24. Gostissa, M. et al. IgH class switching exploits a general property of two DNA breaks to be joined in cis over long chromosomal distances. *Proc. Natl. Acad. Sci. U.S.A.* 111, 2644-2649 (2014).
25. Schmidt, M. et al. High-resolution insertion-site analysis by linear amplification-mediated PCR (LAM-PCR). *Nat. Meth.* 4, 1051-1057 (2007).
26. Paruzynski, A. et al. Genome-wide high-throughput integrome analyses by nrLAM-PCR and next-generation sequencing. *Nat. Protoc.* 5, 1379-1395 (2010).
27. Hu, J., Tepsuporn, S., Meyers, R. M., Gostissa, M. & Alt, F. W. Developmental propagation of V(D)J recombination-associated DNA breaks and translocations in 28. Langmead, B. & Salzberg, S. L. Fast gapped-read alignment with Bowtie 2. *Nat. Meth.* 9, 357-359 (2012).

29. Faust, G. G. & Hall, I. M. YAHA: fast and flexible long-read alignment with optimal breakpoint detection. *Bioinformatics* 28, 2417-2424 (2012).

30. Chevalier, B. S. et al. Design, activity, and structure of a highly specific artificial endonuclease. *Mol. Cell* 10, 895-905 (2002).

31. Kim, Y. G., Cha, J. & Chandrasegaran, S. Hybrid restriction enzymes: zinc finger fusions to Fok I cleavage domain. *Proc. Natl. Acad. Sci. U.S.A.* 93, 1156-1160 (1996).

32. Doyon, Y. et al. Enhancing zinc-finger-nuclease activity with improved obligate heterodimeric architectures. *Nat. Meth.* 8, 74-79 (2011).

33. Christian, M. et al. Targeting DNA double-strand breaks with TAL effector nucleases. *Genetics* 186, 757-761 (2010).

34. Cermak, T. et al. Efficient design and assembly of custom TALEN and other TAL effector-based constructs for DNA targeting. *Nucleic Acids Res.* 39, e82 (2011).

35. Jinek, M. et al. A programmable dual-RNA-guided DNA endonuclease in adaptive bacterial immunity, *Science* 337, 816-821 (2012).

36. Mali, P. et al. RNA-guided human genome engineering via Cas9. *Science* 339, 823-826 (2013).

37. Cong, L. et al. Multiplex genome engineering using CRISPR/Cas systems. *Science* 339, 819-823 (2013).

38. Kim, H. & Kim, J.-S. A guide to genome engineering with programmable nucleases. *Nat. Rev. Genet.* 15, 321-334 (2014).

39. Canela, A., Stanlie, A. & Nussenzweig, A. Collateral DNA damage produced by genome-editing drones: exception or rule? *Mol. Cell* 58, 565-567 (2015).

40. Zetsche, B. et al. Cpf1 Is a Single RNA-Guided Endonuclease of a Class 2 CRISPR-Cas System. *Cell* 163, 759-771 (2015).

41. Boboila, C. et al. Alternative end-joining catalyzes class switch recombination in the absence of both Ku70 and DNA ligase 4. *J. Exp. Med.* 207, 417-427 (2010).

42. Teng, G. et al. RAG Represents a Widespread Threat to the Lymphocyte Genome. *Cell* 162, 751-765 (2015).

43. Ran, F. A. et al. In vivo genome editing using Staphylococcus aureus Cas9. *Nature* 520, 186-191 (2015).

44. Asaithamby, A. & Chen, D. J. Cellular responses to DNA double-strand breaks after low-dose gamma-irradiation. *Nucleic Acids Res.* 37, 3912-3923 (2009).

45. Roukos, V. et al. Spatial dynamics of chromosome translocations in living cells. *Science* 341, 660-664 (2013).

46. Judo, M. S., Wedel, A. B. & Wilson, C. Stimulation and suppression of PCR-mediated recombination. *Nucleic Acids Res.* 26, 1819-1825 (1998).

47. Clepet, C., Le Clainche, I. & Caboche, M. Improved full-length cDNA production based on RNA tagging by T4 DNA ligase. *Nucleic Acids Res.* 32, e6 (2004).

48. Ran, F. A. et al. Genome engineering using the CRISPR-Cas9 system. *Nat. Protoc.* 8, 2281-2308 (2013).

Example 4: Orientation-Specific Joining of AID-Initiated DNA Breaks Promotes Antibody Class Switching During B-cell development, RAG endonuclease cleaves immunoglobulin heavy chain (IgH) V, D, and J gene segments and orchestrates their fusion as deletional events that assemble a V(D)J exon in the same transcriptional orientation as adjacent Cm constant region exons1,2. In mice, six additional sets of constant region exons (CHs) lie 100-200 kilobases downstream in the same transcriptional orientation as V(D)J and Cm exons2. Long repetitive switch (S) regions precede Cm and downstream CHs. In mature B cells, class switch recombination (CSR) generates different antibody classes by replacing Cm with a downstream CH (ref 2). Activation-induced cytidine deaminase (AID) initiates CSR by promoting deamination lesions within Sμ and a downstream acceptor S region2,3; these lesions are converted into DNA double-strand breaks (DSBs) by general DNA repair factors3. Productive CSR must occur in a deletional orientation by joining the upstream end of an Sμ DSB to the downstream end of an acceptor S-region DSB. However, the relative frequency of deletional to inversional CSR junctions has not been measured. Thus, whether orientation-specific joining is a programmed mechanistic feature of CSR as it is for V(D)J recombination and, if so, how this is achieved is unknown. To address this question, we adapt highthroughput genome-wide translocation sequencing4 into a highly sensitive DSB end-joining assay and apply it to endogenous AlDinitiated S-region DSBs in mouse B cells. We show that CSR is programmed to occur in a productive deletional orientation and does so via an unprecedented mechanism that involves in cis Igh organizational features in combination with frequent S-region DSBs initiated by AID. We further implicate ATM-dependent DSB-response factors in enforcing this mechanism and provide an explanation of why CSR is so reliant on the 53BP1 DSB-response factor.

Figure 22A:
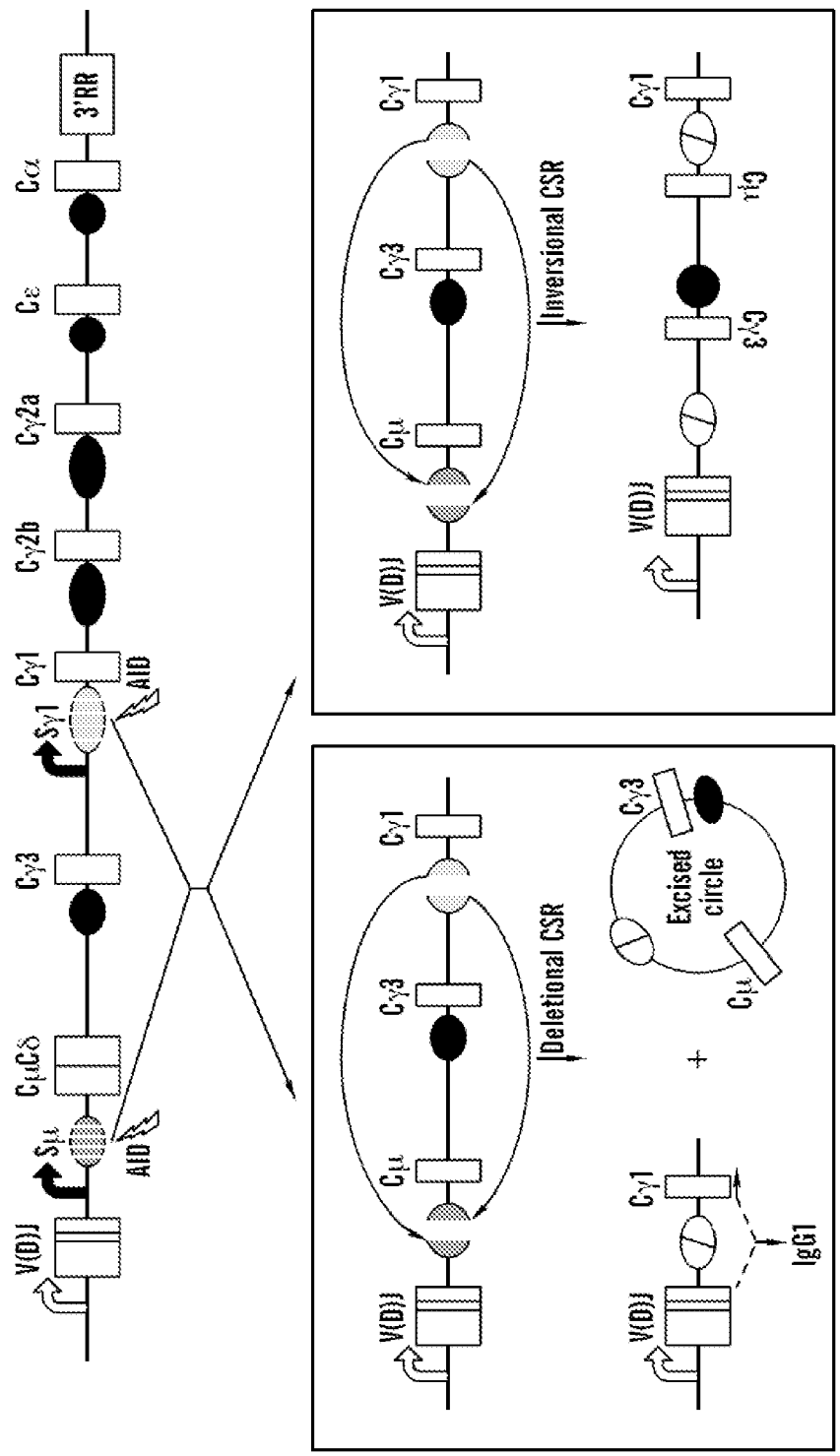
FIGS. 22A-22E demonstrate that S-region-dependent orientation biased joining in CSR-stimulated B cells.

Most chromosomal DSB ends join to ends of separate DSBs genomewide without orientation (end) specificity4,5. Similarly, non-productive 'inversional' CSR joins have been found in transformed B cells6-9, suggesting CSR also may not be orientation-specific10 (FIG. 22A). To address this possibility, we employed digestion-circularization PCR (DC-PCR, data not shown) to identify the orientation of CSR joins between Sμ and Sγ1 in purified mouse B cells stimulated with anti-CD40 plus IL4 to activate AID-targeting to Sγ1 and Se, and class-switching to IgG1 (and IgE). Most Sμ to Sγ1 junctions identified by this semi-quantitative approach were deletional (data not shown).

Figures 22B, 22C, 22D, 22E:
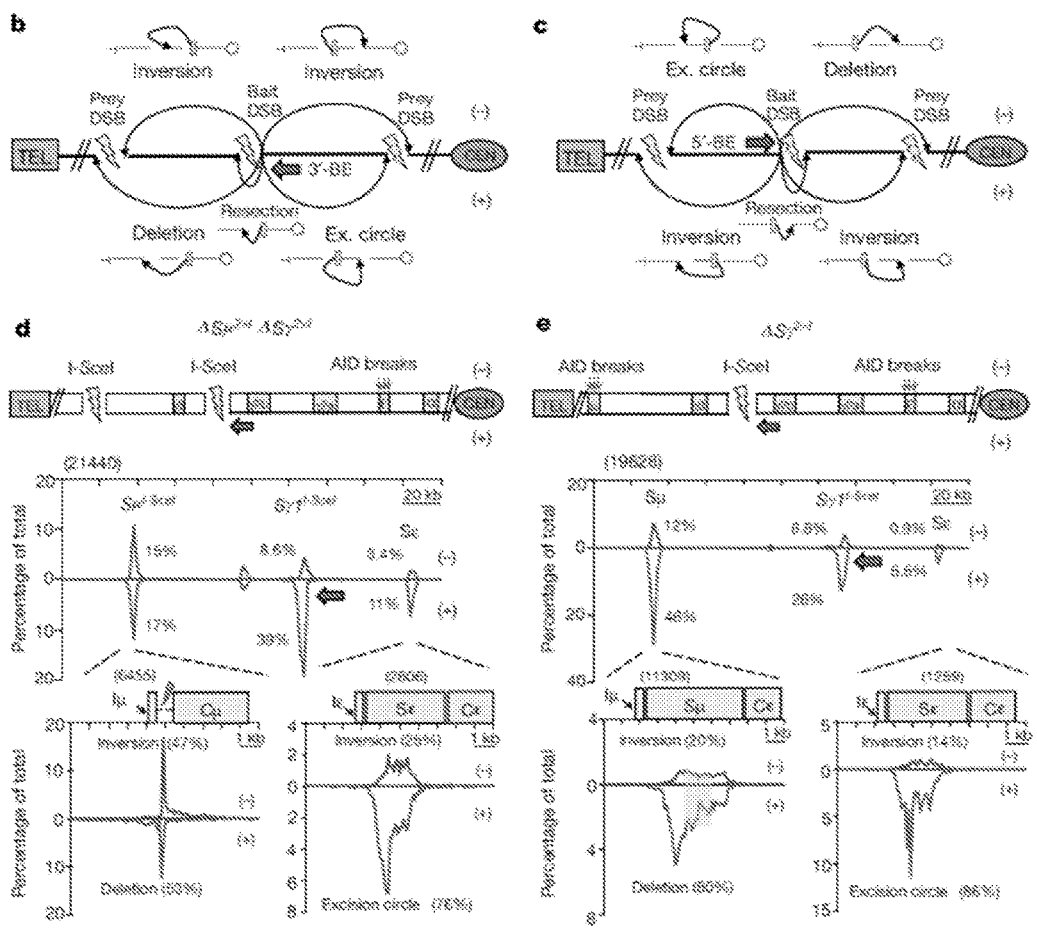

To confirm DC-PCR findings and analyse potential mechanisms, we used high-throughput genome-wide translocation sequencing (HTGTS), an unbiased genome-wide approach that identifies 'prey' DSB junctions to a fixed 'bait' DSB with nucleotide resolution4,5 (data not shown). We refer to broken ends of bait Igh DSBs as 5'- and 3'-broken ends; specific primers allow use of each as bait4 (FIG. 22B, 22C). Prey junctions are denoted 1 if prey is read from the junction in a centromere-to-telomere direction and 2 if in the opposite direction4 (FIG. 22B, 22C). The 1 and 2 outcomes for intrachromosomal joining of broken ends of different DSBs on the same chromosome include rejoining of a DSB subsequent to resection, or joining the broken ends of two separate DSBs to form intrachromosomal inversions, deletions, or excision circles4,5 (FIG. 22B, 22C). To assess the relative frequency at which non-AID-initiated Igh DSBs join in deletional versus inversional orientation, we expressed I-SceI endonuclease in anti-CD40/IL4-activated AID-deficient B cells in which I-SceI targets were inserted upstream of Sμ and downstream of Sγ1(IghI-96k allele11; data not shown), or in AID-sufficient B cells in which Sγ1 and Sμ were replaced with I-SceI targets ($\Delta S\mu^{2xI}/\Delta S\gamma 1^{2xI}$ allele12; FIG. 22D). HTGTS with primers that captured junctions involving 3'- or 5'-broken ends of I-SceI bait DSBs in the Sγ1 locale revealed that a major class of recovered junctions were re-joins of bait DSBs following resection (FIG. 22D). A second major class of bait junctions in the Sγ1 locale involved intact or resected 3'- or 5'-broken ends of I-SceI-generated DSB in the Sμ locale, which comprised relatively similar numbers of deletional (1) and inversional (2) junctions for bait 3'-broken ends (FIG. 22D) and similar numbers of excision circle (2) versus inversional (1) junctions for bait 5'-broken ends (data not shown). As expected4 , bait 3'- and 5'-broken ends from the Sγ1 locale recovered similar levels of 1 and 2 junctions genome-wide (data not shown). We conclude that joining between two I-SceI DSBs in different Igh S-region locations in CSR-activated B cells lacks any notable preference for or against inversional versus deletional joins.

In AID-deficient IghI-96k B cells, I-SceI 5'- and 3'-broken end baits downstream of Sγ1 did not capture Igh DSB hotspots beyond I-SceIgenerated broken ends upstream of Sμ (data not shown). In contrast, I-SceI5'- and 3'-broken ends from the $\Delta S\mu^{2xI}/\Delta S\gamma 1^{2xI}$ allele in AID-sufficient B cells joined frequently to AID-initiated Sε DSBs 60 kilobases (kb) downstream (FIG. 22D), with the majority (80%) of 3' and 5' $\Delta S\mu^{2xI}/\Delta S\gamma 1^{2xI}$ broken end joins distributed across the 4-kb Sε in orientations that generate, respectively, excision circles (FIG. 22D) or deletions (data not shown). We also performed HTGTS on activated, I-SceI-expressing B cells in which only Sγ1 was replaced by an I-SceI cassette ($\Delta S\gamma 1^{2xI}$ allele12 ; FIG. 22E). Beyond break-site junctions, major Igh hotspot regions of 3' $\Delta S\gamma 1^{2xI}$ broken ends were Sμ and Sε (FIG. 22E). Junctions occurred broadly across Sμ, with 80% in a deletional orientation; while 90% of Sε junctions were in the reciprocal excision circle orientation (FIG. 22E). CH12F3 B lymphoma cells in which Sα was replaced with an I-SceI site had a similar orientation bias of Sα I-SceI 3'-broken end joining to Sμ DSBs (data not shown). Joining of the 5'-broken ends of $\Delta S\mu^{2xI}$ (on the $\Delta S\mu^{2xI}/\Delta S\gamma c1^{2xI}$ allele) to AID-initiated DSBs in Sγc3, Sγc2b and Sγc2a in lipopolysaccharide plus anti-IgD-dextran-activated B cells were similarly orientation-biased (data not shown). However, joining of the 5'-broken ends of $\Delta S\mu^{2xI}$ across an array of 28× I-SceI sites replacing SΔcl[13] was not orientation-biased (data not shown). Together, these findings suggest that orientation-specific CSR joining requires an S-region sequence and/or unique aspects of S-region DSBs.

Figures 23A, 23B, 23C, 23D, 23E:
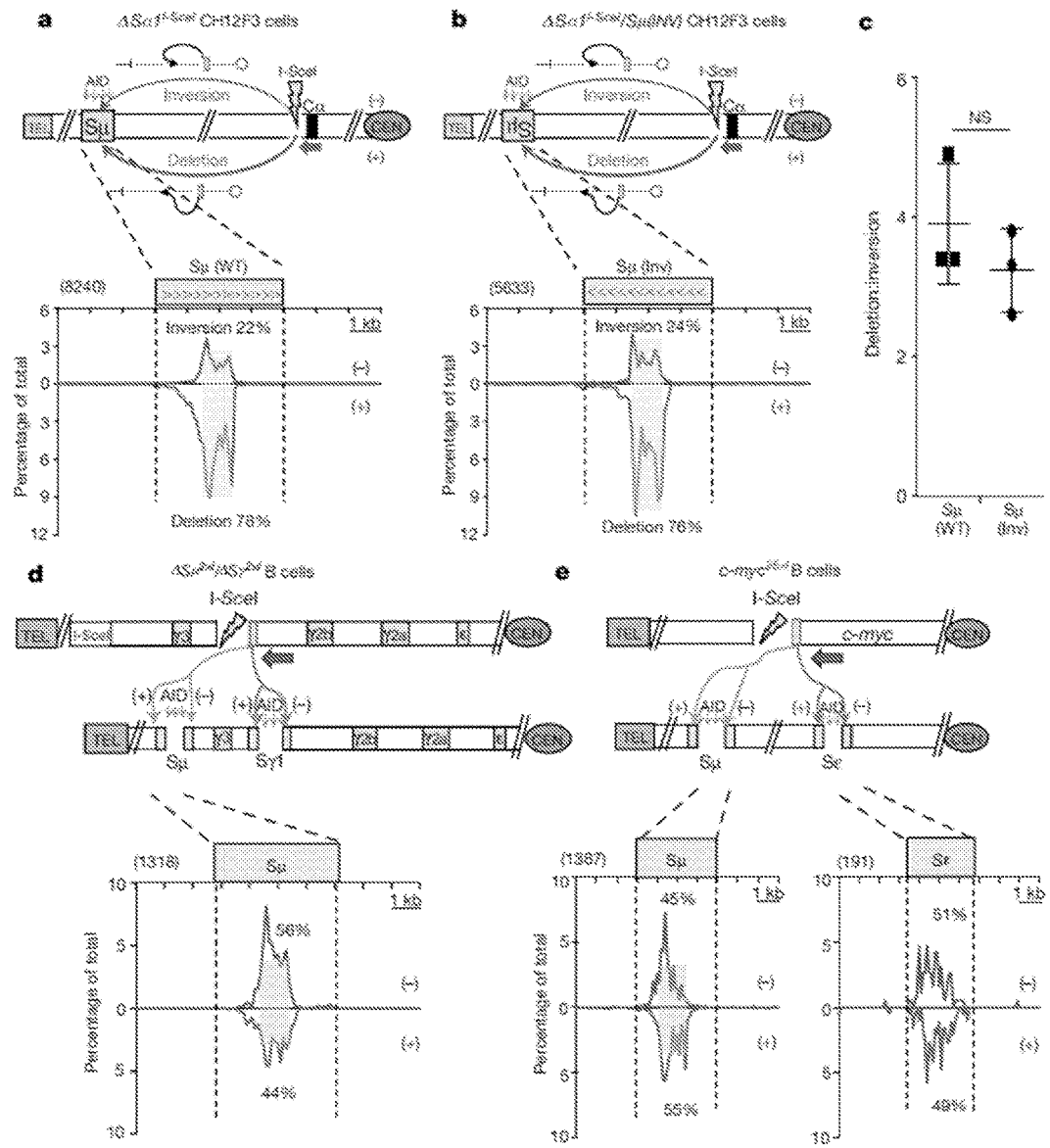
FIGS. 23A-23E demonstrate that S regions are not sufficient to promote orientation-biased CSR joining.

Mammalian S regions are G-rich on the non-template strand, giving AID-initiated 5' and 3' S-region broken ends a potential end-sequence bias. Also, when transcribed in the sense direction, S regions generate stable R-loops14,15 , which could differentially affect 5' and 3' S-region broken end structure. To test the potential roles of S regions in orientation-specific CSR, we used a Cas9/gRNA approach to invert Sμ on the productive allele of CH12F3 B cells, which modestly reduced CSR (data not shown). We then assayed CH12F3 cells in which Sα was replaced with an I-SceI site and Sμ was in a normal or inverted orientation. These assays revealed that joins of I-SceI-generated 3'-broken ends at the Sα locale to Sμ DSBs were similarly biased for deletional junctions independent of Sμ orientation (FIGS. 23A-23C). Consistent with low-level trans CSR16 , HTGTS libraries from activated $\Delta S\mu^{2xI}/\Delta S\gamma c1^{2xI}$ B cells contained numerous junctions from $\Delta S\gamma c1^{2xI}$ 3'-broken ends across the trans Sμ; which, in contrast to cis $\Delta S\gamma c1^{2xI}$ 3'-broken end Sμ junctions, occurred in 1 and 2 orientations at a similar frequency (FIG. 23D). Likewise, bait 3'-broken ends from the $\Delta S\gamma c1^{2xI}$ Igh allele identified approximately equal numbers of (1) versus (2) junctions to AID off-target DSBs in Il4ra on chromosome 7 (data not shown). Finally, translocations between bait 5' I-SceI DSB broken ends in c-myc4 and prey AID-initiated Sμ and Sε broken ends in CSR-activated B cells lacked orientation bias (FIG. 23E). We conclude that orientation dependent CSR joining does not require orientation-associated features of Sμ sequence, transcription, or transcripts. Moreover, AID-initiated DSBs per se are not sufficient to promote orientation specificity, as demonstrated by orientation-independence of DSB joining to them in trans. Thus, beyond S-region sequences and/or high frequency AID initiated DSBs within them, aspects of Igh locus organization in cis must play a critical role in promoting orientation-dependent CSR joining.

Figures 24A, 24B, 24C, 24D, 24E:
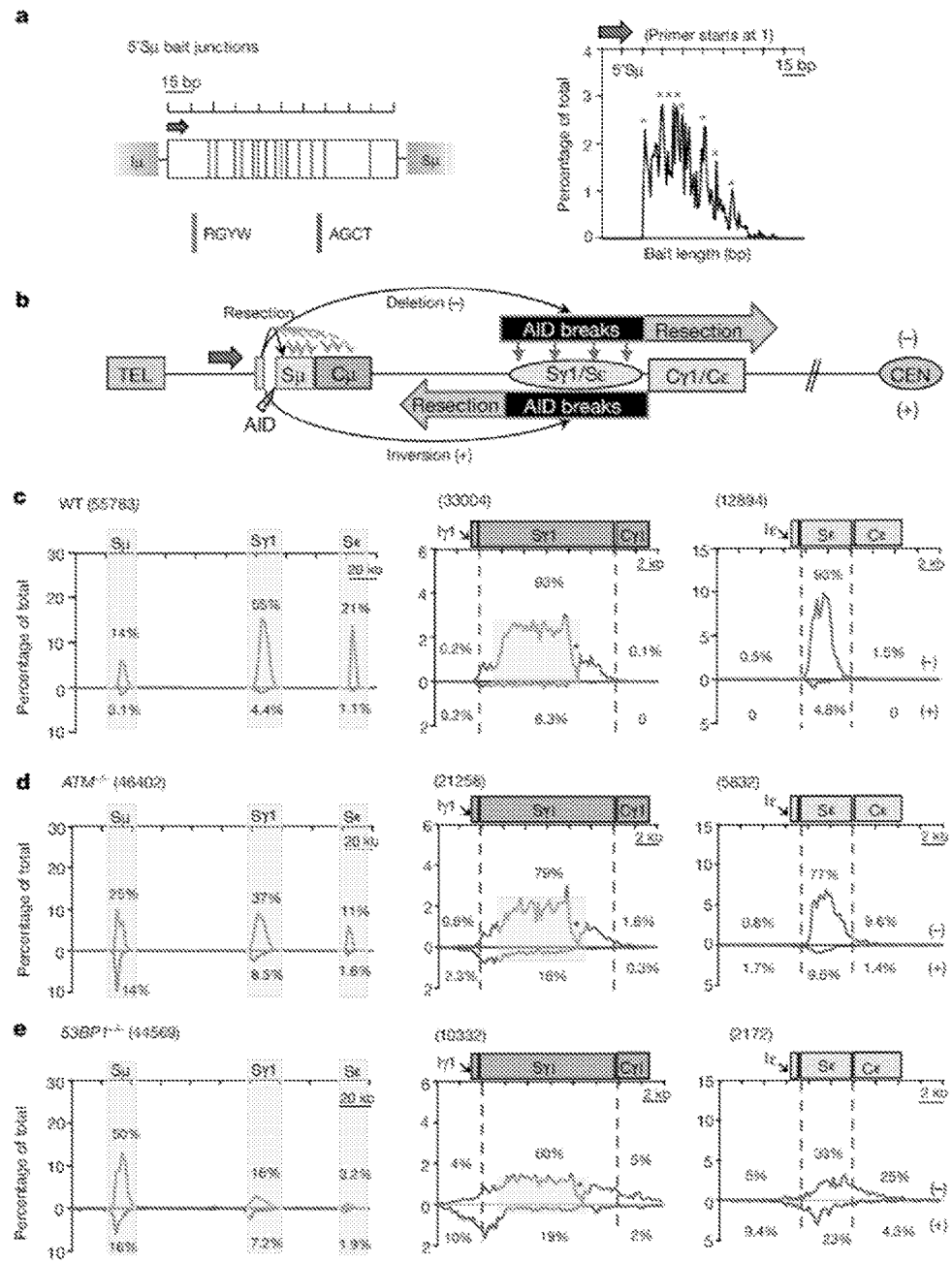
FIGS. 24A-24E demonstrate orientation-biased joining of AID-initiated endogenous S-region breaks.

We tested whether joining between two sets of endogenous AID initiated S-region DSBs is orientation-dependent. Use of core S-region DSBs as HTGTS bait is confounded by their highly repetitive nature. Therefore, we used as bait a 150-base-pair (bp) sequence at the 5' end of Sμ (5'Sμ), which retains 14 of approximately 500 Sμ AID-target motifs (FIG. 24A, left panel). HTGTS of anti-CD40/IL4-stimulated B cells with the 5'Sμ broken end primer revealed break-site junctions, as well as Sγc1 and Sε junctions (FIG. 24B, 24C). Consistent with AID initiation, bait junctions were enriched at AID-targets within the 5'Sμ a bait (FIG. 24A, right panel). 5' Sμ broken end junctions spread broadly over prey S regions, with up to 95% in a deletional orientation (FIG. 24C). For comparison, we tested a 150-bp 5' remnant of Sμ (rSμ; data not shown), retained when the rest of Sμ was deletedl7. B cells homozygous for rSμ have reduced IgG1 CSR but nearly normal IgE CSR18. HTGTS with either 5' rSμ or 3' rSμ broken end primers of anti-CD40/IL4- and lipopolysaccharide/anti-IgDdextran-stimulated B cells, respectively, revealed junctions to Sγc1 and Sε and to Sγc3, Sγc2b, and Sγc2a (data not shown). 5' rSμ broken end junctions spread over target S regions, with >90% in a deletional orientation (data not shown); while >90% of 3' rSμ broken end junctions were in the complementary excision circle orientation (data not shown). Within the bait rSμ, junctions again were enriched at AID targets (data not shown). Consistent with IgH class-switching patterns, rSμ HTGTS junctions occurred more frequently to Sε than those from the 5' Sμ bait in the context of full-length Sμ (data not shown). Analyses of rSμ mutant CH12F3 cells gave similar results (data not shown). Thus, AID-initiated Sμ DSB joining to all downstream acceptor S regions is strongly biased towards the deletional orientation. CSR DSBs generate a DSB response (DSBR) in which ATM activates histone H2AX and 53BP1 in chromatin flanking DSBs, thereby contributing to end-joining19-21. ATM or H2AX deficiency moderately reduces CSR (data not shown) 2,19. However, 53BP1 deficiency causes a more drastic reduction (data not shown), suggesting specialized CSR roles2,19,22 , such as promoting S-region synapsis or protecting S-region DSBs from resection11, 23-25.

Figures 25A, 25B, 25C, 25D:
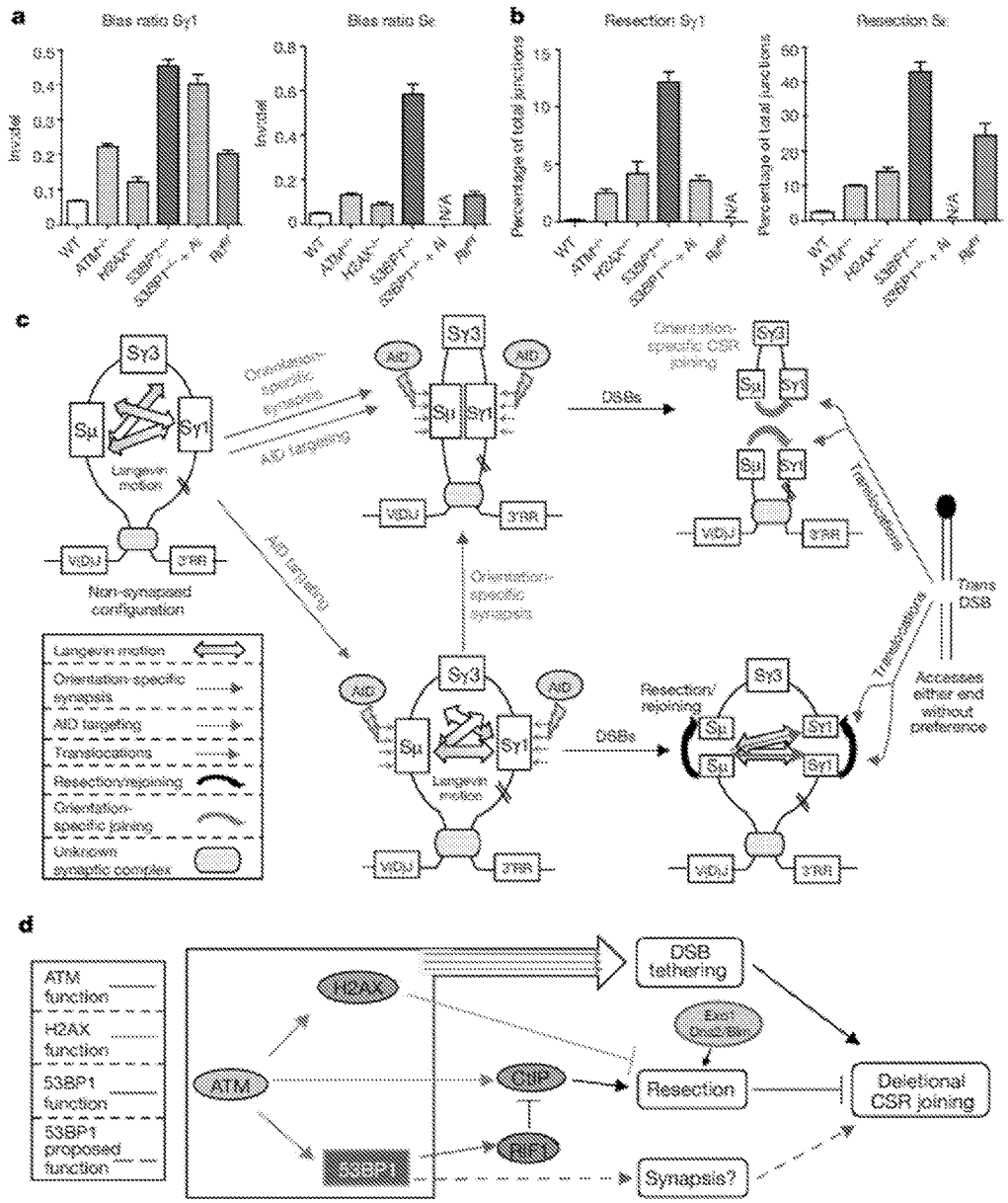
FIGS. 25A-25D depict mechanisitic roles of Igh organization and DSBR factors in deletional CSR.
Figure 26:
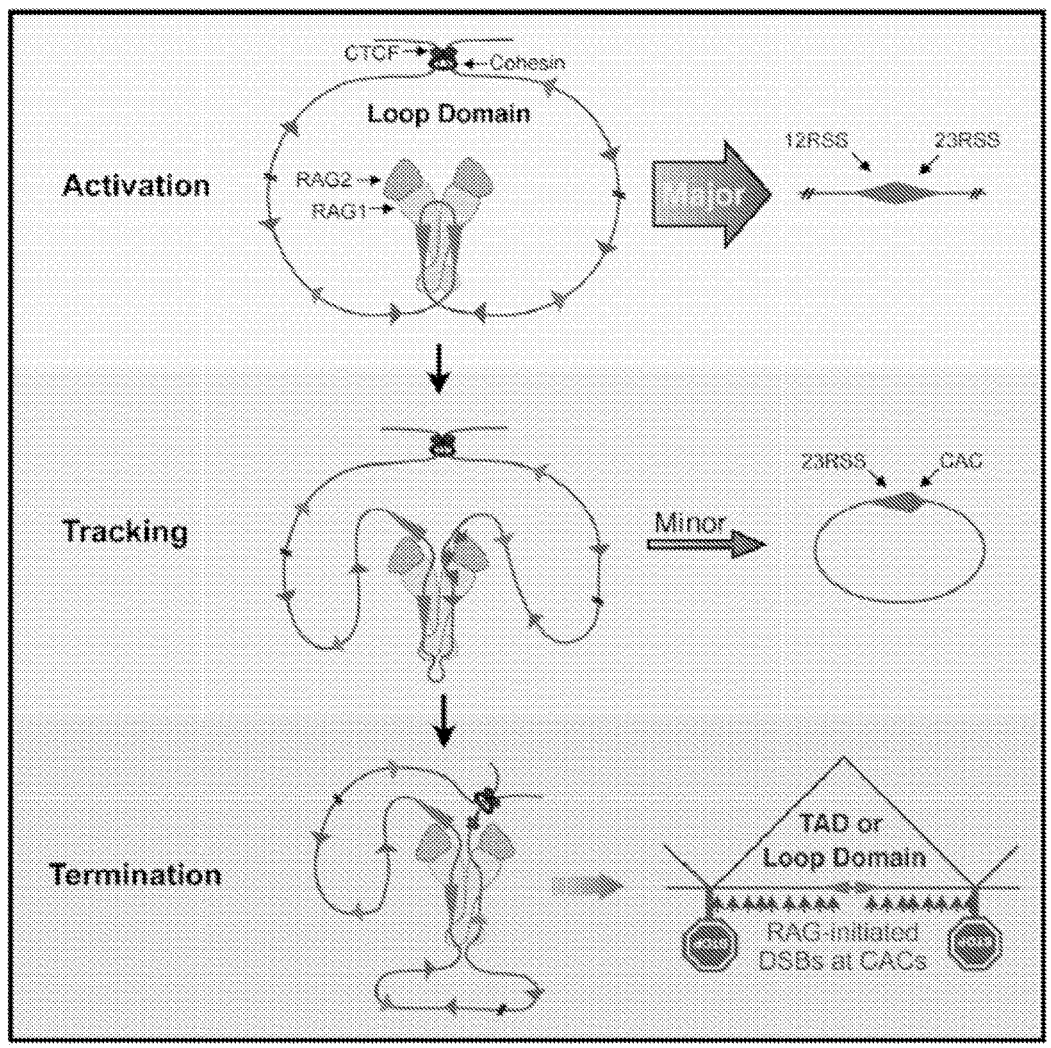
FIG. 26 depicts a schematic of chromosomal loop domains directing the recombination of antigen receptor genes.

To elucidate influences on orientation-specific CSR, we employed HTGTS to assay joining of AID-initiated 5'Sμ broken ends to AID initiated Sγc1 and Sε DSBs in anti-CD40/IL4-activated ATM-, H2AX-, and 53BP1-deficient B cells, as well as in B cells deficient for Rif-1, a 53BP1-associated factor that mediates resection blocking26,27. ATM-, H2AX-, and Rif1-deficient B cells had reduced Sγc1 and Sε junctions compared to wild type; 53BP1-deficient B cells had a greater reduction, with most localizing to the break-site region (FIGS. 24D, 24E). Most break-site junctions were resections, which were longest (up to about 6 kb) for 53BP1 deficiency (data not shown). Compared to wild type, bait 5' Sµ junctions to Sγc1 and Sε DSBs in different DSBR-deficient backgrounds had varying decreases in orientation specificity, with H2AX deficiency having the Smallest and 53BP1 deficiency the largest (FIGS. 24D, 24E, and 25A). Indeed, residual junctions of 5' Sµ to Sγc1 and Sε locales in 53BP1-deficient B cells showed relatively normalized inversion:deletion ratios (FIG. 25A), a finding confirmed by DC-PCR (data not shown). Finally, 53BP1-deficiency did not impact joining orientation of 5' Sµ and 3' Sγc1 I-SceI-generated broken ends in AID-deficient IghI-96k B cells (data not shown). Owing to the potential difficulty in measuring relative resection of recurrent re-joins at or near the break-site, we focused on prey S-region broken end resections (data not shown). Because S regions are long and AID-initiated DSB locations within them are diverse, we estimated relative resection by quantifying bait broken end to prey broken end junctions downstream of S-region positions where the incidence of wild-type junctions decreases to background (FIGS. 24B-24E). Based on this 'long' S-region resection assay, ATM- and H2AX-deficient cells had modest resection increases, Rif1-deficient cells slightly greater increases, and 53BP1—deficient B cells far greater increases that were also apparent as a 'flattening' of Sγc1 and Sε junction profiles relative to other backgrounds (FIGS. 24C-24E and 25B). HTGTS assays of rSµ bait broken end junctions to Sγc1 and Sε (data not shown) and I-SceI-generated 3' ΔSγc1$^{2xI}$ broken end bait junctions to Sµ and Sε (data not shown) gave similar results. In H2AX- or Rif1-deficient B cells, a large fraction of 5' Sµ junctions were within S regions, with the main difference from wild type being a subset of junctions extending beyond S regions, probably reflecting extensive resection of broken ends not rapidly fused (FIG. 25B). Treatment of 53BP1-deficient activated B cells with ATM kinase inhibitor substantially diminished very long S-region resections, but did not restore orientation-dependent joining (FIGS. 25A, 25B). This finding may reflect shorter resections in inhibitor-treated 53BP1-deficient versus ATM-deficient B cells that are not revealed by our long resection assay. Another possibility would involve a putative specialized role for 53BP1 in stabilizing synapsed S regions23.

We demonstrate that CSR is mechanistically programmed to occur in a productive deletional orientation. Based on our findings, we propose a working model for orientation-specific CSR, in which a key component is the organization of S regions within topologicallyassociated domains (TADs) that promote their frequent S-region synapsis2,12,13 via Langevin motion2,13,28 (FIG. 25C). Within such TADs, we implicate additional Igh-specific organizational features, not yet fully elucidated, in playing a fundamental role in mediating synapsis in an orientation that promotes deletional joining (FIG. 25C). We find that functions of such organizational features are complemented by S regions, potentially associated with their ability to promote AID-initiated DSBs, multiple frequent DSBs, or both. Our studies also implicate DSBR factors in enforcing this mechanism (FIG. 25D). The broader DSBR probably contributes by tethering un-synapsed S-region DSBs for efficient re-joining, keeping them from separating into chromosomal breaks that could frequently translocate with orientation independence to S-region broken ends within the TAD2,20 ; this function would also allow subsequent AID-initiated breakage and joining to a synapsed S region (FIG. 25C). DSBR factors also prevent long end-resections that could cause S-region broken ends to linger in resection complexes, preventing synapsis with other S-region broken ends and/or diminishing ability to be joined by classical non-homologous end joining (FIG. 25D). Different DSBR factors have differential impact in tethering versus resection inhibition and, thus, may impact orientation dependence via different routes. For example, ATM deficiency inhibits resection by impairing CtIP activation29, but promotes resection via other nucleases by impairing inhibitory activities of H2AX, 53BP1 and, indirectly, Rif126,27 (FIG. 25D). 53BP1-deficiency is unique in that it both impairs tethering for rejoining and activates resection of un-joined ends by failure to activate Rif1, leading to extreme resections and the greatest impairment of CSR and orientation-dependent joining (FIG. 25D). As common and unique impacts of 53BP1 deficiency markedly affect both donor and acceptor S regions, they would be multiplicative and, thereby, explain the profound impact of 53BP1-deficiency on CSR.

Methods

No statistical methods were used to predetermine sample size. The experiments were not randomized and the investigators were not blinded to allocation during experiments and outcome assessment.

Plasmids and oligonucleotides. Oligonucleotides for gRNAs for CRISPR/Cas9-mediated targeting of various Igh regions were cloned into pX330 vector (Addgene plasmid ID 42230) as described[34].

A 200-bp GFP-derived sequence was amplified and ligated to an I-SceI recognition sequence and subsequently introduced into the pLH28 vector to make the pLH-13 I-SceI exchange vector. To obtain the I-SceI expression plasmid for transducing CH12 cell lines, I-SceI-IRES-GFP fragment was shuttled from a retroviral construct (pMX-I-SceI-IRES-GFP) into pCDNA3.0 (Invitrogen) vector. B-cell culture, transduction and FACS analysis. Mature splenic B cells isolated using a CD43-negative selection kit (MACS) were cultured in lymphocyte medium R15 (RPMI1640, 15% FBS, L-glutamate, 1× penicillin and streptomycin).

B-cell stimulation was performed with anti-CD40 (1 mgml21 , eBioscience) plus IL4 (20 ng ml21 , PeproTech) or LPS (25 ng ml21 , Sigma) plus anti-IgD-dextran (3 ng ml21) for 96 h. Infection with I-SceI expression or control retrovirus was carried out at day 1 post-stimulation by the standard spinning method with the presence of 4 mgml$^{21}$ polybrene as previously described[13]. Efficiency of retrovirus infection and switching levels were evaluated by flow cytometry as previously described[13]. Where indicated, ATM inhibitor KU-55933 (Tocris) was added to stimulated cells at day 1 post-stimulation to a final concentration of 10 mM and was maintained during the course of the experiment until collection of the cells for FACS and HTGTS libraries.

Cell lines and nucleofection. CH12F3 cell line stimulation to IgA was performed as described[35]. CH12F3 cells with recombinase-mediated cassette exchange (RMCE) in place of the endogenous Sa region, referred to as 1F7 cells[35] were maintained at 37 uC, 5% CO2 and cultured in RPMI media with 10% FCS, 0.5% penicillin/streptomycin, 50 mM b-mercaptoethanol. Exchange vector with heterologous loxP sites containing 1× I-SceI site embedded in 200 bp of GFP-derived sequence was cloned. RMCE was performed as previously described[35]. Exchanged ΔSa$^{1xI}$ clones were verified by PCR, Sanger sequencing and Southern blotting. ΔSa$^{1xI}$ cells were then stimulated with anti-CD40, IL4 and TGF-b for 15 h followed by nucleofection with pcDNA-I-Sce1-IRES-GFP expression vector using 4D nucleofector X (Lonza, solution SF, protocol CA-137) and re-plated in stimulation-conditioned media. On day 3 post-stimulation cells, were collected and gDNA was isolated for HTGTS library preparation. Cells were not tested for mycoplasma contamination.

To obtain CH12F3 (productive allele SμINV), non-productive allele DS$_I$LL-Sa) cells, wild-type CH12F3 cells were first nucleofected using the 4D-nucleofector X (Lonza, solution SF protocol CA-137) with the gRNA vectors to excise the sequences between JH4 intron and ,130 bp downstream of Ca polyadenylation on the non-coding allele that has already switched to Sα. Single-cell subclones were seeded into 96-well plates 12 h post-nucleofection, and the resulting clones were screened by PCR and Southern blot. One confirmed positive clone was further modified by gRNA vectors targeted at the 5'Sμ_1 and 3'Sμ regions to invert the Sμ (4 kb) sequence. Initial screening for positive clones was performed by PCR, followed by Southern blotting and Sanger sequencing for the inversion junction. The resultant cells were stimulated with anti-CD40, IL4 and TGF-b, IgA CSR was measured by FACS on days 2 and 3 post-stimulation. ASa$^{1\times1}$ Sμ(INV) cells were obtained by targeting the aforementioned 1× I-SceI RMCE-positive cells with gRNA targeting 5'Sμ_2 and 3'Sμ a for inverting the Sμ sequence same as above. The resultant positive clones were verified by PCR, Southern blotting and Sanger sequencing for the inversion junction. To make rSμ-CH12F3 cells, the aforementioned CH12F3 (non-productive allele DSμ-Sα) cells were used to further truncate Sμ sequences on the coding allele with gRNA targeting 5'Sμ_2 and 3'Sμ. Single cell deletion subclones were screened and confirmed by PCR and Southern blot.

The resultant rSμ-CH12F3 cells were stimulated with anti-CD40, IL4 and TGF-b and harvested on days 2 and 3 for gDNA isolation for HTGTS library preparation. DC-PCR. The DC-PCR assay was performed as described previously[36].

In brief, genomic DNA was isolated and subsequently purified by phenol chloroform extraction from day 4 anti-CD40/IL4 stimulated B cells. Five micrograms of genomic DNA was digested overnight with 20 U of EcoRI (Roche). Ligations were performed under diluted conditions to promote circularization. Digested DNA was ligated overnight at 16 uC with a concentration of 1.8-9 ng ml$^{21}$ in a total volume of 100 ml per reaction. Three to four ligation reactions were pooled, column purified, concentrated and serially diluted at a 1:5 ratio. PCR was then performed in 50 ml per reaction using 2.5 U Taq (Qiagen) with serially diluted DNA starting from ~50-150 ng. Primers were designed to amplify the Sμ-Sγ1 rearrangements that occur during CSR to IgG1 in direct chromosomal joining of Sμ-Sγ1 with excision of circular DNA or inversion of sequences between broken ends of Sμ and Sγ1. As a control for EcoRI digestion and circularization of input DNA, amplification of an EcoRI fragment of nicotinic acetylcholine receptor B subunit gene (CHRNB1) was performed, which, after EcoRI digestion and circularization, generates a 753-bp DC-PCR product.

To quantify the amount of direct or inversion joins amplified by PCR, DC-PCR products of direct or inversion joins were cloned into the pcR2.1 Topo TA vector. Precise plasmid concentrations were determined and a standard curve was generated ranging from 4 to 10,000 copies per reaction. After running on 1% agarose gel, PCR fragments were transferred to nitrocellulose membrane and hybridized to a 3'Sγ1 probe according to standard Southern blotting procedures. Primers for direct joining PCR: forward, 5'CAT GAGAGCTGGAGCTAGTATGAAGGTG-3' (SEQ ID NO: 314); reverse, 5'-ACTGACTGACTGA GTGTCCTCT-CAAC-3' (SEQ ID NO: 315). Primers for inversional joining PCR: forward, 5'-CAG TCACAGAGAAACTGATC-CAGGTGAG-3' (SEQ ID NO: 316); reverse, 5'-CCATAGCAGTTGG TCAATCCTTGTCTCC-3' (SEQ ID NO: 317). Primers for control CHRNB1 DC-PCR36 : forward, 5'-GCGCCATCGATGGACTGCT-GTGGGTTTCACCCAG-3' (SEQ ID NO: 318); reverse, 5'-GGC CGGTCGACAGGCGCGCACTGACAC-CACTAAG-3' (SEQ ID NO: 319). Oligonucleotide probe for the detection of both deletional and inversional CSR joining products: Sγ1-CCTGGGTAGGTTACAGGT-CAAGGCT (SEQ ID NO: 320).

High-throughput genome-wide translocation sequencing (HTGTS). HTGTS libraries were generated by emulsion-mediated PCR (EM-PCR) and linearamplification-mediated PCR (LAM-PCR) methods as described in ref 5. In brief, sonicated (Bioruptor, Diagenode) gDNA was subjected to LAM-PCR using 1 U Taq polymerase (Qiagen) per reaction with a single biotinylated primer for 50 cycles of 94 uC for 180 s; 94 uC for 30 s; 58 uC for 30 s; 72 uC for 90 s. One more unit of Taq polymerase was added to the reaction mixture to execute PCR for an additional 50 cycles. Biotinylated DNA fragments were captured with Dynabeads MyOne streptavidin Cl beads (Invitrogen) at room temperature for 1 h, followed by on-bead ligation at 25 uC for 2 h with bridge adapters in the presence of 15% PEG-8000 (Sigma) and 1 mM hexammine cobalt chloride (Sigma). After washing beads with B&W buffer as described by the manufacturer, ligated products were subjected to 15 cycles of on-bead PCR with Phusion polymerase (Fisher), locusspecific and adaptor primer followed by blocking digestion with appropriate restriction enzymes to remove uncut germline gDNA. A third round of tagging PCR to add Illumina Miseq-compatible adapters at 5' and 3' ends of the secondround PCR product was carried out for another 10 cycles with Phusion polymerase.

PCR products were size-fractionated for DNA fragments between 300-1000 bp on a 1% agrose gel, column purified (Qiagen) before loading onto Illumina Miseq machine for sequencing.

Data analyses. Data analysis of MiSeq sequencing reads has been described in ref 5. In brief, de-multiplexing for the MiSeq reads was performed using the fastq-multx tool from ea-utils (code.google.com/p/ea-utils/) and adaptor sequence trimming was performed using the SeqPrep utility (github. com/jstjohn/SeqPrep). Reads were mapped using Bowtie2 (bowtie-bio.sourceforge. net/bowtie2/manual.shtml) to either mm9 (for libraries generated with Rif1 knockout cells and CH12F3-derived cells) or modified mm9 reference genome (for all other genotypes) containing the 176-kb Igh constant region of 129S genome, in which the region between chr12:114493849-114665808 of mm9 was replaced with DNA sequence ranging from 1416975 to 1593283 on the 129S Igh reference sequences AJ851868.3. In cases where necessary, for instance when aligning reads to the Sμ13I locus on the IghI-96k allele and other circumstances, we further modified the custom 129S_IgHC genome to insert the cassette sequences to accurately reflect the changes of genomic information before aligning MiSeq reads by Bowtie2.

CH12F3 clone was derived from CH12.LX lymphoma cell line[37]. CH12.LX cells were subcloned from the original CH12 lymphoma cell line[38], which originated from a C57BL/10 mouse substrain double congenic for H-2a H-4b (ref 39). C57BL/10 and C57BL/6 are both substrains of C57BL and thus we use BL/6 (mm9) as reference genome when running our HTGTS data analyses pipeline on libraries made with CH12F3 cells. To reflect additional genome modifications (for example, Sµ(INV) shown in FIG. 23B), the mm9 genome sequence was modified accordingly.

A best-path searching algorithm (based on YAHA read aligner and break point detector[40]) was used to select optimal sequence alignments from Bowtie2-reported top alignments with an alignment score above 50, which represents a perfect 25-nucleotide (nt) local alignment. To avoid detecting possible mis-priming events, we set a bait alignment threshold of at least ten perfectly aligned nucleotides extending from the end of cloning primer. Aligned reads were subsequently filtered on following criteria: (1) reads must include both a bait alignment and a prey alignment; and (2) the bait alignment cannot extend more than 10 nt beyond the targeted site. For reads mapped to the repetitive low-mappability regions, multiple competing alignments with identical or similar scores exist and the coordinates for best alignment are randomly chosen among the competing ones.

For junctions mapped to each individual repetitive S region, there are no competing alignments from outside of that region as shown by simulation (see details below), although the exact junction coordinate within the region could not be identified. We also applied filter to remove duplicates (referred to as 'de-dup' hereafter) wherein the coordinates of the end of the bait alignment were compared to the start of the prey alignment across all reads. A read is marked as a duplicate if it has bait and prey alignment coordinates within 2 nt of another read's bait and prey alignments. To plot all the S-region junctions, we took the ones filtered by a mappability filter but unequivocally mapped to S regions and removed the repeats through the de-dup program mentioned above, before combining with 'good' reads passing both the mappability and de-dup filters. A grey box over S regions (for example, Sµ and Sγ1) in the figures is used to denote the repetitive regions in these S sequences wherein the randomly assigned mappability-filtered reads were included. Additionally, we applied post-filtering stringencies to remove junctions mapped to simple sequence repeats, telomere repeats and reads with excessive microhomology>20 nt and insertions>30 nt before further analysis. In the end, the combined and cleaned junctions were then plotted genome-wide or onto desired S regions by using the PlotRegion tool (for details see section below).

S-region junction plotting. As described above, junctions filtered by the mappability filter are retrieved and de-duped before combining with normal junctions. To plot junction coordinates onto individual S regions or the entire Igh constant region, combined junctions are binned using the PlotRegion tool into 100 bins (bin size varies depending on the length of target region that libraries are plotted to) on the basis of the junction coordinates and orientation of joining. The bincount file (histogram information for junction distribution in both joining orientation) generated by the PlotRegion tool is used to calculate the percentage of junctions in each bin in either 1 or 2 orientation of the total number of junctions mapped to the region of interest. The results were then plotted as linear graphs by the Prism software. Note that the scale on top of each graph indicates the size of region plotted and is fixed as 1/10 of the size of the plotted region, thus is always 103 bin size.

Calculation of joining orientation bias and acceptor S-region resection. For simplicity, joining from 59Sµ to downstream Sγ1 and Sε breaks are used for the explanation of orientation bias and resection of acceptor S-region DSBs. Junction mapped to Sγ1 and Sε can be divided into six regions (denoted by a-f) in either 1 or 2 orientation:

$$\frac{a|b|c(-)}{d|e|f(+)}$$

Junctions encompassing core Sγ1/Sε are illustrated as b and e regions for 2 and 1 junctions respectively, c region (deletional joining, 2 orientation) or d region (inversional joining, 1 orientation) represent joining of bait DSB broken ends to resected acceptor Sγ1/Sε DSBs. Junctions falling into regions a or f represent joining to non-AID-generated de novo breaks of unknown source and are often very small in number, and thus were omitted from the calculation of both resection and orientation bias. Since in most genetic backgrounds other than 53BP1$^{-/-}$ inversion joins are much rarer than deletions, the level of resection junctions into the d region fluctuates much more than resection junctions into the c region. We thus chose the c region for calculating resection in all genotypes as follows:

$$\text{resecton rate} = \frac{c}{b+c} \times 100$$

The degree of orientation bias, for the purpose of positively correlating with the level of resection, is calculated as the ratio of inversional joins versus deletional joins as below:

$$\text{bias ratio} = \frac{d+e}{b+c} \times 100$$

To make a bar graph for comparison of orientation bias degree and resection levels in the CSR junctions obtained from libraries with different genetic backgrounds, individual replicate HTGTS libraries were first size-normalized to the one with smallest junction number in the region of interest among the replicates; resection and bias ratio values from individual experiments were calculated separately and averages were used for statistical analysis with unpaired two-tailed t-tests. Experiments for each genotype were performed at least three times.

REFERENCES

1. Schatz, D. G. & Swanson, P. C. V(D)J recombination: mechanisms of initiation. Annu. Rev. Genet. 45, 167-202 (2011).
2. Alt, F. W., Zhang, Y., Meng, F. L., Guo, C. & Schwer, B. Mechanisms of programmed DNA lesions and genomic instability in the immune system. Cell 152, 417-429 (2013).
3. Di Noia, J. M. & Neuberger, M. S. Molecular mechanisms of antibody somatic hypermutation. Annu. Rev. Biochem. 76, 1-22 (2007).
4. Chiarle, R. et al. Genome-wide translocation sequencing reveals mechanisms of chromosome breaks and rearrangements in B cells. Cell 147, 107-119 (2011).
5. Frock, R. L. et al. Genome-wide detection of DNA double-stranded breaks induced by engineered nucleases. Nature Biotechnol. 33, 179-186 (2015).
6. Yancopoulos, G. D. et al. Secondary genomic rearrangement events in pre-B cells: VHDJH replacement by a LINE-1 sequence and directed class switching. EMBO J. 5, 3259-3266 (1986).

7. Jack, H. M. et al. Looping out and deletion mechanism for the immunoglobulin heavy-chain class switch. Proc. Natl Acad. Sci. USA 85, 1581-1585 (1988).
8. Vaandrager, J. W. et al. DNA fiber fluorescence in situ hybridization analysis of immunoglobulin class switching in B-cell neoplasia: aberrant CH gene rearrangements in follicle center-cell lymphoma. Blood 92, 2871-2878 (1998).
9. Lenz, G. et al. Aberrant immunoglobulin class switch recombination and switch translocations in activated B cell-like diffuse large B cell lymphoma. J. Exp. Med. 204, 633-643 (2007).
10. Harriman, W., Vo "Ik, H., Defranoux, N. & Wabl, M Immunoglobulin class switch recombination. Annu. Rev. Immunol 11, 361-384 (1993).
11. Bothmer, A. et al. 53BP1 regulates DNA resection and the choice between classical and alternative end joining during class switch recombination. J. Exp. Med. 207, 855-865 (2010).
12. Zarrin, A. A. et al. Antibody class switching mediated by yeast endonuclease generated DNA breaks. Science 315, 377-381 (2007).
13. Gostissa, M. et al. IgH class switching exploits a general property of two DNA breaks to be joined in cis over long chromosomal distances. Proc. Natl Acad. Sci. USA 111, 2644-2649 (2014).
14. Tian, M. & Alt, F. W. Transcription-induced cleavage of immunoglobulin switch regions by nucleotide excision repair nucleases in vitro. J. Biol. Chem. 275, 24163-24172 (2000).
15. Yu, K., Chedin, F., Hsieh, C. L., Wilson, T. E. & Lieber, M. R. R-loops at immunoglobulin class switch regions in the chromosomes of stimulated B cells. Nature Immunol 4, 442-451 (2003).
16. Reynaud, S. et al. Interallelic class switch recombination contributes significantly to class switching in mouse B cells. J. Immunol 174, 6176-6183 (2005).
17. Khamlichi, A. A. et al Immunoglobulin class-switch recombination in mice devoid of any Sm tandem repeat. Blood 103, 3828-3836 (2004).
18. Zhang, T. et al. Downstream class switching leads to IgE antibody production by B lymphocytes lacking IgM switch regions. Proc. Natl Acad. Sci. USA 107, 3040-3045 (2010).
19. Nussenzweig, A. & Nussenzweig, M. C. Origin of chromosomal translocations in lymphoid cancer. Cell 141, 27-38 (2010).
20. Franco, S. et al. H2AX prevents DNA breaks from progressing to chromosome breaks and translocations. Mol. Cell 21, 201-214 (2006).
21. Bredemeyer, A. L. et al. ATM stabilizes DNA double-strand-break complexes during V(D)J recombination. Nature 442, 466-470 (2006).
22. Daniel, J. A. & Nussenzweig, A. The AID-induced DNA damage response in chromatin. Mol. Cell 50, 309-321 (2013).
23. Reina-San-Martin, B., Chen, J., Nussenzweig, A. & Nussenzweig, M C Enhanced intra-switch region recombination during immunoglobulin class switch recombination in 53BP1−/− B cells. Eur. J. Immunol 37, 235-239 (2007).
24. Bassing, C. H. & Alt, F. W. The cellular response to general and programmed DNA double-strand breaks. DNA Repair (Amst.) 3, 781-796 (2004).
25. Yamane, A. et al. RPA accumulation during class switch recombination represents 59-39 DNA-end resection during the S-G2/M phase of the cell cycle. Cell Rep. 3, 138-147 (2013).
26. Panier, S. & Boulton, S. J. Double-strand break repair: 53BP1 comes into focus. Nature Rev. Mol. Cell Biol. 15, 7-18 (2014).
27. Zimmermann, M. & de Lange, T. 53BP1: pro choice in DNA repair. Trends Cell Biol. 24, 108-117 (2014).
28. Lucas, J. S., Zhang, Y., Dudko, O. K. & Murre, C. 3D trajectories adopted by coding and regulatory DNA elements: first-passage times for genomic interactions. Cell 158, 339-352 (2014).
29. Helmink, B. A. et al. H2AX prevents CtIP-mediated DNA end resection and aberrant repair in G1-phase lymphocytes. Nature 469, 245-249 (2011).
30. Borghesani, P. R. et al. Abnormal development of Purkinje cells and lymphocytes in Atm mutant mice. Proc. Natl Acad. Sci. USA 97, 3336-3341 (2000).
31. Bassing, C. H. et al. Histone H2AX: a dosage-dependent suppressor of oncogenic translocations and tumors. Cell 114, 359-370 (2003).
32. Morales, J. C. et al. Role for the BRCA1 C-terminal repeats (BRCT) protein 53BP1 in maintaining genomic stability. J. Biol. Chem. 278, 14971-14977 (2003).
33. Di Virgilio, M. et al. Rifl prevents resection of DNA breaks and promotes immunoglobulin class switching. Science 339, 711-715 (2013).
34. Cong, L. et al. Multiplex genome engineering using CRISPR/Cas systems. Science 339, 819-823 (2013).
35. Han, L., Masani, S. & Yu, K. Overlapping activation-induced cytidine deaminase hotspot motifs in Ig class-switch recombination. Proc. Natl Acad. Sci. USA 108, 11584-11589 (2011).
36. Chu, C. C., Paul, W. E. & Max, E. E. Quantitation of immunoglobulin m-cl heavy chain switch region recombination by a digestion-circularization polymerase chain reaction method. Proc. Natl Acad. Sci. USA 89, 6978-6982 (1992).
37. Nakamura, M. et al. High frequency class switching of an IgM1 B lymphoma clone CH12F3 to IgA1 cells. Int. Immunol 8, 193-201 (1996).
38. Bishop, G. A. & Haughton, G. Induced differentiation of a transformed clone of Ly-1 B cells by clonal T cells and antigen. Proc. Natl Acad. Sci. USA 83, 7410-7414 (1986).
39. Haughton, G., Arnold, L. W., Bishop, G. A. & Mercolino, T. J. The CH series of murine B cell lymphomas: neoplastic analogues of Ly-11 normal B cells. Immunol Rev. 93, 35-52 (1986). 40. Faust, G. G. & Hall, I. M. YAHA: fast and flexible long-read alignment with optimal breakpoint detection. Bioinformatics 28, 2417-2424 (2012).

Example 5

Chromosomal Loop Domains Direct the Recombination of Antigen Receptor Genes

RAG initiates antibody V(D)J recombination in developing lymphocytes by generating "on-target" DNA breaks at matched pairs of bona fide recombination signal sequences (RSSs). We employ bait RAG-generated breaks in endogenous or ectopically inserted RSS pairs to identify huge numbers of RAG "off-target" breaks. Such breaks occur at the simple CAC motif that defines the RSS cleavage site and are largely confined within convergent CTCF-binding element (CBE)-flanked loop domains containing bait RSS pairs. Marked orientation dependence of RAG off-target activity within loops spanning up to 2 megabases implies involvement of linear tracking. In this regard, major RAG off-targets in chromosomal translocations occur as convergent RSS pairs at enhancers within a loop. Finally, deletion of a CBE-based IgH locus element disrupts V(D)J recombination domains and, correspondingly, alters RAG on- and off-target distributions within IgH. Our findings reveal how RAG activity is developmentally focused and implicate mechanisms by which chromatin domains harness biological processes within them.

INTRODUCTION. During B and T lymphocyte development, exons encoding antigen-binding immunoglobulin (Ig) or T cell receptor (TCR) variable regions are assembled from V, D, and J gene segments by V(D)J recombination (Alt et al., 2013). V(D)J recombination is initiated by RAG endonuclease, which introduces DNA double-stranded breaks (DSBs) between a pair of V, D, and J coding gene segments and their flanking recombination signal sequences (RSSs) (Schatz and Swanson, 2011). A bona fide RSS comprises a conserved palindromic heptamer represented by the canonical CACAGTG sequence, a degenerate spacer of 12 or 23 base pairs (bp), and a less-conserved A-rich nonamer (FIG. 27A; Schatz and Swanson, 2011). RSSs with 12- or 23-bp spacers are termed 12RSSs and 23RSSs, respectively. Efficient RAG cleavage is restricted to a pair of participating coding segments flanked, respectively, by a 12RSS and a 23RSS, referred to here as paired bona fide RSSs. This 12/23 RSS restriction helps direct RAG to appropriate targets within antigen receptor loci (Alt et al., 2013).

Figures 27A, 27B, 27C, 27D, 27E, 27F, 27G:
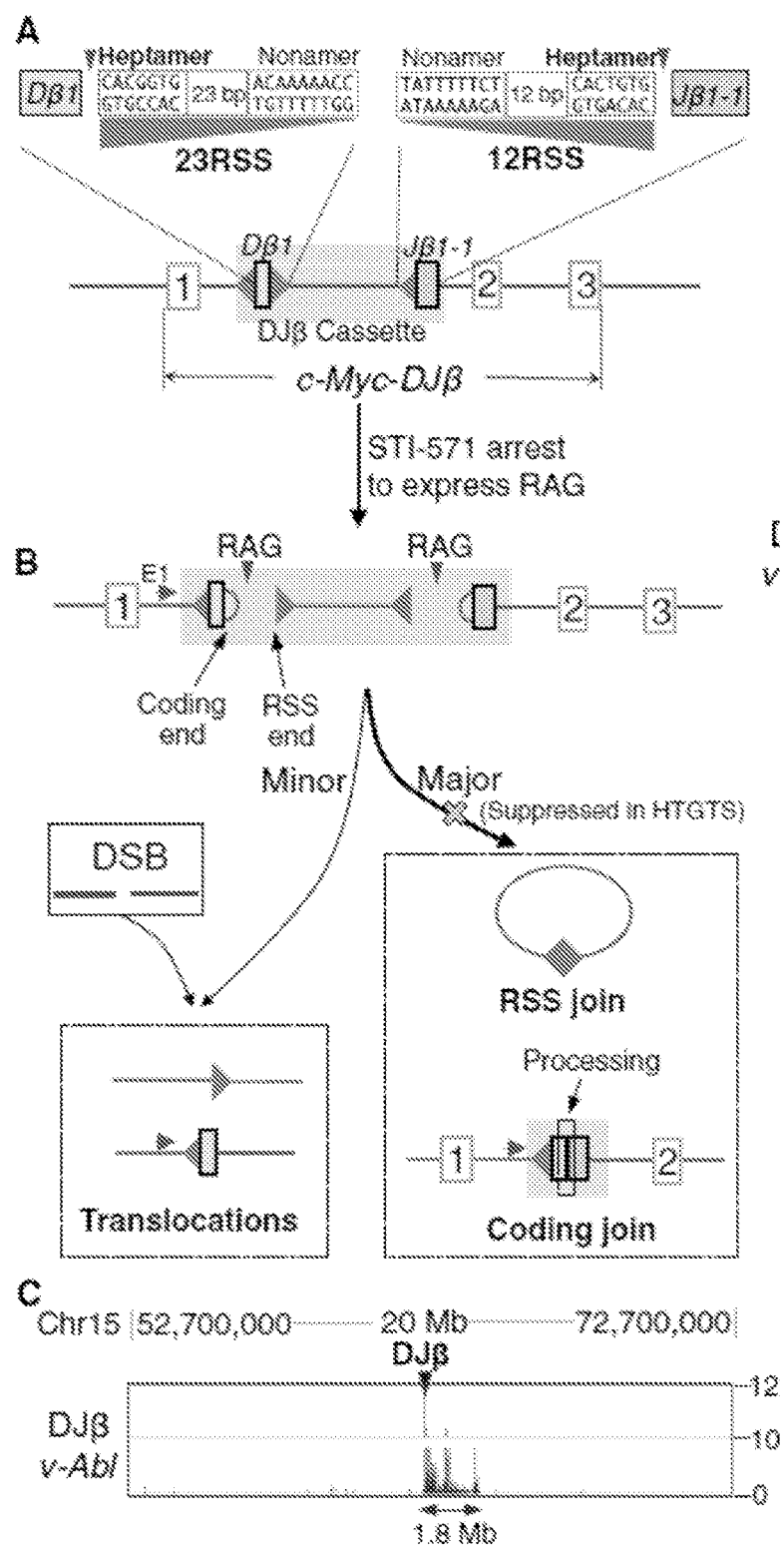
FIGS. 27A-27G demonstrate abundant DSBs in the 1.8-Mb c-Myc-DJβ Loop Domain in v-Abl Pro-B Cells.
Figures 27A, 27B, 27C, 27D, 27E, 27F, 27G:
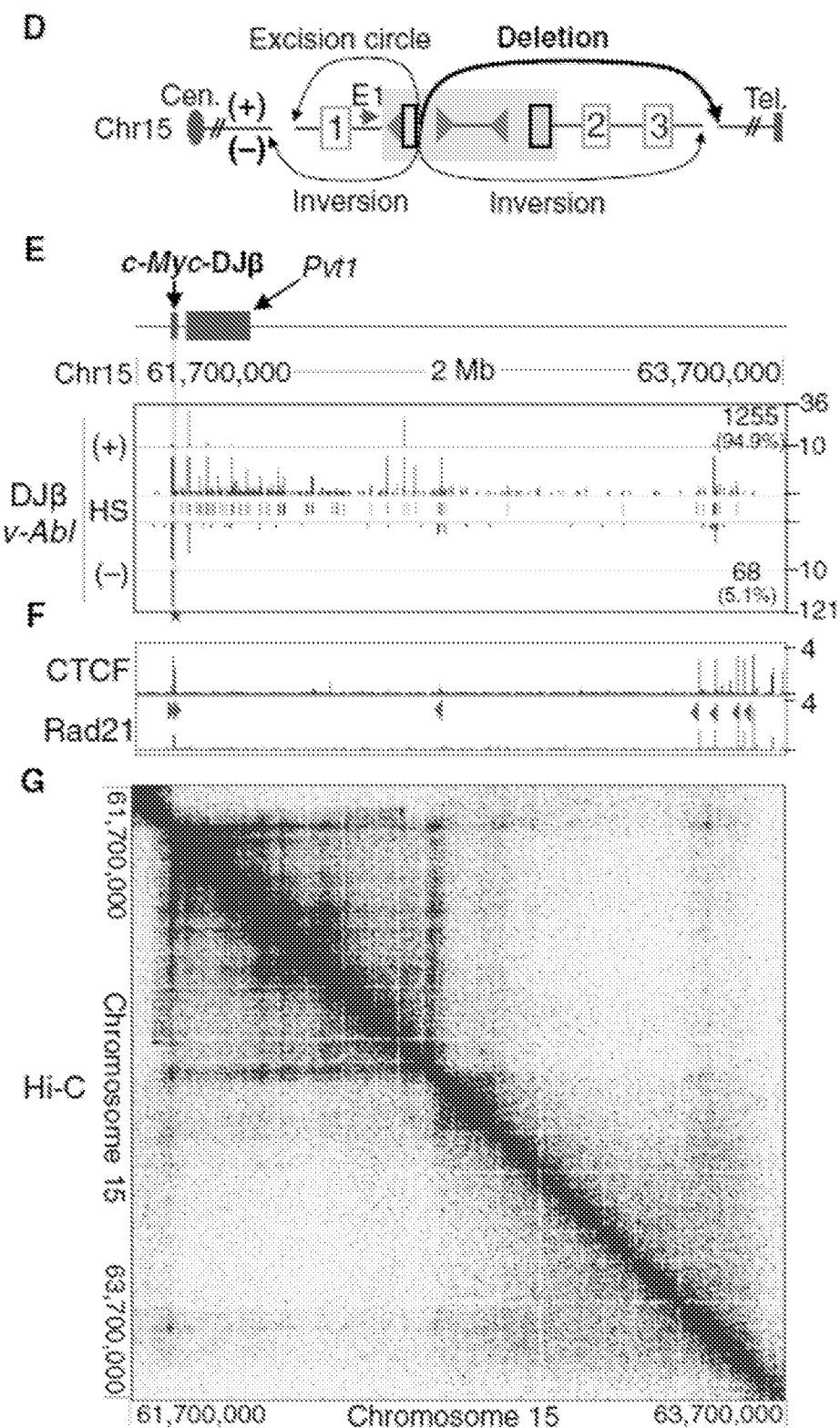

RAG cleavage generates a pair of blunt broken RSS ends and a pair of hairpin-sealed coding ends (FIG. 27B; Schatz and Swanson, 2011). Classical non-homologous end joining (C-NHEJ) fuses the two RSS ends precisely to form RSS joins and opens the two coding-end hairpins and joins them to form coding joins, which may be "processed" to lose or gain several nucleotides from each end (FIG. 27B; Alt et al., 2013). While potential bona fide RSS-related sequences occur frequently across the genome, only a small number are documented RAG off-targets ("cryptic RSSs") (Merelli et al., 2010). Such RAG off-target activity contributes to oncogenic deletions or translocations in immature B and T cell cancers (Boehm et al., 1989; Larmonie et al., 2013; Onozawa and Aplan, 2012; Papaemmanuil et al., 2014). While RAG1 and RAG2 bind several thousand genomic sites that mostly correspond to active promoters and enhancers (Ji et al., 2010; Teng et al., 2015), lower densities of cryptic RSS heptamers near transcription start sites may help to limit RAG off-target activity (Teng et al., 2015).

The mouse IgH locus spans 2.7 megabases (Mb) with VHs and their downstream 23RSSs embedded in a 2.4-Mb distal portion separated by a 100-kb intergenic region from DHs flanked on both sides by 12RSSs and JHs flanked upstream by 23RSSs. Even though 12/23 restriction should allow VHs to join to un-rearranged DHs, IgH V(D)J recombination is "ordered," with DH to JH joining occurring in early progenitor (pro)-B cells followed by appendage of a VH to a DJH complex (Alt et al., 2013). Ordered rearrangement and other levels of IgH V(D)J recombination regulation are mediated by modulating gene segment accessibility to RAG (Yancopoulos and Alt, 1986). In this regard, IgH contains a critical regulatory element termed intergenic control region 1 (IGCR1) within the VH-to-DH interval (Guo et al., 2011). IGCR1 suppresses proximal VH transcription and rearrangement at the DH-to-JH joining stage and, thereby, mediates broad levels of V(D)J recombination control, including diversification of antibody repertoires, by indirectly promoting increased utilization of distal VHs. The most D-proximal VH (VH81x), while preferentially utilized in wild-type (WT) pro-B cells (Yancopoulos et al., 1984), is even more frequently utilized upon IGCR1 inactivation (Guo et al., 2011).

The CTCF factor binds directionally to an 14-bp DNA target (Nakahashi et al., 2013), referred to as a CTCF-binding element (CBE) (Guo et al., 2011). CTCF is implicated in transcriptional insulation through ability to mediate chromatin loops (Ong and Corces, 2014). IGCR1 function relies on two divergently oriented CBEs within it (Guo et al., 2011). Besides IGCR1 CBEs, the 30 IgH boundary harbors a CBE cluster (termed "30 CBEs"), and single CBEs occur just downstream of proximal VHs and in intergenic regions between distal VHs (Degner et al., 2009). VH CBEs are convergently oriented with respect to the upstream IGCR1 CBE, and 30 CBEs are convergently oriented with respect to the downstream IGCR1 CBE (Guo et al., 2011). Mutational studies of individual IGCR1 CBEs indicated that loop(s) mediated by the downstream CBE focus RAG activity in early pro-B cells within a domain containing the DHs and JHs, while a second domain mediated by the upstream CBE sequesters proximal VHs from RAG activity (Lin et al., 2015).

Eukaryotic genomes are organized into a hierarchy of architectures. Hi-C shows that chromatin is organized into topologically associated domains (TADs) that occur on Mb or sub-Mb scales and that have high-frequency chromatin interactions within them (Dixon et al., 2012; Nora et al., 2012). Boundaries of such domains are often co-anchored by long-range interactions of sites bound by CTCF in association with cohesion (Phillips-Cremins et al., 2013; Zuin et al., 2014). Recent higher resolution in situ Hi-C further revealed that mammalian genomes are divided into contact domains at an average scale of 185 kb (Rao et al., 2014). Contact domains with endpoints that generate a loop are termed loop domains (Rao et al., 2014). Loop domains genome-wide are commonly associated with pairs of convergent CBEs bound by CTCF and cohesin (Rao et al., 2014; Vietri Rudan et al., 2015). TADs have been implicated in replication timing (Pope et al., 2014), super-enhancer-driven transcription (Dowen et al., 2014), and DSB synapsis during antibody classswitch recombination (CSR) (Dong et al., 2015; Zarrin et al., 2007), as well as in promoting normal limb development (Lupia' n~ ez et al., 2015).

Mechanistic aspects of how loop domains and TADs function are not well understood. Our recent studies suggested an unanticipated source of RAG off-target activity within long chromatin domains. To study oncogenic consequences, we generated mice with Tcrb Dβ1 and Jβ1-1 segments inserted into intron one of the c-Myc oncogene ("c-Myc-DJβcassette"). Despite frequent c-Myc-DJβ cassette recombination in developing lymphocytes, these mice do not develop lymphoma (Ranganath et al., 2008). However, ATM deficient, c-Myc-DJβ cassette mice develop B cell lymphomas with c-Myc translocations/amplifications that fuse RAG-generated IgH DSBs to sequences over a several-hundred-kb region downstream of c-Myc (Tepsuporn et al., 2014). These downstream translocations occur exclusively on the cassette allele but do not involve the cassette, suggesting that RAG activity at bona fide RSS pairs within c-Myc promotes cutting at linked downstream cryptic RSSs (Tepsuporn et al., 2014). On this basis, we identify an immense number of previously unsuspected RAG off-targets generated by a mechanism that has broader implications for gene regulation within loop domains.

Results

HTGTS Assay for RAG On-Target and Off-Target DSBs and Translocations. To test the hypothesis that the c-Myc-DJβ cassette promotes cutting at cryptic RSSs downstream of c-Myc, we generated a v-Abl-transformed pro-B cell line from mice homozygous for the c-Myc-DJβ cassette allele (referred to as "c-Myc-DJβ pro-B line"). In such lines, RAG expression can be induced in the context of G1 cell-cycle arrest following treatment with the v-Abl kinase inhibitor STI-571 (Bredemeyer et al., 2006). Due to propensity of cycling v-Abl transformants to form D1β1-to-Jβ-1 cassette rearrangements at low level, we were able to isolate just one v-Abl pro-B clone with an un-rearranged cassette allele (FIG. 27A). This clone had a second cassette allele in DJβ-rearranged rearranged configuration, which is inert for rearrangement (see below). Upon G1 arrest and RAG expression, the c-Myc-DJβ construct undergoes high-frequency bona fide Dβ11-to-Jβ1-1 rearrangements, which fuse the downstream coding end of Dβ1 (23RSS-associated) to the Jβ1-1 12RSS-associated coding end in the chromosome and, correspondingly fuse the Dβ1 23RSS to the Jβ1-1 12RSS within an excision circle (FIGS. 27A and 27B).

To detect potential cryptic RSSs activated by the c-Myc-DJβ cassette in these v-Abl pro-B cells, we employed high-throughput genome-wide translocation sequencing (HTGTS). HTGTS is a highly sensitive DSB and translocation assay that identifies junctions between a broken end of a fixed "bait" DSB and ends of other prey DSBs genome-wide (Chiarle et al., 2011; Dong et al., 2015; Frock et al., 2015). For these analyses, we used an HTGTS bait primer termed "c-Myc E1" that anneals with sequences 213 bp upstream of the cassette Dβ1 23RSS. This primer detects D1β1 downstream coding end joins to Jβ1-1 coding ends and to other DSBs genome-wide (FIG. 27B).

In the c-Myc-DJβ pro-B line, the vast majority of recovered HTGTS junctions represented expected bona fide cassette Dβ1-to-Jβ1-1 coding joins. To enhance off-target detection, we experimentally suppressed recovery of bona fide cassette DJβ joins (FIG. 27B). The vast majority of remaining Dβ1 downstream coding-end junctions, representing 1%-3% of total junctions, occurred to sequences up to 1.8 Mb downstream of c-Myc, with additional joins to sequences about 1 kb upstream. Notably, the junctions in this 1.8-Mb region abruptly ended in both directions (FIG. 27C; see below).

Indeed, the only other clear-cut hotspot region genome-wide occurred at about 0.02% of total junctions and involved low-level translocations to Igk (data not shown), a major bona fide RAG target in v-Abl pro-B cells (Zhang et al., 2012). Approximately 20% of the apparent RAG off-target sites in the 1.8-Mb domain represented recurrent ("hotspot") junctions that, in some cases, were recovered dozens of times in independent libraries (data not shown). HTGTS analysis of bone marrow (BM) pro-B cells from c-Myc-DJβ mice gave similar results (data not shown).

We also isolated an ATM-deficient v-Abl c-Myc-DJβ pro-B line in which one allele had an inversion that joined the Dβ1 RSS to a cryptic RSS (50-CACAGTT) in the Jβ1-1 segment (data not shown). In this line, the second c-MycDJβ allele was in the inert DJβ configuration. Following G1 arrest, HTGTS employing the c-Myc E1 primer revealed that the major "bona fide" V(D)J joining event in this line (>97% of recovered junctions) was inversional joining of the D1β1 12RSS (the upstream Dβ1 RSS) to the inverted Dβ1 RSS 693 bp downstream (data not shown). The vast majority of remaining joins (~3% of total junctions) fused the Dβ1 RSS to other DSBs along the 1.8-MB cassette-containing domain with a distribution similar to that of Dβ1 downstream coding-end joins in the ATM-proficient c-Myc-DJβ pro-B line and primary pro-B cells (data not shown). Notably, there was increased but still low levels of translocations to Igk (~0.2% of total junctions) as compared to ATM-proficient pro-B cells. ATM-deficient BM c-Myc-DJβ pro-B cells also had similar patterns of Dβ1 RSS coding-end junctions to those of ATM-proficient pro-B lines, exce low-level translocations to IgH (~0.07%) and TCRa/d (~0.05%) (data not shown). Finally, an ATM-deficient v-Abl c-Myc-DJβ pro-B line in which both cassette alleles were in the DJβ configuration generated few junctions, confirming that single 12RSScontaining alleles are inert (data not shown).

Abundant DSBs across the 1.8-Mb c-Myc-DJβ Loop Domain. We investigated the orientation of the thousands of Dβ1 downstream coding-end junctions within the 1.8-Mb c-Myc region in the c-Myc-DJβ1 v-Abl pro-B cell line. Junctions are denoted as in "+" orientation if prey sequence reads in a centromere-to-telomere direction and in "−" orientation if prey reads in the opposite direction (Chiarle et al., 2011). As the c-Myc E1 primer is centromeric to the bait Dβ1 downstream coding end, it captures junctions resulting in upstream excision circles and downstream deletions as + events and captures inversional junctions either upstream or downstream as − events (FIG. 27D). Dβ1 downstream coding-end junctions near (within 5 kb) c-Myc occurred at similar frequency in + and − orientations (data not shown); strikingly, however, ~95% of junctions to sequences further downstream of c-Myc occurred in deletional (+) orientation (FIG. 27E). Similar results also were obtained with ATM-deficient c-Myc-DJβ pro-B cell lines, even though their junctions involved Dβ1-12RSS ends (data not shown).

To gain insight into the basis for the well-defined boundaries of the DSB hotspot region flanking the c-Myc-DJβ cassette, we analyzed existing ChIP-seq data from BM pro-B cells (Lin et al., 2012) and found a cluster of CTCF and cohesin subunit Rad21-binding sites on both boundaries of this 1.8-Mb domain (FIG. 27F). Moreover, the two clusters of CBEs were in convergent orientation (FIG. 27F). Indeed, recent high-resolution in situ Hi-C data performed in mouse CH12-LX B cell lines (Rao et al., 2014) confirmed that this 1.8-Mb region is a well-defined convergent CBE-based loop domain that contains within it a strong 840-kb sub-loop that also extends to a convergent CBE (FIGS. 27F and 27G). HTGTS junction density within the 1.8-Mb domain in both ATM-proficient (FIGS. 27E-27G) and deficient c-Myc-DJβ pro-B cells (data not shown) correlated well with Hi-C interactions within the two loop domains.

Figures 28A, 28B, 28C, 28D, 28E, 28F:
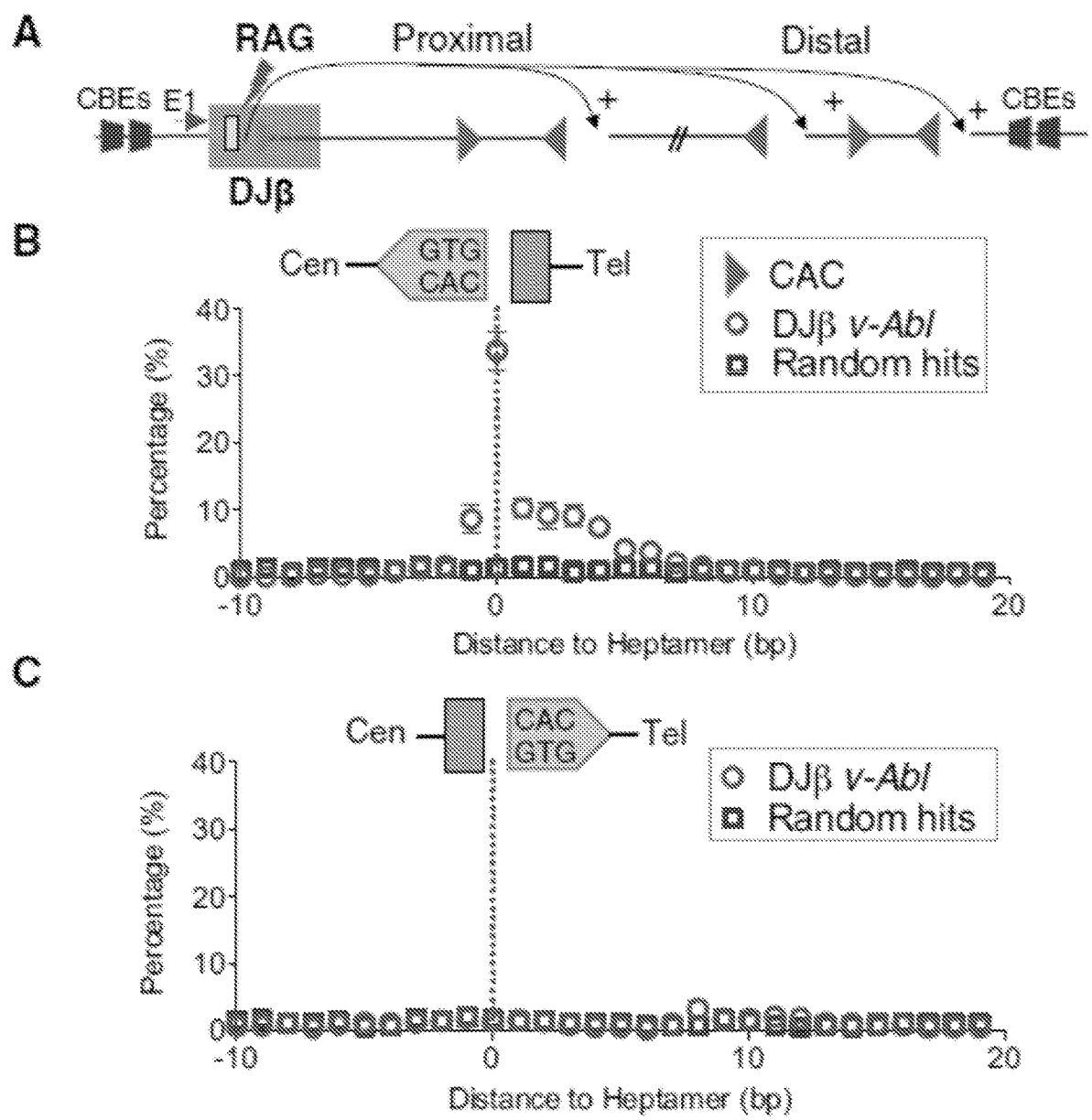
FIGS. 28A-28F demonstrate that RAG Generates DSBs across the 1.8-Mb c-Myc-DJβ Loop Domain.

RAG Generates DSBs in the 1.8-Mb c-Myc-DJβ Loop Domain. To test the relationship of frequent prey DSBs within the 1.8-Mb c-Myc loop domain to RAG-generated DSBs, we searched ATM-proficient and ATM-deficient c-Myc-DJβ junctions for sequence motifs in their vicinity. In this regard, the conserved 50-CAC motif of the RSS heptamer is a position indicator for RAG cleavage, with cleavage invariably occurring 50 to the CAC motif (FIG. 27A). For convention, a CAC is considered in "forward" orientation if the presumed associated "coding" sequence is centromeric to the RSS and in "reverse" orientation if the presumed coding sequence is telomeric. For widespread CACs, sequences in the coding position would not generally be gene segments; thus, we refer to them as surrogate coding ends. For analysis, we pooled and analyzed, respectively, all + junctions from the two v-Abl pro-B cell types and found that the majority occurred in putative surrogate coding sequences at or within pt that they had 5 bp of a reverse CAC, with ~30% joined directly to the surrogate coding sequence immediately flanking a CAC (FIGS. 28A, 28B). There was no significant correlation with forward CACs (FIG. 28C). These results indicate that the frequent DSBs within the 1.8-MB c-Myc domain occur at "cryptic RSSs" represented predominantly by a conserved CAC. Moreover, surrogate coding ends fused to the bait ends were processed similarly to normal coding ends during V(D)J recombination. The most highly recurrent hotspot DSBs within the 1.8-Mb domain tended to involve CACs within more canonical heptamers (data not shown). Finally, remarkably similar results were obtained from ATM-proficient and ATM-deficient c-Myc-DJβ BM pro-B cells (data not shown).

To unequivocally test the role of RAG in generating DSBs in the 1.8-Mb c-Myc loop domains, we deleted Rag2 in the ATM-deficient c-Myc-DJβ pro-B cell line (data not shown). For HTGTS bait, we employed a Cas9/gRNA to generate DSBs 519 bp downstream of the c-Myc-DJβ cassette and designed a primer that allowed 50 broken ends of these DSBs to be used as bait ("50Cas9 bait ends"; FIG. 28D). We then performed HTGTS on RAG-sufficient and RAG2-deficient Gl-arrested pro-B cells. Recovered 50Cas9 HTGTS junctions from RAG-sufficient ATM-deficient c-Myc-DJβ v-Abl pro-B cells correlated with reverse CACs in the 1.8-Mb domain as expected; however, unlike RAG-generated bait broken ends, the Cas9/gRNA-generated bait ends recovered junctions equally in + and − orientation (FIGS. 28D-28F). Performing these assays in ATM-deficient v-Abl pro-B cells that either lacked the c-Myc-DJβ cassette or were RAG2 deficient generated only a very few junctions within the 1.8-Mb domain, and these had no correlation with CACs (FIGS. 28D-28F). These findings confirm that RAG generates the off-target DSBs across the 1.8-Mb c-Myc domain in a c-Myc-DJβ-cassette-dependent fashion and also demonstrate that the asymmetric prey-joining preferences observed are specific to RAG-generated bait ends.

Figures 29A, 29B, 29C, 29D, 29E, 29F, 29G, 29H, 29I, 29J, 29K:
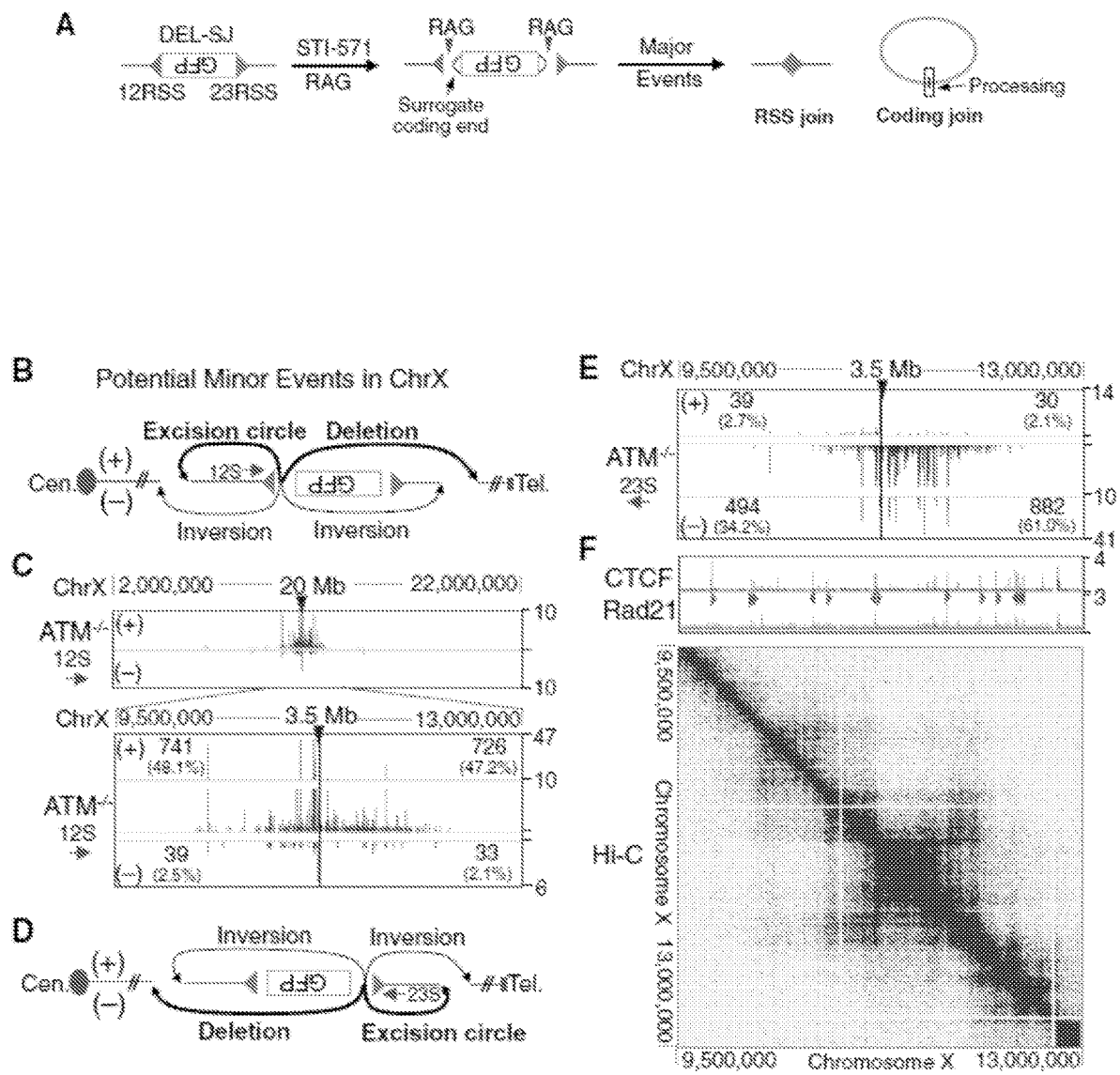
FIGS. 29A-29K demonstrate DSBs Restricted in Genome-wide DEL-SJ-Containing Loop Domains.
Figures 29A, 29B, 29C, 29D, 29E, 29F, 29G, 29H, 29I, 29J, 29K:
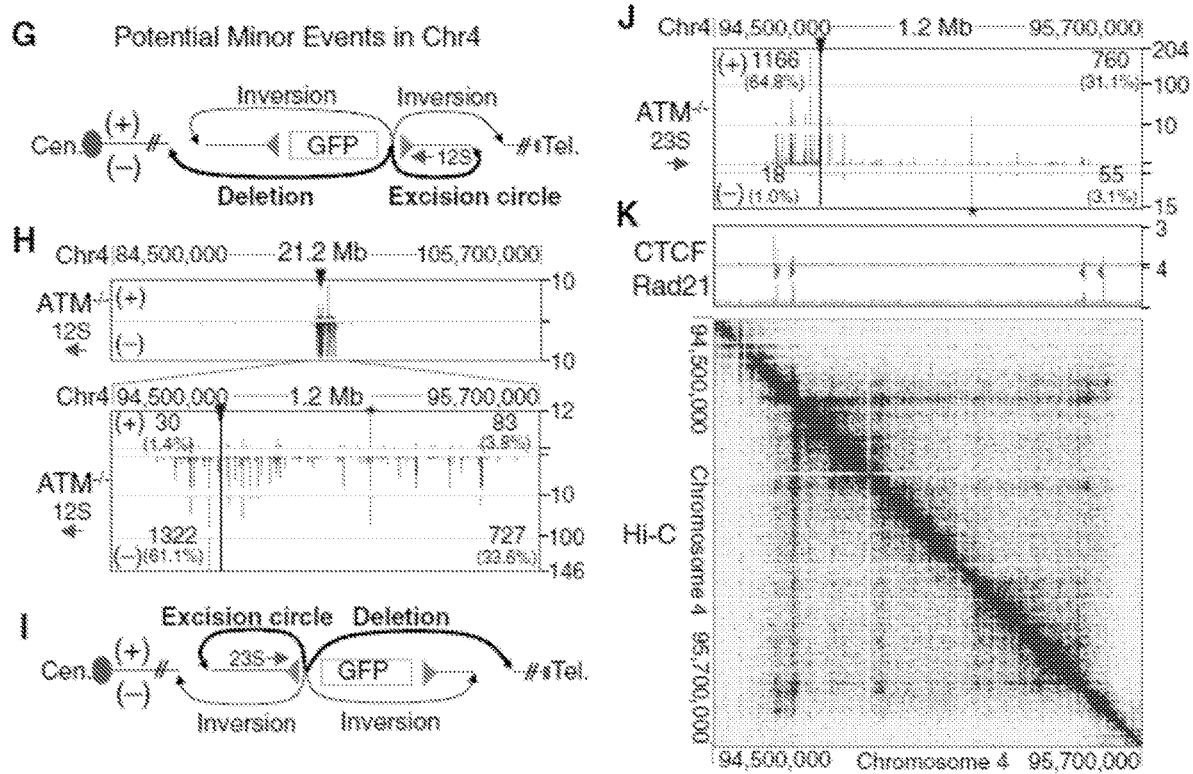

Paired Bona Fide RSSs Generate RAG Off-Target Activity in Loop Domains Genome-wide. We next tested whether other loop domains genome-wide could similarly be targets for such widespread RAG-generated DSBs if they contain bona fide RSS pairs. To insert bait RSSs into multiple genomic sites, we infected ATM-proficient and—deficient v-Abl pro-B lines with the pMX-DEL-SJ virus (referred to as "DEL-SJ"), which harbors a pair of divergent bona fide RSSs flanking an inverted GFP sequence (FIG. 29A; Bredemeyer et al., 2006). V(D)J recombination between the divergent DELSJ RSSs fuses them in the chromosome and liberates the intervening GFP DNA within an excision circle generated via fusion of the surrogate coding ends (FIG. 29A). We isolated six independent sub-clones from each genotype, each with a unique DELSJ-integration, treated them with STI-571, and generated HTGTS libraries with primers adjacent to either the construct 12RSS (12S primer) or 23RSS (23S primer) (data not shown). In all 12 DEL-SJ integration sites, the 12RSS and 23RSS junctions were confined within convergent CBE-based loop domains that ranged from 174 kb to 2.64 Mb in size (data not shown) and which often contained sub-domains flanked by convergent CBEs. For all integration sites, translocation junction density correlated well with interaction intensities revealed by Hi-C. Representative findings from chromosome X, 4, 12, and 19 integrations are shown (FIGS. 29B-29K). Notably, junctions detected from either 12RSS- or 23RSS-specific primers mostly occurred in deletional orientation independent of the orientation in which the DEL-SJ was integrated relative to the centromere (FIGS. 29B-29K). As for the c-Myc-DJβ 1.8-Mb domain, hotspots also were apparent (FIGS. 29B-29K).

Figures 30A, 30B, 30C, 30D, 30E, 30F, 30G, 30H:
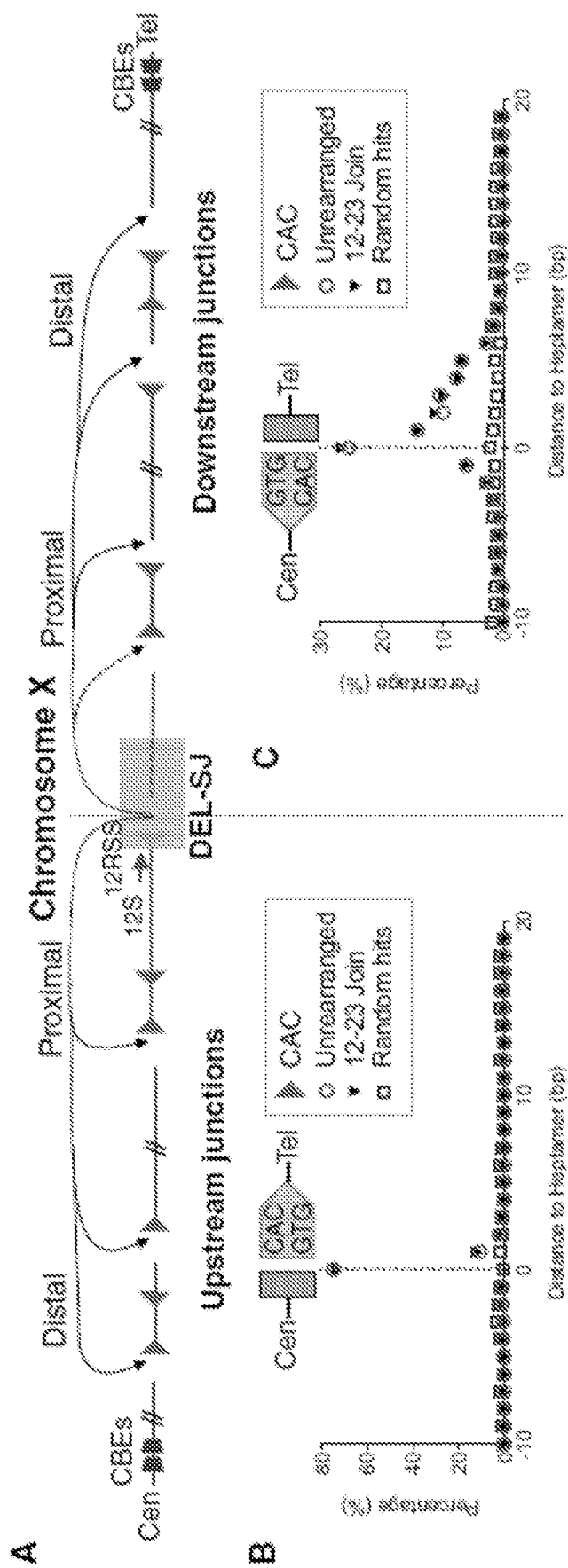
FIGS. 30A-30H demonstrate Orientation-Biased Joining of RAG-Initiated DSBs in Loop Domains.
Figures 30A, 30B, 30C, 30D, 30E, 30F, 30G, 30H:
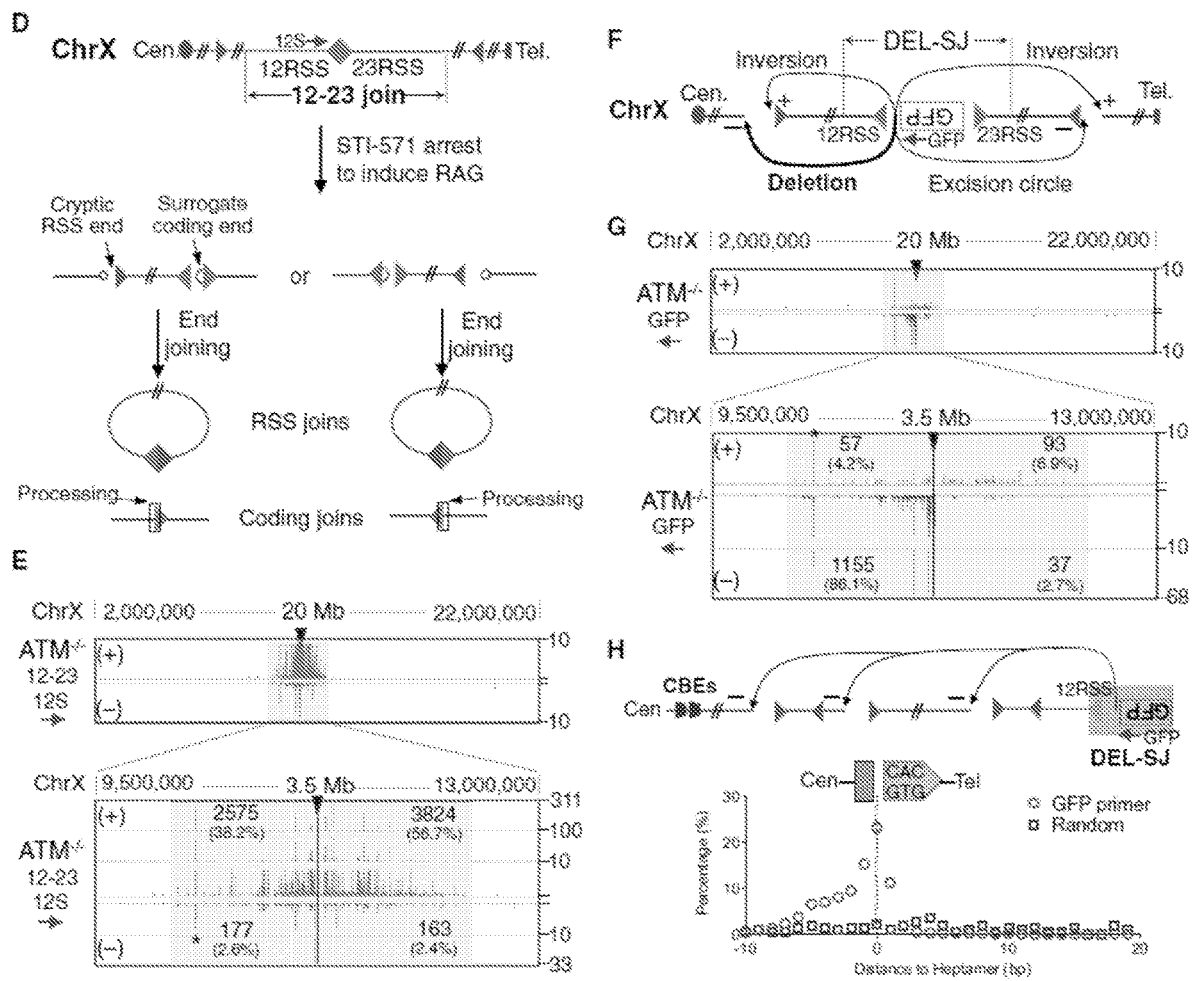

We examined junction sequences within the two DEL-SJ loop domains on chromosome X and 4, respectively, for potential correlations with forward or reverse CACs. Deletional and excision circle junctions represented>95% of events for any given integration site (FIGS. 29B-29K). Strikingly, the vast majority of junctions were highly correlated with CACs; however, while bait RSSs joined to convergent upstream cryptic CACs, they joined to surrogate coding ends associated with downstream CACs in the same orientation to form apparent "hybrid" RSS-to-coding-end joins (FIGS. 30A-30C; but see below). Analysis of several other DEL-SJ-containing domains (on chromosomes 12 and 19) revealed precisely the same patterns despite diverse locations and relative chromosomal orientations (data not shown). Notably, upstream CACs were generally joined precisely to bait RSSs, but downstream joins to surrogate coding ends were often imprecise, with deletions of several nucleotides from the CAC border (FIGS. 30A-30C). The latter result, together with junctional sequence analysis of bait RSS ends (data not shown), indicates that RSS ends from the DEL-SJ construct that join downstream behave like surrogate coding ends in a V(D)J recombination-type of joining reaction.

Normal DEL-SJ V(D)J recombination generates fused RSS pairs at a high frequency (FIG. 29A) that can be re-cleaved by RAG, with one cleavage product then being treated as an RSS end and the other as a surrogate coding end (FIG. 30D; Meier and Lewis, 1993). Thus, the apparent downstream "hybrid joins" observed with the bait 12RSS, consistent with their end structure, could be generated from the fused intermediate. To test this possibility, we used as bait the 12RSSs of perfectly fused 12-23 joins of DEL-SJ within the chromosome X and 4 integrations, respectively. Indeed, this fused RSS pair faithfully recapitulated the joining patterns of the parental un-rearranged DEL-SJ construct in this location (FIGS. 30B, 30C, 30E), demonstrating that the joining orientation of the two fused RSSs determines whether one or the other acts as an RSS end or surrogate coding end in the off-target V(D)J recombination joining reaction. Finally, we also generated HTGTS libraries from the surrogate coding ends (GFP primer) associated with 12RSS of DEL-SJ integrated into chromosome X. Such surrogate coding end junctions would not be re-cleaved by RAG. Correspondingly, nearly 90% of the 12RSS-associated coding ends joined downstream of the GFP primer to surrogate coding ends adjacent to CACs (FIGS. 30F-30H). Together, our findings show that, for bona fide RSS pairs within a loop domain, both the RSS and the associated coding sequence join to convergent cryptic RSSs (CACs) and associated surrogate coding ends within a loop domain via a V(D)J recombination-like reaction.

Figure 31A:
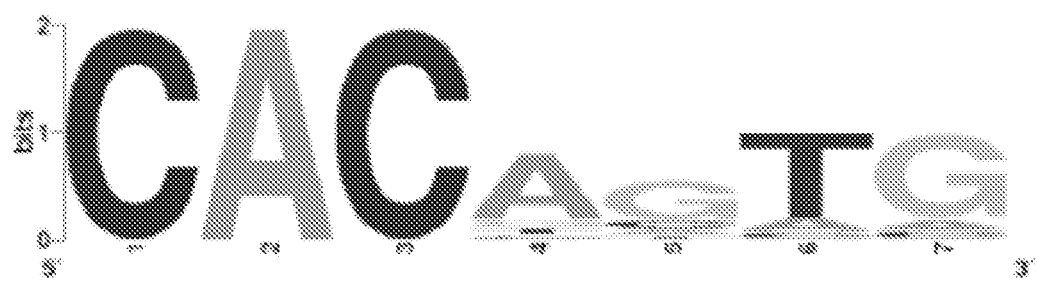
FIGS. 31A-31D depict Genome-wide RAG Off-Targets.
Figure 31B:
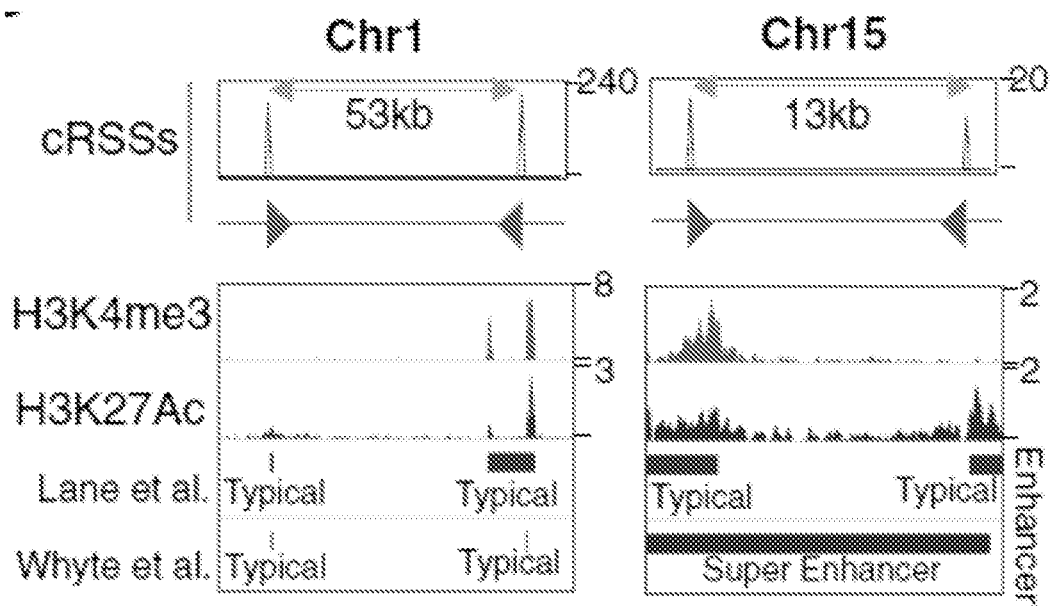
Figure 31C:
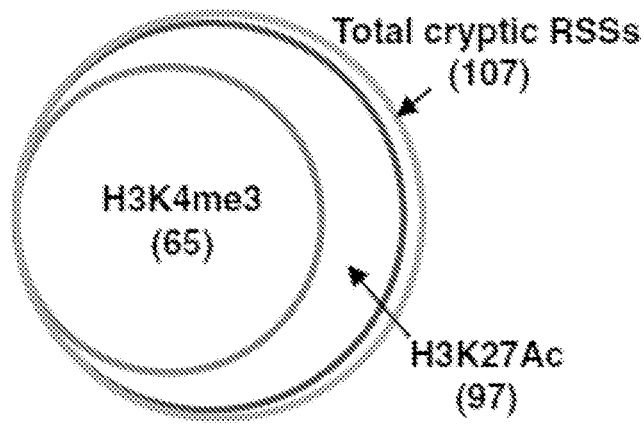
Figure 31D:
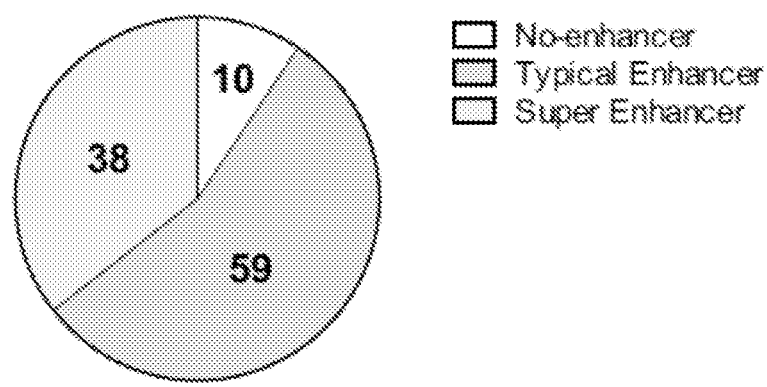

Robust Detection of RAG Off-Targets Genome-wide Outside of Chromatin Domains. We further analyzed the 12RSS-associated coding end (GFP)-primed DEL-SJ HTGTS libraries from the X chromosome integration in ATM-deficient v-Abl lines and additional libraries from an integration on chromosome 1 in a different ATM-deficient v-Abl line (data not shown). Beyond the expected joining patterns within the DEL-SJ-containing loop domains (data not shown), these libraries also revealed 107 translocation hotspots across the genome that all occurred at or near heptamers related to the canonical CACAGTG motif (FIG. 31A). Notably, 60 of the 107 identified cryptic RSSs occurred in pairs in convergent orientation within <100 kb in the same domain (FIG. 31B). HTGTS employing a primer upstream of the cryptic RSS in one such pair on chromosome 1 (FIG. 31B) revealed thousands of deletional junctions involving two cryptic RSSs (data not shown). We compared locations of these 107 cryptic RSSs with existing pro-B H3K4me3 ChIP-seq data, which marks promoters, or H3K27Ac data that marks promoters and enhancers (Lane et al., 2014; Whyte et al., 2013). Strikingly, 97 of the 107 RAG off-targets overlapped with H3K27Ac-marked regions, with 38 overlapping with super-enhancers and 59 with typical enhancers. Of these, 65 overlapped with regions marked by both H3K4me3 and H3K27Ac (FIGS. 31C and 31D). These remarkably high correlations demonstrate that accessibility, beyond RAG binding, also is important for efficient RAG cleavage at cryptic RSSs.

IgH Employs CBE-Based Subdomains to Regulate RAG On- and Off-Target Activity. We applied HTGTS to test whether RAG on- and off-target activity in IgH is confined within IGCR1 CBE-based domains (data not shown). We employed an ATM-deficient v-Abl pro-B cell line that harbors a DFL16.1-JH3 rearrangement, providing a population of cells harboring a 50D 12RSS expected to join to accessible upstream VHs 23RSSs (Alt et al., 2013). We used an HTGTS primer 82 bp upstream of the 50 DFL16.1 12RSS to capture joins involving bait 50DFL16.1-JH3 RSS ends (data not shown). The majority of 27,000 recovered IgH HTGTS junctions were ontargets at IgH bona fide RSSs (85%), with most fusing the DFL16.1 50RSS to a VH 23RSS in physiologic (excision circle) orientation (data not shown). While such junctions involved multiple VHs across the 2.4-Mb VH domain, they were biased toward proximal VHs, particularly VH81× (38% of on-targets) (data not shown). We also observed substantial-inversional (+) joining between the DFL16.1 50RSS and JH4 23RSS (20% of IgH ontargets) (data not shown). Strikingly, IGCR1 deletion dramatically increased the number of DFL16.1 50RSS junctions recovered (28-fold) (data not shown), largely from markedly increased utilization of proximal VHs (48-fold) and, in particular, VH81× (92% of junctions) (data not shown). Correspondingly, there was an 18-fold decrease in distal/middle VH utilization and a 20-fold decrease in JH4 junctions (data not shown).

These IgH HTGTS studies also revealed low but highly reproducible off-target joining of DFL16.1 12RSS ends to DSBs within IgH that correlated with CACs (data not shown). Strikingly, ~95% of the off-target IgH junctions were within a tightly focused 12.3-kb region that contains the DFL16.1-JH3 and is bounded upstream by IGCR1 and downstream by iEm/Sm (data not shown). We refer to this region as the iEm/Sm-to-IGCR1 "recombination domain." Strikingly, deletion of IGCR1 from this ATMdeficient pro-B line dramatically changed the profile of off-target DSBs, permitting them to spread ~120 kb upstream into the proximal VHs while decreasing the percentage of off-target junctions in the former iEm/Sm to IGCR1 domain to 13% (data not shown). Thus, IGCR1 deletion established a new iEm/Sm-toproximal-VH recombination domain in which RAG activity on both cryptic RSSs and proximal VHs bona fide RSSs is refocused. As in other domains, RAG off-target activity was highly dependent on convergent CAC orientation once several kb from the DFL16.1 50RSS break site (data not shown).

Discussion

Mechanism of RAG Off-Target Activity. We report a major form of RAG off-target activity that eluded prior investigations. Remarkably, this activity is largely confined to loop domains containing paired bona fide RSSs, with cleavage requiring only recognition of a simple CAC motif. Also remarkable, this off-target RAG activity is directionally oriented such that RSS ends from paired bona fide RSSs join to convergent CAC-containing motifs, while coding ends from paired bona fide RSSs join to surrogate coding ends associated with a CAC. Thus, RSSs and corresponding coding ends join with the same patterns and in the same locations, consistent with V(D)J recombination (FIGS. 30A-30H). Such orientation dependence is most readily explained by a linear tracking mechanism (Yancopoulos et al., 1984; FIG. 7). Based on RAG structural information (Kim et al., 2015), we propose a working model. This model assumes that formation and activation of the tetrameric RAG1/2 complex (Lapkouski et al., 2015) requires binding of paired bona fide RSSs (data not shown). We hypothesize that one or the other of these occasionally escapes the activated complex, allowing cryptic RSSs to replace them. The replacement process could involve diffusion of proximal cryptic RSSs or unidirectional tracking to more distal cryptic RSSs downstream. Once appropriately positioned in the activated complex, cryptic RSSs and surrogate coding ends could, likely at reduced frequency, be cleaved and joined to their remaining bona fide counterpart via a reaction that preserves most aspects of normal V(D)J recombination (data not shown). This general tracking model explains all aspects of our findings, including tracking from the two bona fide RSSs of a pair in opposite directions around the loop.

Implications for Normal Loop Domain Functions. An obvious and important question arises as to why RAG activity is so highly restricted within loop domains containing the initiating paired bona fide RSSs. One contributing factor could be high interaction frequency of DNA in chromatin across these domains (Alt et al., 2013). In this regard, DSB ends find and join to ends of other DSBs within such domains at higher frequency than elsewhere in the genome (Alt et al., 2013; Zhang et al., 2012). During IgH CSR, this phenomenon promotes proper and frequent joining of AID-initiated DSBs (Dong et al., 2015; Zarrin et al., 2007). Such DSB interactions are evident in our current studies in which Cas9/gRNA-generated DSBs frequently join to RAG off-target DSBs within the same loop. However, distinct from RAG-generated RSS or coding ends, a given Cas9/gRNA bait end joins to both cryptic RSS ends and surrogate coding ends of RAG off-target DSBs. Another apparent difference is that site-specific nuclease- or AID-generated DSBs appear to find off-targets in other regions across the genome much more readily than do RAG-generated DSBs, even in WT cells (Chiarle et al., 2011; Dong et al., 2015; Frock et al., 2015). The almost exclusive restriction of RAG off-targets to paired bona fide RSS-containing loops implies that an additional mechanism enforces such RAG activity.

The tracking mechanism can explain the additional restriction of RAG activity within a given loop (data not shown). We do not know the mechanism that propels RAG tracking, although transcription and/or cohesin might be involved (e.g., Nichols and Corces, 2015). However, it is reasonable to assume that tracking is terminated when it encounters a block imposed by the CTCF/cohesin-bound convergent CBE pair or similar loop-forming interactions (data not shown). Such blockage would terminate tracking in each direction from paired bona fide RSSs and limit off-target RAG activity to the loop. In support of this model, deletion of the CBE-based IGCR1 allows RAG off-target activity to extend from its initial highly restricted location in the D-JH recombination domain to >100 kb upstream, where new boundaries may form via VH CBEs and/or associated factors (data not shown). Beyond regulating V(D)J recombination, related loop domain functions might impact on other activities constrained within them, including replication (Pope et al., 2014) and promoter/enhancer interactions (Dowen et al., 2014).

IgH Locus Regulation. Regulated IgH VH-to-DJH recombination depends on the integrity of the two divergent CBEs within IGCR1, likely via formation of loop domains that focus RAG activity on DHs and JHs (Guo et al., 2011; Lin et al., 2015). Our HTGTS studies provide additional insights into IgH V(D)J recombination regulation (data not shown). In a DJH-rearranged pro-B cell line, on-target rearrangements of the 50DRSS occur to RSSs of VHs across the locus but predominantly to 30 VHs (data not shown). As most RAG off-target activity is focused in a small 12.3-kb recombination domain from IGCR1 to the iEm/Sm boundary, the recombination domain in these cells does not extend downstream to 30CBEs as perhaps anticipated.

This restriction could be due to IGCR1CBElooping with non-CBE elements at iEm/Sm (Guo et al., 2011) and/or by tracking limitations imposed by a unidirectional mechanism. In the DJH-rearranged cells, bona fide V(D)J recombination at upstream VHs in the absence of corresponding off-target activity, even in proximal portions of the locus, is consistent with VHs entering the recombinationdomain by a specialized mechanism operating subsequent to locus contraction (Bossen et al., 2012). Based on off-target activity as an assay, IGCR1 deletion extends the recombination domain linearly into proximal VHs, resulting in a huge overall V(D)J recombination increase, involvingVH81× and other proximal VHs (data not shown). This increase may be facilitated by increased interaction frequency gained by placing VH 23RSSs in the same loop domain as the 50 DFL16.1 12RSS and/or by a tracking contribution. Finally, a unidirectional RAG tracking mechanism also might explain why 30D 12RSSs, but not 50D 12RSSs, are used developmentally in D-to-JH rearrangements.

RAG Off-Target Activity, Chromosomal Rearrangements, and Cancer. We prove our hypothesis that inserting paired bona fide RSSs into c-Myc activates RAG-generated DSBs at cryptic RSSs over a long region downstream that, in the context of ATM deficiency, promotes oncogenic translocations. These findings explain how paired bona fide RSSs within a Tcra excision circle fragment integrated into the HPRT locus in leukemia cells causes further genomic aberrations (Messier et al., 2006) and also support the hypothesis that translocations downstream of c-Myc in human B cell lymphomas involve cryptic RSSs (Kroenlein et al., 2012). Given that cryptic RSS targeting downstream of c-Myc occurs in both WT and ATM-deficient pro-B cells, one role of ATM in suppressing such translocations would be through stabilizing ends in RAG post-cleavage complexes to facilitate their joining via V(D)J recombination (Bredemeyer et al., 2006). Thus, ATM limits potential RAG-initiated translocations by promoting joining of RAG-initiated DSBs at RSSs and cryptic RSSs within a loop. Our findings also provide a mechanism for oncogenic translocations to sequences far downstream of c-Myc in C-NHEJ/p53 double-deficient pro-B cells (Alt et al., 2013). In this regard, we find cryptic RSSs in the c-Myc 1.8-Mb domain that are closer to consensus (Merelli et al., 2010) and, therefore, may drive RAG-initiated DSBs at other cryptic RSSs in this domain that become liberated from post-cleavage complexes in the absence of C-NHEJ.

We also found 107 genome-wide cryptic RSSs, not related to antigen receptor loci or paired bona fide RSSs-containing domains, that were DSB and translocation targets in ATM-deficient v-Ab1 pro-B cells (FIGS. 31A-31D). This set of cryptic RSSs tended to have heptamers even closer to consensus than recurrent hotspots within paired bona fide RSSs-containing loops (FIG. 31A). Many of these translocation target RSSs occurred in pairs separated by <100 kb, with each member of the pair falling directly within enhancer and/or promoter regions (FIGS. 31B-31D).

Enhancer/promoter loops also might increase the frequency with which such paired cryptic RSSs are juxtaposed to form stable RAG synaptic complexes. Strikingly, all 30 pairs of these cryptic RSS translocation targets were in convergent orientation, similar to most proximal paired bona fide RSSs within antigen receptor loci (Bossen et al., 2012) and the majority of cryptic RSSs captured by bona fide RSSs within loop domains. Thus, to serve as a strong genome-wide translocation target, cryptic RSS require a good heptamer, location in enhancers and/or promoters, and convergent pairing with another good cryptic RSS in the same loop. Finally, our findings provide a mechanistic basis for recurrent oncogenic chromosomal interstitial deletions in tumors arising from developing human lymphocytes (Larmonie et al., 2013; Mullighan et al., 2008; Papaemmanuil et al., 2014).

Experimental Procedures

Cell Lines. BM pro-B cells were purified by aB220 selection from ATM-proficient and—deficient c-Myc-Dβ mice (Tepsuporn et al., 2014) and were cultured in opti-MEM medium with 10% (v/v) FBS plus IL-7 (2 ng/ml) and SCF (2 ng/ml) for 4 days. The v-Ab1 pro-B cells were cultured in RPMI medium with 15% (v/v) FBS; cells were treated with STI-571 (3 mM) for 4 days to express RAG. WT and ATM-deficient v-Ab1 pro-B cell lines were described previously (Zha et al., 2011). ATM-proficient and -deficient c-Myc-DJβ v-Ab1 pro-B cell lines were made specifically for this studyfromEm-Bcl-2 transgenic miceof the corresponding genotypes. We included the Em-Bcl-2 transgene in these cells to protect STI-571-treated (G1-arrested) v-Ab1 pro-B cells from apoptosis; prior work showed that Bcl-2 expression has no effect on V(D)J recombination (Zha et al., 2011).

RAG On- and Off-Targets HTGTS was performed and analyzed as previously described with modifications (Frock et al., 2015). Due to the very low junctional diversity of bona fide V(D)J recombination RSS joins and coding joins, we included duplicate junctions in our analyses of G1-arrested v-Ab1 cells to better reflect the actual frequencies of the various classes of bona fide and off-target junctions. Where approximate percentage and/or numbers of different classes of junctions are indicated (e.g., c-Myc-D43 or IgH), we controlled for reproducibility by performing at least three independent experiments. RAG off-target hotspots were identified by MACS2 (Zhang et al., 2008), with extend size (extsize) at 20 bp and false discovery rate (FDR) cut-off at 10^9.

ChIP-Seq and Hi-C Data. CTCF and Rad21 ChIP-seq data were extracted from Lin et al. (2012) (GEO: GSE40173); H3K4me3 and H3K27Ac ChIP-seq data were extracted from Lane et al. (2014) (GEO: GSE48555). These data are from BM pro-B cells. We re-analyzed ChIP-seq data with Chilin software (available on the world wide web at cistrome.org/chilin/) in the simple model against mm9. Enhancer annotation was either extracted directly from Whyte et al. (2013) (GEO: GSE44288) or identified by Homer™ software (Heinz et al., 2010) from re-analyzed H3K27Ac ChIP-seq data (Lane et al., 2014). In situ Hi-C data for CH12-LX B cells was extracted and displayed (KR normalization) by Juicebox™ software (Rao et al., 2014).

Preparing HTGTS Libraries. For preparing HTGTS libraries with DFL16.15'12RSS bait at IgH locus, we used the same protocol described previously (Frock et al., 2015). For HTGTS libraries from c-Myc-DJβ cassette- or DEL-SJcontaining cells, we made some modifications to the original protocol as below, which showed the same pattern but with a higher efficiency. In the linear amplification-mediated PCR step, we used Phusion polymerase (Thermo) instead of Taq polymerase (Roche) to perform an 85-cycle PCR with 75-µM dNTPs. In the adapter ligation step, we used a new adapter (comprised of "GCGAC-TATAGGGCACGCGTGG-NH2" (SEQ ID NO: 308) and "/5'Phosphorylation/-CCACGCGTG CCCTATAGTCGC-NH2" (SEQ ID NO: 309)) at the concentration of 2.5 µM instead. Restriction enzyme was used to suppress bona fide V(D)J recombination products within the paired bona fide RSSs-containing cassettes: PstI for c-Myc E1 primer in c-Myc-DJβ cassette, ScaI for 12S primer in DEL-SJ, and MluI for 23S primer in DEL-SJ. No restriction enzyme blocking was performed for IgH and DEL-SJ GFP-primer HTGTS libraries. All the HTGTS libraries were sequenced by Miseq with paired ends each at a read length of 250 bp.

HTGTS Data Analyzing and Normalization. The pipeline used for running HTGTS was the same as described previously (Frock et al., 2015). Miseq sequencing reads were aligned to mm9 genome, with modified genomes in some cases depicted in details below. We further filtered the junctions by removing those with more than 30-bp un-aligned sequences between bait and prey sequences.

For HTGTS libraries from c-Myc-DJβ cassette- or DEL-SJ-containing cells, the sequencing reads were separately aligned to mm9 genome or paired bona fide RSSs-containing cassettes. The former detects genome-wide transloca-tions and the latter detects bona fide RSSmediated rear-rangements in the cassettes. Junctions in the paired bona fide RSSs-containing loop domains were displayed by IGV (Robinson et al., 2011) without adding the bona fide rear-rangements. The junction diversity between RAG-initiated DSBs is very limited (Gellert, 2002), thus we took the duplicate junctions into account to reflect more accurate frequencies of translocations between bait bona fide RSSs and other RSSs. When junctions have the same bait length and prey length with the same length of inserted sequences if any, we defined them as duplicate junctions. The BM pro-B cells can proliferate to duplicate early translocation junctions, thus no duplicate junctions were contained for analysis in HTGTS libraries from these cells.

For HTGTS libraries from the G1-arrested v-Abl pro-B cells, duplicate junctions with different prey length result from random sonication shearing on independent transloca-tion junction-containing fragments. Therefore, these dupli-cate junctions were considered as independent biological events and were contained for analysis. For libraries from 12S or 23S primers in DEL-SJ-integrated cells, we prepared one library from pooled genomic DNA of 6 strains with independent integration locations for ATM-proficient and deficient v-Abl cells, respectively. All 12 DEL-SJ contain-ing loop domains showed very similar general patterns (see the text for details) providing robust controls for reproduc-ibility of the main conclusions. For libraries with DFL16.1 5'12RSS bait at IgH locus, to accurately map the junctions, Miseq reads were aligned to modified mm9 genome (mm9_8653), in which the IgH sequence between DFL16.1 and JH3 (mm9 coordinates: chr12: 114667296-114720403) was replaced by the DFL16.1-JH3 join sequence (CTGCA-GAGACAGTGACCAGAGTCCCTTGGCCCCAG-TAAGCAAACCAGGGTAGCTACTAC CGTAG-TAATAAA (SEQ ID NO: 321)) harbored in the ATM-/-v-Abl pro-B cells (8653). RAG ontarget analysis included junctions within ±20 bp of the cleavage site of IgH bona fide RSSs and associated resection. Annotation of VH RSSs was from Choi et al., 2013.

Annotation of DH and JH RSSs was obtained from IMGT/GENE-DB (Giudicelli et al., 2005). IgH junctions excluding on-targets were used for RAG off-target analysis. All duplicates were included for IgH junction analysis as on-target V(D)J recombination generates a vast majority of RSS joins that are perfectly fused and coding joins with very limited diversity as outlined above, thus, most independent V(D)J joins represented as duplicates in sequencing reads. We compared IgH offtarget junctions containing all the duplicates with those containing only duplicates of diverse prey lengths and observed similar pattern between the two.

To compare HTGTS libraries of ATM-deficient cells with and without IGCR1, the same amount (50 ug) of DNA were used for library preparation and junctions were further normalized to number of bait aligned reads that reflect the same amount of sequenced bait-containing alleles (Table S4). We also performed HTGTS from cycling cells before G1 arrest, which yielded less than 5% of junctions of G1-arrested cells, confirming that most of the junctions recovered from G1-arrested cells occurred de novo after G1 arrest. Note that the ChIP-seq data displayed for IgH locus was lifted-over to the mm9_8653 genome from the source (GSE40173).

The Gene Expression Omnibus (GEO) accession number for the datasets reported in this paper is GEO: GSE73007.

TABLE 12

Oligos used

| Name | Sequence (SEQ ID NOS 322-356, respectively, in order of appearance) | Purpose |
|---|---|---|
| Myc-E1-bio | /5bio/TGATGTTGGGCTAGCGCAG | HTGTS bio primers for DJβ cassette |
| Myc-E1-red | AGGGATGTGACCGATTCGTTG | HTGTS nested primers for DJβ cassette |
| 12S-bio | /5bio/GACCTTACACAGTCCTGCTG | HTGTS bio primers for DEL-SJ 12RSS |
| 12S-red | GTAGACGGCATCGCAGCTTG | HTGTS nested primers for DEL-SJ 12RSS |
| 23S-bio | /5bio/CAAAAGACGGCAATATGGTGG | HTGTS bio primers for DEL-SJ 23RSS |

TABLE 12-continued

Oligos used

| Name | Sequence (SEQ ID NOS 322-356, respectively, in order of appearance) | Purpose |
| --- | --- | --- |
| 23S-red | ACGCACACCGGCCTTATTCC | HTGTS nested primers for DEL-SJ 23RSS |
| GFP-bio | /5bio/GACAACCACTACCTGAGCAC | HTGTS bio primers for DEL-SJ GFP |
| GFP-red | CCAACGAGAAGCGCGATCAC | HTGTS nested primers for DEL-SJ GFP |
| Rag2-up | GAATAGGTCTTTTATCTGAA | Upstream Cas9 site for Rag2 deletion |
| Rag2-down | GAGCAATATACCTGAGTCTG | Downstream Cas9 site for Rag2 deletion |
| Myc-Cas9 | GACGAGCGTCACTGATAGTA | For Cas9 site downstream of DJβ cassette |
| Myc-bio | /5bio/GCCTCGGCTCTTAGCAGACTG | HTGTS bio primers for myc-Cas9 |
| Myc-red | CCTCTGAAGCCAAGGCCGATG | HTGTS nested primers for myc-Cas9 |
| hCD4-Cas9 | GCAGTGTCTGCTGAGTGACT | For Cas9 site at hCD4 in DEL-SJ |
| hCD4-bio | /5bio/TGATGAGAGCCACTCAGCTC | HTGTS bio primers for hCD4-Cas9 |
| hCD4-red | CCTAAGCTGATGCTGAGCTTG | HTGTS nested primers for hCD4-Cas9 |
| IS-hCD4 | CAATGGCCCTGATTGTGCTG | In the DEL-SJ for verifying integration site |
| IS-Chr1 | CCTATTTTCTCCGACTAGCC | For verifying DEL-SJ integration site |
| IS-Chr4 | GAAGCACACATGTGGCTTGC | For verifying DEL-SJ integration site |
| IS-Chr5 | CTGGTGCTTACACCATTAGAG | For verifying DEL-SJ integration site |
| IS-Chr6 | GTGAGGTATGAAGCCATGACC | For verifying DEL-SJ integration site |
| IS-Chr8 | TGTCGGGAGTTAGCTTCCAG | For verifying DEL-SJ integration site |
| IS-Chr9 | CTGTCCTCACACTCAGGTTC | For verifying DEL-SJ integration site |
| IS-Chr10 | CAAGTGGCGAACATGACCTAGC | For verifying DEL-SJ integration site |
| IS-Chr12 | CTGCTACTATTGCTCCTCTG | For verifying DEL-SJ integration site |
| IS-Chr12 | CTAAGACAGTAAGGTAGACACAC | For verifying DEL-SJ integration site |
| IS-Chr17 | CTAGTTGGTTATGCGTATGAC | For verifying DEL-SJ integration site |
| IS-Chr19 | GAAGTAGAACAGAAGGGAAAG | For verifying DEL-SJ integration site |
| IS-ChrX | CCGCACTCTTTGACACAGAC | For verifying DEL-SJ integration site |
| cRSS-bio | /5bio/GTTCATATTCAAAGTTTAGTCGCC | HTGTS bio primers for cryptic RSS at Chr1 |
| cRSS-red | CTCTAGCCAAAAGCTGGCTTC | HTGTS nested primers for cryptic RSS at Chr1 |

TABLE 12-continued

Oligos used

| Name | Sequence (SEQ ID NOS 322-356, respectively, in order of appearance) | Purpose |
| --- | --- | --- |
| IGCR1_up | GGAAAACTCTGTAGGACTAC | Upstream Cas9 site for IGCR1 deletion |
| IGCR1_down | TGGGACATGTAAACTGTAAC | Downstream Cas9 site for IGCR1 deletion |
| DFL16.1-bio | /5bio/CTTGCTCCCTAGGACCTTCC | HTGTS bio primer for DFL16.1 5' 12RSS |
| DFL16.1-red | ACTGAAACTCAACCGTGCTG | HTGTS nested primer for DFL16.1 5' 12RSS |

REFERENCES

Alt, F. W., Zhang, Y., Meng, F.-L., Guo, C., and Schwer, B. (2013). Mechanisms of programmed DNA lesions and genomic instability in the immune system. Cell 152, 417-429.

Boehm, T., Mengle-Gaw, L., Kees, U. R., Spun, N., Lavenir, I., Forster, A., and Rabbitts, T. H. (1989). Alternating purine-pyrimidine tracts may promote chromosomal translocations seen in a variety of human lymphoid tumours. EMBO J. 8, 2621-2631.

Bossen, C., Mansson, R., and Murre, C. (2012). Chromatin topology and the regulation of antigen receptor assembly. Annu. Rev. Immunol 30, 337-356.

Bredemeyer, A. L., Sharma, G. G., Huang, C.-Y., Helmink, B. A., Walker, L. M., Khor, K. C., Nuskey, B., Sullivan, K. E., Pandita, T. K., Bassing, C. H., and Sleckman, B. P. (2006). ATM stabilizes DNA double-strand-break complexes during V(D)J recombination. Nature 442, 466-470.

Chiarle, R., Zhang, Y., Frock, R. L., Lewis, S. M., Molinie, B., Ho, Y.-J., Myers, D. R., Choi, V. W., Compagno, M., Malkin, D. J., et al. (2011). Genome-wide translocation sequencing reveals mechanisms of chromosome breaks and rearrangements in B cells. Cell 147, 107-119.

Degner, S. C., Wong, T. P., Jankevicius, G., and Feeney, A. J. (2009). Cutting edge: developmental stage-specific recruitment of cohesin to CTCF sites throughout immunoglobulin loci during B lymphocyte development. J. Immunol 182, 44-48.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Dong, J., Panchakshari, R. A., Zhang, T., Zhang, Y., Hu, J., Volpi, S. A., Meyers, R. M., Ho, Y.-J., Du, Z., Robbiani, D. F., et al. (2015). Orientation-specific joining of AID-initiated DNA breaks promotes antibody class switching. Nature 525, 134-139.

Dowen, J. M., Fan, Z. P., Hnisz, D., Ren, G., Abraham, B. J., Zhang, L. N., Weintraub, A. S., Schuijers, J., Lee, T. I., Zhao, K., and Young, R. A. (2014). Control of cell identity genes occurs in insulated neighborhoods in mammalian chromosomes. Cell 159, 374-387.

Frock, R. L., Hu, J., Meyers, R. M., Ho, Y.-J., Kfi, E., and Alt, F. W. (2015). Genome-wide detection of DNA double-stranded breaks induced by engineered nucleases. Nat. Biotechnol. 33, 179-186.

Guo, C., Yoon, H. S., Franklin, A., Jain, S., Ebert, A., Cheng, H.-L., Hansen, E., Despo, O., Bossen, C., Vettermann, C., et al. (2011). CTCF-binding elements mediate control of V(D)J recombination. Nature 477, 424-430.

Heinz, S., Benner, C., Spann, N., Bertolino, E., Lin, Y. C., Laslo, P., Cheng, J. X., Murre, C., Singh, H., and Glass, C. K. (2010). Simple combinations of lineagedetermining transcription factors prime cis-regulatory elements required for macrophage and B cell identities. Mol. Cell 38, 576-589.

Ji, Y., Resch, W., Corbett, E., Yamane, A., Casellas, R., and Schatz, D. G. (2010). The in vivo pattern of binding of RAG1 and RAG2 to antigen receptor loci. Cell 141, 419-431.

Kim, M.-S., Lapkouski, M., Yang, W., and Gellert, M. (2015). Crystal structure of the V(D)J recombinase RAG1-RAG2. Nature 518, 507-511.

Kroenlein, H., Schwartz, S., Reinhardt, R., Rieder, H., Molkentin, M., Go"kbuget, N., Hoelzer, D., Thiel, E., and Burmeister, T. (2012). Molecular analysis of the t(2;8)/MYC-IGK translocation in high-grade lymphoma/leukemia by long-distance inverse PCR. Genes Chromosomes Cancer 51, 290-299. Lane, A. A., Chapuy, B., Lin, C. Y., Tivey, T., Li, H., Townsend, E. C., van Bodegom, D., Day, T. A., Wu, S.-C., Liu, H., et al. (2014). Triplication of a 21q22 region contributes to B cell transformation through HMGN1 overexpression and loss of histone H3 Lys27 trimethylation. Nat. Genet. 46, 618-623.

Lapkouski, M., Chuenchor, W., Kim, M.-S., Gellert, M., and Yang, W. (2015). Assembly Pathway and Characterization of the RAG1/2-DNA Paired and Signal-end Complexes. J. Biol. Chem. 290, 14618-14625.

Larmonie, N. S. D., Dik, W. A., Meijerink, J. P. P., Homminga, I., van Dongen, J. J. M., and Langerak, A. W. (2013). Breakpoint sites disclose the role of the V(D)J recombination machinery in the formation of T-cell receptor (TCR) and non-TCR associated aberrations in T-cell acute lymphoblastic leukemia. Haematologica 98, 1173-1184.

Lin, Y. C., Benner, C., Mansson, R., Heinz, S., Miyazaki, K., Miyazaki, M., Chandra, V., Bossen, C., Glass, C. K., and Murre, C. (2012). Global changes in the nuclear positioning of genes and intra- and interdomain genomic interactions that orchestrate B cell fate. Nat. Immunol 13, 1196-1204.

Lin, S. G., Guo, C., Su, A., Zhang, Y., and Alt, F. W. (2015). CTCF-binding elements 1 and 2 in the Igh intergenic control region cooperatively regulate V(D)J recombination. Proc. Natl. Acad. Sci. USA 112, 1815-1820.

Lupia' n˜ez, D. G., Kraft, K., Heinrich, V., Krawitz, P., Brancati, F., Klopocki, E., Horn, D., Kayserili, H., Opitz, J. M., Laxova, R., et al. (2015). Disruptions of topological chromatin domains cause pathogenic rewiring of gene-enhancer interactions. Cell 161, 1012-1025.

Meier, J. T., and Lewis, S. M. (1993). P nucleotides in V(D)J recombination: a fine-structure analysis. Mol. Cell. Biol. 13, 1078-1092.

Merelli, I., Guffanti, A., Fabbri, M., Cocito, A., Furia, L., Grazini, U., Bonnal, R. J., Milanesi, L., and McBlane, F. (2010). RSSsite: a reference database and prediction tool for the identification of cryptic Recombination Signal Sequences in human and murine genomes. Nucleic Acids Res. 38, W262-W267.

Messier, T. L., O'Neill, J. P., and Finette, B. A. (2006). V(D)J recombinase mediated inter-chromosomal HPRT alterations at cryptic recombination signal sequences in peripheral human T cells. Hum. Mutat. 27, 829.

Mullighan, C. G., Miller, C. B., Radtke, I., Phillips, L. A., Dalton, J., Ma, J., White, D., Hughes, T. P., Le Beau, M. M., Pui, C.-H., et al. (2008). BCR-ABL1 lymphoblastic leukaemia is characterized by the deletion of Ikaros. Nature 453, 110-114.

Nakahashi, H., Kwon, K.-R. K., Resch, W., Vian, L., Dose, M., Stavreva, D., Hakim, O., Pruett, N., Nelson, S., Yamane, A., et al. (2013). A genome-wide map of CTCF multivalency redefines the CTCF code. Cell Rep. 3, 1678-1689.

Nichols, M. H., and Corces, V. G. (2015). A CTCF Code for 3D Genome Architecture. Cell 162, 703-705.

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Ong, C.-T., and Corces, V. G. (2014). CTCF: an architectural protein bridging genome topology and function. Nat. Rev. Genet. 15, 234-246.

Onozawa, M., and Aplan, P. D. (2012). Illegitimate V(D)J recombination involving nonantigen receptor loci in lymphoid malignancy. Genes Chromosomes Cancer 51, 525-535.

Papaemmanuil, E., Rapado, I., Li, Y., Potter, N. E., Wedge, D. C., Tubio, J., Alexandrov, L. B., Van Loo, P., Cooke, S. L., Marshall, J., et al. (2014). RAGmediated recombination is the predominant driver of oncogenic rearrangement in ETV6-RUNX1 acute lymphoblastic leukemia. Nat. Genet. 46, 116-125.

Phillips-Cremins, J E, Sauria, M. E. G., Sanyal, A., Gerasimova, T. I., Lajoie, B. R., Bell, J. S. K., Ong, C.-T., Hookway, T. A., Guo, C., Sun, Y., et al. (2013). Architectural protein subclasses shape 3D organization of genomes during lineage commitment. Cell 153, 1281-1295.

Pope, B. D., Ryba, T., Dileep, V., Yue, F., Wu, W., Denas, O., Vera, D. L., Wang, Y., Hansen, R. S., Canfield, T. K., et al. (2014). Topologically associating domains are stable units of replication-timing regulation. Nature 515, 402-405.

Ranganath, S., Carpenter, A. C., Gleason, M., Shaw, A. C., Bassing, C. H., and Alt, F. W. (2008). Productive coupling of accessible Vbeta14 segments and DJβeta complexes determines the frequency of Vbeta14 rearrangement. J. Immunol 180, 2339-2346.

Rao, S. S. P., Huntley, M. H., Durand, N. C., Stamenova, E. K., Bochkov, I. D., Robinson, J. T., Sanborn, A. L., Machol, I., Omer, A. D., Lander, E. S., and Aiden, E. L. (2014). A 3D map of the human genome at kilobase resolution reveals principles of chromatin looping. Cell 159, 1665-1680.

Schatz, D. G., and Swanson, P. C. (2011). V(D)J recombination: mechanisms of initiation. Annu. Rev. Genet. 45, 167-202.

Teng, G., Maman, Y., Resch, W., Kim, M., Yamane, A., Qian, J., Kieffer-Kwon, K.-R., Mandal, M., Ji, Y., Meffre, E., et al. (2015). RAG represents a widespread threat to the lymphocyte genome. Cell 162, 751-765.

Tepsuporn, S., Hu, J., Gostissa, M., and Alt, F. W. (2014). Mechanisms that can promote peripheral B-cell lymphoma in ATM-deficient mice. Cancer Immunol Res. 2, 857-866.

Vietri Rudan, M., Barrington, C., Henderson, S., Ernst, C., Odom, D. T., Tanay, A., and Hadjur, S. (2015). Comparative Hi-C reveals that CTCF underlies evolution of chromosomal domain architecture. Cell Rep. 10, 1297-1309.

Whyte, W. A., Orlando, D. A., Hnisz, D., Abraham, B. J., Lin, C. Y., Kagey, M. H., Rahl, P. B., Lee, T. I., and Young, R. A. (2013). Master transcription factors and mediator establish super-enhancers at key cell identity genes. Cell 153, 307-319.

Yancopoulos, G. D., and Alt, F. W. (1986). Regulation of the assembly and expression of variable-region genes. Annu. Rev. Immunol 4, 339-368.

Yancopoulos, G. D., Desiderio, S. V., Paskind, M., Kearney, J. F., Baltimore, D., and Alt, F. W. (1984). Preferential utilization of the most JH-proximal VH gene segments in pre-B-cell lines. Nature 311, 727-733.

Zarrin, A. A., Del Vecchio, C., Tseng, E., Gleason, M., Zarin, P., Tian, M., and Alt, F. W. (2007). Antibody class switching mediated by yeast endonucleasegenerated DNA breaks. Science 315, 377-381.

Zha, S., Guo, C., Boboila, C., Oksenych, V., Cheng, H.-L., Zhang, Y., Wesemann, D. R., Yuen, G., Patel, H., Goff, P. H., et al. (2011). ATM damage response and XLF repair factor are functionally redundant in joining DNA breaks. Nature 469, 250-254.

Zhang, Y., Liu, T., Meyer, C. A., Eeckhoute, J., Johnson, D. S., Bernstein, B. E., Nusbaum, C., Myers, R. M., Brown, M., Li, W., and Liu, X. S. (2008). Modelbased analysis of ChIP-Seq (MACS). Genome Biol. 9, R137.

Zhang, Y., McCord, R. P., Ho, Y.-J., Lajoie, B. R., Hildebrand, D. G., Simon, A. C., Becker, M. S., Alt, F. W., and Dekker, J. (2012). Spatial organization of the mouse genome and its role in recurrent chromosomal translocations. Cell 148, 908-921.

Zuin, J., Dixon, J. R., van der Reijden, M. I. J. A., Ye, Z., Kolovos, P., Brouwer, R. W. W., van de Corput, M. P. C., van de Werken, H. J. G., Knoch, T. A., van IJcken, W. F. J., et al. (2014). Cohesin and CTCF differentially affect chromatin architecture and gene expression in human cells. Proc. Natl. Acad. Sci. USA 111, 996-1001.

What is claimed herein is:

1. A method for high throughput, genome-wide translocation sequencing (HTGTS) and detection of double-stranded DNA break (DSB) locations, the method comprising the steps of:
   a. exposing a cell to an agent known or suspected of being capable of producing at least one DSB;
   b. optionally, allowing the cell to divide for at least a half cell cycle after exposure;
   c. extracting genomic DNA from the cells;
   d. optionally, producing a fragmented DNA sample;
   e. producing a single-stranded PCR product by Linear Amplification Mediated (LAM)-PCR with a first locus-specific primer;
   f. producing a ligated DNA product by ligating the single-stranded PCR product produced in step (e) to an adapter, wherein the adapter comprises:
      a distal portion of known DNA sequence that can be used to design PCR primers for a nested PCR amplification;
      a proximal portion of random nucleotides; and
      a 3' overhang;
   g. producing a nested PCR product by performing a nested-PCR with an adapter- and a locus-specific primer using the ligated DNA product thereby amplifying the nucleic acid sequence surrounding the junction around the at least one DSB;
   h. optionally, digesting the ligated DNA sample with a blocking enzyme;
   i. producing a sequenced nested PCR product by sequencing the nested PCR product;
   j. aligning the sequenced nested PCR product against a reference sequence to identify a chromosomal location of the translocation and the chromosomal location of the at least one DSB.

2. The method of claim 1, wherein the first locus-specific primer comprises an affinity tag.

3. The method of claim 2, wherein the method further comprises isolating the PCR products produced in step (e) by affinity purification.

4. The method of claim 1, wherein the affinity tag is biotin and affinity purification comprises binding biotin with streptavidin.

5. The method of claim 1, wherein the affinity purification comprises binding the PCR products produced in step (d) to a substrate.

6. The method of claim 1, wherein the primers used for the nested PCR step comprise barcode sequences.

7. The method of claim 1, wherein the fragmenting is performed by sonication; restriction digest; randomly shearing genomic DNA; and/or with a frequently cutting restriction enzyme.

8. The method of claim 1, wherein ligating the single-stranded PCR products to an adapter comprises contacting the PCR product with a population of adapters having the same distal portion and random proximal portion sequences.

9. The method of claim 1, wherein the adaptor comprises barcode sequences between distal and proximal portions.

10. The method of claim 1, wherein the PCR products produced in step (i) are size selected prior to sequencing.

11. The method of claim 1 wherein the agent is selected from the group consisting of:
    Cas9 nuclease; Cas9:gRNA nuclease; a nuclease; a custom nuclease; a meganuclease; a TALEN; a zinc-finger nuclease; a CRISPR; a Cpf1 CRISPR effector; an integrating virus or viral vector; an endonuclease; a chemotherapeutic; and radiation.

12. The method of claim 1, wherein the agent will generate at least one DSB within 400 bp of the hybridization target of the locus-specific primer.

13. The method of claim 1, wherein the agent will generate at least one DSB on the same chromosome as the hybridization target of the locus-specific primer.

14. The method of claim 1, wherein the cell is exposed to two agents, wherein a first agent will generate at least one DSB on the same chromosome as a DSB generated by a second agent.

15. The method of claim 1, further comprising a step of inserting into a cell to be analyzed at least one target sequence for the agent that is known to be absent in the genome of the cell to be analyzed prior to step (a) of claim 1.

16. The method of claim 1, wherein the cells are allowed to divide for at least 12 hours.

17. The method of claim 1, wherein the cell is a mammalian or plant cell.

18. The method of claim 1, wherein the cell division step (b) or the blocking digestion step (h) is omitted.

19. The method of claim 1, wherein end repair is not performed between steps (d) and (e).

20. The method of claim 1, wherein the fragmenting is performed by sonication.

* * * * *